US008030270B2

(12) United States Patent
Chu et al.

(10) Patent No.: US 8,030,270 B2
(45) Date of Patent: *Oct. 4, 2011

(54) METHODS FOR IDENTIFYING GLP-1 SECRETAGOGUES

(75) Inventors: Zhi-Liang Chu, San Diego, CA (US); James N. Leonard, San Diego, CA (US); Hussien A. Al-Shamma, Encinitas, CA (US); Robert M. Jones, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 18 days.

This patent is subject to a terminal disclaimer.

(21) Appl. No.: 12/610,674

(22) Filed: Nov. 2, 2009

(65) Prior Publication Data

US 2010/0285495 A1    Nov. 11, 2010

Related U.S. Application Data

(63) Continuation of application No. 12/609,599, filed on Oct. 30, 2009, which is a continuation of application No. 11/603,417, filed on Nov. 22, 2006, now Pat. No. 7,803,754, which is a continuation of application No. 11/328,405, filed on Jan. 9, 2006.

(60) Provisional application No. 60/726,880, filed on Oct. 14, 2005, provisional application No. 60/683,172, filed on May 19, 2005, provisional application No. 60/643,086, filed on Jan. 10, 2005.

(51) Int. Cl.
*A61K 38/00* (2006.01)
*A61K 51/00* (2006.01)

(52) U.S. Cl. .................. 514/1.1; 530/300; 424/1.69

(58) Field of Classification Search .............. None
See application file for complete search history.

(56) References Cited

U.S. PATENT DOCUMENTS

| | | | |
|---|---|---|---|
| 4,166,452 | A | 9/1979 | Generales, Jr. et al. |
| 4,256,108 | A | 3/1981 | Teeuwes et al. |
| 4,265,874 | A | 5/1981 | Bonson et al. |
| 4,704,362 | A | 11/1987 | Itakaru et al. |
| 5,462,856 | A | 10/1995 | Lerner et al. |
| 5,922,576 | A | 7/1999 | He et al. |
| 6,040,145 | A | 3/2000 | Huber |
| 6,051,386 | A | 4/2000 | Lerner et al. |
| 6,100,042 | A | 8/2000 | Fowlkes et al. |
| 6,100,234 | A | 8/2000 | Huber |
| 6,166,063 | A | 12/2000 | Villhauer |
| 6,183,974 | B1 | 2/2001 | Bringhurst et al. |
| 6,221,660 | B1 | 4/2001 | Bonini et al. |
| 6,242,422 | B1 | 6/2001 | Karanewsky |
| 6,303,661 | B1 | 10/2001 | Demuth et al. |
| 6,380,398 | B2 | 4/2002 | Kanstrup et al. |
| 6,395,767 | B2 | 5/2002 | Robl et al. |
| 6,410,508 | B1 | 6/2002 | Isales et al. |
| 6,432,969 | B1 | 8/2002 | Villhauer et al. |
| 6,468,756 | B1 * | 10/2002 | Bonini et al. ............ 435/7.1 |
| 6,573,287 | B2 | 6/2003 | Sulsky et al. |
| 6,617,340 | B1 | 9/2003 | Villhauer et al. |
| 6,645,995 | B2 | 11/2003 | Kanstrup et al. |
| 6,653,064 | B1 | 11/2003 | Jochum et al. |
| 6,699,871 | B2 | 3/2004 | Edmondson et al. |
| 6,706,742 | B2 | 3/2004 | de Nanteuil et al. |
| 6,710,040 | B1 | 3/2004 | Hulin et al. |
| 6,716,843 | B2 | 4/2004 | de Nanteuil et al. |
| 6,727,261 | B2 | 4/2004 | Gobbi et al. |
| 6,800,650 | B2 | 10/2004 | Boehringer et al. |
| 6,803,357 | B1 | 10/2004 | Bachovchin et al. |
| 6,812,350 | B2 | 11/2004 | Hulin et al. |
| 6,844,316 | B2 | 1/2005 | Niestroj et al. |
| 6,849,622 | B2 | 2/2005 | Yasuda et al. |
| 6,861,440 | B2 | 3/2005 | Boehringer et al. |
| 6,867,205 | B2 | 3/2005 | Boehringer et al. |
| 6,869,947 | B2 | 3/2005 | Kanstrup et al. |
| 6,897,222 | B2 | 5/2005 | Gobbi et al. |
| 6,946,480 | B2 | 9/2005 | Demuth et al. |
| 6,949,515 | B2 | 9/2005 | Demuth et al. |
| 6,995,183 | B2 | 2/2006 | Hamann et al. |
| 7,008,957 | B2 | 3/2006 | Wagner et al. |
| 7,022,718 | B2 | 4/2006 | Boehringer et al. |
| 7,026,316 | B2 | 4/2006 | Ashton et al. |
| 7,053,055 | B2 | 5/2006 | Demuth et al. |

(Continued)

FOREIGN PATENT DOCUMENTS

CA          2 123 128          5/1993

(Continued)

OTHER PUBLICATIONS

Cox et al., "Multiple Y receptors mediate pancreatic polypeptide responses in mouse colon mucosa," *Peptides*, 22:445-452 (2001).
Fu et al., "Oleylethanolamide regulates feeding and body weight through activation of the nuclear receptor PPAR-alpha," *Nature*, 425:90-93 (2003).
"Impact of Modeling on GPR119 Agonist Development," PDM, Pfizer Global Research and Development, Groton, CT and Rosa and Co., LLC, San Carlos, CA, Poster and Press Release, Biorbis World PK/PD Summit, 3 pages (Apr. 26, 2011).
Bjenning et al., "G protein-coupled receptors as therapeutic targets for obesity and type 2 diabetes," *Curr. Opin. Investig. Drugs*, 5(10):1051-62 (2004).
Fagerholm et al., "alpha2A-adrenoceptor antagonism increases insulin secretion and synergistically augments the insulinotropic effect of glibenclamide in mice," *Br. J. Pharmacol.*, 154:1287-1296 (2008).

(Continued)

*Primary Examiner* — Maury Audet
(74) *Attorney, Agent, or Firm* — Fish & Richardson P.C.

(57) ABSTRACT

The present invention concerns combination of an amount of a GPR119 agonist with an amount of a dipeptidyl peptidase IV (DPP-IV) inhibitor such that the combination provides an effect in lowering a blood glucose level or in increasing a blood GLP-1 level in a subject over that provided by the amount of the GPR119 agonist or the amount of the DPP-IV inhibitor alone and the use of such a combination for treating or preventing diabetes and conditions related thereto or conditions ameliorated by increasing a blood GLP-1 level. The present invention also relates to the use of a G protein-coupled receptor to screen for GLP-1 secretagogues.

9 Claims, 13 Drawing Sheets

U.S. PATENT DOCUMENTS

| | | |
|---|---|---|
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,083,933 B1 | 8/2006 | Griffin et al. |
| 7,084,120 B2 | 8/2006 | Demuth et al. |
| 7,094,800 B2 | 8/2006 | Shoenafinger et al. |
| 7,122,555 B2 | 10/2006 | Boehringer et al. |
| 7,132,426 B2 | 11/2006 | Jones et al. |
| 7,217,711 B2 | 5/2007 | Eckhardt et al. |
| 7,238,670 B2 | 7/2007 | Natarajan et al. |
| 7,238,671 B2 | 7/2007 | Natarajan et al. |
| 7,348,327 B2 | 3/2008 | Aranyi et al. |
| 7,470,699 B2 | 12/2008 | Jones et al. |
| 7,495,002 B2 | 2/2009 | Langkopf et al. |
| 7,501,426 B2 | 3/2009 | Himmelsbach et al. |
| 7,550,455 B2 | 6/2009 | Himmelsbach et al. |
| 7,645,763 B2 | 1/2010 | Himmelsbach et al. |
| 7,833,730 B2 * | 11/2010 | Chu et al. .................. 435/7.2 |
| 2002/0006899 A1 | 1/2002 | Pospisilk et al. |
| 2002/0019411 A1 | 2/2002 | Robl et al. |
| 2002/0042441 A1 | 4/2002 | Acton, III et al. |
| 2002/0049164 A1 | 4/2002 | Demuth et al. |
| 2002/0103384 A1 | 8/2002 | Kanstrup et al. |
| 2002/0183367 A1 | 12/2002 | Sulsky et al. |
| 2002/0198205 A1 | 12/2002 | Himmelsbach et al. |
| 2003/0018081 A1 | 1/2003 | Piomelli et al. |
| 2003/0078247 A1 | 4/2003 | DeNanteuil et al. |
| 2003/0087950 A1 | 5/2003 | DeNanteuil et al. |
| 2003/0100563 A1 | 5/2003 | Edmondson et al. |
| 2003/0105077 A1 | 6/2003 | Kanstrup et al. |
| 2003/0119738 A1 | 6/2003 | Niestroj et al. |
| 2003/0119750 A1 | 6/2003 | Demuth et al. |
| 2003/0125304 A1 | 7/2003 | Demuth et al. |
| 2003/0125539 A1 | 7/2003 | Bonini et al. |
| 2003/0130199 A1 | 7/2003 | Von Hoersten et al. |
| 2003/0130281 A1 | 7/2003 | Boehringer et al. |
| 2003/0134802 A1 | 7/2003 | Demuth et al. |
| 2003/0162820 A1 | 8/2003 | Demuth et al. |
| 2003/0180813 A1 | 9/2003 | Ohishi et al. |
| 2003/0195188 A1 | 10/2003 | Boehringer et al. |
| 2003/0199528 A1 | 10/2003 | Kanstrup et al. |
| 2003/0216382 A1 | 11/2003 | Boehringer et al. |
| 2003/0216450 A1 | 11/2003 | Evans et al. |
| 2003/0225102 A1 | 12/2003 | Sankaranarayanan et al. |
| 2003/0232788 A1 | 12/2003 | Karanwesky et al. |
| 2004/0034014 A1 | 2/2004 | Kanstrup et al. |
| 2004/0063935 A1 | 4/2004 | Yasuda et al. |
| 2004/0072892 A1 | 4/2004 | Fukushima et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097510 A1 | 5/2004 | Himmelsbach et al. |
| 2004/0106656 A1 | 6/2004 | Ashton et al. |
| 2004/0110817 A1 | 6/2004 | Hulin et al. |
| 2004/0116328 A1 | 6/2004 | Yoshikawa et al. |
| 2004/0138214 A1 | 7/2004 | Himmelsbach et al. |
| 2004/0176406 A1 | 9/2004 | Gobbi et al. |
| 2004/0180925 A1 | 9/2004 | Matsuno et al. |
| 2004/0224875 A1 | 11/2004 | Schilling et al. |
| 2004/0229926 A1 | 11/2004 | Yasuda et al. |
| 2004/0242898 A1 | 12/2004 | Hulin et al. |
| 2004/0254226 A1 | 12/2004 | Feng et al. |
| 2004/0259883 A1 | 12/2004 | Sakashita et al. |
| 2004/0259902 A1 | 12/2004 | Boehringer et al. |
| 2004/0259903 A1 | 12/2004 | Boehringer et al. |
| 2005/0004205 A1 | 1/2005 | Evans et al. |
| 2005/0032804 A1 | 2/2005 | Cypes et al. |
| 2005/0038020 A1 | 2/2005 | Hamann et al. |
| 2005/0043292 A1 | 2/2005 | Parker et al. |
| 2005/0059650 A1 | 3/2005 | Jones et al. |
| 2005/0059724 A1 | 3/2005 | Schoenafinger et al. |
| 2005/0070562 A1 | 3/2005 | Jones et al. |
| 2005/0101542 A1 | 5/2005 | Piomelli et al. |
| 2006/0014764 A1 | 1/2006 | Feng et al. |
| 2006/0024313 A1 | 2/2006 | Chen et al. |
| 2006/0039974 A1 | 2/2006 | Akiyama et al. |
| 2006/0040963 A1 | 2/2006 | Mathvink et al. |
| 2006/0046978 A1 | 3/2006 | Pierau et al. |
| 2006/0052382 A1 | 3/2006 | Duffy et al. |
| 2006/0069116 A1 | 3/2006 | Ashton et al. |
| 2006/0074087 A1 | 4/2006 | Ashton et al. |
| 2006/0111336 A1 | 5/2006 | Duffy et al. |
| 2006/0135512 A1 | 6/2006 | Boehringer et al. |
| 2006/0135767 A1 | 6/2006 | Feng et al. |
| 2006/0142262 A1 | 6/2006 | Jones et al. |
| 2006/0142576 A1 | 6/2006 | Meng et al. |
| 2006/0154866 A1 | 7/2006 | Chu et al. |
| 2006/0217379 A1 | 9/2006 | Jones et al. |
| 2007/0032420 A1 | 2/2007 | Polidori et al. |
| 2007/0066590 A1 | 3/2007 | Jones et al. |
| 2007/0072803 A1 | 3/2007 | Chu et al. |
| 2007/0072804 A1 | 3/2007 | Chu et al. |
| 2007/0072844 A1 | 3/2007 | Jones et al. |
| 2007/0078150 A1 | 4/2007 | Jones et al. |
| 2007/0082874 A1 | 4/2007 | Jones et al. |
| 2007/0155763 A1 | 7/2007 | Jones et al. |
| 2007/0167473 A1 | 7/2007 | Jones et al. |
| 2007/0287670 A1 | 12/2007 | Natarajan et al. |
| 2008/0058339 A1 | 3/2008 | Brandt et al. |
| 2008/0076805 A1 | 3/2008 | Lin et al. |
| 2009/0036434 A1 | 2/2009 | Jones et al. |
| 2009/0253153 A1 | 10/2009 | Chu et al. |
| 2010/0137293 A1 * | 6/2010 | Chu et al. .................. 514/227.5 |

FOREIGN PATENT DOCUMENTS

| | | |
|---|---|---|
| CA | 2 289 124 | 11/1998 |
| CA | 2 289 125 | 11/1998 |
| CA | 2 339 537 | 3/2000 |
| CA | 2 433 090 | 7/2002 |
| CA | 2 466 870 | 6/2003 |
| DE | 296075 | 11/1991 |
| DE | 19616486 | 10/1997 |
| DE | 19823831 | 12/1999 |
| DE | 19828113 | 1/2000 |
| DE | 19834591 | 2/2000 |
| DE | 10143840 | 3/2003 |
| DE | 10238243 | 3/2004 |
| DE | 10238470 | 3/2004 |
| DE | 10238477 | 3/2004 |
| DE | 10251927 | 5/2004 |
| DE | 10256264 | 6/2004 |
| DE | 10327439 | 1/2005 |
| DE | 10333935 | 2/2005 |
| DE | 200410282263 | 1/2006 |
| EP | 0 995 440 | 4/2000 |
| EP | 1 043 328 | 10/2000 |
| EP | 1 050 540 | 11/2000 |
| EP | 1 092 727 | 4/2001 |
| EP | 1 215 207 | 6/2002 |
| EP | 1 228 061 | 8/2002 |
| EP | 1 245 568 | 10/2002 |
| EP | 1 248 604 | 10/2002 |
| EP | 1 258 476 | 11/2002 |
| EP | 1 280 797 | 2/2003 |
| EP | 1 296 974 | 4/2003 |
| EP | 1 301 187 | 4/2003 |
| EP | 1 323 710 | 7/2003 |
| EP | 1 333 025 | 8/2003 |
| EP | 1 338 651 | 8/2003 |
| EP | 1338 592 | 8/2003 |
| EP | 1 354 882 | 10/2003 |
| EP | 1 304 327 | 4/2004 |
| EP | 1 426 366 | 4/2004 |
| EP | 1 465 891 | 10/2004 |
| EP | 1 469 873 | 10/2004 |
| EP | 1 489 088 | 12/2004 |
| EP | 1 490 335 | 12/2004 |
| EP | 1 538 217 | 6/2005 |
| EP | 1 624 874 | 2/2006 |
| EP | 1 627 870 | 2/2006 |
| EP | 1 659 123 | 5/2006 |
| EP | 1 664 031 | 6/2006 |
| EP | 1 671 649 | 6/2006 |
| EP | 1 287 133 | 12/2006 |
| EP | 1 902 730 | 3/2008 |
| FR | 2822826 | 10/2002 |
| FR | 2824825 | 11/2002 |

| | | | | | |
|---|---|---|---|---|---|
| JP | 1998081666 | 3/1998 | WO | WO 03/000180 | 1/2003 |
| JP | 1998182613 | 7/1998 | WO | WO 03/000181 | 1/2003 |
| JP | 2000191616 | 7/2000 | WO | WO 03/000250 | 1/2003 |
| JP | 2000511559 | 9/2000 | WO | WO 03/002530 | 1/2003 |
| JP | 2000327689 | 11/2000 | WO | WO 03/002531 | 1/2003 |
| JP | 2001510442 | 7/2001 | WO | WO 03/002553 | 1/2003 |
| JP | 2002265439 | 9/2002 | WO | WO 03/002593 | 1/2003 |
| JP | 2002356471 | 12/2002 | WO | WO 03/002595 | 1/2003 |
| JP | 2002356472 | 12/2002 | WO | WO 03/002596 | 1/2003 |
| JP | 2002363157 | 12/2002 | WO | WO 03/004496 | 1/2003 |
| JP | 2003238566 | 8/2003 | WO | WO 03/004498 | 1/2003 |
| JP | 2003300977 | 10/2003 | WO | WO 03/015775 | 2/2003 |
| JP | 2003327532 | 11/2003 | WO | WO 03/022871 | 3/2003 |
| JP | 2004002367 | 1/2004 | WO | WO 03/024942 | 3/2003 |
| JP | 2004002368 | 1/2004 | WO | WO 03/024965 | 3/2003 |
| JP | 2004026678 | 1/2004 | WO | WO 03/026661 | 4/2003 |
| JP | 2004026820 | 1/2004 | WO | WO 03/035057 | 5/2003 |
| JP | 2004035574 | 2/2004 | WO | WO 03/035067 | 5/2003 |
| JP | 2004043429 | 2/2004 | WO | WO 03/037327 | 5/2003 |
| JP | 2004244412 | 9/2004 | WO | WO 03/038123 | 5/2003 |
| JP | 2004269468 | 9/2004 | WO | WO 03/040174 | 5/2003 |
| JP | 2004269469 | 9/2004 | WO | WO 03/045228 | 6/2003 |
| JP | 2004315496 | 11/2004 | WO | WO 03/045977 | 6/2003 |
| JP | 2005023038 | 1/2005 | WO | WO 03/055881 | 7/2003 |
| WO | WO 91/16339 | 10/1991 | WO | WO 03/057144 | 7/2003 |
| WO | WO 93/08259 | 4/1993 | WO | WO 03/057666 | 7/2003 |
| WO | WO 93/10127 | 5/1993 | WO | WO 03/068748 | 8/2003 |
| WO | WO 95/15309 | 6/1995 | WO | WO 03/068757 | 8/2003 |
| WO | WO 95/29691 | 11/1995 | WO | WO 03/072528 | 9/2003 |
| WO | WO 97/40832 | 11/1997 | WO | WO 03/072556 | 9/2003 |
| WO | WO 98/18763 | 5/1998 | WO | WO 03/074500 | 9/2003 |
| WO | WO 98/19998 | 5/1998 | WO | WO 03/080633 | 10/2003 |
| WO | WO 98/50046 | 11/1998 | WO | WO 03/082817 | 10/2003 |
| WO | WO 98/50066 | 11/1998 | WO | WO 03/084940 | 10/2003 |
| WO | WO 99/14344 | 3/1999 | WO | WO 03/095425 | 11/2003 |
| WO | WO 99/16864 | 4/1999 | WO | WO 03/099279 | 12/2003 |
| WO | WO 99/25719 | 5/1999 | WO | WO 03/101448 | 12/2003 |
| WO | WO 99/38501 | 8/1999 | WO | WO 03/101958 | 12/2003 |
| WO | WO 99/56753 | 11/1999 | WO | WO 03/104229 | 12/2003 |
| WO | WO 99/61431 | 12/1999 | WO | WO 03/105763 | 12/2003 |
| WO | WO 99/62914 | 12/1999 | WO | WO 03/106456 | 12/2003 |
| WO | WO 99/67278 | 12/1999 | WO | WO 04/000327 | 12/2003 |
| WO | WO 00/10549 | 3/2000 | WO | WO 2004/004661 | 1/2004 |
| WO | WO 00/12704 | 3/2000 | WO | WO 2004/007446 | 1/2004 |
| WO | WO00/22129 | 4/2000 | WO | WO 2004/007468 | 1/2004 |
| WO | WO 00/23421 | 4/2000 | WO | WO 2004/009544 | 1/2004 |
| WO | WO 00/31258 | 6/2000 | WO | WO 2004/014860 | 2/2004 |
| WO | WO 00/34241 | 6/2000 | WO | WO 2004/018467 | 3/2004 |
| WO | WO 00/50562 | 8/2000 | WO | WO 2004/018468 | 3/2004 |
| WO | WO 00/53171 | 9/2000 | WO | WO 2004/018469 | 3/2004 |
| WO | WO 00/56296 | 9/2000 | WO | WO 2004/020407 | 3/2004 |
| WO | WO 00/56297 | 9/2000 | WO | WO 2004/024943 | 3/2004 |
| WO | WO 00/69868 | 11/2000 | WO | WO 2004/032836 | 4/2004 |
| WO | WO 00/71135 | 11/2000 | WO | WO 2004/033455 | 4/2004 |
| WO | WO 01/34594 | 5/2001 | WO | WO 2004/037169 | 5/2004 |
| WO | WO 01/52825 | 7/2001 | WO | WO 2004/037181 | 5/2004 |
| WO | WO 01/55105 | 8/2001 | WO | WO 2004/041795 | 5/2004 |
| WO | WO 01/68603 | 9/2001 | WO | WO 2004/041820 | 5/2004 |
| WO | WO 01/81304 | 11/2001 | WO | WO 2004/043940 | 5/2004 |
| WO | WO 01/81337 | 11/2001 | WO | WO 2004/046106 | 6/2004 |
| WO | WO 01/87929 | 11/2001 | WO | WO 2004/048379 | 6/2004 |
| WO | WO 01/96295 | 12/2001 | WO | WO 2004/050022 | 6/2004 |
| WO | WO 01/97808 | 12/2001 | WO | WO 2004/050658 | 6/2004 |
| WO | WO 02/02560 | 1/2002 | WO | WO 2004/052362 | 6/2004 |
| WO | WO 02/14271 | 2/2002 | WO | WO 2004/052850 | 6/2004 |
| WO | WO 02/30890 | 4/2002 | WO | WO 2004/058266 | 7/2004 |
| WO | WO 02/30891 | 4/2002 | WO | WO 2004/064778 | 8/2004 |
| WO | WO 02/34900 | 5/2002 | WO | WO 2004/065380 | 8/2004 |
| WO | WO 02/38541 | 5/2002 | WO | WO 2004/067509 | 8/2004 |
| WO | WO 02/42461 | 5/2002 | WO | WO 2004/069162 | 8/2004 |
| WO | WO 02/44362 | 6/2002 | WO | WO 2004/071454 | 8/2004 |
| WO | WO 02/49648 | 6/2002 | WO | WO 2004/076413 | 9/2004 |
| WO | WO 02/051836 | 7/2002 | WO | WO 2004/076433 | 9/2004 |
| WO | WO 02/055088 | 7/2002 | WO | WO 2004/076434 | 9/2004 |
| WO | WO 02/062764 | 8/2002 | WO | WO 2004/085378 | 10/2004 |
| WO | WO 02/068420 | 9/2002 | WO | WO 2004/085661 | 10/2004 |
| WO | WO 02/076450 | 10/2002 | WO | WO 2004/087053 | 10/2004 |
| WO | WO 02/083109 | 10/2002 | WO | WO 2004/087650 | 10/2004 |
| WO | WO 02/083128 | 10/2002 | WO | WO 2004/092128 | 10/2004 |

| | | |
|---|---|---|
| WO | WO 2004/096806 | 11/2004 |
| WO | WO 2004/099134 | 11/2004 |
| WO | WO 2004/103276 | 12/2004 |
| WO | WO 2004/103993 | 12/2004 |
| WO | WO 2004/104215 | 12/2004 |
| WO | WO 2004/104216 | 12/2004 |
| WO | WO 2004/106289 | 12/2004 |
| WO | WO 2004/108730 | 12/2004 |
| WO | WO 2004/110375 | 12/2004 |
| WO | WO 2004/110436 | 12/2004 |
| WO | WO 2004/110988 | 12/2004 |
| WO | WO 2004/111041 | 12/2004 |
| WO | WO 2004/111051 | 12/2004 |
| WO | WO 2004/112701 | 12/2004 |
| WO | WO 2005/000846 | 1/2005 |
| WO | WO 2005/000848 | 1/2005 |
| WO | WO 2005/003135 | 1/2005 |
| WO | WO 2005/007647 | 1/2005 |
| WO | WO 2005/007658 | 1/2005 |
| WO | WO 2005/009956 | 2/2005 |
| WO | WO 2005/011581 | 2/2005 |
| WO | WO 2005/012249 | 2/2005 |
| WO | WO 2005/012308 | 2/2005 |
| WO | WO 2005/012312 | 2/2005 |
| WO | WO 2005/019168 | 3/2005 |
| WO | WO 2005/020920 | 3/2005 |
| WO | WO 2005/021536 | 3/2005 |
| WO | WO 2005/023762 | 3/2005 |
| WO | WO 2005/025554 | 3/2005 |
| WO | WO 2005/026148 | 3/2005 |
| WO | WO 2005/030127 | 4/2005 |
| WO | WO 2005/030751 | 4/2005 |
| WO | WO 2005/032590 | 4/2005 |
| WO | WO 2005/033099 | 4/2005 |
| WO | WO 2005/034940 | 4/2005 |
| WO | WO 2005/037779 | 4/2005 |
| WO | WO 2005/037828 | 4/2005 |
| WO | WO 2005/040095 | 5/2005 |
| WO | WO 2005/042488 | 5/2005 |
| WO | WO 2005/042533 | 5/2005 |
| WO | WO 2005/044195 | 5/2005 |
| WO | WO 2005/047297 | 5/2005 |
| WO | WO 2005/049022 | 6/2005 |
| WO | WO 2005/051950 | 6/2005 |
| WO | WO 2005/058849 | 6/2005 |
| WO | WO 2005/058901 | 6/2005 |
| WO | WO 2005/061489 | 7/2005 |
| WO | WO 2005/063750 | 7/2005 |
| WO | WO 2005/072530 | 8/2005 |
| WO | WO 2005/075426 | 8/2005 |
| WO | WO 2005/079795 | 9/2005 |
| WO | WO 2005/082348 | 9/2005 |
| WO | WO 2005/082849 | 9/2005 |
| WO | WO 2005/082906 | 9/2005 |
| WO | WO 2005/085246 | 9/2005 |
| WO | WO 2005/087235 | 9/2005 |
| WO | WO 2005/094323 | 10/2005 |
| WO | WO 2005/095339 | 10/2005 |
| WO | WO 2005/095381 | 10/2005 |
| WO | WO 2005/100334 | 10/2005 |
| WO | WO 2005/106011 | 11/2005 |
| WO | WO 2005/108382 | 11/2005 |
| WO | WO 2005/115982 | 12/2005 |
| WO | WO 2005/116014 | 12/2005 |
| WO | WO 2005/116029 | 12/2005 |
| WO | WO 2005/118555 | 12/2005 |
| WO | WO 2005/120494 | 12/2005 |
| WO | WO 2005/121089 | 12/2005 |
| WO | WO 2005/121121 | 12/2005 |
| WO | WO 2005/121131 | 12/2005 |
| WO | WO 2005/123685 | 12/2005 |
| WO | WO 2006/000576 | 1/2006 |
| WO | WO 2006/009886 | 1/2006 |
| WO | WO 2006/011035 | 2/2006 |
| WO | WO 2006/012395 | 2/2006 |
| WO | WO 2006/012441 | 2/2006 |
| WO | WO 2006/013104 | 2/2006 |
| WO | WO 2006/015691 | 2/2006 |
| WO | WO 2006/015699 | 2/2006 |
| WO | WO 2006/020017 | 2/2006 |
| WO | WO 2006/023750 | 3/2006 |
| WO | WO 2006/027204 | 3/2006 |
| WO | WO 2006/029769 | 3/2006 |
| WO | WO 2006/030847 | 3/2006 |
| WO | WO 2006/033848 | 3/2006 |
| WO | WO 2006/039325 | 4/2006 |
| WO | WO 2006/040625 | 4/2006 |
| WO | WO 2006/040966 | 4/2006 |
| WO | WO 2006/043490 | 4/2006 |
| WO | WO 2006/047248 | 5/2006 |
| WO | WO 2006/058064 | 6/2006 |
| WO | WO 2006/058628 | 6/2006 |
| WO | WO 2006/067531 | 6/2006 |
| WO | WO 2006/067532 | 6/2006 |
| WO | WO 2006/068163 | 6/2006 |
| WO | WO 2006/068978 | 6/2006 |
| WO | WO 2006/070208 | 6/2006 |
| WO | WO 2006/070208 | 7/2006 |
| WO | WO 2006/071752 | 7/2006 |
| WO | WO 2006/071762 | 7/2006 |
| WO | WO 2006/076231 | 7/2006 |
| WO | WO 2006/083491 | 8/2006 |
| WO | WO 2006/086727 | 8/2006 |
| WO | WO 2007/003960 | 1/2007 |
| WO | WO 2007/003961 | 1/2007 |
| WO | WO 2007/003962 | 1/2007 |
| WO | WO 2007/003964 | 1/2007 |
| WO | WO 2007/035355 | 3/2007 |
| WO | WO 2007/116229 | 10/2007 |
| WO | WO 2007/116230 | 10/2007 |
| WO | WO 2007/120689 | 10/2007 |
| WO | WO 2007/120702 | 10/2007 |
| WO | WO 2007/138362 | 12/2007 |
| WO | WO 2008/005569 | 1/2008 |
| WO | WO 2008/005576 | 1/2008 |
| WO | WO 2008/008887 | 1/2008 |
| WO | WO 2008/008895 | 1/2008 |
| WO | WO 2008/025798 | 3/2008 |
| WO | WO 2008/025799 | 3/2008 |
| WO | WO 2008/025800 | 3/2008 |
| WO | WO 2008/070692 | 6/2008 |
| WO | WO 2008/076243 | 6/2008 |
| WO | WO 2009/012275 | 1/2009 |
| WO | WO 2009/038974 | 3/2009 |
| WO | WO 2009/123992 | 10/2009 |
| WO | WO 2009/150144 | 12/2009 |
| WO | WO 2010/001166 | 1/2010 |
| WO | WO 2010/029089 | 3/2010 |
| WO | WO 2010/072776 | 7/2010 |
| WO | WO 2010/074271 | 7/2010 |
| WO | WO 2010/086411 | 8/2010 |
| WO | WO 2010/092163 | 8/2010 |
| WO | WO 2010/093845 | 8/2010 |
| WO | WO 2010/108902 | 9/2010 |
| WO | WO 2010/108903 | 9/2010 |
| WO | WO 2010/149170 | 12/2010 |
| WO | WO 2011/008663 | 1/2011 |

OTHER PUBLICATIONS

Goodman et al., "The Novel GPR119-Receptor Agonist PSN821 Shows Glucose Lowering and Decreased Energy Intake in Patients with T2DM after 14 Days Treatment," Presented During Session: Pharmacologic Treatment of Diabetes—Novel Therapies, Abstract No. 0306-OR, 1 page (Jun. 17, 2011).

Irwin et al., "Antidiabetic effects of sub-chronic activation of the GIP receptor alone and in combination with background exendin-4 therapy in high fat fed mice," Regul. Pept., 153:70-76 (2009).

Lebovitz et al., "Combination insulin-sulfonylurea therapy," Diabetes Care, 13(6):667-675 (1990).

Mace et al., "The Novel GPR119-Receptor Agonist PSN821 Stimulates Basal and Nutrient-Induced GIP, GLP-1 and PYY Secretion from Rat Small Intestine," Presented During: General Poster Session I, Abstract No. 1132-P, 1 page (Jun. 17, 2011).

Novartis, Starlix® (nateglinide) tablets, Prescribing Information Description, 12 pages (Jul. 2008).

Nunez et al., "Evaluation of GSK1292263, a Novel GPR119 Agonist, in Type 2 Diabetes Mellitus (T2DM): Safety, Tolerability, Pharmacokinetics (PK) and Pharmacodynamics (PD) of Single and Multiple Doses," Presented During: Pharmacologic Treatment of Diabetes—Novel Therapies I, Abstract No. 0996-P, 2 pages (Jun. 17, 2011).

Tian et al., "Stimulating Beta Cell Replication and Improving Islet Graft Function by AR231453, a GPR119 Agonist," Presented During Session: Experimental Islet Transplantation/Glycemic Control after Kidney Transplantation, Abstract No. 0166-OR, 1 page (Jun. 17, 2011).

Yoshida et al., "The Novel, Potent and Orally Available GPR119 Agonist AS1790091 Enhances Insulin Secretion and Insulin Promoter Activity, Preserves B-Cell Function, Improves Insulin Resistance, and Reduces Body Weight Gain in Type 2 Diabetic Mice," Presented During: Pharmacologic Treatment of Diabetes—Novel Therapies II, Abstract No. 1001-P, 1 page (Jun. 17, 2011).

U.S. Appl. No. 60/342,015, filed Oct. 18, 2001, Natarajan et al.

Abe et al., "First synthesis and determination of the absolute configuration of sulphostin, a novel inhibitor of dipeptidyl peptidase IV," *J Nat Prod.*, 67:99-1004 (2004).

Abramowicz et al., "Drugs for diabetes," *Treatment Guidelines from the Medical Letter*, 3(36):57-62 (2005).

Abbott et al., "Blockade of the neuropeptide Y Y2 receptor with the specific antagonist BIIE0246 attenuates the effect of endogenous and exogenous peptide $YY_{(3-36)}$ on food intake," *Brain Res.*, 1043:139-144 (2005).

Adachi et al., "Free fatty acids administered into the colon promote the secretion of glucagon-like peptide-1 and insulin," *Biochem. Biophys. Res. Commun.*, 340:332-337 (2006).

Adler, Bone Diseases, Springer-Verlag, Germany (2000).

Adrian et al., "Human distribution and release of a putative new gut hormone, peptide YY,"*Gastroenterology*, 89:1070-1077 (1985).

Adult Treatment Panel III (ATP III: National Institutes of Health: Third Report of the National Cholesterol Education Program Expert Panel on Detection, Evaluation, and Treatment of High Blood Cholesterol in Adults (Adult Treatment Panel IIIJ), Executive Summary, Bethesda, MD., National Institutes of Health, National Heart, Lung and Blood Institute (NIH pub. No. 01-3670) (2001).

Ahren et al., "Inhibition of Dipeptidyl Peptidase-4 Augments Insulin Secretion in Response to Exogenously Administered Glucagon-Like Peptide-1, Glucose-Dependent Insulinotropic Polypeptide, Pituitary Adenylate Cyclase-Activating Polypeptide, and Gastrin-Releasing Peptide in Mice," *Endocrinology*, 146(4):2055-2059 (2005).

Ahren et al., "Inhibition of dipeptidyl peptidase-4 reduces glycemia, sustains insulin levels, and reduces glucagon levels in type 2 diabetes," *J .Clin. Endocrinol. Metab.*, 89:2078-2084 (2004).

Ahren et al., "Inhibition of dipeptidyl peptidase IV improves metabolic control over a 4-week study period in type 2 diabetes," *Diabetes Care*, 25:869-875 (2002).

Anini et al., "Role of leptin in the regulation of glucagon-like peptide-1 secretion," *Diabetes*, 52:252-259 (2003).

Altschul et al., "Basic Local Alignment Search Tool," *J. Mol. Biol.*, 215:403-410 (1990).

Altschul et al., "Gapped BLAST and PSI-BLAST: a new generation of protein database search programs," *Nucleic Acids Research*, 25:3389-3402 (1997).

Arehart et al., "Acceleration of cardiovascular disease by a dysfunctional prostacyclin receptor mutation: potential implications for cyclooxygenase-2 inhibition," *Circ. Res.*, 102(8):986-993 (2008).

Atik et al., "Burden of osteoporosis", *Clinical Orthopaedics and Related Research*, 443:19-24 (2006).

Ausubel et al., Short Protocols in Molecular Biology, $3^{rd}$ Edition, Wiley & Sons (1995).

Bak et al., "The effect of aging on fracture healing in the rat," *Calcified Tissue International*, 45:292-297 (1989).

Balasubramaniam et al., "Structure-activity studies including a (CH-NH) scan of peptide YY (PYY) active site, PYY(22-36), for interaction with rat intestinal PYY receptors: development of analogues with potent in vivo activity in the intestine," *J. Med. Chem.*, 43:3420-3427 (2000).

Balasubramaniam et al., "Neuropeptide Y (NPY) $Y_2$ receptor-selective agonist inhibits food intake and promotes fat metabolism in mice: combined anorectic effects of $Y_2$ and $Y_4$ receptor-selective agonists," *Peptides*, 28:235-240 (2007).

Balena et al., "Eight Weeks of Treatment with the Long Acting, Human GLP-1 Analogue R1583 Improves Glycemic Control and Lowers Body Weight in Subjects with Type 2 Diabetes Mellitus (T2DM) Treated with Metformin: A Double-Blind Placebo-Controlled Phase 2 Study," *Diabetes* Abstract ADA08L-1604: contact View, [108-OR] (2008).

Banish et al., "The use of stable isotope labeling and liquid chromatography/tandem mass spectrometry techniques to study the pharmacokinetics and bioavailability of the antimigraine drug, MK-0462 (rizatriptan) in dogs," *Rapid Commun. Mass Spectrom.*, 10:1033-1037 (1996).

Batterham et al., "Gut hormone $PYY_{3-36}$ physiologically inhibits food intake," *Nature*, 418:650-654 (2002).

Bas et al., "Radioiodinated Analogs of EP 00652218 for the Exploration of the Tachykinin NK1 Receptor by Spect," *J. Labelled Compd. Radiopharm.*, 44:S280-S282 (2001).

Behre, "Adiponectin, obesity and atherosclerosis," *Scand. J. Clin. Lab. Invest.*, 67:449-458 (2007).

Benoist et al., "In vivo sequence requirements of the SV40 early promotor region," *Nature*, 290:304-310 (1981).

Berge et al., "Pharmaceutical salts," *Journal of Pharmaceutical Sciences*, 66:1-19 (1977).

Bilchik et al., "Peptide YY is a physiological regulator of water and electrolyte absorption in the canine small bowel in vivo," *Gastroenterology*, 105:1441-1448 (1993).

Bilchik et al., "Peptide YY augments postprandial small intestinal absorption in the conscious dog," *Am. J. Surg.*, 167:570-574 (1994).

Boey et al., "Peptide YY ablation in mice leads to the development of hyperinsulinaemia and obesity," *Diabetologia*, 49:1360-1370 (2006).

Boey et al., "PYY transgenic mice are protected against diet-induced and genetic obesity," *Neuropeptides*, 42:19-30 (2008).

Bollag et al., "Osteoblast-derived cells express functional glucose-dependent insulinotropic peptide receptors," *Endocrinology*, 141:1228-1235 (2000).

Bollag et al., "Glucose-dependent insulinotropic peptide is an integrative hormone with osteotropic effects," *Molecular and Cellular Endocrinology*, 177:35-41 (2001).

Bose et al., "Glucagon-like peptide 1 can directly protect the heart against ischemia/reperfusion injury," *Diabetes*, 54:146-151 (2005).

Bradley, "TNF-mediated inflammatory disease," *J. Pathol.*, 214:149-160 (2008).

Brubaker et al., "Regulation of glucagon-like peptide-1 synthesis and secretion in the GLUTag enteroendoctrine cell line," *Endocrinology*, 139:4108-4114 (1998).

Brutlag et al., "Improved sensitivity of biological sequence database searches," *Cabios Comput Appl. Biosci.*, 6(3):237-245 (1990).

Buchan et al., "Clinical pharmacokinetics of frovatriptan," *Headache Suppl.*, 42(suppl. 2):S54-S62 (2002).

Caldwell et al., "Fluoropyrrolidine amides as dipeptidyl peptidase IV inhibitors," *Biorg. Med. Chem. Lett.*, 14(5):1265-1268 (2004).

Campbell el al., "Selective $A_1$-adenosine receptor antagonists identified using yeast *Saccharomyces cerevisiae* functional assays," *Bioorganic & Medical Chemistry Letters*, 9:2413-2418 (1999).

Carpenter et al., "The in vitro and in vivo effects of a GPR119 agonist," Poster, *Diabetes Mellitus, Insulin Action and Resistance*, Keystone Symposia, Breckenridge, Colorado (Jan. 22, 2008-Jan. 27, 2008).

Cello et al., "Chemical synthesis of poliovirus cDNA: generation of infectious virus in the absence of natural template," *Science*, 297:1016-1018 (2002).

Center WatchSM, "Clinical Trial Result Information," dated May 7, 2007 [online]. Retrieved on Feb. 5, 2009]. Retrieved from the Internet: http://www.centerwatch.com/clinical-trials/results/db/stur10066.html.

Chavez-Eng et al., "High-performance liquid chromatographic-tandem mass spectrometric evaluation and determination of stable isotope labeled analogs of rofecoxib in human plasma samples from oral bioavailability studies," *J. Chromatogr. B. Analyt. Technol. Biomed. Life. Sci.*, 767:117-129 (2002).

Chaudhri et al., "Gastrointestinal satiety signals," *Annu. Rev. Physiol.*, 70:239-255 (2008).

Chen et al., "CD26," *J. Biol. Regul. Homest. Agents*, 8:47-54 (2004).

Chen et al., "Glucose responsiveness of a reporter gene transduced into hepatocytic cells using a retroviral vector," *FEBS Letters*, 365:223-226 (1995).

Childs, "Diabetes medications update," *The Kansas Nurse*, 79(5):4-6 (2004).

Chu et al., "A role for intestinal endocrine cell-expressed, GPR119 in glycemic control by enhancing GLP-1 and GIP release," *Endocrinology*, 149(5):2038-2047 (2008).

Chu et al., "A role for β-cell-expressed G protein-coupled receptor 119 in glycemic control by enhancing glucose-dependent insulin release," *Endocrinology*, 148:2601-2609 (2007).

Chu et al., "Agonists of the orphan GPCR 19AJ promote insulin secretion by stimulating both GLP-1—producing endocrine cells and pancreatic β-cells," Abstract #112, p. 42, *Diabetes Mellitus: Molecular Mechanisms, Genetics and New Therapies*, Keystone Symposia, Keystone, Colorado (Jan. 27, 2005-Feb. 2, 2005).

Chu et al., "AR231453 mediates improved glycemic control exclusively via GDIR/GPR119," Abstract # 117 & Poster, *Diabetes: Molecular Genetics, Signaling Pathways and Integrated Physiology*, Keystone Symposia, Keystone, Colorado (Jan. 14, 2007-Jan. 19, 2007).

Chu et al., "Identification of an orphan, β-cell-specific GPCR that enhances glucose-dependent insulin release," Abstract #107, p. 56, *Toward Understanding Islet Biology*, Keystone Symposia, Keystone, Colorado (Jan. 21, 2003-Jan. 26, 2003).

Chu et al., "Novel lipid amide activators of GDIR/GPR119 and their role in glucose homeostasis," Abstract # 230 & Poster, *Diabetes: Molecular Genetics, Signaling Pathways and Integrated Physiology*, Keystone Symposia, Keystone, Colorado (Jan. 14, 2007-Jan. 19, 2007).

Chu et al., "Transgenic mice with β-cell-targeted expression of the human orphan GPCR 19AJ are resistant to high fat diet-induced hyperglycemia," Abstract #228, p. 54, *Diabetes Mellitus: Molecular Mechanisms, Genetics and New Therapies*, Keystone Symposia, Keystone, Colorado (Jan. 27, 2005-Feb. 2, 2005).

Collier et al., "Radiosynthesis and in-vivo evaluation of the pseudopeptide σ-opioid anatagonist 125 $[I^{125}]$-ITIPP(ψ)," *J. Labelled Comd Radiopharm.*, 42: S264-S266 (1999).

ConjuChem Press Release Dec. 3, 2008 (3 pages).

Cox, "Peptide YY: a neuroendocrine neighbor of note," *Peptides*, 28:345-351 (2007).

Crespo et al., "Morphometric and mechanical properties of femora in young adult male turkeys with and without femoral fractures," *Poultry Science*, 79:602-608 (2000).

Cruze et al., "The $Y_2$ receptor mediates increases in collateral-dependent blood flow in a model of peripheral arterial insufficiency," *Peptides*, 28:269-280 (2007).

Deacon et al., "Degradation of endogenous and exogenous gastric inhibitory polypeptide in healthy and in type 2 diabetic subjects as revealed using a new assay for the intact peptide," *The Journal of Clinical Endocrinology & Metabolism*, 85:3575-3581 (2000).

Deacon et al., "Dipeptidyl peptidase IV inhibition potentiates the insulinotropic effect of glucagon-like peptide 1 in the anesthetized pig," *Diabetes*, 47(5):764-769 (1998).

Deacon, "What do we know about the secretion and degradation of incretin hormones," *Regulatory Peptides*, 128:117-124 (2005).

D'Alessio et al., "Glucagon-like peptide 1: evolution of an incretin into a treatment for diabetes," *Am. J. Physiol. Endocrinol. Metab.*, 286(6):E882-E890 (2004).

Ding et al., "Impact of glucose-dependent peptide on age-induced bone loss," *Journal of Bone and Mineral Research* (published online Dec. 10, 2007).

Drucker, "The biology of incretin hormones", *Cell Metabolism*, 3:153-165, (2006).

Drucker, "Enhancing incretin action for the treatment of type 2 diabetes," *Diabetes Care*, 26(10):2929-2940 (2003).

During et al., "Glucagon-like peptide-1 receptor is involved in learning and neuroprotection," *Nat Med*., 9:1173-1179 (2003).

E-mail communication, Deno Dialynas and Kellie McConnell (Aug. 14, 2006).

Eberlein et al., "A new molecular form of PYY: structural characterization of human $PYY_{3-36}$ and $PYY_{1-36}$," *Peptides*, 10:797-803 (1989).

Ekstrand et al., "Deletion of neuropeptide Y (NPY) 2 receptor in mice results in blockage of NPY-induced angiogenesis and delayed wound healing," *Proc. Natl. Acad. Sci. USA*, 100:6033-6038 (2003).

Edmondson et al., "Potent and selective proline derived dipeptidyl peptidase IV inhibitors," *Bioorg Med Chem Lett.*,14:5151-5155 (2004).

Ekblad et al., "Distribution of pancreatic polypeptide and peptide YY," *Peptides*, 23:251-261 (2002).

El Bahh et al., "The anti-epileptic actions of neuropeptide Y in the hippocampus are mediated by $Y_2$ and not $Y_5$ receptors," *Eur. J. Neurosci.*, 22:1417-1430 (2005).

Engelstoft et al., "A gut feeling for obesity: 7TM sensors on enteroendocrine cells," *Cell Metabolism*, 8(6):447-449 (2008).

Felig et al., Eds., Endocrinology and Metabolism $4^{th}$ Edition, McGraw-Hill Book Company (2001).

Fayad et al., "Noninvasive In vivo high-resolution magnetic resonance imaging of atherosclerotic lesions in genetically engineered mice," *Circulation*, 98:1541-1547 (1998).

Fredriksson R. et al., "Seven evolutionarily conserved human rhodopain G protein-coupled receptors lacking close relatives," *FEBS Lett.*, 554(3):381-388 (2003).

Fyfe et al., "GPR119 Agonists are Potential Novel Oral Agents for the Treatment of Diabesity", *Diabetes* (2007) 56 (Supplement 1):A142, (Abstract #532-P; American Diabetes Association).

Fyfe et al., "Synthesis, SAR, and in vivo efficacy of novel GPR119 agonists with a 4-[3-(4-methanesulfinylphenoxy)propyl]-1-Boc-piperidine core," Abstract # MEDI 62, Division of Medicinal Chemistry, 234th ACS National Meeting, Boston, MA (Aug. 19-23, 2007).

Fyfe et al., "Discovery of novel, orally active, synthetic GPR119 agonists as potential agents for treatment of obesity and associated metaobolic disorders," *Diabetes*, 55 (Suppl. 1):p. A81 (Jun. 2006).

Fyfe et al., "New nonpeptide-binding GPCRs as targets for diabetes and the metabolic syndrome," *Ann. Rep. Med Chem.*, 42:129-145 (2007).

GenBank® Accession No. AAN95195, rat G Protein-coupled receptor 119 (Gpr119) protein (date of last modification: Dec. 20, 2002).

GenBank® Accession No. AY288423, Mus musculus G Protein-coupled receptor 119 (Gpr119) mRNA, complete cds. (date of last modification: Dec. 8, 2003).

GenBank® Accession No. AAP72125, G Protein-coupled receptor 119 [*Homo sapiens*] (date of last modification: Dec. 8, 2003).

Gish et al., "Identification of protein coding regions by database similarity search," *Nature Genet,*, 3:266-272 (1993).

Greig et al., "New therapeutic strategies and drug candidates for neurodegenerative diseases: p53 and TNF-alpha inhibitors, and GLP-1 receptor agonists," *Ann NY Acad Sci*,1035:290-315 (2004).

Gomez et al., "Intestinal peptide YY: ontogeny of gene expression in rat bowel and trophic actions on rat and mouse bowel," *Am. J. Physiol.*, 268:G71-G81 (1995).

Gong et al., "An antagonist of monocyte chemoattractant protein 1 (MCP-1) inhibits arthritis in the MRL-lpr mouse model," *J. Exp. Med.*, 186:131-137 (1997).

Graham et al., "Characteristics of a human cell line transformed by DNA from human adenovirus type 5," *J. Gen Virol.*, 36:59 (1977).

Grandt et al., "Two molecular forms of peptide YY (PYY) are abundant in human blood: characterization of a radioimmunoassay recognizing PYY 1-36 and PYY 3-36," *Regul. Pept.*, 51:151-159 (1994).

Grise et al., "Peptide YY inhibits growth of human breast cancer in vitro and in vivo," *J. Surg. Res.*, 82:151-155 (1999).

Guerre-Millo, "Adiponectin: an update," *Diabetes & Metab.*, 34:12-18 (2008).

Gulyas et al., "Drug distribution in man: a positron emission tomography study after oral administration of the labelled neuroprotective drug vinpocetine," *Eur. J. Nucl. Med. Mol. Imaging*, 29:1031-1038 (2002).

Hamer et al., "Regulation in vivo of a cloned mammalian gene: cadmium induces the transcription of a mouse metallothionein gene in SV40 vectors," *J. Mol. Appl. Gen.*,1(4):273-288 (1982).

Handbook of Pharmaceutical Excipients (Rowe et al., eds), $4^{th}$ Edition, 2003, Pharmaceutical Press.

Hansmann et al., "Pulmonary arterial hypertension is linked to insulin resistance and reversed by peroxisome proliferator-activated receptor-γ activation," *Circulation*, 115:1275-1284 (2007).

Hara et al., "Measurement of the high-molecular weight form of adiponectin in plasma is useful for the prediction of insulin resistance and metabolic syndrome," *Diabetes Care*, 29:1357-1362 (2006).

Hay et al., "Inflammatory bowel disease: costs-of-illness," *J. Clin. Gastroenterol.*, 14:309-317 (1992).

He et al., "A simplified system for generating recombinant adenoviruses," *Proc. Natl. Acad. Sci. USA*, 95:2509-2514 (1998).

Hirasawa et al., "Free fatty acids regulate gut incretin glucagon-like peptide 1 secretion through GPR 120," *Nature Medicine*, 11(1):90-98 (2005).

Holz et al., "Glucagon-like peptide-1 synthetic analogs: new therapeutical agents for use in the treatment of diabetes mellitus," *Curr. Med. Chem.*, 10(22):2471-2483 (2003).

Irwin et al., "Comparison of the metabolic effects of GIP receptor antagonism and PYY(3-36) receptor activation in high fat fed mice," *Peptides*, 28(11):2192-2198 (2007).

Jee et al., "Overview: animal models of osteopenia and osteoporosis," *J. Musculoskel. Neuron. Interact.*, 1(3):193-207 (2001).

Jetter et al., "Effects of grapefruit juice on the pharmacokinetics of sildenafil," *Clin. Pharmacol. Ther.*, 71:21-29 (2002).

Johnston et al., "Isolation of the yeast regulatory gene GAL4 and analysis of its dosage effects on the galactose/melibiose regulon," *Proc. Natl. Acad. Sci. USA*, 79:6971-6975 (1982).

Karlin et al., "Methods for assessing the statistical significance of molecular sequence features by using general scoring schemes," *Proc. Natl. Acad. Sci. USA*, 87:2264-2268 (1990).

Keighley et al., "Inflammatory bowel disease," *Ailment Pharmacol. Ther.*, 18:Suppl 3:66-70 (2003).

Keire et al., "Primary structures of PYY, [Pro$^{34}$]PYY, and PYY-(3-36) confer different conformations and receptor selectivity," *Am. J. Physiol. Gastrointest. Liver Physiol.*, 279:G126-G131 (2000).

Kenakin, "Are receptors promiscuous? Intrinsic efficacy as a transduction phenomenon," *Life Sciences*, 43:1095-1101 (1988).

King et al. "Control of yeast mating signal transduction by a mammalian beta 2-adrenergic receptor and Gs alpha subunit," *Science*, New Series, 250(4977):121-123 (1990).

Kopelman P.G., "Obesity as a medical problem," *Nature*, 404(6778):635-643 (2000).

Kubota et al., "Disruption of adiponectin causes insulin resistance and neointimal formation," *J. Biol. Chem.*, 277:25863-25866 (2002).

Lumb et al., "Novel selective neuropeptide Y2 receptor PEGylated peptide agonists reduce food intake and body weight in mice," *J. Med. Chem.*, 50:2264-2268 (2007).

Lauffer et al., "GPR119: "double-dipping" for better glycemic control," *Endocrinology*, 149(5) 2035-2037 (2008).

Le Bas et al., "Radioiodinated analogs of EP 00652218 for the exploration of the tachykinin NK1 receptor by spect," *J. Labelled Compd Radiopharm.*, 44:S280-S282 (2001).

Lee et al., "Impaired angiogenesis in neuropeptide Y (NPY)-Y2 receptor knockout mice," *Peptides*, 24:99-106 (2003).

Lee et al., "Neuropeptide Y induces ischemic angiogenesis and restores function of ischemic skeletal muscles," *J. Clin. Invest.*, 111:1853-1862 (2003).

Leiting et al., "Catalytic properties and inhibition of proline-specific dipeptidyl peptidases II, IV and VII," *Biochem. J.*, 371:525-532 (2003).

Leonard, "GPR119—Overseer of Gut and Pancreatic Endocrine Systems in Glucose Homeostasis," 68$^{th}$ *Scientific Sessions, American Diabetes Association* (2008).

Lippincott Williams & Wilkins; and Handbook of Pharmaceutical Excipients (Rowe et al., eds), 4$^{th}$ Edition, *Pharmaceutical Press* (2003).

Liu et al., "Pancreatic peptide YY mRNA levels increase during adaptation after small intestinal resection," *J. Surg. Res.*, 58:6-11 (1995).

Liu et al., "Y2 receptors decrease human pancreatic cancer growth and intracellular cyclic adenosine monophosphate levels," *Surgery*, 118:229-236 (1995).

Liu et al., "Peptide YY: a potential proabsorptive hormone for the treatment of malabsorptive disorders," *Am. Surg.*, 62:232-236 (1996).

Lundberg et al., "Localization of peptide YY (PYY) in gastrointestinal endocrine cells and effects on intestinal blood flow and motility," *Proc. Natl. Acad. Sci. USA*, 79:4471-4475 (1982).

Maeda et al., "Diet-induced insulin resistance in mice lacking adiponectin/ACRP30," *Nat. Med.*, 8:731-737 (2002).

Marsh et al., "Role of the Y5 neuropeptide Y receptor in limbic seizures," *Proc. Natl. Acad. Sci. USA*, 96:13518-13523 (1999).

Marso et al., "Low adiponectin levels are associated with atherogenic dyslipidemia and lipid-rich plaque in nondiabetic coronary arteries," *Diabetes Care*, 31(5):989-994 (2008).

Mather, "Establishment and characterization of two distinct mouse testicular epithelial cell lines," *Biol. Reprod.*, 23:243-251 (1980).

Mather et al., "Culture of testicular cells in hormone-supplemented serum-free medium," *Ann. N.Y. Acad. Sci.*, 383:44-68 (1982).

Matsuda et al., "Role of adiponectin in preventing vascular stenosis. The missing link of adipo-vascular axis," *J. Biol. Chem.*, 277:37487-37491 (2002).

Mayet et al., *Diabetologia*, 48(Suppl.):A166, Abstract (2005).

McCormack, ((OSI)™ Pharmaceuticals Inc.), "Update on PSN821," SEC File No. 0-15190; Accession No. 950123-7-16093 (Nov. 29, 2007).

McFadden et al., "Peptide YY inhibits the growth of Barrett's esophageal adenocarcinoma in vitro," *Am. J. Surg.*, 188:516-519 (2004).

McGinnis et al., "Actual causes of death in the United States," *JAMA*, 270:2207-2212 (1993).

McIntosh et al., "Dipeptidyl peptidase IV inhibitors: How do they work as new antidiabetic agents?," *Regulatory Peptides*, 128:159-165 (2005).

Mclean et al., "Visualizing Differences in Ligand Regulation of Wild-Type and Constitutively Active Mutant $\beta_2$-Adrenoceptor-Green Fluorescent Protein Fusion Proteins," *Molecular Pharmacology*, 56:1182-1191 (1999).

McKnight, "Functional relationships between transcriptional control signals of the thymidine kinase gene of herpes simplex virus," *Cell*, 31:355-365 (1982).

Mentlein, "Therapeutic assessment of glucagon-like peptide-1 agonists compared with dipeptidyl peptidase IV inhibitors as potential antidiabetic drugs," *Expert Opin. Investig. Drugs*, 14:57-64 (2005).

Merck Sante S.A.S., "Glucovance, film-coted tablets," *Pediatric Public Assessment Report EU Work Sharing Procedure-Assessment of Pediatric data*, 1-8 (2008).

Milligan et al., "Chimaeric G alpha proteins: their potential use in drug discovery," *Trends in Pharmaceutical Sciences*, 20:118-24 (1999).

Miret et al. "Functional Expression of Heteromeric Calcitonin Gene-related Peptide and Adrenomedullin Receptors in Yeast," *The Journal of Biological Chemistry*, 277(9):6881-6887 (2002).

Morley et al., "An investigation of tolerance to the actions of leptogenic and anorexigenic drugs in mice," *Life Sci.*, 41:2157-2165 (1987).

Morris et al., "Hapten-induced model of chronic inflammation and ulceration in the rat colon," *Gastroenterology*, 96:795-803 (1989).

Mosekilde et al., "The effects of growth hormone on fracture healing in rats: a histological description," *Bone*, 14:19-27 (1993).

Mulcahy et al., "Sustained Glycaemic Control over 6 Years in a Large Outpatient Cohort Using a Repeatedly Implemented Aggressive Treatment Protocol," Abstract No. 531-P in Diabetes, Abstract Book, 67$^{th}$ Scientific Sessions, Friday, Jun. 22-Tuesday, Jun. 26, 2007, Chicago, IL, vol. 56, supplement 1, p. A142 (Jun. 2007).

Nauck et al., "Incretins and their analogues as new antidiabetic drugs," *Drug News Perspect.*, 16:413-422 (2003).

Nauck et al., "Gastric inhibitory polypeptide and glucagon-like peptide-1 in the pathogenesis of type 2 diabetes," *Diabetes*, 53(Suppl 3):S190-196 (2004).

Nichols et al, eds. Sinauer Associates, Inc., "Indirect Mechanisms of Synaptic Transmission," Chapter 8, *Neuron to Brain* (3$^{rd}$ Ed.) (1992).

Nightingale et al., "Gastrointestinal hormones in short bowel syndrome. Peptide YY may he the 'colonic brake' to gastric emptying," *Gut*, 39:267-272 (1996).

Nishimura at al., "Adiponectin prevents cerebral ischemic injury through endothelial nitric oxide synthase dependent mechanisms," *Circulation*, 117:216-223 (2008).
Offermanns et al., "G alpha 15 and G alpha 16 couple a wide variety of receptors to phosphollpase C." *J. Biol. Chem.*, 270:15175-80 (1995).
Ohashi et al., "Adiponectin replenishment ameliorates obesity-related hypertension," *Hypertension*, 47:1108-1116 (2006).
Okada et al., "Program & Abstracts," *The Endocrine Society*, Supplement 180 (1993).
Okamoto et al., "Adiponectin reduces atherosclerosis in apolipoprotein E-deficient mice," *Circulation*, 106:2767-2770 (2002).
Oku et al., "Adiponectin deficiency suppresses ABCA1 expression and ApoA-I synthesis in the liver," *FEBS Lett.*, 581:5029-5033 (2007).
Ortiz at al., "A novel long-acting selective neuropeptide Y2 receptor polyethylene glycol-conjugated peptide agonist reduces food intake and body weight and improves glucose metabolism in rodents," *J. Pharmacol. Exp. Ther.*, 323:692-700 (2007).
Ouchi et al., "Novel modulator for endothelial adhesion molecules: adipocyte-derived plasma protein adiponectin," *Circulation*, 100:2473-2476 (1999).
Ouchi et al., "Adiponectin as an anti-inflammatory factor," *Clin. Chim. Acta.*, 380:24-30 (2007).
Overton et al., "Deorphanization of a G protein-coupled receptor for oleoylethanolamide and its use in the discovery of small-molecule hypophagic agents", *Cell Metabolism*, 3:167-175 (2006).
Overton et al., "GPR119, a novel G protein-coupled receptor target for the treatment of type 2 diabetes and obesity," *Br. J. Pharmacol.*, 1-6 (2007).
Overton et al., "GPR119, a novel G protein-coupled receptor target for the treatment of type 2 diabetes and obesity," *Br. J. Pharmacol.*, 153:S76-S81 (2008).
Parker et al., "Neuropeptide Y Y2 receptor in health and disease," *Br. J. Pharmacol.*, 153:420-431 (2008).
Pearson, "Inflammatory bowel disease," *Nurs. Times*, 100:86-90 (2004).
Pederson et al., "Improved glucose tolerance in Zucker fatty rats by oral administration of the dipeptidyl peptidase IV inhibitor isoleucine thiazolidide," *Diabetes*, 47(8):1253-1258 (1998).
Peters et al., "Aminomethyl-pyrimidines as novel DPP-IV inhibitors: a 10(5)-fold activity increase by optimization of aromatic substituents," *Bioorg. Med. Chem. Lett.*, 14:1491-1493 (2004).
Pittner et al., "Effects of PYY[3-36] in rodent models of diabetes and obesity," *Int. J. Obes. Relat. Metab. Disord.*, 28:963-971 (2004).
Polymorphism in Pharmaceutical Solids (1999) Britain, ed., Marcel Dekker, Inc.
Potenza et al., "A rapid quantitative bioassay for evaluating the effects of ligands upon receptors that modulate cAMP levels in a melanophere cell line," *Pigment Cell Research*, 5(6)-372-378 (1992).
Prevention and Management of Osteoporosis, World Health Organization Technical Report Series, 921, Geneva (2003).
Raisz, "Pathogenesis of osteoporosis: concepts, conflicts, and prospects," *The Journal of Clinical Investigation*, 115(12):3318-3325 (2005).
Ramsay et al., "Detection of receptor ligands by monitoring slecctive stabilization of a *Renilla* luciferase-tagged, constitutively active mutant, G-protein-coupled receptor," *British Journal of Pharmacology*, 315-323 (2001).
Remington: The Science and Practice of Pharmacy, (A.R. Gennaro, ed.), 20th Edition, 2000, Lippincott Williams & Wilkins.
Rendell et al., "Combination therapy with pioglitazone plus metformin or sulfonylurea in patients with Type 2 diabetes influence of prior antidiabetic drug regimen," *Journal of Diabetes and Its Complications*, 17:211-217 (2003).
Renshaw et al., "Peptide YY: a potential therapy for obesity," *Curr. Drug Targets*, 6:171-179 (2005).
Ruggeri, "Platelets in atherothrombosis," *Nat. Med.*, 8:1227-1234 (2002).

Sakamoto et al., "Expression and distribution of Gpr119 in the pancreatic islets of mice and rats: predominant localization in pancreatic polypeptide-secreting PP-cells," *Biochem. Biophys. Res. Commun.*, 351:474-480 (Dec. 2006).
Sambrook et al., Molecular Cloning: A Laboratory Manual, Second Edition, Cold-Spring Harbor, N.Y. (1989).
Sambrook et al., Molecular Cloning: A Laboratory Manual, Third Edition, Cold-Spring Harbor, N.Y. (2001).
Sanofi Aventis *AVE0010—R&D Meeting* (Sep. 17, 2007).
Schwartz et al., "Safety profile and metabolic effects of 14 days of treatment with DIO-902: results of a phase IIa multicenter, randomized, double-blind, placebo-controlled, parallel-group trial in patients with type 2 diabetes mellitus," *Clin. Ther.*, 30(6):1081-1088 (2008).
Shibata et al., "Adiponectin stimulates angiogenesis in response to tissue ischemia through stimulation of amp-activated protein kinase signaling," *J. Biol. Chem.*, 279:28670-28674 (2004).
Shibata et al., "Adiponectin stimulates angiogenesis in response to tissue ischemia through stimulation of amp-activated protein kinase signaling," *Nat. Med.*, 11:1096-1103 (2005).
Shibata et al., "Adiponectin protects against the development of systolic dysfunction following myocardial infarction," *J. Mol. Cell. Cardiol.*, 42:1065-1074 (2007).
Shore et al., "Adiponectin attenuates allergen-induced airway inflammation and hyperresponsiveness in mice," *J. Allergy Clin. Immunol.*, 118:389-395 (2006).
Sierra-Ascencio et al., "Exenatide: use in humans," *Gas Med Mex.*, 142(6):483-491 (2006) (Abstract).
Silver et al., "Amino terminus of the yeast GAL4gene product is sufficient for nuclear localization," *Proc. Natl. Acad. Sci. USA*, 81:5951-5955 (1984).
Soga et al., "Lysophosphatidylcholine enhances glucose-dependent insulin secretion via an orphan G-protein-coupled receptor," *Biochemical and Biophysical Research Communications*, 326:744-751 (2005).
Sondhi et al., "cDNA array reveals increased expression of glucose-dependent insulinotropic polypeptide following chronic clozapine treatment: role in atypical antipsychotic drug-induced adverse metabolic effects," *The Pharmacogenomics Journal*, 6:131-140 (2006).
Souli et al., "Several receptors mediate the antisecretory effect of peptide YY, neuropeptide Y, and pancreatic polypeptide on VIP-induced fluid secretion in the rat jejunum in vivo," *Peptides*, 18:551-557 (1997).
Stewart et al., Pharmacokinetics, Safety, and Tolerability of Albiglutide (Syncria®), a Long-Acting GLP-1 Mimetic, in Healthy Volunteers, Abstract ADA08L__1316: Contact View, [522-P] (2008).
Summer et al., "Alveolar macrophage activation and an emphysema-like phenotype in adiponectin-deficient mice," *Am. J. Physiol. Lung Cell Mol. Physiol.*, 294(6):L1035-L1042 (Epub. Mar. 7, 2008).
Suzuki et al., "Regulatable promoters for use in gene therapy applications: modification of the 5'-flanking region of the CFTR gene with multiple cAMP response elements to support basal, low-level gene expression that can be upregulated by exogenous agents that raise intracellular levels of cAMP," *Hum. Gene Ther.*, 7:1883-1893 (1996).
Tao et al., "Adiponectin cardioprotection after myocardial ischemia/reperfusion involves the reduction of oxidative/nitrative stress," *Circulation*, 115:1408-1416 (2007).
Takasaki et al., "Effects of combination treatment with dipeptidyl peptidase IV inhibitor and sulfonylurea on glucose levels in rats," *J. Pharmacol Sciences*, 95(2):291-293 (2004).
Tatemoto et al., "Isolation of two novel candidate hormones using a chemical method for finding naturally occurring polypeptides," *Nature*, 285:417-418 (1980).
Tilg et al., "Adipocytokines: mediators linking adipose tissue, inflammation and immunity," *Nat. Rev. Immunol.*, 6:772-783 (2006).
Traynor et al., "Modulation by μ-Opioid Agonists of Guanosine-5'-O-(3-[$^{35}$S]thio)triphosphate Binding to membranes from Human Neuroblastoma SH-SY5Y Cells," *Molecular Pharmacology*, 47:848-854 (1995).
Trümper et al., "Glucose-Dependent Insulinotropic Polypeptide is a Growth Factor for β (INS-1) Cells by Pleiotropic Signaling," *Mol. Endocrinol.*, 15(9):1559-1570 (2001).

Tseng et al., "Peptide YY and cancer: current findings and potential clinical applications," *Peptides*, 23:389-395 (2002).

Tsukiyama et al., "Gastric Inhibitory Polypeptide as an endogenous Factor Promoting New bone Formation after Food Ingestion," *Molecular Endocrinology*, 20(7):1644-1651 (2006).

Ueno et al., "The role of PYY in feeding regulation," *Regul. Pept.*, 145:12-16 (2008).

Urlaub and Chasin, "Isolation of Chinese hamster cell mutants deficient in dihydrofolate reductase activity," *Proc. Natl. Acad. Sci. (USA)*, 77:4216 (1980).

Uttenthal, "The anorectic gut hormones: GLP-1 and co-secreted peptides," *CLI*, 4 pages (2007).

Villhauer et al., "1-AA(3-hydroxy-1-adamantyl)amino]acetyl-2-cyano-(S)-pyrrolidine: a potent, selective, and orally bioavailable dipeptidyl peptidase IV inhibitor with antihyperglycemic properties," *J. Med. Chem.* 46: 2774-2789 (2003).

Villhauer et al., 1-A2-A(5-Cyanopyridin-2-yl) aminolethylamino]acetyl-2-(S)-pyrrolidinecarbonitrile; a potent, selective and orally bioavailable dipeptidyl peptidase JV inhibitor with antihyperglycemic properties, *J Med Chem.*, 45:2362-2365 (2002).

Vona-Davis et al., "PYY and the pancreas: inhibition of tumor growth and inflammation," *Peptides*, 28:334-338 (2007).

Wang Y. et al., "BI-1356. Dipeptidyl-Peptidase IV Inhibitor, Antidiabetic Agent," *Drugs of the Future*, 33(6):473-477 (2008).

Weber, "Dipeptidyl peptidase IV inhibitors for the treatment of diabetes," *J. Med. Chem.*, 47(17):4135-4141 (2004).

Weber et al., "MK-0431 is a potent, selective, dipeptidyl peptidase IV inhibitor for the treatment of type 2 diabetes," *Diabetes*, 53(Suppl. 2):A151, 633-P (Abstract) (2004).

Williams Textbook of Endocrinology, 10th Edition, Larsen et al., Eds., W.B. Saunders Company (2002).

Woldbye et al., "Differential suppression of seizures via Y2 and Y5 neuropeptide Y receptors," *Neurobiology of Dis.*, 20:760-772 (2005).

Wise et al., "The identification of ligands at orphan G-protein coupled receptors," *Annu. Rev. Pharmacol. Toxicol.*, 44:43-66 (2004).

Wong et al., "Nonpeptide factor Xa inhibitors: DPC423, a highly potent and orally bioavailable pyrazole antithrombotic agent," *Cardiovasc. Drug Rev.*, 20:137-52 (2002).

Wortley et al., "Peptide YY regulates bone turnover in rodents," *Gastroenterology*, 133:1534-1543 (2007).

Yamada et al., *Endocrinology & Diabetology*, 23:237-243 (Sep. 2006) (Translation).

Yamamoto et al., "Correlation of the adipocyte-derived protein adiponectin with insulin resistance index and serum high-density lipoprotein-cholesterol, independent of body mass index, in the Japanese population," *Clin. Sci.* (Lond), 103:137-142 (2002).

Yang et al., "Efficacy and specificity of bFGF increased collateral flow in experimental peripheral arterial insufficiency," *Am. J. Physiol. Heart Circ. Physiol.*, 278:H1966-H1973 (2000).

Yasuda et al., "Metformin causes reduction of food intake and body weight gain and improvement of glucose intolerance in combination with dipeptidyl peptidase IV inhibitor in Zucker fa/fa rats," *J. Pharmacol. Exp. Ther.*, 310(2): 614-619 (2004).

Yasuda et al., "Enhanced secretion of glucagon-like peptide 1 by biguanide compounds," *Biochem. Biophys. Res. Commun.*, 298:779-784 (2002).

Yokota et al., "Adiponectin, a new member of the family of soluble defense collagens, negatively regulates the growth of myelomonocytic progenitors and the functions of macrophages," *Blood*, 96:1723-1732 (2000).

Xie et al., "Glucose-dependent insulinotropic peptide-overexpressing transgenic mice have increased bone mass," *Bone xx* (2007).

Xie et al., "Glucose-dependent insulinotropic polypeptide receptor knockout mice have altered bone turnover," *Bone*, 37:759-769 (2005).

Xu, "Metabolic Disease Drug Discovery-Strategic Research Institute's Third International World Summit, Dipeptidyl peptidase-IV inhibitors," *IDrugs*, 7(9):839-840 (2004).

Zander et al., "Effect of 6-week course of glucagon-like peptide 1 on glycaemic control, insulin sensitivity, and beta-cell function in type 2 diabetes: a parallel-group study," *Lancet*, 359:824-830 (2002).

Zhong et al., "Effects of glucose-dependent insulinotropic peptide on osteoclast function," *Am. J. Physiol. Endocrinol. Metab.*, 292:E543-E548 (2007).

Zhu et al., "Synthesis and mode of action of (125)I and (3)H-labeled thieno [2,3-c] pyridine antagonists of cell adhesions molecule expressions," *J. Org. Chem.*, 67(3):943-948 (2002).

Zimmerman et al., "The effect of a high-fat meal on the oral bioavailability of the immunosuppressant sirolimus (rapamycin)," *J. Clin. Pharmacol.*, 39:1155-1161 (1999).

U.S. Appl. No. 60/486,728, filed Jul. 11, 2003, Jones et al.
U.S. Appl. No. 60/487,443, filed Jul. 14, 2003, Jones et al.
U.S. Appl. No. 60/577,354, filed Jun. 4, 2004, Jones et al.
U.S. Appl. No. 60/643,086, filed Jan. 10, 2005, Chu.

American Diabetes Association, "Implications of the United Kingdom Prospective Diabetes Study," *Diabetes Care*, 25 (Suppl 1), Jan. 2002, 5 pages.

Ammala et al., "GPR119 dependent hormone secretion: Insulin, GLP-1 and more," Keystone Symposia, Islet and Beta Cell Biology, Poster Presentation, Poster Session 1, Apr. 7, 2008.

Ammala et al., "GPR119 dependent hormone secretion: Insulin, GLP-1 and more," Abstract 102, Keystone Symposia, Islet and Beta Cell Biology, conference held Apr. 6-11, 2008 at Snowbird, Utah (according to conference organizers, the abstract was made available to attendees in an abstract book distributed at the conference).

Balkan et al., "Inhibition of dipeptidyl peptidase IV with NVP-DPP728 increases plasma GLP-1 (7-36 amide) concentrations and improves oral glucose tolerance in obese Zucker rats," *Diabetologia*, 42(11):1324-1331 (1999).

Balkan, "Effects of glucagon-like peptide-1 (GLP-1) on glucose homeostasis and food intake," *Appetite*, 35(3):269-270 (2000).

Beers et al., "The Merck Manual of Diagnosis and Therapy Seventeenth Edition," *Merck Research Laboratories*, Whitehouse Station, NJ, 469-471 (1999).

Charpentier, "Oral combination therapy for type 2 diabetes," *Diabetes Metab. Res. Rev.*, 18:S70-S76 (2002).

Deacon et al., "Preservation of active incretin hormones by inhibition of dipeptidyl peptidase IV suppresses meal-induced incretin secretion in dogs," *J. Endocrinol.*, 172(2):355-362 (2002).

Deacon et al., "Inhibitors of dipeptidyl peptidase IV: a novel approach for the prevention and treatment of Type 2 diabetes?," *Expert Opin. Investig. Drugs*, 13(9):1091-1102 (2004).

Declaration of James N. Leonard, dated Dec. 12, 2008, 13 pages.

Drucker, "Therapeutic potential of dipeptidyl peptidase IV inhibitors for the treatment of type 2 diabetes," *Expert Opin. Investig. Drugs*, 12(1):87-100 (2003).

Duffy et al., "Effects of antidiabetic drugs on dipeptidyl peptidase IV activity: nateglinide is an inhibitor of DPP IV and augments the antidiabetic activity of glucagon-like peptide-1," *Eur. J. Pharmacol.*, 568:278-286 (2007).

Evans, "Dipeptidyl peptidase IV inhibitors," *IDrugs*, 5(6):577-585 (2002).

Findlay et al., "Mechanisms of bone loss in rheumatoid arthritis," *Mod. Rheumatol.*, 15:232-240 (2005).

Hoist, "Treatment of Type 2 diabetes mellitus with agonists of the GLP-1 receptor or DPP-IV inhibitors," *Expert Opinion on Emerging Drugs*, 9(1):155-166 (2004).

Hoist et al., "Inhibition of the Activity of Dipeptidyl-Peptidase IV as a Treatment for Type 2 Diabetes," *Diabetes*, 47:1663-1670 (1998).

Hughes et al., "NVP-DPP728 (1-[[[2-[(5-cyanopyridin-2-yl)amino]ethyl]amino]acetyl]-2-cyano-(S)-pyrrolidine), a slow-binding inhibitor of dipeptidyl peptidase IV," *Biochemistry*, 38(36):11597-11603 (1999).

Inzucchi, "Oral Antihyperglycemic Therapy for Type 2 Diabetes," *JAMA*, 287:360-372 (2002).

Jones et al., "GPR 119 agonists for the treatment of type 2 diabetes," *Expert Opinion Therapeutic Patents*, 19(10):1339-1359 (2009).

Kim et al., "(2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine: a potent, orally active dipeptidyl peptidase IV inhibitor for the treatment of type 2 diabetes," *J. Med. Chem.*, 48:141-151 (2005).

Lankas et al., "Dipeptidyl Peptidase IV Inhibition for the Treatment of Type 2 Diabetes," *Diabetes*, 54:2988-2994 (2005).

Mitani et al., "Dipeptidyl peptidase IV inhibition improves impaired glucose tolerance in high-fat diet-fed rats: study using a Fischer 344 rat substrain deficient in its enzyme activity," *Jpn. J. Pharmacol.*, 88(4):442-450 (2002).

Ning et al., "Endogenous and synthetic agonists of GPR119 differ in signaling pathways and their effects on insulin secretion in MIN6c4 insulinoma cells," *Brit. J. Pharmacol.*, 155:1056-1065 (2008).

Pei et al., "Discovery and Structure—Activity Relationships of Piperidinone- and Piperidine-Constrained Phenethylamines as Novel, Potent, and Selective Dipeptidyl Peptidase IV Inhibitors," *J. Med. Chem.*, 50:1983-1987 (2007).

Reimer et al., "Long-term inhibition of dipeptidyl peptidase IV improves glucose tolerance and preserves islet function in mice," *Eur. J. Endocrinol.*, 146(5):717-727 (2002).

Rendell, "Advances in diabetes for the millennium: drug therapy of type 2 diabetes," *MedGenMed.*, 6(3 Suppl):9 (2004).

Riddle, "Oral pharmacologic management of type 2 diabetes," *Am. Fam. Physician*, 60(9):2613-2620 (1999).

Semple et al., "Discovery of the First Potent and Orally Efficacious Agonist of the Orphan G-Protein Coupled Receptor 119," *J. Med. Chem.*, 51:5172-5175 (2008).

Sudre et al., "Chronic inhibition of circulating dipeptidyl peptidase IV by FE 999011 delays the occurrence of diabetes in male zucker diabetic fatty rats," *Diabetes*, 51(5):1461-1469 (2002).

Takasaki et al., "K579, a slow-binding inhibitor of dipeptidyl peptidase IV, is a long-acting hypoglycemic agent," *Eur. J Pharmacol.*, 486:335-342 (2004).

Wiedeman et al., "Dipeptidyl peptidase IV inhibitors for the treatment of impaired glucose tolerance and type 2 diabetes," *Curr. Opin. Investig. Drugs*, 4(4):412-420 (2003).

Pauly et al., "Improved glucose tolerance in rats treated with the dipeptidyl peptidase IV (CD26) inhibitor Ile-thiazolidide," *Metabolism*, 48(3):385-389 (1999).

"Approach to the Management of Diabetes Mellitus," *Diabetes Care and Education Committee of the Banting and Best Diabetes Centre, Faculty of Medicine, University of Toronto*, 7th Edition, 112 pages (2009).

"DPPIV-Glo™ Protease Assay," *Promega Corporation*, Technical Bulletin No. 339, 10 pages (2004).

Ahren, "GLP-1 and Extra-islet Effects," *Horm. Metab. Res.*, 36:842-845 (2004).

Aquilante, "Sulfonylurea pharmacogenomics in Type 2 diabetes: the influence of drug target and diabetes risk polymorphisms," *Expert Rev. Cardiovasc Ther.*, 8(3):359-372 (2010).

Augeri et al., "Discovery and preclinical profile of Saxagliptin (BMS-477118): a highly potent, long-acting, orally active dipeptidyl peptidase IV inhibitor for the treatment of type 2 diabetes," *J. Med. Chem.*, 48:5025-5037 (2005).

Brandt et al., "Inhibition of dipeptidyl-peptidase IV catalyzed peptide truncation by Vildagliptin ((2S)-{[(3-hydroxyadamantan-1-yl)amino]acetyl}-pyrrolidine-2-carbonitrile)," *Biochem. Pharmacol.*, 701:134-43 (2005).

Brubaker, "Minireview: update on incretin biology: focus on glucagon-like peptide-1," *Endocrinology*, 151(5):0000-0000 (2010).

Campbell, "Drugs in type 2 diabetes: their properties and recommended use," *Prescriber*, 5:19-41 (2010).

Cluny et al., "The identification of peroxisome proliferator-activated receptor alpha-independent effects of oleoylethanolamide on intestinal transit in mice," *Neurogastroenterol. Motil.*, 21:420-429 (2009).

Cox et al., "Peptide YY is Critical for Acylethanolamine Receptor Gpr119-Induced Activation of Gastrointestinal Mucosal Responses," *Cell Metabolism*, 11:532-421 (2010).

de Heer et al., "Sulfonylurea compounds uncouple the glucose dependence of the insulinotropic effect of glucagon-like peptide 1," *Diabetes*, 56:438-443 (2007).

Deacon, "Dipeptidyl peptidase-4 inhibitors in the treatment of type 2 diabetes: a comparative review," *Diabetes Obes Metab.*, 13:7-18 (2011).

Effects of a DPP4 Inhibitor and GPR 119 Agonist Alone or in Combination on Plasma Glucose in an OGTT in SD Rat—Study Protocol, 5 pages, Study protocol of Bristol/Myers Squibb Company submitted to European Patent Office in EP1808168 (Mar. 2, 2010).

Effect of DPP4 Inhibitor and GPR 119 Agonists on Plasma Glucose in Male C57BL/6J Mouse—Study Protocol, 7 pages, Study protocol of Bristol/Myers Squibb Company submitted to European Patent Office in EP1808168 (Mar. 2, 2010).

Fields et al., "Glucagon-like peptide-1 and myocardial protection: more than glycemic control," *Clin. Cardiol.*, 32(5):236-243 (2009).

Flatt et al., "Dipeptidyl peptidase IV (DPP IV) and related molecules in type 2 diabetes," *Front Biosci.*, 13:3648-3660 (2008).

Flock et al., "GPR119 regulates murine glucose homeostasis through incretin receptor-dependent and independent mechanisms," *Endocrinology*, 152(1):0000-0000 (2011).

Fyfe et al., "PSN821: A Novel Oral GPR119 Agonist for the Treatment of Type 2 Diabetes Producing Substantial Glucose Lowering and Weight Loss in Rats," *American Diabetes Association*, Abstract No. 297-OR (2008).

Green et al., "Dipeptidyl peptidase IV (DPP IV) inhibitors: A newly emerging drug class for the treatment of type 2 diabetes," *Diab Vasc Dis Res.*, 3:159-165 (2006).

Harkavyi et al., "Glucagon-like peptide 1 receptor stimulation as a means of neuroprotection," *Br. J. Pharmacol.*, 159:495-501 (2010).

Holscher, "Incretin analogues that have been developed to treat type 2 diabetes hold promise as a novel treatment strategy for Alzheimer's disease," *Recent Pat. CNS Drug Discov.*, 5:000-000 (2010).

Houjou, "DPP-4 Inhibitor: MK-0431," *BioClinica*, 21:73-76 (2006) [English translation included], 10 pages.

Ibrahim, "Diabetes Mellitus Type II: Review of Oral Treatment Options," *Int. J. Pharm. Sci.*, 2(Suppl 1):21-30 (2010).

Kirkham, "American Chemical Society—239th National Meeting—Investigating New Therapeutic Candidates: Part 2. Mar. 21-25, 2010, San Francisco, CA, USA," *IDrugs*, 13(5):292-294 (2010).

Krentz, "Thiazolidinediones: effects on the development and progression of type 2 diabetes and associated vascular complications," *Diabetes Metab Res Rev.*, 25:112-126 (2009).

Kushner, "Minimizing the risk of hypoglycemia in patients with type 2 diabetes mellitus," *Diabetes, Metabolic Syndrome and Obesity: Targets and Therapy*, 3:49-53 (2010).

Lauffer et al., "GPR119 is essential for oleoylethanolamide-induced glucagon-like peptide-1 secretion from the intestinal enteroendocrine L-cell," *Diabetes*, 58(5):1058-1066 (2009).

Lenhard et al., "Reduced serum dipeptidyl peptidase-IV after metformin and pioglitazone treatments," *Biochem Biophys Res Comm.*, 324:92-97 (2004).

Lorenzati et al., "Oral Hypoglycemic Drugs: Pathophysiological Basis of Their Mechanism of Action," *Pharmaceuticals*, 3:3005-3020 (2010).

McKillop et al., "Insulinotropic actions of nateglinide in type 2 diabetic patients and effects on dipeptidyl peptidase-IV activity and glucose-dependent insulinotropic polypeptide degradation," *Eur J Endocrinol.*, 161:877-885 (2009).

MDS Pharma Services (Catalog # 163910; King of Prussia, PA), 2 pages (2006).

Migoya et al., "Minutes of the 42nd General Assembly of the European Association for the Study of Diabetes," *Diabetologia*, 50:[Suppl 1]SI-S538 (2007).

Migoya et al., "Sitagliptin, a selective DPP-4 inhibitor, and metformin have complementary effects to increase active GLP-1 concentrations," *Diabetologia*, 50:[Suppl 1]:SI-S538, Abstract A0111 (2007).

Mitri et al., "Diabetes medications and body weight," *Expert Opin. Drug Saf.*, 8(5):573-584 (2009).

Miura et al., "Combination therapy with nateglinide and vildagliptin improves postprandial metabolic derangements in Zucker fatty rats," *Horm Metab Res.*, 42:731-735 (2010).

Noyan-Ashraf et al., "GLP-1R agonist liraglutide activates cytoprotective pathways and improves outcomes after experimental myocardial infarction in mice," *Diabetes*, 58:975-983 (2009).

Perry et al., "A new Alzheimer's disease interventive strategy: GLP-1," *Curr. Drug Targets*, 5:565-571 (2004).

Rizos et al., "How safe is the use of thiazolidinediones in clinical practice?," *Expert Opin. Drug Saf.*, 8(1):15-32 (2009).

Schwartz et al., "An Enteroendocrine Full Package Solution," *Cell Metabolism*, 11:445-447 (2010).

Schwartz et al., "The lipid messenger OEA links dietary fat intake to satiety," *Cell Metab.*, 8:281-288 (2008).

Senten et al., "Design, synthesis, and SAR of potent and selective dipeptide-derived inhibitors for dipeptidyl peptidases," *J Med Chem.*, 46:5005-5014 (2003).

Shomali, "Add-on therapies to metformin for type 2 diabetes," *Expert Opin Pharmacother.*, 12(1):47-62 (2011).

Voulgari et al., "Combination of nateglinide with thiazolidinediones in Type 2 diabetes," *Expert Rev. Endocrinol. Metab.*, 4(6):537-552 (2009).

Whittaker, "A review of oral diabetic medication," *SA Pharmaceutical Journal*, 20-25 (2010).

Xu et al., "Influence of genetic polymorphisms on the pharmacokinetics and pharmaco-dynamics of sulfonylurea drugs," *Curr Drug Metab.*, 10:643-658 (2009).

Yoshiro et al., "Nateglinide Stimulates GLP-1 Release by Human Intestinal L Cells Via a KATP Channel-Independent Mechanism," *American Diabetes Association*, Abstract No. 1427-P (2009).

* cited by examiner

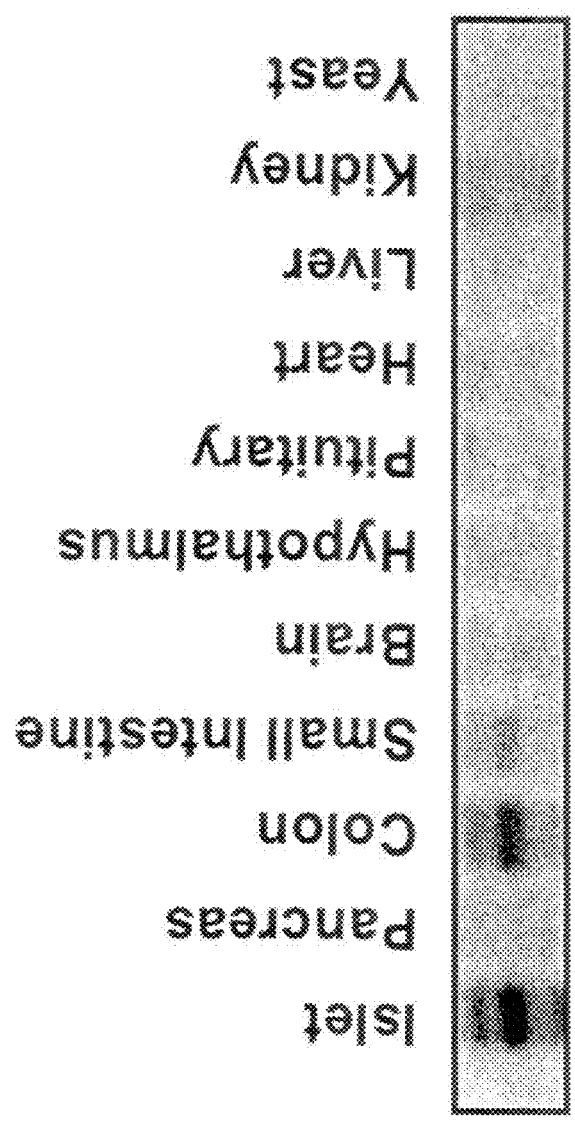
Figure 3. Expression of GPR119 in Gut

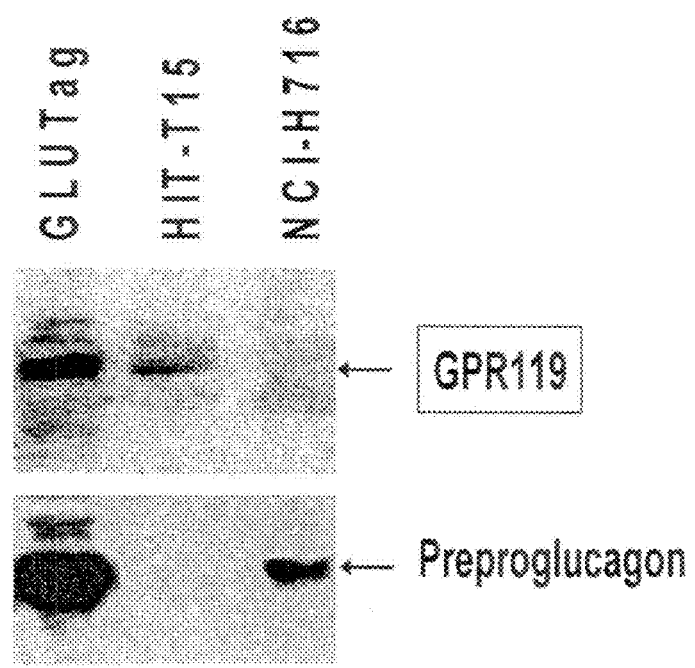
Figure 4. Expression of GPR119 in GLUTag Cells

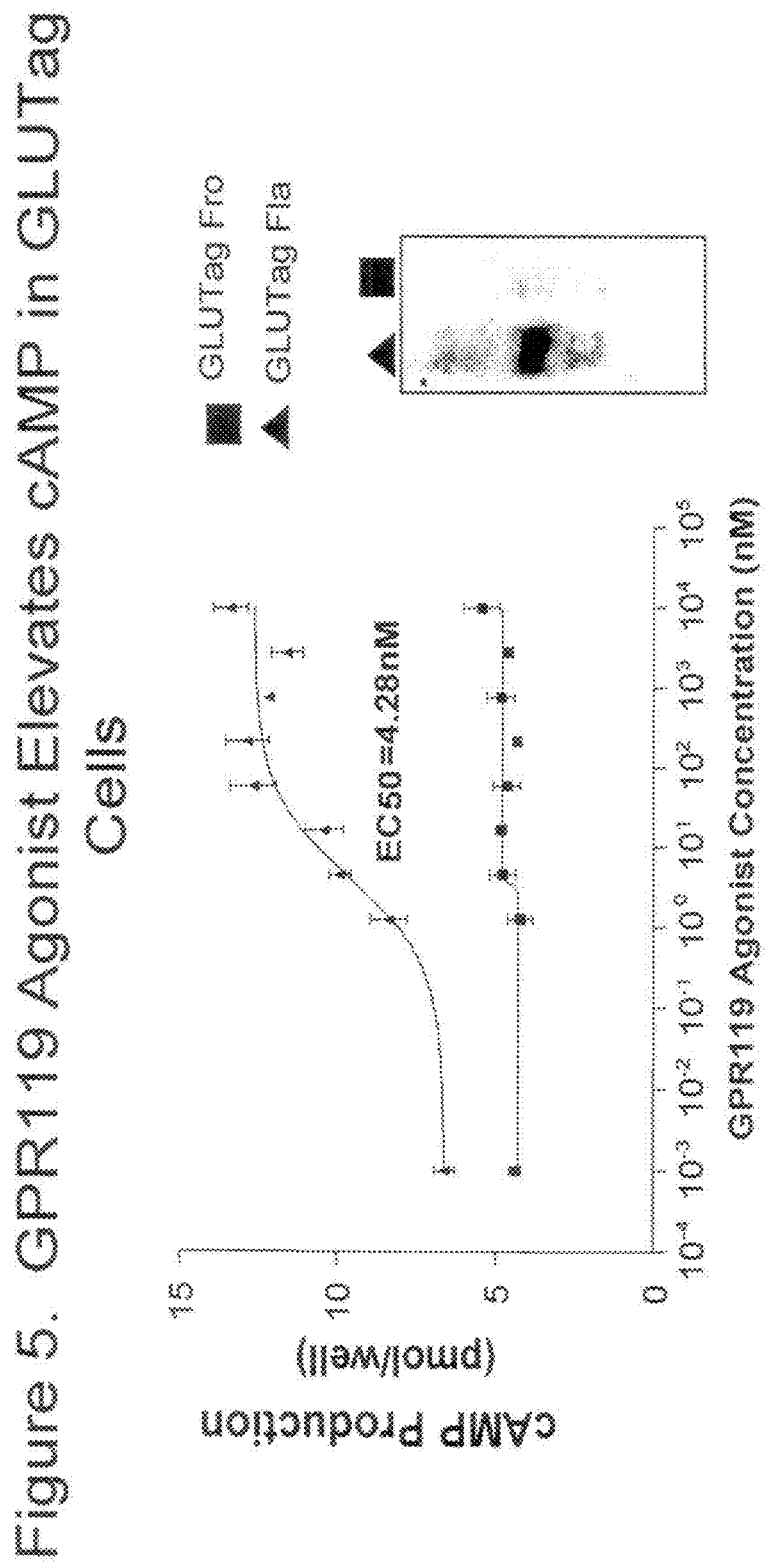

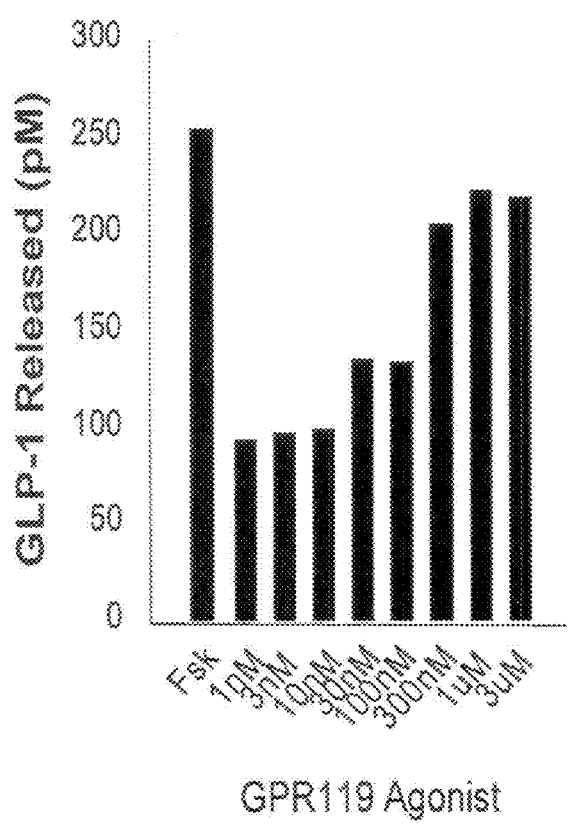
Figure 6. GPR119 Agonist Stimulates GLP-1 Secretion in GLUTag Cells

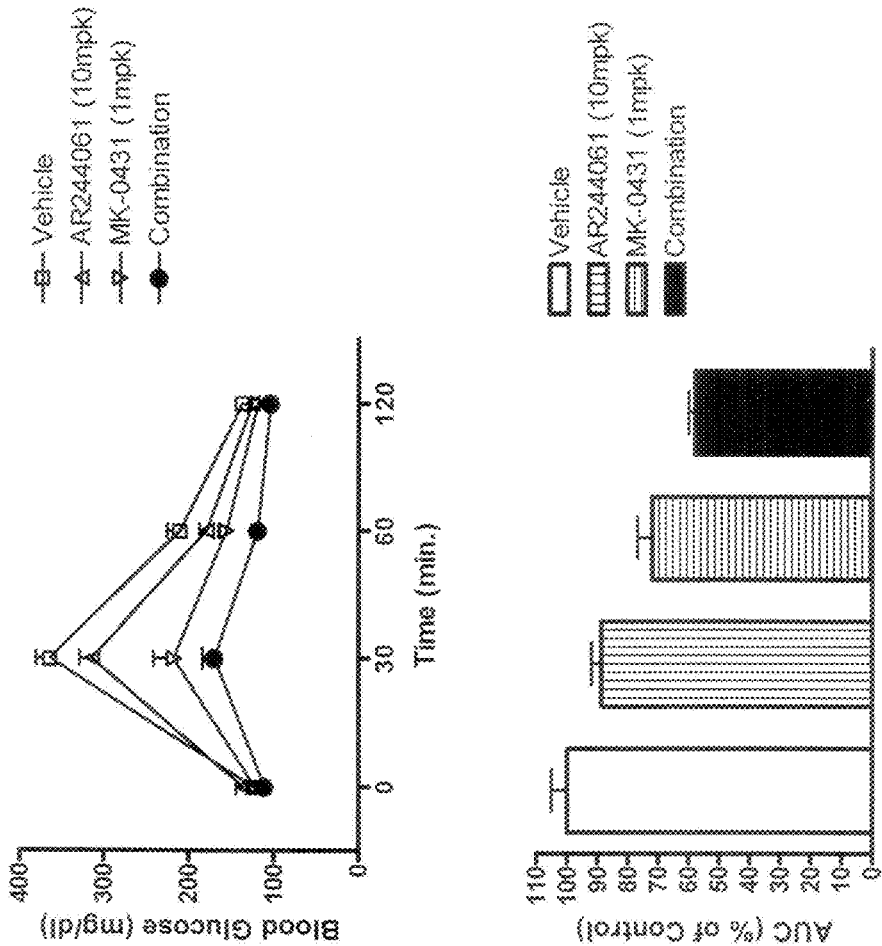

GPR119 Agonist AR244061 and MK-0431
Combination-2

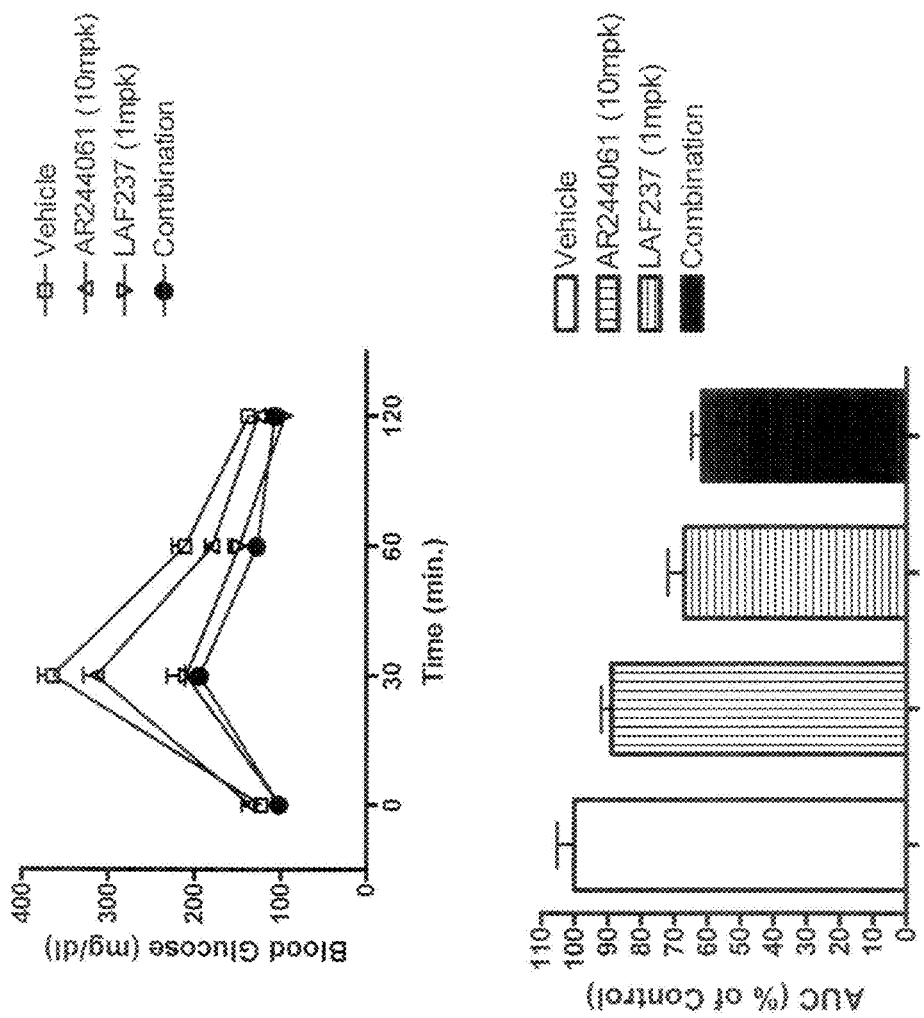

GPR119 Agonist AR244061 and LAF237
Combination-2

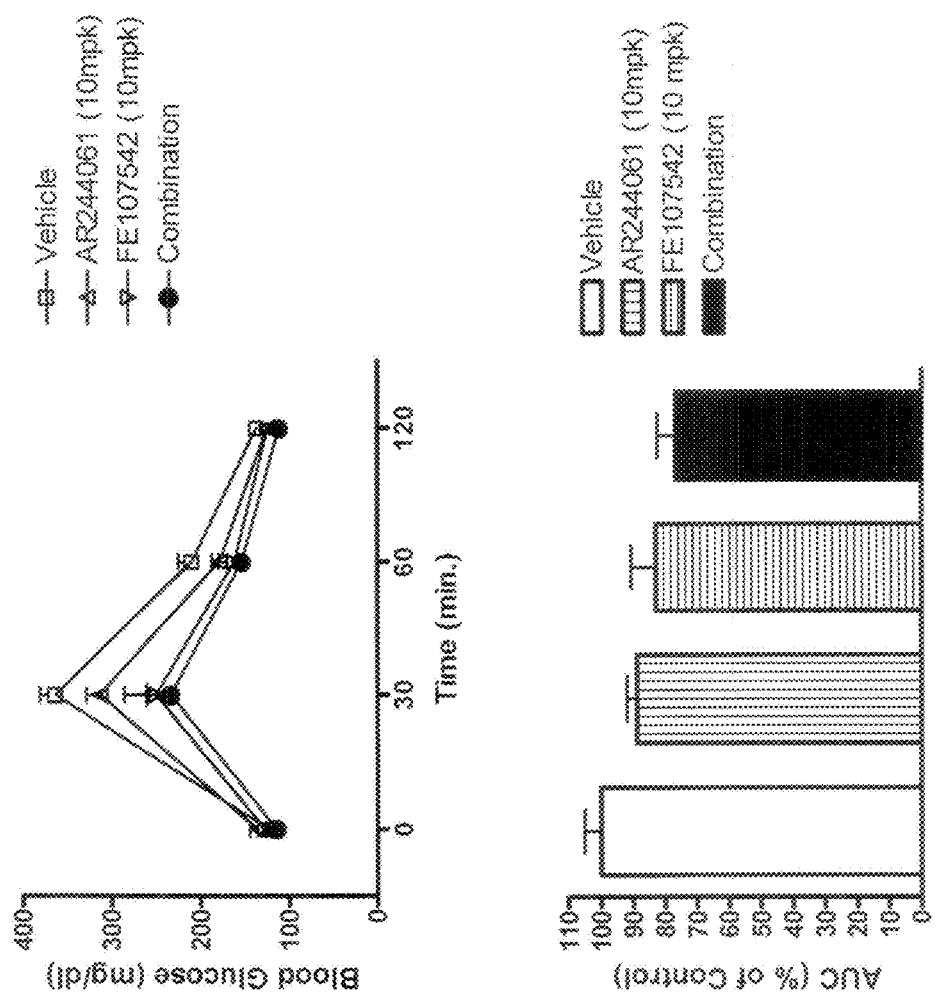

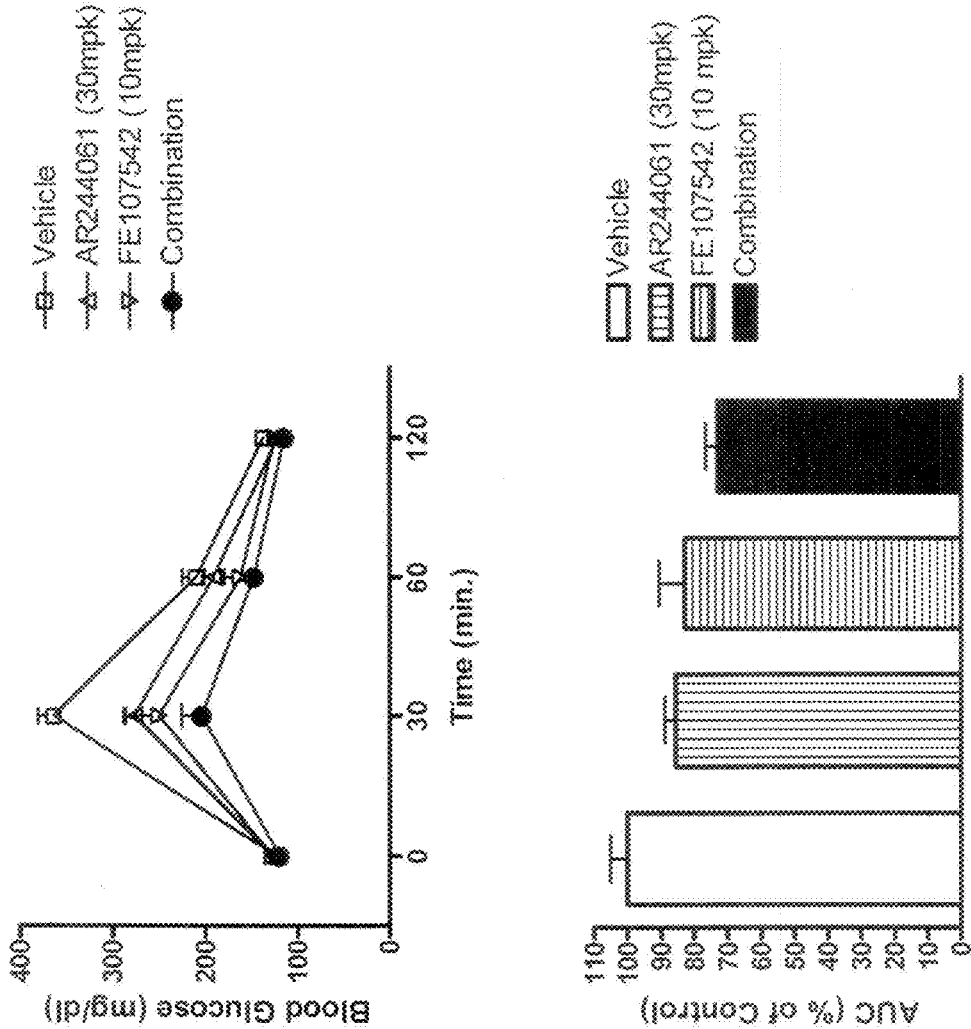

METHODS FOR IDENTIFYING GLP-1 SECRETAGOGUES

CROSS REFERENCE TO RELATED APPLICATIONS

This application is a continuation of U.S. application Ser. No. 12/609,599, filed Oct. 30, 2009, which is a continuation of U.S. application Ser. No. 11/603,417, filed Nov. 22, 2006 (now U.S. Pat. No. 7,803,754), which is a continuation of U.S. application Ser. No. 11/328,405, filed on Jan. 9, 2006, which in turn claims the benefit of U.S. Provisional Appl. Nos. 60/643,086, filed Jan. 10, 2005, 60/683,172, filed May 19, 2005, and 60/726,880, filed Oct. 14, 2005, each of which is hereby incorporated by reference in its entirety.

FIELD OF THE INVENTION

The present invention relates to compositions and methods for treating or preventing diabetes and conditions related thereto. The present invention further relates to compositions and methods for increasing a blood GLP-1 level in a mammal. The present invention also relates to methods of using a G protein-coupled receptor to screen for GLP-1 secretagogues.

BACKGROUND OF THE INVENTION

The following discussion is intended to facilitate the understanding of the invention, but is not intended nor admitted to be prior art to the invention.

A. Diabetes

Type 2 diabetes is one of the most common chronic diseases. Type 2 diabetes is characterized by fasting and postprandial hyperglycemia and by relative insulin insufficiency. Hyperglycemia may cause long-term microvascular and macrovascular complications, such as nephropathy, neuropathy, retinopathy, and peripheral vascular disease. In addition, Type 2 diabetes is a comorbid disease that frequently compounds hyperlipidemia, atherosclerosis and hypertension. Hyperlipidemia is a primary risk factor for cardiovascular disease due to atherosclerosis. Obesity is a well known common risk factor for the development of atherosclerosis, stroke, hypertension and Type 2 diabetes. Type 2 diabetes causes significant morbidity and mortality at considerable expense to patients, their families and society. The incidence of Type 2 diabetes in the United States is about 7% and accounts for as much as 10% of all health care dollars. Furthermore, the incidence of Type 2 diabetes worldwide is increasing such that Type 2 diabetes is now considered to be a worldwide epidemic.

B. Glucagon-Like Peptide-1 (GLP-1)

Glucagon-like peptide-1 (GLP-1) is an incretin hormone derived from the posttranslational modification of proglucagon and secreted by gut endocrine cells. GLP-1 mediates its actions through a specific G protein-coupled receptor (GPCR), namely GLP-1R. GLP-1 is best characterized as a hormone that regulates glucose homeostasis. GLP-1 has been shown to stimulate glucose-dependent insulin secretion and to increase pancreatic beta cell mass. GLP-1 has also been shown to reduce the rate of gastric emptying and to promote satiety. The efficacy of GLP-1 peptide agonists in controlling blood glucose in Type 2 diabetics has been demonstrated in several clinical studies [see, e.g., Nauck et al., Drug News Perspect (2003) 16:413-422], as has its efficacy in reducing body mass [Zander et al., Lancet (2002) 359:824-830].

GLP-1 receptor agonists are additionally useful in protecting against myocardial infarction and against cognitive and neurodegenerative disorders. GLP-1 has been shown to be cardioprotective in a rat model of myocardial infarction [Bose et al., Diabetes (2005) 54:146-151], and GLP-1R has been shown in rodent models to be involved in learning and neuroprotection [During et al., Nat Med (2003) 9:1173-1179; and Greig et al., Ann N Y Acad Sci (2004) 1035:290-315].

Certain disorders such as Type 2 diabetes are characterized by a deficiency in GLP-1 [see, e.g., Nauck et al., Diabetes (2004) 53 Suppl 3:S190-196].

Current GLP-1 peptide agonists suffer from a lack of oral bioavailability, negatively impacting patient compliance. Efforts to develop orally bioavailable non-peptidergic, small-molecule agonists of GLP-1R have so far been unsuccessful [Mentlein, Expert Opin Investig Drugs (2005) 14:57-64]. An attractive alternative approach is to develop an orally active composition for increasing an endogenous level of GLP-1 in the blood.

C. GPR119

GPR119 G protein-coupled receptor (GPR119; e.g., human GPR119, GenBank® Accession No. AAP72125 and alleles thereof; e.g., mouse GPR119, GenBank® Accession No. AY288423 and alleles thereof) is selectively expressed on pancreatic beta cells. GPR119 activation leads to elevation of a level of intracellular cAMP, consistent with GPR119 being coupled to Gs. Agonists to GPR119 stimulate glucose-dependent insulin secretion in vitro and lower an elevated blood glucose level in vivo. See, e.g., International Applications WO 04/065380, WO 04/076413, and EP 1338651, the disclosure of each of which is herein incorporated by reference in its entirety. In the patent literature, GPR119 has been referred to as RUP3 (see, e.g., International Application WO 00/31258).

D. Dipeptidyl Peptidase IV (DPP-IV)

Dipeptidyl peptidase IV (DPP-IV, EC 3.4.14.5) exhibits catalytic activity against a broad range of peptide substrates that includes peptide hormones, neuropeptides, and chemokines. The incretins glucagon-like peptide 1 (GLP-1) and glucose-dependent insulinotropic polypeptide (GIP), which stimulate glucose-dependent insulin secretion and otherwise promote blood glucose homeostasis, are rapidly cleaved by DPP-IV at the position 2 alanine leading to inactivation of their biological activity. Both pharmacological and genetic attenuation of DPP-IV activity is associated with enhanced incretin action, increased insulin, and lower blood glucose in vivo. Genetic attenuation of DPP-IV activity has been shown to provide resistance to obesity and to improve insulin sensitivity. A second-generation DPP-IV inhibitor, LAF237 (Ahren et al., J Clin Endocrinol Metab (2004) 89:2078-2084; and Villhauer et al., J Med Chem (2003) 46:2774-2789; the disclosure of each of which is herein incorporated by reference in its entirety), is currently in phase 3 clinical trials for Type 2 diabetes and additional DPP-IV inhibitors are in clinical development, including MK-0431, BMS-477118, PSN-9301 and SYR-322.

Because the incretin hormones are not, the only substrates for DPP-IV, there is concern that inhibition of the cleavage of other endogenous DPP-IV substrates may give rise to undesirable side effects [see, e.g., Chen et al, J Biol Regul Homeost Agents (2004) 18:47-54, the disclosure of which is herein incorporated by reference in its entirety]. It therefore would be advantageous to identify an activity promoting blood glucose homeostasis which is associated with substantially lower concentrations of DPP-IV inhibitor.

E. G Protein-Coupled Receptors

GPCRs share a common structural motif, having seven sequences of between 22 to 24 hydrophobic amino acids that form seven alpha helices, each of which spans the membrane (each span is identified by number, i.e., transmembrane-1 (TM-1), transmembrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when an agonist binds to a G protein-coupled receptor (often referred to as "activation" of the receptor), there is a change in the conformation of the receptor that facilitates coupling between the intracellular region and an intracellular "G-protein." It has been reported that GPCRs are "promiscuous" with respect to G proteins, i.e., that a GPCR can interact with more than one G protein. See, Kenakin, T., 43 Life Sciences 1095 (1988). Although other G proteins may exist, currently, Gq, Gs, Gi, Gz and Go are G proteins that have been identified. Ligand-activated GPCR coupling with the G-protein initiates a signaling cascade process (referred to as "signal transduction"). Under normal conditions, signal transduction ultimately results in cellular activation or cellular inhibition.

Gs stimulates the enzyme adenylyl cyclase. Gi (and Gz and Go), on the other hand, inhibit adenylyl cyclase. Adenylyl cyclase catalyzes the conversion of ATP to cAMP; thus, activated GPCRs that couple the Gs protein are associated with increased cellular levels of cAMP. On the other hand, activated GPCRs that couple Gi (or Gz, Go) protein are associated with decreased cellular levels of cAMP. See, generally, "Indirect Mechanisms of Synaptic Transmission," Chpt. 8, From Neuron To Brain (3$^{rd}$ Ed.) Nichols, J. G. et al eds. Sinauer Associates, Inc. (1992). Thus, assays that detect cAMP can be utilized to determine if a candidate compound is, e.g., an agonist to the receptor (i.e., such a compound would increase the levels of cAMP). Gq and Go are associated with activation of the enzyme phospholipase C, which in turn hydrolyzes the phospholipid $PIP_2$, releasing two intracellular messengers: diacyclglycerol (DAG) and inositol 1,4, 5-triphosphate (IP3). Increased accumulation of IP3 is associated with activation of Gq- and Go-associated receptors. See, generally, "Indirect Mechanisms of Synaptic Transmission," Chpt. 8, From Neuron To Brain (3$^{rd}$ Ed.) Nichols, J. G. et al eds. Sinauer Associates, Inc. (1992). Assays that detect IP3 accumulation can be utilized to determine if a candidate compound is, e.g., an agonist to a Gq- or Go-associated receptor (i.e., such a compound would increase the levels of IP3). Assay that detect the level of intracellular free calcium can also be utilized to determine if a candidate compound is, e.g., an agonist to a Gq or Go-associated receptor (i.e., such a compound would increase the levels of intracellular free calcium) See, e.g., Table A ("N/A": "not applicable").

TABLE A

| G protein | Effect on cAMP Production upon Activation of GPCR (i.e., constitutive activation or agonist binding) | Effect on IP3 Accumulation upon Activation of GPCR (i.e., constitutive activation or agonist binding) | Effect on cAMP Production upon contact with an Inverse Agonist | Effect on IP3 Accumulation upon contact with an Inverse Agonist |
|---|---|---|---|---|
| Gs | Increase | N/A | Decrease | N/A |
| Gi | Decrease | N/A | Increase | N/A |
| Gz | Decrease | N/A | Increase | N/A |
| Go | Decrease | Increase | Increase | Decrease |
| Gq | N/A | Increase | N/A | Decrease |

There are also promiscuous G proteins, which appear to couple several classes of GPCRs to the phospholipase C pathway, such as Gα15 or Gα16 [Offermanns & Simon, J Biol Chem (1995) 270:15175-80], or chimeric G proteins designed to couple a large number of different GPCRs to the same pathway, e.g. phospholipase C [Milligan & Rees, Trends in Pharmaceutical Sciences (1999) 20:118-24].

Under physiological conditions, GPCRs exist in the cell membrane in equilibrium between two different conformations: an "inactive" state and an "active" state. A receptor in an inactive state is unable to link to the intracellular signaling transduction pathway to initiate signal transduction leading to a biological response. Changing the receptor conformation to the active state allows linkage to the transduction pathway (via the G-protein) and produces a biological response.

A receptor may be stabilized in an active state by a ligand or a compound such as a drug. Recent discoveries, including but not exclusively limited to modifications to the amino acid sequence of the receptor, provide means other than ligands or drugs to promote and stabilize the receptor in the active state conformation. These means effectively stabilize the receptor in an active state by simulating the effect of a ligand binding to the receptor. Stabilization by such ligand-independent means is termed "constitutive receptor activation." An endogenous receptor exhibiting activity in the absence of ligand is referred to as a constitutively active endogenous receptor.

SUMMARY OF THE INVENTION

The present invention concerns combination of an amount of a GPR119 agonist with an amount of a dipeptidyl peptidase IV (DPP-IV) inhibitor such that the combination provides an effect in lowering a blood glucose level in a subject over that provided by the amount of the GPR119 agonist or the amount of the DPP-IV inhibitor alone and the use of such a combination for treating or preventing diabetes and conditions related thereto. The present invention further concerns combination of an amount of a GPR119 agonist with an amount of a dipeptidyl peptidase IV (DPP-IV) inhibitor such that the combination provides an effect in increasing a blood GLP-1 level in a subject over that provided by the amount of the GPR119 agonist or the amount of the DPP-IV inhibitor alone and the use of such a combination for treating or preventing a condition ameliorated by increasing a blood GLP-1 level or for increasing a blood GLP-1 level in a subject deficient in GLP-1. The present invention also relates to methods of using GPR119 G protein-coupled receptor to screen for GLP-1 secretagogues.

In a first aspect, the present invention features a method of treating or preventing diabetes or a condition related thereto comprising administering to a subject in need thereof a therapeutically effective amount of a composition comprising or consisting essentially of a GPR119 agonist and a DPP-IV inhibitor. In certain embodiments, the GPR119 agonist and the DPP-IV inhibitor are administered in amounts sufficient to lower a blood glucose level in the subject. In certain embodiments, the blood glucose level is an elevated blood glucose level.

The present invention additionally features a method of treating or preventing a condition ameliorated by increasing a blood GLP-1 level comprising administering to a subject in need thereof a therapeutically effective amount of a composition comprising or consisting essentially of a GPR119 agonist and a DPP-IV inhibitor. In certain embodiments, the GPR119 agonist and the DPP-IV inhibitor are administered in amounts sufficient to increase a blood GLP-1 level in the subject.

The present invention additionally features a method of increasing a blood GLP-1 level comprising administering to a subject deficient in GLP-1 a therapeutically effective amount of a composition comprising or consisting essentially of a GPR119 agonist and a DPP-IV inhibitor. In certain embodiments, the GPR119 agonist and the DPP-IV inhibitor are administered in amounts sufficient to increase a blood GLP-1 level in the subject.

In certain embodiments, diabetes is Type 2 diabetes.

In certain embodiments, the condition related to diabetes is selected from the group consisting of hyperglycemia, impaired glucose tolerance, insulin resistance, pancreatic beta-cell insufficiency, enteroendocrine cell insufficiency, glucosuria, metabolic acidosis, cataracts, diabetic nephropathy, diabetic neuropathy, diabetic retinopathy, diabetic coronary artery disease, diabetic cerebrovascular disease, diabetic peripheral vascular disease, metabolic syndrome, hyperlipidemia, atherosclerosis, stroke, hypertension, and obesity.

In certain embodiments, the condition ameliorated by increasing a blood GLP-1 level is selected from the group consisting of diabetes, a condition related to diabetes, myocardial infarction, learning impairment, memory impairment, and a neurodegenerative disorder.

In certain embodiments, the condition ameliorated by increasing a blood GLP-1 level is a neurodegenerative disorder selected from the group consisting of excitotoxic brain damage caused by severe epileptic seizures, Alzheimer's disease, Parkinson's disease, Huntington's disease, prion-associated disease, stroke, motor-neuron disease, learning or memory impairment, traumatic brain injury, spinal cord injury, and peripheral neuropathy.

In certain embodiments, the subject is a human.

In a second aspect, the present invention features a composition comprising or consisting essentially of a GPR119 agonist and a DPP-IV inhibitor. In certain embodiments, the present invention relates to a dosage form of the composition wherein the GPR119 agonist and the DPP-IV inhibitor are in amounts sufficient to lower a blood glucose level in a subject. In certain embodiments, the blood glucose level is an elevated blood glucose level. In certain embodiments, the present invention relates to a dosage form of the composition wherein the GPR119 agonist and the DPP-IV inhibitor are in amounts sufficient to increase a blood GLP-1 level in a subject.

In certain embodiments, the subject is a human.

In a third aspect, the present invention features a composition comprising or consisting essentially of a GPR119 agonist and a DPP-IV inhibitor for use in a method of treatment of the human or animal body by therapy. In certain embodiments, the present invention relates to a dosage form of the composition wherein the GPR119 agonist and the DPP-IV inhibitor are in amounts sufficient to lower a blood glucose level in a subject. In certain embodiments, the blood glucose level is an elevated blood glucose level. In certain embodiments, the present invention relates to a dosage form of the composition wherein the GPR119 agonist and the DPP-IV inhibitor are in amounts sufficient to increase a blood GLP-1 level in a subject.

The present invention additionally features a composition comprising or consisting essentially of a GPR119 agonist and a DPP-IV inhibitor for use in a method of treatment or prevention of diabetes or a condition related thereto of the human or animal body by therapy. In certain embodiments, the present invention relates to a dosage form of the composition wherein the GPR119 agonist and the DPP-IV inhibitor are in amounts sufficient to lower a blood glucose level in a subject. In certain embodiments, the blood glucose level is an elevated blood glucose level.

The present invention additionally features a composition comprising or consisting essentially of a GPR119 agonist and a DPP-IV inhibitor for use in a method of treatment or prevention of a condition ameliorated by increasing a blood GLP-1 level of the human or animal body by therapy. In certain embodiments, the present invention relates to a dosage form of the composition wherein the GPR119 agonist and the DPP-IV inhibitor are in amounts sufficient to increase a blood GLP-1 level in a subject.

The present invention additionally features a composition comprising or consisting essentially of a GPR119 agonist and a DPP-IV inhibitor for use in a method of treatment or prevention of a deficiency of GLP-1 of the human or animal body by therapy. In certain embodiments, the present invention relates to a dosage form of the composition wherein the GPR119 agonist and the DPP-IV inhibitor are in amounts sufficient to increase a blood GLP-1 level in a subject.

In certain embodiments, the subject is a human.

In a fourth aspect, the present invention features a method of preparing a pharmaceutical composition, said method comprising or consisting essentially of admixing a GPR119 agonist and a DPP-IV inhibitor, together with at least one pharmaceutically acceptable carrier. In certain embodiments, the method further comprises the step of preparing a dosage form of the pharmaceutical composition wherein the GPR119 agonist and the DPP-IV inhibitor are in amounts sufficient to lower a blood glucose level in a subject. In certain embodiments, the blood glucose level is an elevated blood glucose level. In certain embodiments, the method further comprises the step of preparing a dosage form of the pharmaceutical composition wherein the GPR119 agonist and the DPP-IV inhibitor are in amounts sufficient to increase a blood GLP-1 level in a subject.

In certain embodiments, the subject is a human.

In a fifth aspect, the present invention features a pharmaceutical composition comprising or consisting essentially of a GPR119 agonist and a DPP-IV inhibitor, together with at least one pharmaceutically acceptable carrier. In certain embodiments, the present invention relates to a dosage form of the pharmaceutical composition wherein the GPR119 agonist and the DPP-IV inhibitor are in amounts sufficient to lower a blood glucose level in a subject. In certain embodiments, the blood glucose level is an elevated blood glucose level. In certain embodiments, the present invention relates to a dosage form of the pharmaceutical composition wherein the GPR119 agonist and the DPP-IV inhibitor are in amounts sufficient to increase a blood GLP-1 level in a subject.

In certain embodiments, the subject is a human.

In a sixth aspect, the present invention features a method of treating or preventing diabetes or a condition related thereto comprising administering to a subject in need thereof a therapeutically effective amount of a pharmaceutical composition in accordance with the fifth aspect. In certain embodiments, the GPR119 agonist and the DPP-IV inhibitor are administered in amounts sufficient to lower a blood glucose level in the subject. In certain embodiments, the blood glucose level is an elevated blood glucose level.

The present invention additionally features a method of treating or preventing a condition ameliorated by increasing a blood GLP-1 level comprising administering to a subject in need thereof a therapeutically effective amount of a pharmaceutical composition in accordance with the fifth aspect. In certain embodiments, the GPR119 agonist and the DPP-IV inhibitor are administered in amounts sufficient to increase a blood GLP-1 level in the subject.

The present invention additionally features a method of increasing a blood GLP-1 level comprising administering to a subject deficient in GLP-1 a therapeutically effective amount of a pharmaceutical composition in accordance with the fifth aspect. In certain embodiments, the GPR119 agonist and the DPP-IV inhibitor are administered in amounts sufficient to increase a blood GLP-1 level in the subject.

In certain embodiments, the subject is a human.

In a seventh aspect, the present invention features use of a composition comprising or consisting essentially of a GPR119 agonist and a DPP-IV inhibitor for the manufacture of a medicament for the treatment or prevention of diabetes or a condition related thereto. In certain embodiments, the present invention relates to a dosage form of the medicament wherein the GPR119 agonist and the DPP-IV inhibitor are in amounts sufficient to lower a blood glucose level in a subject. In certain embodiments, the blood glucose level is an elevated blood glucose level.

The present invention additionally features use of a composition comprising or consisting essentially of a GPR119 agonist and a DPP-IV inhibitor for the manufacture of a medicament for the treatment or prevention of a condition ameliorated by increasing a blood GLP-1 level. In certain embodiments, the present invention relates to a dosage form of the medicament wherein the GPR119 agonist and the DPP-IV inhibitor are in amounts sufficient to increase a blood GLP-1 level in a subject.

The present invention additionally features use of a composition comprising or consisting essentially of a GPR119 agonist and a DPP-IV inhibitor for the manufacture of a medicament for the treatment or prevention of a deficiency of GLP-1. In certain embodiments, the present invention relates to a dosage form of the medicament wherein the GPR119 agonist and the DPP-IV inhibitor are in amounts sufficient to increase a blood GLP-1 level in a subject.

In certain embodiments, the subject is a human.

In an eighth aspect, the invention features a method for identifying GLP-1 secretagogues or compounds useful for treating or preventing a condition ameliorated by increasing a blood GLP-1 level, comprising the steps of:
  (a) contacting a test compound with a host cell or with membrane of a host cell that expresses a G protein-coupled receptor, wherein the G protein-coupled receptor comprises an amino acid sequence selected from the group consisting of:
    (i) amino acids 1-335 of SEQ ID NO:2;
    (ii) amino acids 2-335 of SEQ ID NO:2;
    (iii) amino acids 2-335 of SEQ ID NO:2, with the proviso that the receptor does not comprise the amino acid sequence of SEQ ID NO:2;
    (iv) the amino acid sequence of a G protein-coupled receptor encoded by a polynucleotide comprising a nucleotide sequence, said nucleotide sequence being the sequence obtainable by a process comprising performing polymerase chain reaction (PCR) on a human DNA sample using specific primers SEQ ID NO:3 and SEQ ID NO:4;
    (v) the amino acid sequence of a G protein-coupled receptor encoded by a polynucleotide comprising a nucleotide sequence, said nucleotide sequence hybridizing under stringent conditions to the complement of SEQ ID NO:1; and
    (vi) a biologically active fragment of any one of (i) to (v); and
  (b) determining the ability of the test compound to stimulate functionality of the receptor; wherein the ability of the test compound to stimulate functionality of the receptor is indicative of the test compound being a GLP-1 secretagogue or a compound useful for preventing or treating a condition ameliorated by increasing a blood GLP-1 level.

The invention additionally features a method for identifying GLP-1 secretagogues or compounds useful for treating or preventing a condition ameliorated by increasing a blood GLP-1 level, comprising steps (a) and (b) of this eighth aspect, and further comprising:
  (c) contacting a compound which stimulates functionality of the receptor in step (b) in vitro with a mammalian enteroendocrine cell; and
  (d) determining whether the compound stimulates GLP-1 secretion from the mammalian enteroendocrine cell;
wherein the ability of the test compound to stimulate GLP-1 secretion from the mammalian enteroendocrine cell is indicative of the test compound being a GLP-1 secretagogue or a compound useful for treating or preventing a condition ameliorated by increasing a blood GLP-1 level.

The invention additionally features a method for identifying GLP-1 secretagogues or compounds useful for treating or preventing a condition ameliorated by increasing a blood GLP-1 level, comprising steps (a) and (b) of this eighth aspect, and further comprising:
  (c) administering a compound which stimulates functionality of the receptor in step (b) to a mammal; and
  (d) determining whether the compound increases a blood GLP-1 level in the mammal;
wherein the ability of the test compound to increase a blood GLP-1 level in the mammal is indicative of the test compound being a GLP-1 secretagogue or a compound useful for treating or preventing a condition ameliorated by increasing a blood GLP-1 level. In certain embodiments, the mammal is a non-human mammal.

In certain embodiments, the identified GLP-1 secretagogue or the identified compound useful for treating or preventing a condition ameliorated by increasing a blood GLP-1 level is an agonist of the receptor. In some embodiments, the agonist is a partial agonist.

In certain embodiments, the receptor is coupled to a G protein. In certain embodiments, the G protein is Gs.

In certain embodiments, the human DNA sample is human genomic DNA.

In certain embodiments, the process is RT-PCR (reverse transcription-polymerase chain reaction). RT-PCR techniques are well known to the skilled artisan.

In certain embodiments, the human DNA sample is human cDNA. In certain embodiments, the cDNA is from a human tissue that expresses GPR119. In some embodiments, the human tissue that expresses GPR119 is pancreas, pancreatic islet, colon, small intestine, or fetal liver. In certain embodiments, the cDNA is from a human cell type that expresses GPR119. In some embodiments, the cDNA is from a pancreatic beta cell line or an enteroendocrine cell line.

In certain embodiments, stringent hybridization conditions comprise hybridization at 42° C. in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing at 65° C. in a solution comprising 0.1×SSC. Hybridization techniques are well known to the skilled artisan.

In certain embodiments, the G protein-coupled receptor encoded by a polynucleotide comprising a nucleotide sequence, said nucleotide sequence hybridizing under stringent conditions to the complement of SEQ ID NO:1, exhibits a biological activity selected from the group consisting of increasing a level of intracellular cAMP and binding a known ligand of GPR119. In certain embodiments, the encoded G protein-coupled receptor increases a level of intracellular cAMP and binds a known ligand of GPR119.

In some embodiments, the G protein-coupled receptor is part of a fusion protein comprising a G protein. Techniques for making a GPCR:G fusion construct are well known to the skilled artisan (see, e.g., International Application WO 02/42461).

In some embodiments, the G protein-coupled receptor is recombinant.

In certain embodiments, the host cell comprises an expression vector, said expression vector comprising a polynucleotide encoding the G protein-coupled receptor. In some embodiments, the expression vector is pCMV. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351. Other suitable expression vectors will be readily apparent to those of ordinary skill in the art, and a wide variety of expression vectors are commercially available (e.g., from Clontech, Palo Alto, Calif.; Stratagene, La Jolla, Calif.; and Invitrogen, Carlsbad, Calif.).

In some embodiments, the host cell is mammalian. In some embodiments, the mammalian host cell is selected from the group consisting of 293, 293T, CHO, MCB3901, and COS-7. In some embodiments, the host cell is melanophore. In some embodiments, the host cell is an enteroendocrine cell. In some embodiments, the enteroendocrine cell is GLUTag-Fro cell line. Other suitable host cells will be readily apparent to those of ordinary skill in the art, and a wide variety of cell lines are available from the American Type Culture Collection, 10801 University Boulevard, Manassas, Va. 20110-2209.

In certain embodiments, said determining is consistent with the G protein-coupled receptor being a Gs-coupled receptor.

In some embodiments, said determining is consistent with the G protein-coupled receptor being coupled through a promiscuous G protein, such as Gα15 or Gα16, to the phopholipase C pathway. Promiscuous G proteins are well known to the skilled artisan [see, e.g., Offermanns et al., J Biol Chem (1995) 270:15175-15180]. In some embodiments, said determining is consistent with the G protein-coupled receptor being coupled through a chimeric G protein, e.g. to the phospholipase C pathway. Chimeric G proteins are well known to the skilled artisan [see, e.g., Milligan et al., Trends in Pharmaceutical Sciences (1999) 20:118-124; and WO 02/42461].

In some embodiments, said determining is through the measurement of a level of a second messenger selected from the group consisting of cyclic AMP (cAMP), cyclic GMP (cGMP), inositol 1,4,5-triphosphate (IP3), diacylglycerol (DAG), MAP kinase activity, MAPK/ERK kinase kinase-1 (MEKK1) activity, and Ca2+. In some preferred embodiments, the second messenger is cAMP. In certain preferred embodiments, a level of intracellular cAMP is elevated.

In certain embodiments, said determining is carried out with membrane comprising the G protein-coupled receptor.

In certain embodiments, said determining is through the use of a melanophore assay. In some preferred embodiments, a level of pigment dispersion is elevated.

In some embodiments, said determining is through the measurement of an activity mediated by elevation of a level of intracellular cAMP. In some embodiments, said activity is stimulation of GLP-1 secretion.

In some embodiments, said determining is through CRE-Luc reporter assay. In some preferred embodiments, a level of luciferase activity is elevated.

In some embodiments, said determining is through the measurement of GTPγS binding to membrane comprising the G protein-coupled receptor. In some preferred embodiments, said GTPγS is labeled with [$^{35}$S]. In some preferred embodiments, said GTPγS binding to membrane comprising the GPCR is elevated.

In some embodiments, the test compound is a small molecule. In some embodiments, the test compound is a small molecule, with the proviso that the small molecule is not a polypeptide. In some embodiments, the test compound is a small molecule, with the proviso that the small molecule is not an antibody or an antigen-binding fragment thereof. In some embodiments, the test compound is a small molecule, with the proviso that the small molecule is not a lipid. In some embodiments, the test compound is a small molecule, with the proviso that the small molecule is not a polypeptide or a lipid. In some embodiments, the test compound is a polypeptide. In some embodiments, the test compound is a polypeptide, with the proviso that the polypeptide is not an antibody or an antigen-binding fragment thereof. In some embodiments, the test compound is a lipid. In some embodiments, the test compound is not an antibody or an antigen-binding fragment thereof. In some embodiments, the test compound is an antibody or an antigen-binding fragment thereof.

In some embodiments, the method further comprises synthesizing the GLP-1 secretagogue or the compound useful for treating or preventing a condition ameliorated by increasing a blood GLP-1 level.

In some embodiments, the method further comprises: optionally, determining the structure of the GLP-1 secretagogue or the compound useful for treating or preventing a condition ameliorated by increasing a blood GLP-1 level; and providing the GLP-1 secretagogue or the compound useful for treating or preventing a condition ameliorated by increasing a blood GLP-1 level or providing the name or structure of the GLP-1 secretagogue or the compound useful for treating or preventing a condition ameliorated by increasing a blood GLP-1 level.

In some embodiments, said method further comprises: optionally, determining the structure of the GLP-1 secretagogue or the compound useful for treating or preventing a condition ameliorated by increasing a blood GLP-1 level; optionally, providing the name or structure of the GLP-1 secretagogue or the compound useful for treating or preventing a condition ameliorated by increasing a blood GLP-1 level; and producing or synthesizing the GLP-1 secretagogue or the compound useful for treating or preventing a condition ameliorated by increasing a blood GLP-1 level.

In some embodiments, said method further comprises the step of formulating the GLP-1 secretagogue or the compound useful for treating or preventing a condition ameliorated by increasing a blood GLP-1 level into a pharmaceutical composition.

In a ninth aspect, the invention features a method for identifying GLP-1 secretagogues or compounds useful for treating or preventing a condition ameliorated by increasing a blood GLP-1 level, comprising the steps of:

(a) contacting a G protein-coupled receptor with an optionally labeled known ligand to the receptor in the presence or absence of a test compound, wherein the G protein-coupled receptor comprises an amino acid sequence selected from the group consisting of:
  (i) amino acids 1-335 of SEQ ID NO:2;
  (ii) amino acids 2-335 of SEQ ID NO:2;
  (iii) amino acids 2-335 of SEQ ID NO:2, with the proviso that the receptor does not comprise the amino acid sequence of SEQ ID NO:2;
  (iv) the amino acid sequence of a G protein-coupled receptor encoded by a polynucleotide comprising a nucleotide sequence, said nucleotide sequence being the sequence obtainable by a process comprising performing polymerase chain reaction (PCR) on a human DNA sample using specific primers SEQ ID NO:3 and SEQ ID NO:4;
  (v) the amino acid sequence of a G protein-coupled receptor encoded by a polynucleotide comprising a nucleotide sequence, said nucleotide sequence hybridizing under stringent conditions to the complement of SEQ ID NO:1; and
  (vi) a biologically active fragment of any one of (i) to (v); and
(b) detecting the complex between said known ligand and said receptor; and
(c) determining whether less of said complex is formed in the presence of the test compound than in the absence of the test compound;
wherein said determination is indicative of the test compound being a GLP-1 secretagogue or a compound useful for preventing or treating a condition ameliorated by increasing a blood GLP-1 level.

In certain embodiments, the optionally labeled known ligand is a labeled known ligand. In certain embodiments, the labeled known ligand is a radiolabeled known ligand. Techniques for radiolabeling a compound, such as for labeling a known ligand of a G protein-coupled receptor of the invention, are well known to the skilled artisan. See, e.g., International Application WO 04/065380.

Techniques for detecting the complex between a G protein-coupled receptor and a compound known to be a ligand of the G protein-coupled receptor are well known to the skilled artisan. See, e.g., International Application WO 04/065380.

The invention additionally features a method for identifying GLP-1 secretagogues or compounds useful for treating or preventing a condition ameliorated by increasing a blood GLP-1 level, comprising steps (a) to (c) of this ninth aspect, and further comprising:

(d) contacting a compound in the presence of which less of said complex is formed in step (c) in vitro with a mammalian enteroendocrine cell; and
(e) determining whether the compound stimulates GLP-1 secretion from the mammalian enteroendocrine cell;
wherein the ability of the test compound to stimulate GLP-1 secretion from the mammalian enteroendocrine cell is indicative of the test compound being a GLP-1 secretagogue or a compound useful for treating or preventing a condition ameliorated by increasing a blood GLP-1 level.

The invention additionally features a method for identifying GLP-1 secretagogues or compounds useful for treating or preventing a condition ameliorated by increasing a blood GLP-1 level, comprising steps (a) to (c) of this ninth aspect, and further comprising:

(d) administering a compound in the presence of which less of said complex is formed in step (c) to a mammal; and
(e) determining whether the compound increases a blood GLP-1 level in the mammal;
wherein the ability of the test compound to increase a blood GLP-1 level in the mammal is indicative of the test compound being a GLP-1 secretagogue or a compound useful for treating or preventing a condition ameliorated by increasing a blood GLP-1 level. In certain embodiments, the mammal is a non-human mammal.

In certain embodiments, the receptor is recombinant.

In some embodiments, the test compound is a small molecule. In some embodiments, the test compound is a small molecule, with the proviso that the small molecule is not a polypeptide. In some embodiments, the test compound is a small molecule, with the proviso that the small molecule is not an antibody or an antigen-binding fragment thereof. In some embodiments, the test compound is a small molecule, with the proviso that the small molecule is not a lipid. In some embodiments, the test compound is a small molecule, with the proviso that the small molecule is not a polypeptide or a lipid. In some embodiments, the test compound is a polypeptide. In some embodiments, the test compound is a polypeptide, with the proviso that the polypeptide is not an antibody or an antigen-binding fragment thereof. In some embodiments, the test compound is a lipid. In some embodiments, the test compound is not an antibody or an antigen-binding fragment thereof. In some embodiments, the test compound is an antibody or an antigen-binding fragment thereof.

In some embodiments, the method further comprises synthesizing the GLP-1 secretagogue or the compound useful for treating or preventing a condition ameliorated by increasing a blood GLP-1 level.

In some embodiments, the method further comprises: optionally, determining the structure of the GLP-1 secretagogue or the compound useful for treating or preventing a condition ameliorated by increasing a blood GLP-1 level; and providing the GLP-1 secretagogue or the compound useful for treating or preventing a condition ameliorated by increasing a blood GLP-1 level or providing the name or structure of the GLP-1 secretagogue or the compound useful for treating or preventing a condition ameliorated by increasing a blood GLP-1 level.

In some embodiments, said method further comprises: optionally, determining the structure of the GLP-1 secretagogue or the compound useful for treating or preventing a condition ameliorated by increasing a blood GLP-1 level; optionally, providing the name or structure of the GLP-1 secretagogue or the compound useful for treating or preventing a condition ameliorated by increasing a blood GLP-1 level; and producing or synthesizing the GLP-1 secretagogue or the compound useful for treating or preventing a condition ameliorated by increasing a blood GLP-1 level.

In some embodiments, said method further comprises the step of formulating the GLP-1 secretagogue or the compound useful for treating or preventing a condition ameliorated by increasing a blood GLP-1 level into a pharmaceutical composition.

This application claims the benefit of priority from the following provisional applications, filed via U.S. Express mail with the United States Patent and Trademark Office on the indicated dates: U.S. Provisional No. 60/643,086, filed Jan. 10, 2005; U.S. Provisional No. 60/683,172, filed May 19, 2005; and U.S. Provisional No. 60/726,880, filed Oct. 14, 2005. The disclosure of each of the foregoing applications is herein incorporated by reference in its entirety.

BRIEF DESCRIPTION OF THE DRAWINGS

The invention is illustrated in connection with the figures appended hereto in which:

FIG. 3 shows expression of GPR119 in gut. See Example 10.

FIG. 4 shows expression of GPR119 in GLUTag enteroendocrine cell line. See Example 11.

FIG. 5 shows elevation of the level of intracellular cAMP in GLUTag enteroendocrine cells by GPR119 agonist. See Example 12.

FIG. 6 shows stimulation of GLP-1 secretion in GLUTag enterendocrine cells by GPR119 agonist. See Example 13.

FIG. 9 shows an effect of GPR119 agonist AR244061 and DPP-IV inhibitor FE107542 in lowering blood glucose level in oral glucose tolerance test (oGTT) in mice. See Example 14.

DETAILED DESCRIPTION OF THE INVENTION

Figures 1A, 1B:
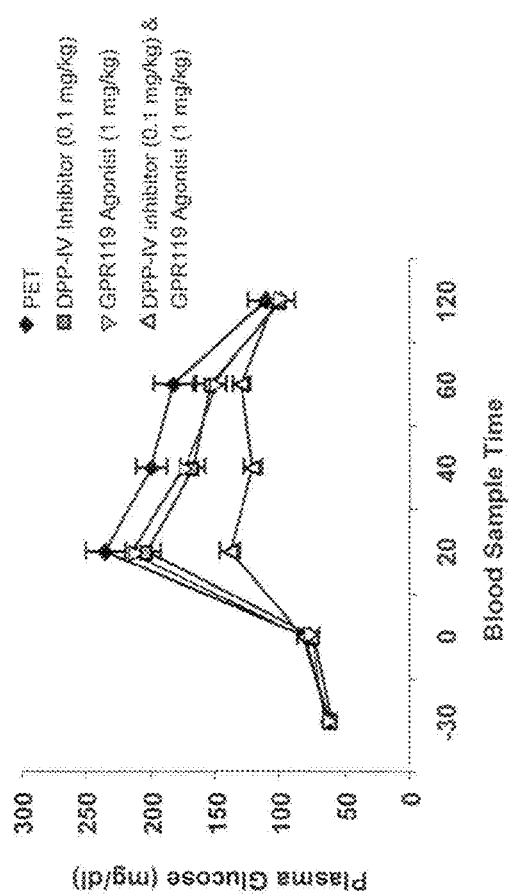
FIG. 1 shows a synergistic effect of GPR119 agonist and DPP-IV inhibitor in lowering an elevated blood glucose level in oral glucose tolerance test (oGTT) in mice. See Example 1.

This invention is concerned with the combination of certain compounds, or pharmaceutically acceptable salts thereof, for the treatment or prevention of diabetes and conditions related thereto. This invention is further concerned with the combination of certain compounds, or pharmaceutically acceptable salts thereof, for the treatment or prevention of a condition ameliorated by increasing a blood GLP-1 level. Applicant has found that an amount of a GPR119 agonist in combination with an amount of a DPP-IV inhibitor can provide an unexpected synergistic effect in lowering a blood glucose level in a subject over that provided by the amount of the GPR119 agonist alone or by the amount of the DPP-IV inhibitor alone. Applicant has additionally found that an amount of a GPR119 agonist in combination with an amount of a DPP-IV inhibitor can provide an unexpected synergistic effect in increasing a blood GLP-1 level in a subject over that provided by the amount of the GPR119 agonist alone or by the amount of the DPP-IV inhibitor alone. Applicant has additionally discovered that GPR119 is a GLP-1 secretagogue receptor.

By the use of a combination of a GPR119 agonist and a DPP-IV inhibitor in accordance with the present invention, it is possible to treat or prevent diabetes and conditions related thereto with a dose of a DPP-IV inhibitor substantially lower than that currently contemplated for use in therapy for diabetes and conditions related thereto, thereby reducing the likelihood of unwanted side-effects associated with inhibition of DPP-IV activity. By the use of a combination of a GPR119 agonist and a DPP-IV inhibitor in accordance with the present invention, it is possible to treat or prevent a condition ameliorated by increasing a blood GLP-1 level with a dose of a DPP-IV inhibitor substantially lower than that currently contemplated for use in therapy for said condition, thereby reducing the likelihood of unwanted side-effects associated with inhibition of DPP-IV activity. Furthermore, by the use of a combination of a GPR119 agonist and a DPP-IV inhibitor in accordance with the present invention, it is possible to treat or prevent diabetes and conditions related thereto with a dose of a GPR119 agonist substantially lower than that currently contemplated for use in therapy for diabetes and conditions related thereto, thereby reducing the likelihood of unwanted side-effects should any be found to be associated with activation of GPR119 receptor. The present invention provides a new, unexpected and advantageous approach to lowering a blood glucose level in a subject. The present invention additionally provides a new, unexpected and advantageous approach to increasing a blood GLP-1 level in a subject.

The term "ligand", as used herein, shall mean a molecule that specifically binds to a GPCR. A ligand may be, for example, a polypeptide, a lipid, a small molecule, an antibody. An endogenous ligand is a ligand that is an endogenous, natural ligand for a native GPCR. A ligand may be a GPCR "antagonist", "agonist", "partial agonist", or "inverse agonist", or the like.

The term "agonist", as used herein, shall mean an agent (e.g., ligand, candidate compound) that by virtue of binding to a GPCR activates the GPCR so as to elicit an intracellular response mediated by the GPCR.

The term "partial agonist", as used herein, shall mean an agent (e.g., ligand, candidate compound) that by virtue of binding to a GPCR activates the GPCR so as to elicit an intracellular response mediated by the GPCR, albeit to a lesser exent or degree than does a full agonist.

The term "antagonist" shall mean an agent (e.g., ligand, candidate compound) that binds, and preferably binds competitively, to a GPCR at about the same site as an agonist or partial agonist but which does not activate an intracellular response initiated by the active form of the GPCR, and can thereby inhibit the intracellular response by agonist or partial agonist. An anatagonist typically does not diminish the baseline intracellular response in the absence of an agonist or partial agonist.

The term "inverse agonist" shall mean an agent (e.g., ligand, candidate compound) which binds to a GPCR and which inhibits the baseline intracellular response initiated by the active form of the receptor below the normal base level activity which is observed in the absence of an agonist or partial agonist.

The term "GPR119 agonist," as used herein, refers to a compound that binds to GPR119 receptor and acts as an agonist.

The term "selective GPR119 agonist," as used herein, refers to a GPR119 agonist having selectivity for GPR119 receptor over one or more closely related receptors, such as corticotrophin-releasing factor-1 (CRF-1) receptor.

The term "DPP-IV inhibitor," as used herein, refers to a compound that binds to DPP-IV and inhibits DPP-IV dipeptidyl peptidase activity.

The term "selective DPP-IV inhibitor," as used herein, refers to a DPP-IV inhibitor having selectivity for DPP-IV over closely related peptidases, such as one or more of post-proline-cleaving enzyme (PPCE), dipeptidyl peptidase II (DPP-II), dipeptidyl peptidase 8 (DPP-8), and dipeptidyl peptidase 9 (DPP-9).

The term "blood glucose level" or "blood GLP-1 level" shall mean blood glucose concentration or blood GLP-1 concentration, respectively. In certain embodiments, blood GLP-1 level is a level in blood of biologically active GLP-1, wherein GLP-1 having agonist activity at GLP-1R is biologically active. In certain embodiments, a blood glucose level or blood GLP-1 level is a plasma glucose level or a plasma GLP-1 level.

The term "elevated blood glucose level" shall mean an elevated blood glucose level such as that found in a subject demonstrating clinically inappropriate basal and postprandial hyperglycemia or such as that found in a subject in oral glucose tolerance test (oGTT).

The term "subject," as used herein, shall refer to a mammal, including but not limited to a mouse, a rat, a rabbit, a pig, a dog, a cat, a non-human primate and a human, more preferably to a mouse or rat, most preferably to a human.

The term "in need of prevention or treatment" as used herein refers to a judgement made by a caregiver (e.g. physician, nurse, nurse practitioner in the case of humans; veterinarian in the case of non-human mammals) that a subject requires or will benefit from treatment.

The term "therapeutically effective amount" or "therapeutically effective dose" is intended to mean that amount of drug that will elicit the desired biological or medical response. In certain embodiments, a therapeutically effective amount is that amount of drug which will create an AUC inhibition above 30% in mouse oGTT assay.

The term "therapeutically ineffective amount" or "therapeutically ineffective dose" is intended to mean an amount of drug less than the therapeutically effective amount of the drug. In certain embodiments, a therapeutically ineffective amount is an amount of drug which will create an AUC inhibition less than or equal to 30% in mouse oGTT assay.

The term "amount that is effective to prevent" refers to that amount of drug that will prevent or reduce the risk of occurrence of the biological or medical event that is sought to be prevented. In many instances, the amount that is effective to prevent is the same as the therapeutically effective amount.

The term "composition" shall mean a material comprising at least one component.

The term "active ingredient" shall mean any component that provides pharmacological activity or other direct effect in the diagnosis, cure, mitigation, treatment, or prevention of disease.

The term "pharmaceutical composition" shall mean a composition comprising at least one active ingredient, whereby the composition is amenable to investigation and treatment in a mammal.

The term "dosage form" shall mean the physical form in which a drug is produced and dispensed, such as a tablet, capsule, or an injectable.

As used herein, the term "diabetes" encompasses both insulin-dependent diabetes mellitus (also known as Type 1 diabetes) and non-insulin-dependent diabetes mellitus (also known as Type 2 diabetes).

The term "condition related to diabetes" is intended to include but not be limited to hyperglycemia, impaired glucose tolerance, insulin resistance, pancreatic beta-cell insufficiency, enteroendocrine cell insufficiency, glucosuria, metabolic acidosis, cataracts, diabetic nephropathy, diabetic neuropathy, diabetic retinopathy, diabetic coronary artery disease, diabetic cerebrovascular disease, diabetic peripheral vascular disease, metabolic syndrome, hyperlipidemia, atherosclerosis, stroke, hypertension, and obesity, where it is understood that conditions related to diabetes can be included in embodiments individually or in any combination.

The term "condition ameliorated by increasing a blood GLP-1 level" is intended to include but not be limited to diabetes, a condition related to diabetes, myocardial infarction, learning impairment, memory impairment, and a neurodegenerative disorder, where it is understood that conditions ameliorated by increasing a blood GLP-1 level can be included in embodiments individually or in any combination.

The term "atherosclerosis" as used herein refers to a form of vascular disease characterized by the deposition of atheromatous plaques containing cholesterol and lipids on the innermost layer of the walls of large and medium-sized arteries.

The term "metabolic syndrome" as defined herein, and according to the Adult Treatment Panel III (ATP III; National Institutes of Health: Third Report of the National Cholesterol Education Program Expert Panel on Detection, Evaluation, and Treatment of High Blood Cholesterol in Adults (Adult Treatment Panel III), Executive Summary; Bethesda, Md., National Institutes of Health, National Heart, Lung and Blood Institute, 2001 (NIH pub. No 01-3670), occurs when a person meets three or more of five criteria related to obesity, hypertriglyceridemia, low HDL cholesterol, high blood pressure, and high fasting glucose.

The term "neurodegenerative disorder" is intended to include but not be limited to excitotoxic brain damage caused by severe epileptic seizures, Alzheimer's disease, Parkinson's disease, Huntington's disease, prion-associated disease, stroke, motor-neuron disease, learning or memory impairment, traumatic brain injury, spinal cord injury, and peripheral neuropathy.

The term "obesity," as used herein, is defined as a body mass index (BMI) of 30.0 or greater, in accordance with the WHO classifications of weight [Kopelman, Nature (2000) 404:635-643; the disclosure of which is herein incorporated by reference in its entirety].

The term "$C_{1-5}$ acyl" denotes a $C_{1-5}$ alkyl radical attached to a carbonyl wherein the definition of alkyl has the same definition as described herein; some examples include but not limited to, acetyl, propionyl, n-butanoyl, iso-butanoyl, sec-butanoyl, t-butanoyl (i.e., pivaloyl), pentanoyl and the like.

The term "$C_{1-5}$ acyloxy" denotes an acyl radical attached to an oxygen atom wherein acyl has the same definition has described herein; some examples include but not limited to acetyloxy, propionyloxy, butanoyloxy, iso-butanoyloxy, sec-butanoyloxy, t-butanoyloxy and the like.

The term "$C_{1-6}$ acylsulfonamide" refers to a $C_{1-6}$ acyl attached directly to the nitrogen of the sulfonamide, wherein the definitions for $C_{1-6}$ acyl and sulfonamide have the same meaning as described herein, and a $C_{1-6}$ acylsulfonamide can be represented by the following formula:

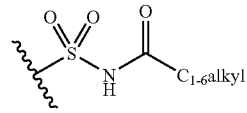

Some embodiments of the present invention are when acylsulfonamide is a $C_{1-5}$ acylsulfonamide, some embodiments are $C_{1-4}$ acylsulfonamide, some embodiments are $C_{1-3}$ acylsulfonamide, and some embodiments are $C_{1-2}$ acylsulfonamide. Examples of an acylsulfonamide include, but not limited to, acetylsulfamoyl[-S(=O)$_2$NHC(=O)Me], propionylsulfamoyl[-S(=O)$_2$NHC(=O)Et], isobutyrylsulfamoyl, butyrylsulfamoyl, 2-methyl-butyrylsulfamoyl, 3-methyl-butyrylsulfamoyl, 2,2-dimethyl-propionylsulfamoyl, pentanoylsulfamoyl, 2-methyl-pentanoylsulfamoyl, 3-methyl-pentanoylsulfamoyl, 4-methyl-pentanoylsulfamoyl, and the like.

The term "$C_{2-6}$ alkenyl" denotes a radical containing 2 to 6 carbons wherein at least one carbon-carbon double bond is present, some embodiments are 2 to 4 carbons, some embodiments are 2 to 3 carbons, and some embodiments have 2 carbons. Both E and Z isomers are embraced by the term "alkenyl." Furthermore, the term "alkenyl" includes di- and tri-alkenyls. Accordingly, if more than one double bond is present then the bonds may be all E or Z or a mixtures of E and Z. Examples of an alkenyl include vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2,4-hexadienyl and the like.

The term "$C_{1-4}$ alkoxy" as used herein denotes a radical alkyl, as defined herein, attached directly to an oxygen atom. Examples include methoxy, ethoxy, n-propoxy, iso-propoxy, n-butoxy, t-butoxy, iso-butoxy, sec-butoxy and the like.

The term "$C_{1-8}$ alkyl" denotes a straight or branched carbon radical containing 1 to 8 carbons, some embodiments are 1 to 6 carbons, some embodiments are 1 to 3 carbons, and some embodiments are 1 or 2 carbons. Examples of an alkyl include, but not limited to, methyl, ethyl, n-propyl, iso-propyl, n-butyl, sec-butyl, iso-butyl, t-butyl, pentyl, iso-pentyl, t-pentyl, neo-pentyl, 1-methylbutyl [i.e., —CH(CH$_3$)CH$_2$CH$_2$CH$_3$], 2-methylbutyl [i.e., —CH$_2$CH(CH$_3$)CH$_2$CH$_3$], n-hexyl and the like.

The term "$C_{1-4}$ alkylcarboxamido" or "$C_{1-4}$ alkylcarboxamide" denotes a single $C_{1-4}$ alkyl group attached to the nitrogen of an amide group, wherein alkyl has the same definition as found herein. The $C_{1-5}$ alkylcarboxamido may be represented by the following:

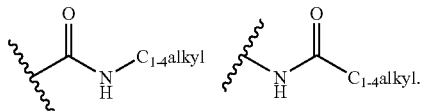

Examples include, but not limited to, N-methylcarboxamide, N-ethylcarboxamide, N-n-propylcarboxamide, N-iso-propylcarboxamide, N-n-butylcarboxamide, N-sec-butylcarboxamide, N-iso-butylcarboxamide, N-t-butylcarboxamide and the like.

The term "$C_{1-3}$ alkylene" refers to a $C_{1-3}$ divalent straight carbon group. In some embodiments $C_{1-3}$ alkylene refers to, for example, —CH$_2$—, —CH$_2$CH$_2$—, —CH$_2$CH$_2$CH$_2$—, and the like. In some embodiments, $C_{1-3}$ alkylene refers to —CH—, —CHCH$_2$—, —CHCH$_2$CH$_2$—, and the like wherein these examples relate generally to "A".

The term "$C_{1-4}$ alkylsulfinyl" denotes a $C_{1-4}$ alkyl radical attached to a sulfoxide radical of the formula: —S(O)— wherein the alkyl radical has the same definition as described herein. Examples include, but not limited to, methylsulfinyl, ethylsulfinyl, n-propylsulfinyl, iso-propylsulfinyl, n-butylsulfinyl, sec-butylsulfinyl, iso-butylsulfinyl, t-butyl, and the like.

The term "$C_{1-4}$ alkylsulfonamide" refers to the groups

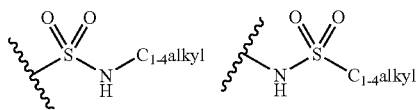

wherein $C_{1-4}$ alkyl has the same definition as described herein.

The term "$C_{1-4}$ alkylsulfonyl" denotes a $C_{1-4}$ alkyl radical attached to a sulfone radical of the formula: —S(O)$_2$— wherein the alkyl radical has the same definiti+on as described herein. Examples include, but not limited to, methylsulfonyl, ethylsulfonyl, n-propylsulfonyl, iso-propylsulfonyl, n-butylsulfonyl, sec-butylsulfonyl, iso-butylsulfonyl, t-butyl, and the like.

The term "$C_{1-4}$ alkylthio" denotes a $C_{1-4}$ alkyl radical attached to a sulfide of the formula: —S— wherein the alkyl radical has the same definition as described herein. Examples include, but not limited to, methylsulfanyl (i.e., CH$_3$S—), ethylsulfanyl, n-propylsulfanyl, iso-propylsulfanyl, n-butylsulfanyl, sec-butylsulfanyl, iso-butylsulfanyl, t-butyl, and the like.

The term "$C_{1-4}$ alkylthiocarboxamide" denotes a thioamide of the following formulae:

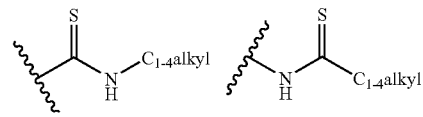

wherein $C_{1-4}$ alkyl has the same definition as described herein.

The term "$C_{1-4}$ alkylthioureyl" denotes the group of the formula: —NC(S)N— wherein one are both of the nitrogens are substituted with the same or different $C_{1-4}$ alkyl groups and alkyl has the same definition as described herein. Examples of an alkylthioureyl include, but not limited to, CH$_3$NHC(S)NH—, NH$_2$C(S)NCH$_3$—, (CH$_3$)$_2$N(S)NH—, (CH$_3$)$_2$N(S)NH—, (CH$_3$)$_2$N(S)NCH$_3$—, CH$_3$CH$_2$NHC(S)NH—, CH$_3$CH$_2$NHC(S)NCH$_3$—, and the like.

The term "$C_{1-4}$ alkylureyl" denotes the group of the formula: —NC(O)N— wherein one are both of the nitrogens are substituted with the same or different $C_{1-4}$ alkyl group wherein alkyl has the same definition as described herein. Examples of an alkylureyl include, but not limited to, CH$_3$NHC(O)NH—, NH$_2$C(O)NCH$_3$—, (CH$_3$)$_2$N(O)NH—, (CH$_3$)$_2$N(O)NH—, (CH$_3$)$_2$N(O)NCH$_3$—, CH$_3$CH$_2$NHC(O)NH—, CH$_3$CH$_2$NHC(O)NCH$_3$—, and the like.

The term "$C_{2-6}$ alkynyl" denotes a radical containing 2 to 6 carbons and at least one carbon-carbon triple bond, some embodiments are 2 to 4 carbons, some embodiments are 2 to 3 carbons, and some embodiments have 2 carbons. Examples of an alkynyl include, but not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "amino" denotes the group —NH$_2$.

The term "$C_{1-4}$ alkylamino" denotes one alkyl radical attached to an amino radical wherein the alkyl radical has the same meaning as described herein. Some examples include, but not limited to, methylamino, ethylamino, n-propylamino, iso-propylamino, n-butylamino, sec-butylamino, iso-butylamino, t-butylamino, and the like. Some embodiments are "$C_{1-2}$ alkylamino."

The term "aryl" denotes an aromatic ring radical containing 6 to 10 ring carbons. Examples include phenyl and naphthyl.

The term "arylalkyl" defines a $C_1$-$C_4$ alkylene, such as —CH$_2$—, —CH$_2$CH$_2$— and the like, which is further substituted with an aryl group. Examples of an "arylalkyl" include benzyl, phenethylene and the like.

The term "arylcarboxamido" denotes a single aryl group attached to the nitrogen of an amide group, wherein aryl has the same definition as found herein. The example is N-phenylcarboxamide.

The term "arylureyl" denotes the group —NC(O)N— where one of the nitrogens are substituted with an aryl.

The term "benzyl" denotes the group —CH$_2$C$_6$H$_5$.

The term "carbo-C$_{1-6}$-alkoxy" refers to a C$_{1-6}$ alkyl ester of a carboxylic acid, wherein the alkyl group is as defined herein. In some embodiments, the carbo-C$_{1-6}$-alkoxy group is bonded to a nitrogen atom and together form a carbamate group (e.g., N—COO—C$_{1-6}$-alkyl). In some embodiments, the carbo-C$_{1-6}$-alkoxy group is an ester (e.g., —COO—C$_{1-6}$-alkyl). Examples include, but not limited to, carbomethoxy, carboethoxy, carbopropoxy, carboisopropoxy, carbobutoxy, carbo-sec-butoxy, carbo-iso-butoxy, carbo-t-butoxy, carbo-n-pentoxy, carbo-iso-pentoxy, carbo-t-pentoxy, carbo-neo-pentoxy, carbo-n-hexyloxy, and the like.

The term "carboxamide" refers to the group —CONH$_2$.

The term "carboxy" or "carboxyl" denotes the group —CO$_2$H; also referred to as a carboxylic acid group.

The term "cyano" denotes the group —CN.

The term "C$_{3-7}$ cycloalkenyl" denotes a non-aromatic ring radical containing 3 to 6 ring carbons and at least one double bond; some embodiments contain 3 to 5 carbons; some embodiments contain 3 to 4 carbons. Examples include cyclopropenyl, cyclobutenyl, cyclopentenyl, cyclopentenyl, cyclohexenyl, and the like.

The term "C$_{3-7}$ cycloalkyl" denotes a saturated ring radical containing 3 to 6 carbons; some embodiments contain 3 to 5 carbons; some embodiments contain 3 to 4 carbons. Examples include cyclopropyl, cyclobutyl, cyclopentyl, cyclopenyl, cyclohexyl, cycloheptyl and the like.

The term "C$_{4-8}$ diacylamino" denotes an amino group bonded with two acyl groups defined herein wherein the acyl groups may be the same or different, such as:

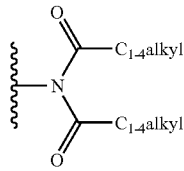

Examples of C$_{4-8}$ diacylamino groups include, but limited to, diacetylamino, dipropionylamino, acetylpropionylamino and the like.

The term "C$_{2-6}$ dialkylamino" denotes an amino substituted with two of the same or different alkyl radicals wherein alkyl radical has the same definition as described herein. Some examples include, but not limited to, dimethylamino, methylethylamino, diethylamino, methylpropylamino, methylisopropylamino, ethylpropylamino, ethylisopropylamino, dipropylamino, propylisopropylamino and the like. Some embodiments are "C$_{2-4}$ dialkylamino."

The term "C$_{1-4}$ dialkylcarboxamido" or "C$_{1-4}$ dialkylcarboxamide" denotes two alkyl radicals, that are the same or different, attached to an amide group, wherein alkyl has the same definition as described herein. A C$_{1-4}$ dialkylcarboxamido may be represented by the following groups:

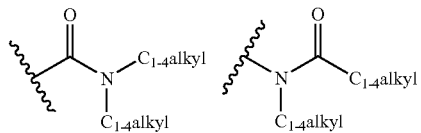

wherein C$_{1-4}$ has the same definition as described herein. Examples of a dialkylcarboxamide include, but not limited to, N,N-dimethylcarboxamide, N-methyl-N-ethylcarboxamide, N,N-diethylcarboxamide, N-methyl-N-isopropylcarboxamide, and the like.

The term "C$_{2-6}$ dialkylsulfonamide" refers to one of the following groups shown below:

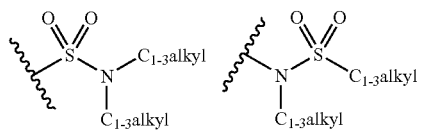

wherein C$_{1-3}$ has the same definition as described herein, for example but not limited to, methyl, ethyl, n-propyl, isopropyl, and the like.

The term "C$_{2-6}$ dialkylthiocarboxamido" or "C$_{2-6}$ dialkylthiocarboxamide" denotes two alkyl radicals, that are the same or different, attached to a thioamide group, wherein alkyl has the same definition as described herein. A C$_{1-4}$ dialkylthiocarboxamido may be represented by the following groups:

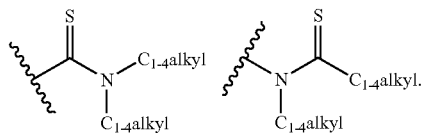

Examples of a dialkylthiocarboxamide include, but not limited to, N,N-dimethylthiocarboxamide, N-methyl-N-ethylthiocarboxamide and the like.

The term "C$_{2-6}$ dialkylsulfonylamino" refers to an amino group bonded with two C$_{1-3}$ alkylsulfonyl groups as defined herein.

The term "ethynylene" refers to the carbon-carbon triple bond group as represented below:

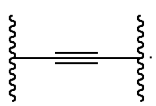

The term "formyl" refers to the group —CHO.

The term "C$_{1-4}$ haloalkoxy" denotes a haloalkyl, as defined herein, which is directly attached to an oxygen atom. Examples include, but not limited to, difluoromethoxy, trifluoromethoxy, 2,2,2-trifluoroethoxy, pentafluoroethoxy and the like.

The term "C$_{1-4}$ haloalkyl" denotes an C$_{1-4}$ alkyl group, defined herein, wherein the alkyl is substituted with one halogen up to fully substituted and a fully substituted C$_{1-4}$ haloalkyl can be represented by the formula C$_n$L$_{2n+1}$ wherein L is a halogen and "n" is 1, 2, 3 or 4; when more than one halogen is present then they may be the same or different and selected from the group consisting of F, Cl, Br and I, preferably F. Examples of $C_{1-4}$ haloalkyl groups include, but not limited to, fluoromethyl, difluoromethyl, trifluoromethyl, chlorodifluoromethyl, 2,2,2-trifluoroethyl, pentafluoroethyl and the like.

The term "$C_{1-4}$ haloalkylcarboxamide" denotes an alkylcarboxamide group, defined herein, wherein the alkyl is substituted with one halogen up to fully substituted represented by the formula wherein L is a halogen and "n" is 1, 2, 3 or 4. When more than one halogen is present they may be the same or different and selected from the group consisting of F, Cl, Br and I, preferably F.

The term "$C_{1-4}$ haloalkylsulfinyl" denotes a haloalkyl radical attached to a sulfoxide group of the formula: —S(O)— wherein the haloalkyl radical has the same definition as described herein. Examples include, but not limited to, trifluoromethylsulfinyl, 2,2,2-trifluoroethylsulfinyl, 2,2-difluoroethylsulfinyl and the like.

The term "$C_{1-4}$ haloalkylsulfonyl" denotes a haloalkyl radical attached to a sulfone group of the formula: —S(O)$_2$— wherein haloalkyl has the same definition as described herein. Examples include, but not limited to, trifluoromethylsulfonyl, 2,2,2-trifluoroethylsulfonyl, 2,2-difluoroethylsulfonyl and the like.

The term "$C_{1-4}$ haloalkylthio" denotes a haloalkyl radicaol directly attached to a sulfur wherein the haloalkyl has the same meaning as described herein. Examples include, but not limited to, trifluoromethylthio (i.e., $CF_3S$—), 1,1-difluoroethylthio, 2,2,2-trifluoroethylthio and the like.

The term "halogen" or "halo" denotes to a fluoro, chloro, bromo or iodo group.

The term "$C_{1-2}$ heteroalkylene" refers to a $C_{1-2}$ alkylene bonded to a heteroatom selected from O, S, S(O), S(O)$_2$ and NH. Some represented examples include, but not limited to, the groups of the following formulae:

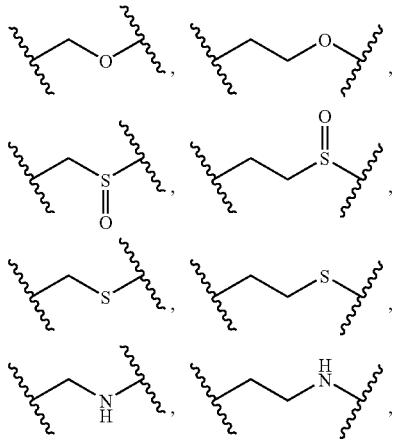

and the like.

The term "heteroaryl" denotes an aromatic ring system that may be a single ring, two fused rings or three fused rings wherein at least one ring carbon is replaced with a heteroatom selected from, but not limited to, the group consisting of O, S and N wherein the N can be optionally substituted with H, $C_{1-4}$ acyl or $C_{1-4}$ alkyl. Examples of heteroaryl groups include, but not limited to, pyridyl, benzofuranyl, pyrazinyl, pyridazinyl, pyrimidinyl, triazinyl, quinoline, benzoxazole, benzothiazole, 1H-benzimidazole, isoquinoline, quinazoline, quinoxaline and the like. In some embodiments, the heteroaryl atom is O, S, NH, examples include, but not limited to, pyrrole, indole, and the like.

The term "heterocyclic" denotes a non-aromatic carbon ring (i.e., cycloalkyl or cycloalkenyl as defined herein) wherein one, two or three ring carbons are replaced by a heteroatom selected from, but not limited to, the group consisting of O, S, N, wherein the N can be optionally substituted with H, $C_{1-4}$ acyl or $C_{1-4}$ alkyl, and ring carbon atoms optionally substituted with oxo or a thiooxo thus forming a carbonyl or thiocarbonyl group. The heterocyclic group is a 3-, 4-, 5-, 6- or 7-membered containing ring. Examples of a heterocyclic group include but not limited to aziridin-1-yl, aziridin-2-yl, azetidin-1-yl, azetidin-2-yl, azetidin-3-yl, piperidin-1-yl, piperidin-4-yl, morpholin-4-yl, piperzin-1-yl, piperzin-4-yl, pyrrolidin-1-yl, pyrrolidin-3-yl, [1,3]-dioxolan-2-yl and the like.

The term "heterocyclic-carbonyl" denotes a heterocyclic group, as defined herein, directly bonded to the carbon of a carbonyl group (i.e., C=O). In some embodiments, a ring nitrogen of the heterocyclic group is bonded to the carbonyl group forming an amide. Examples include, but not limited to,

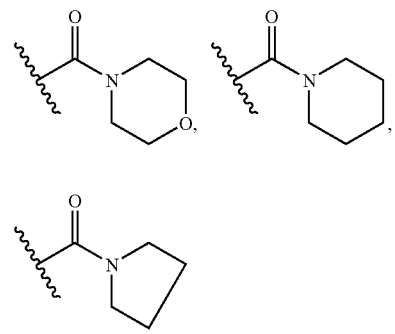

and the like.

In some embodiments, a ring carbon is bonded to the carbonyl group forming a ketone group.

Examples include, but not limited to,

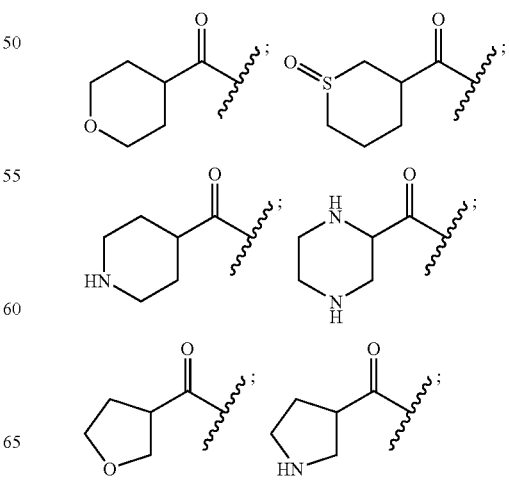

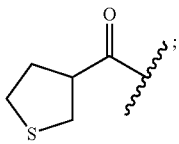

and the like.

The term "heterocyclic-oxy" refers to a heterocyclic group, as defined herein, that is directly bonded to an oxygen atom. Examples include the following:

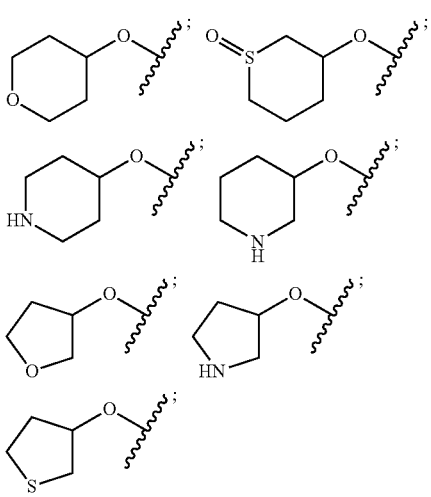

and the like.

The term "heterocycliccarboxamido" denotes a heterocyclic group, as defined herein, with a ring nitrogen where the ring nitrogen is bonded directly to the carbonyl forming an amide. Examples include, but not limited to,

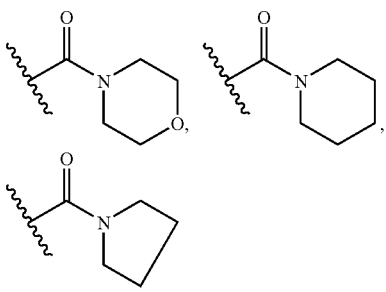

and the like.

The term "heterocyclicsulfonyl" denotes a heterocyclic group, as defined herein, with a ring nitrogen where the ring nitrogen is bonded directly to an $SO_2$ group forming an sulfonamide. Examples include, but not limited to,

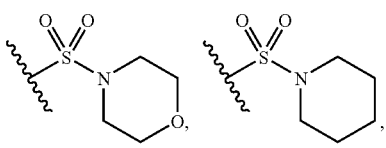

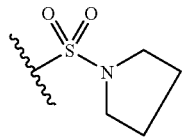

and the like.

The term "hydroxyl" refers to the group —OH.

The term "hydroxylamino" refers to the group —NHOH.

The term "nitro" refers to the group —$NO_2$.

The term "$C_{4-7}$ oxo-cycloalkyl" refers to a $C_{4-7}$ cycloalkyl, as defined herein, wherein one of the ring carbons is replaced with a carbonyl. Examples of $C_{4-7}$ oxo-cycloalkyl include, but are not limited to, 2-oxo-cyclobutyl, 3-oxo-cyclobutyl, 3-oxo-cyclopentyl, 4-oxo-cyclohexyl, and the like and represented by the following structures respectively:

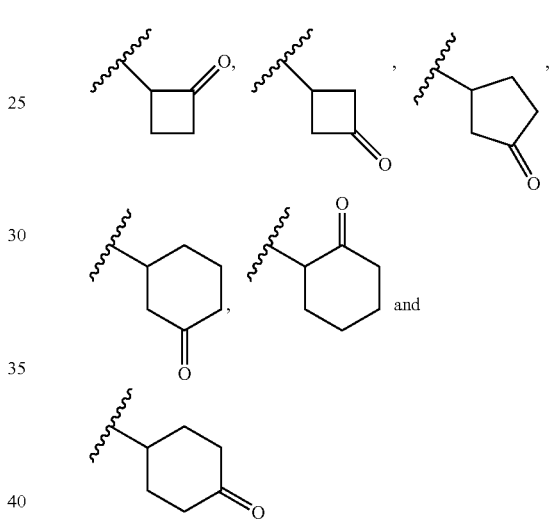

The term "perfluoroalkyl" denotes the group of the formula —$C_nF_{2n+1}$; stated differently, a perfluoroalkyl is an alkyl as defined herein wherein the alkyl is fully substituted with fluorine atoms and is therefore considered a subset of haloalkyl. Examples of perfluoroalkyls include $CF_3$, $CF_2CF_3$, $CF_2CF_2CF_3$, $CF(CF_3)_2$, $CF_2CF_2CF_2CF_3$, $CF_2CF(CF_3)_2$, $CF(CF_3)CF_2CF_3$ and the like.

The term "phenoxy" refers to the group $C_6H_5O$—.

The term "phenyl" refers to the group $C_6H_5$—.

The term "phosphonooxy" refers to a group with the following chemical structure:

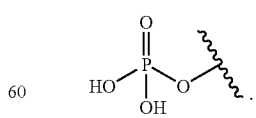

The term "sulfonamide" refers to the group —$SO_2NH_2$.

The term "sulfonic acid" refers to the group —$SO_3H$.

The term "tetrazolyl" refers to the five membered heteroaryl of the following formulae:

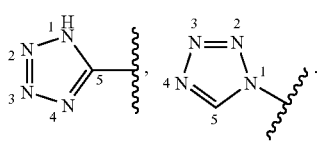

In some embodiments, the tetrazolyl group is further substituted at either the 1 or 5 position respectively with a group selected from the group consisting of $C_{1-3}$ alkyl, $C_{1-3}$ haloalkyl and $C_{1-3}$ alkoxy.

The term "thiol" denotes the group —SH.

The term "GLP-1 secretagogue" shall mean an agent (e.g., a compound) that promotes GLP-1 secretion from a cell, e.g. an enteroendocrine cell.

The term "endogenous" shall mean a material that a mammal naturally produces. The term "biologically active fragment of a G protein-coupled receptor" shall mean a fragment of the GPCR having structural and biochemical functions of a naturally occurring GPCR. In certain embodiments, the biologically active fragment couples to a G protein. In certain embodiments, the biologically active fragment binds to a known ligand of the GPCR.

The term "primer" is used herein to denote a specific oligonucleotide sequence which is complementary to a target nucleotide sequence and used to hybridize to the target nucleotide sequence. A primer serves as an initiation point for nucleotide polymerization catalyzed by DNA polymerase, RNA polymerase, or reverse transcriptase.

The term "expression vector" shall mean a DNA sequence that is required for the transcription of cloned DNA and translation of the transcribed mRNA in an appropriate host cell recombinant for the expression vector. An appropriately constructed expression vector should contain an origin of replication for autonomous replication in host cells, selectable markers, a limited number of useful restriction enzyme sites, a potential for high copy number, and active promoters. The cloned DNA to be transcribed is operably linked to a constitutively or conditionally active promoter within the expression vector.

The term "candidate compound" or "test compound" shall mean a compound (for example and not limitation, a chemical compound) that is amenable to screening.

The term "contact" or "contacting" shall mean bringing at least two moieties together.

The terms "modulate" or "modify" shall be taken to refer to an increase or decrease in the amount, quality, or effect of a particular activity, function or molecule. By way of illustration and not limitation, agonists, partial agonists, inverse agonists, and antagonists of a G protein-coupled receptor are modulators of the receptor.

The term "small molecule" shall be taken to mean a compound having a molecular weight of less than about 10,000 grams per mole, including a peptide, peptidomimetic, amino acid, amino acid analogue, polynucleotide, polynucleotide analogue, nucleotide, nucleotide analogue, organic compound or inorganic compound (i.e. including a heterorganic compound or organometallic compound), and salts, esters and other pharmaceutically acceptable forms thereof. In certain preferred embodiments, small molecules are organic or inorganic compounds having a molecular weight of less than about 5,000 grams per mole. In certain preferred embodiments, small molecules are organic or inorganic compounds having molecular weight of less than about 1,000 grams per mole. In certain preferred embodiments, small molecules are organic or inorganic compounds having a molecular weight of less than about 800 grams per mole. In certain preferred embodiments, small molecules are organic or inorganic compounds having a molecular weight of less than about 600 grams per mole. In certain preferred embodiments, small molecules are organic or inorganic compounds having a molecular weight of less than about 500 grams per mole.

The term "polynucleotide" shall refer to RNA, DNA, or RNA/DNA hybrid sequence of more than one nucleotide in either single chain or duplex form. The polynucleotides of the invention may be prepared by any known method, including synthetic, recombinant, ex vivo generation, or a combination thereof, as well as utilizing any purification methods known in the art.

The term "polypeptide" shall refer to a polymer of amino acids without regard to the length of the polymer. Thus, peptides, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups and the like are expressly encompassed by the term polypeptide.

The term "antibody" is intended herein to encompass monoclonal antibody and polyclonal antibody.

The term "second messenger" shall mean an intracellular response produced as a result of receptor activation. A second messenger can include, for example, inositol 1,4,5-triphosphate (IP3), diacylglycerol (DAG), cyclic AMP (cAMP), cyclic GMP (cGMP), MAP kinase activity, MAPK/ERK kinase kinase-1 (MEKK1) activity, and Ca2+. Second messenger response can be measured for a determination of receptor activation.

The term "receptor functionality" shall refer to the normal operation of a receptor to receive a stimulus and moderate an effect in the cell, including, but not limited to regulating gene transcription, regulating the influx or efflux of ions, effecting a catalytic reaction, and/or modulating activity through G-proteins, such as eliciting a second messenger response.

The term "stimulate" or "stimulating," in relationship to the term "response" or "functionality of the receptor" shall mean that a response or a functionality of the receptor is increased in the presence of a compound as opposed to in the absence of the compound.

The term "inhibit" or "inhibiting," in relationship to the term "response" or "functionality of the receptor" shall mean that a response a functionality of the receptor is decreased or prevented in the presence of a compound as opposed to in the absence of the compound.

Where a range of values is provided, it is understood that each intervening value, to the tenth of the lower limit unless the context clearly indicates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

GPR119 Agonists

Preferably, GPR119 is mammalian GPR119. More preferably, GPR119 is rodent or primate GPR119. Most preferably, GPR119 is human GPR119.

The class of GPR119 agonists useful in the novel therapeutic combinations of the present invention include compounds which exhibit an acceptably high affinity for GPR119 receptor. The GPR119 agonist or pharmaceutically acceptable salt may be any agonist, more preferably a selective GPR119 agonist.

Examples of GPR119 agonists are described in International Application No. PCT/US2004/001267 (published as WO 04/065380), the disclosure of which is herein incorporated by reference in its entirety. Disclosed in International Application No. PCT/US2004/001267 as a GPR119 agonist is a compound of Formula (I):

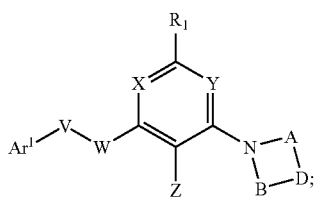

wherein:

A and B are independently $C_{1-3}$ alkylene optionally substituted with 1 to 4 methyl groups;

D is O, S, S(O), S(O)$_2$, CR$_2$R$_3$ or N—R$_2$;

V is selected from the group consisting of $C_{1-3}$ alkylene, ethynylene and $C_{1-2}$ heteroalkylene wherein each are optionally substituted with 1 to 4 substituents selected from the group consisting of $C_{1-3}$ alkyl, $C_{1-4}$ alkoxy, carboxy, cyano, $C_{1-3}$ haloalkyl and halogen; or V is absent;

W is NR$_4$, O, S, S(O) or S(O)$_2$; or

W is absent;

X is N or CR$_5$;

Y is N or CR$_6$;

Z is selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, $C_{1-2}$ alkylamino, $C_{2-4}$ dialkylamino, carbo-$C_{1-6}$-alkoxy, carboxamide, carboxy, cyano, $C_{4-8}$ diacylamino, $C_{2-6}$ dialkylcarboxamide, $C_{1-4}$ dialkylthiocarboxamide, $C_{2-6}$ dialkylsulfonamide, $C_{1-4}$ dialkylsulfonylamino, formyl, $C_{1-4}$ haloalkoxy, $C_{1-4}$ haloalkyl, $C_{1-4}$ haloalkylcarboxamide, $C_{1-4}$ haloalkylsulfinyl, $C_{1-4}$ haloalkylsulfonyl, $C_{1-4}$ haloalkylthio, halogen, aryl, heterocyclic, heteroaryl, hydroxyl, hydroxylamino, nitro and tetrazolyl, wherein $C_{1-8}$ alkyl and $C_{1-5}$ acyl are each optionally substituted with 1, 2, 3 or 4 groups selected from the group consisting of $C_{1-5}$ acyl, $C_{1-5}$ acyloxy, $C_{1-4}$ alkoxy, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-2}$ alkylamino, $C_{2-4}$ dialkylamino, carbo-$C_{1-6}$-alkoxy, carboxamide, carboxy, cyano, formyl, $C_{1-4}$ haloalkoxy, $C_{1-4}$ haloalkylsulfinyl, $C_{1-4}$ haloalkylsulfonyl, $C_{1-4}$ haloalkylthio, halogen, hydroxyl, hydroxylamino and nitro; or Z is a group of Formula (IA):

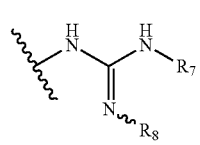

wherein:

R$_7$ is H, $C_{1-8}$ alkyl or $C_{3-6}$ cycloalkyl; and

R$_8$ is H, nitro or nitrile;

Ar$_1$ is aryl or heteroaryl wherein each are optionally substituted with R$_9$-R$_{13}$;

R$_1$ is selected from the group consisting of H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-6}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio and hydroxyl;

R$_2$ is selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, cyano, $C_{3-6}$-cycloalkyl, $C_{2-6}$ dialkylcarboxamide, $C_{1-4}$ haloalkoxy, $C_{1-4}$ haloalkyl, halogen, heteroaryl, hydroxyl and phenyl; and wherein $C_{1-8}$ alkyl, heteroaryl and phenyl are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-alkylene, $C_{3-6}$-cycloalkyl-$C_{1-3}$-heteroalkylene, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; or R$_2$ is —Ar$_2$—Ar$_3$ wherein Ar$_2$ and Ar$_3$ are independently aryl or heteroaryl each optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, cyano, $C_{3-6}$-cycloalkyl, $C_{2-6}$ dialkylcarboxamide, $C_{1-4}$ haloalkoxy, $C_{1-4}$ haloalkyl, halogen, hydroxyl and nitro; or R$_2$ is a group of Formula (IB):

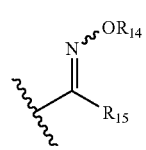

wherein:
R$_{14}$ is C$_{1-8}$ alkyl or C$_{3-6}$ cycloalkyl; and R$_{15}$ is F, Cl, Br or CN; or R$_2$ is a group of Formula (IC):

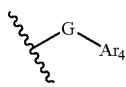

(IC)

wherein:
G is C=O, CR$_{16}$R$_{17}$, O, S, S(O), S(O)$_2$; where R$_{16}$ and R$_{17}$ are independently H or C$_{1-8}$ alkyl; and
Ar$_4$ is phenyl or heteroaryl optionally substituted with 1 to 5 substituents selected from the group consisting of C$_{1-5}$ acyl, C$_{1-5}$ acyloxy, C$_{1-4}$ alkoxy, C$_{1-8}$ alkyl, C$_{1-4}$ alkylcarboxamide, C$_{1-4}$ alkylthiocarboxamide, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylthioureyl, C$_{1-4}$ alkylureyl, amino, carbo-C$_{1-6}$-alkoxy, carboxamide, carboxy, cyano, C$_{3-6}$-cycloalkyl, C$_{2-6}$ dialkylcarboxamide, C$_{1-4}$ dialkylthiocarboxamide, C$_{2-6}$ dialkylsulfonamide, C$_{1-4}$ alkylthioureyl, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkyl, C$_{1-4}$ haloalkylthio, halogen, heteroaryl, hydroxyl, hydroxylamino and nitro;

R$_3$ is H, C$_{1-8}$ alkyl, C$_{1-4}$ alkoxy, halogen or hydroxyl;
R$_4$ is H or C$_{1-8}$ alkyl;
R$_5$ and R$_6$ are independently H, C$_{1-8}$ alkyl or halogen;
R$_9$ is selected from the group consisting of C$_{1-5}$ acyl, C$_{1-5}$ acyloxy, C$_{2-6}$ alkenyl, C$_{1-4}$ alkoxy, C$_{1-8}$ alkyl, C$_{1-4}$ alkylamino, C$_{1-4}$ alkylcarboxamide, C$_{2-6}$ alkynyl, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylureyl, amino, arylsulfonyl, carbo-C$_{1-6}$-alkoxy, carboxamide, carboxy, cyano, C$_{3-6}$ cycloalkyl, C$_{2-6}$ dialkylamino, C$_{2-6}$ dialkylcarboxamide, C$_{2-6}$ dialkylsulfonamide, halogen, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkylthio, heterocyclic, heterocyclicsulfonyl, heteroaryl, hydroxyl, nitro, C$_{4-7}$ oxo-cycloalkyl, phenoxy, phenyl, sulfonamide and sulfonic acid, and wherein C$_{1-5}$ acyl, C$_{1-4}$ alkoxy, C$_{1-8}$ alkyl, C$_{1-4}$ alkylsulfonamide, alkylsulfonyl, arylsulfonyl, heteroaryl, phenoxy and phenyl are each optionally substituted with 1 to 5 substituents selected independently from the group consisting of C$_{1-5}$ acyl, C$_{1-5}$ acyloxy, C$_{2-6}$ alkenyl, C$_{1-4}$ alkoxy, C$_{1-8}$ alkyl, C$_{1-4}$ alkylcarboxamide, C$_{2-6}$ alkynyl, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylureyl, carbo-C$_{1-6}$-alkoxy, carboxamide, carboxy, cyano, C$_{3-6}$ cycloalkyl, C$_{2-6}$ dialkylcarboxamide, halogen, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkylthio, heteroaryl, heterocyclic, hydroxyl, nitro and phenyl; or R$_9$ is a group of Formula (ID):

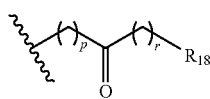

(ID)

wherein:
"p" and "r" are independently 0, 1, 2 or 3; and
R$_{18}$ is H, C$_{1-5}$ acyl, C$_{2-6}$ alkenyl, C$_{1-8}$ alkyl, C$_{1-4}$ alkylcarboxamide, C$_{2-6}$ alkynyl, C$_{1-4}$ alkylsulfonamide, carbo-C$_{1-6}$-alkoxy, carboxamide, carboxy, cyano, C$_{3-6}$ cycloalkyl, C$_{2-6}$ dialkylcarboxamide, halogen, heteroaryl or phenyl, and wherein the heteroaryl and phenyl are each optionally substituted with 1 to 5 substituents selected independently from the group consisting of C$_{1-4}$ alkoxy, amino, C$_{1-4}$ alkylamino, C$_{2-6}$ alkynyl, C$_{2-8}$ dialkylamino, halogen, C$_{1-4}$ haloalkoxy, C$_{1-4}$ haloalkyl and hydroxyl; and R$_{10}$-R$_{13}$ are independently selected form the group consisting of C$_{1-5}$ acyl, C$_{1-5}$ acyloxy, C$_{2-6}$ alkenyl, C$_{1-4}$ alkoxy, C$_{1-8}$ alkyl, C$_{1-4}$ alkylcarboxamide, C$_{2-6}$ alkynyl, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylureyl, carbo-C$_{1-6}$-alkoxy, carboxamide, carboxy, cyano, C$_{3-6}$ cycloalkyl, C$_{2-6}$ dialkylcarboxamide, halogen, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkylthio, hydroxyl and nitro; or
two adjacent R$_{10}$-R$_{11}$ groups together with Ar$_1$ form a 5, 6 or 7 membered cycloalkyl, cycloalkenyl or heterocyclic group wherein the 5, 6 or 7 membered group is optionally substituted with halogen.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/US2004/001267 include the following compounds according to Formula (I) (referred to herein as Group A1): [6-(4-Benzenesulfonyl-piperidin-1-yl)-5-nitro-pyrimidin-4-yl]-(4-methanesulfonyl-phenyl)-amine; {4-[6-(4-Methanesulfonyl-phenylamino)-5-nitro-pyrimidin-4-yl]-piperazin-1-yl}-acetic acid ethyl ester; (2-Fluoro-phenyl)-{5-nitro-6-[4-(pyridin-2-ylsulfanyl)-piperidin-1-yl]-pyrimidin-4-yl}-amine; 1-[6-(4-Imidazol-1-yl-phenoxy)-5-nitro-pyrimidin-4-yl]-piperidine-4-carboxylic acid ethyl ester; 1-[5-Nitro-6-(4-[1,2,4]triazol-1-yl-phenoxy)-pyrimidin-4-yl]-piperidine-4-carboxylic acid ethyl ester; {6-[4-(4-Fluoro-phenoxy)-piperidin-1-yl]-5-nitro-pyrimidin-4-yl}-(4-methanesulfonyl-phenyl)-amine; {6-[4-(3-Isopropyl-[1,2,4]oxadiazol-5-yl)-piperidin-1-yl]-5-nitro-pyrimidin-4-yl}-(4-methanesulfonyl-phenyl)-amine; {6-[4-(3-Cyclopropyl-[1,2,4]oxadiazol-5-yl)-piperidin-1-yl]-5-nitro-pyrimidin-4-yl}-(4-methanesulfonyl-phenyl)-amine; (4-Methanesulfonyl-phenyl)-(5-nitro-6-{4-[3-(3-trifluoromethyl-phenyl)-[1,2,4]oxadiazol-5-yl]-piperidin-1-yl}-pyrimidin-4-yl)-amine; {6-[4-(3-Ethyl-[1,2,4]oxadiazol-5-yl)-piperidin-1-yl]-5-nitro-pyrimidin-4-yl}-(2-fluoro-phenyl)-amine; (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine; {6-[4-(3-Ethyl-[1,2,4]oxadiazol-5-yl)-piperidin-1-yl]-5-nitro-pyrimidin-4-yl}-(2-fluoro-4-methanesulfonyl-phenyl)-amine; (4-Methanesulfonyl-phenyl)-{5-nitro-6-[4-(3-propyl-[1,2,4]oxadiazol-5-yl)-piperidin-1-yl]-pyrimidin-4-yl}-amine; {6-[4-(3-Cyclopropylmethyl-[1,2,4]oxadiazol-5-yl)-piperidin-1-yl]-5-nitro-pyrimidin-4-yl}-(4-methanesulfonyl-phenyl)-amine; (4-Methanesulfonyl-phenyl)-{5-nitro-6-[4-(pyridin-4-yloxy)-piperidin-1-yl]-pyrimidin-4-yl}-amine; (4-Methanesulfonyl-phenyl)-{5-nitro-6-[4-(pyrimidin-2-yloxy)-piperidin-1-yl]-pyrimidin-4-yl}-amine; 1-[6-(4-Carbamoylmethyl-phenoxy)-5-nitro-pyrimidin-4-yl]-piperidine-4-carboxylic acid ethyl ester; 1-{6-[4-(1,3-Dioxo-1,3-dihydro-isoindol-2-yl)-phenoxy]-5-nitro-pyrimidin-4-yl}-piperidine-4-carboxylic acid ethyl ester; 4'-[4-(2-Methoxycarbonyl-acetyl)-phenoxy]-3'-nitro-3,4,5,6-tetrahydro-2H-[1,2']bipyridinyl-4-carboxylic acid ethyl ester; {6-[4-(2-Methoxy-phenylsulfanyl)-piperidin-1-yl]-5-nitro-pyrimidin-4-yl}-(4-[1,2,4]triazol-1-yl-phenyl)-amine; 4'-(2-Amino-4-ethanesulfonyl-phenoxy)-3'-nitro-3,4,5,6-tetrahydro-2H-[1,2']bipyridinyl-4-carboxylic acid ethyl ester; 4'-(4-Imidazol-1-yl-phenoxy)-3'-nitro-3,4,5,6-tetrahydro-2H-[1,2']bipyridinyl-4-carboxylic acid ethyl ester; (4-Methoxy-2-{5-nitro-6-[4-(pyridin-2-ylsulfanyl)-piperidin-1-yl]-pyrimidin-4-yloxy}-phenyl)-phenyl-methanone; 4-{4-[6-(4-Cyclopropylmethoxymethyl-piperidin-1-yl)-5-nitro-pyrimidin-4-yloxy]-phenyl}-butan-2-one; 4-{4-[5-Nitro-6-(4-propoxymethyl-piperidin-1-yl)-pyrimidin-4-yloxy]-phenyl}-butan-2-one; 4-{4-[6-(4-Butoxymethyl-piperidin-1-yl)-5-nitro-pyrimidin-4-yloxy]-phenyl}-butan-2-one; 4-{4-[6-(4-Isobutoxymethyl-piperidin-1-yl)-5-nitro-pyrimidin-4-yloxy]-phenyl}-butan-2-one; {1-[6-(Benzo[1,3]dioxol-5-ylamino)-5-nitro-pyrimidin-4-yl]-piperidin-4-yl}-(4-fluoro-phenyl)-methanone; (2,3-Difluoro-phenyl)-{5-nitro-6-[4-(pyridin-2-ylsulfanyl)-piperidin-1-yl]-pyrimidin-4-yl}-amine; (2,4-Difluoro-phenyl)-{5-nitro-6-[4-(pyridin-2-ylsulfanyl)-piperidin-1-yl]-pyrimidin-4-yl}-amine; 1-{2-Nitro-3-[4-(3-oxo-butyl)-phenoxy]-phenyl}-piperidine-4-carboxylic acid ethyl ester; 1-[6-(4-Acetyl-phenoxy)-5-nitro-pyrimidin-4-yl]-piperidine-4-carboxylic acid ethyl ester; 3'-Nitro-2'-[4-(3-oxo-butyl)-phenoxy]-3,4,5,6-tetrahydro-2H-[1,4']bipyridinyl-4-carboxylic acid ethyl ester; 4-(4-{5-Nitro-6-[4-(pyridin-2-ylsulfanyl)-piperidin-1-yl]-pyrimidin-4-yloxy}-phenyl)-butan-2-one; 4-(4-{5-Nitro-6-[4-(2-trifluoromethyl-phenoxy)-piperidin-1-yl]-pyrimidin-4-yloxy}-phenyl)-butan-2-one; 4-(4-{6-[4-(3-Methyl-[1,2,4]oxadiazol-5-yl)-piperidin-1-yl]-5-nitro-pyrimidin-4-yloxy}-phenyl)-butan-2-one; 4-(2,4-Difluoro-phenoxy)-5-nitro-6-[4-(pyridin-2-ylsulfanyl)-piperidin-1-yl]-pyrimidine; 4-(4-{6-[4-(4-Fluoro-benzoyl)-piperidin-1-yl]-5-nitro-pyrimidin-4-yloxy}-phenyl)-butan-2-one; 4-(4-Methanesulfonyl-phenoxy)-5-nitro-6-[4-(pyridin-2-ylsulfanyl)-cyclohexyl]-pyrimidine; 4-(4-Methanesulfonyl-phenoxy)-5-nitro-6-[4-(pyridin-4-ylsulfanyl)-cyclohexyl]-pyrimidine; 4-(4-Methanesulfonyl-phenoxy)-5-nitro-6-(4-phenylsulfanyl-cyclohexyl)-pyrimidine; 1-{6-[(Benzo[1,3]dioxol-5-ylmethyl)-amino]-5-nitro-pyrimidin-4-yl}-piperidine-4-carboxylic acid ethyl ester; 1-{6-[4-(1,1-Dioxo-1$\lambda^6$-thiomorpholin-4-ylmethyl)-phenylamino]-5-nitro-pyrimidin-4-yl}-piperidine-4-carboxylic acid ethyl ester; 1-[6-(4-Methanesulfonyl-phenylamino)-5-nitro-pyrimidin-4-yl]-piperidine-4-carboxylic acid ethyl ester; 1-[6-(4-Dimethylsulfamoyl-phenylamino)-5-nitro-pyrimidin-4-yl]-piperidine-4-carboxylic acid ethyl ester; 1-[6-(3-Methoxy-phenylamino)-5-nitro-pyrimidin-4-yl]-piperidine-4-carboxylic acid ethyl ester; 1-[6-(2-Methoxy-phenylamino)-5-nitro-pyrimidin-4-yl]-piperidine-4-carboxylic acid ethyl ester; 1-[6-(4-Methanesulfonyl-phenoxy)-5-nitro-pyrimidin-4-yl]-piperidine-4-carboxylic acid ethyl ester; 1-{6-[4-(2-Methoxycarbonyl-acetyl)-phenoxy]-5-nitro-pyrimidin-4-yl}-piperidine-4-carboxylic acid ethyl ester; 1-[6-(2-Amino-4-ethanesulfonyl-phenoxy)-5-nitro-pyrimidin-4-yl]-piperidine-4-carboxylic acid ethyl ester; 1-[6-(2,5-Dimethoxy-phenylamino)-5-nitro-pyrimidin-4-yl]-piperidine-4-carboxylic acid ethyl ester; (4-{5-Nitro-6-[4-(pyridin-2-ylsulfanyl)-piperidin-1-yl]-pyrimidin-4-ylamino}-phenyl)-phenyl-methanone; 1-[6-(4-Cyclohexyl-phenylamino)-5-nitro-pyrimidin-4-yl]-piperidine-4-carboxylic acid ethyl ester; 1-[5-Nitro-6-(4-[1,2,4]triazol-1-yl-phenylamino)-pyrimidin-4-yl]-piperidine-4-carboxylic acid ethyl ester; 1-[5-Nitro-6-(4-trifluoromethanesulfonyl-phenylamino)-pyrimidin-4-yl]-piperidine-4-carboxylic acid ethyl ester; 1-[5-Nitro-6-(4-[1,2,3]thiadiazol-4-yl-phenylamino)-pyrimidin-4-yl]-piperidine-4-carboxylic acid ethyl ester; [6-(4-Ethoxymethyl-piperidin-1-yl)-5-nitro-pyrimidin-4-yl]-(4-methanesulfonyl-phenyl)-amine; [5-Nitro-6-(4-propyl-piperidin-1-yl)-pyrimidin-4-yl]-(4-[1,2,4]triazol-1-yl-phenyl)-amine; {5-Nitro-6-[4-(pyridin-2-ylsulfanyl)-piperidin-1-yl]-pyrimidin-4-yl}-(4-[1,2,4]triazol-1-yl-phenyl)-amine; (2-Fluoro-phenyl)-{6-[4-(3-methyl-[1,2,4]oxadiazol-5-yl)-piperidin-1-yl]-5-nitro-pyrimidin-4-yl}-amine; (4-Methanesulfonyl-phenyl)-{6-[4-(3-methyl-[1,2,4]oxadiazol-5-yl)-piperidin-1-yl]-5-nitro-pyrimidin-4-yl}-amine; {6-[4-(3-Methyl-[1,2,4]oxadiazol-5-yl)-piperidin-1-yl]-5-nitro-pyrimidin-4-yl}-(4-[1,2,4]triazol-1-yl-phenyl)-amine; (4-Methanesulfonyl-phenyl)-{5-nitro-6-[4-(pyridin-2-ylsulfanyl)-piperidin-1-yl]-pyrimidin-4-yl}-amine; (3-Methoxy-phenyl)-{5-nitro-6-[4-(pyridin-2-ylsulfanyl)-piperidin-1-yl]-pyrimidin-4-yl}-amine; 1-[6-(Benzo[1,3]dioxol-5-ylamino)-5-nitro-pyrimidin-4-yl]-piperidine-4-carboxylic acid ethyl ester; 1-[6-(2-Fluoro-phenylamino)-5-nitro-pyrimidin-4-yl]-piperidine-4-carboxylic acid ethyl ester; 1-[6-(3-Fluoro-phenylamino)-5-nitro-pyrimidin-4-yl]-piperidine-4-carboxylic acid ethyl ester; 1-[6-(3,4-Dihydro-2H-benzo[b][1,4]dioxepin-7-ylamino)-5-nitro-pyrimidin-4-yl]-piperidine-4-carboxylic acid ethyl ester; 1-{6-[4-(Morpholine-4-sulfonyl)-phenylamino]-5-nitro-pyrimidin-4-yl}-piperidine-4-carboxylic acid ethyl ester; Benzo[1,3]dioxol-5-yl-[5-nitro-6-(4-propyl-piperidin-1-yl)-pyrimidin-4-yl]-amine; (4-Fluoro-phenyl)-{1-[5-nitro-6-(4-[1,2,4]triazol-1-yl-phenylamino)-pyrimidin-4-yl]-piperidin-4-yl}-methanone; [5-Nitro-6-(4-phenylsulfanyl-piperidin-1-yl)-pyrimidin-4-yl]-(4-[1,2,4]triazol-1-yl-phenyl)-amine; (4-Fluoro-phenyl)-{1-[6-(2-fluoro-phenylamino)-5-nitro-pyrimidin-4-yl]-piperidin-4-yl}-methanone; (4-Methanesulfonyl-phenyl)-[5-nitro-6-(4-phenylsulfanyl-piperidin-1-yl)-pyrimidin-4-yl]-amine; (4-Methanesulfonyl-phenyl)-{5-nitro-6-[4-(pyridin-2-yloxy)-piperidin-1-yl]-pyrimidin-4-yl}-amine; (4-Methanesulfonyl-phenyl)-{5-nitro-6-[4-(pyridin-4-ylsulfanyl)-piperidin-1-yl]-pyrimidin-4-yl}-amine; (4-Methanesulfonyl-phenyl)-{6-[4-(4-methoxyphenylsulfanyl)-piperidin-1-yl]-5-nitro-pyrimidin-4-yl}-amine; 2-Methoxy-phenyl)-{5-nitro-6-[4-(pyridin-2-ylsulfanyl)-piperidin-1-yl]-pyrimidin-4-yl}-amine; (4-Methanesulfonyl-phenyl)-(5-nitro-6-{4-[3-(3-trifluoromethyl-phenyl)-[1,2,4]oxadiazol-5-yl]-piperidin-1-yl}-pyrimidin-4-yl)-amine; {6-[4-(3-Ethyl-[1,2,4]oxadiazol-5-yl)-piperidin-1-yl]-5-nitro-pyrimidin-4-yl}-(4-methanesulfonyl-phenyl)-amine; (6-{4-[5-(4-Fluoro-phenyl)-[1,3,4]oxadiazol-2-yl]-piperidin-1-yl}-5-nitro-pyrimidin-4-yl)-(4-methanesulfonyl-phenyl)-amine; (4-Methanesulfonyl-phenyl)-[5-nitro-6-(4-pyridin-2-ylmethyl-piperidin-1-yl)-pyrimidin-4-yl]amine; 1-{6-[4-(2,5-Dioxo-imidazolidin-4-yl)-phenoxy]-5-nitro-pyrimidin-4-yl}-piperidine-4-carboxylic acid ethyl ester; 1-[5-Nitro-6-(4-propionyl-phenoxy)-pyrimidin-4-yl]-piperidine-4-carboxylic acid ethyl ester; 1-[5-Nitro-6-(4-[1,2,3]thiadiazol-4-yl-phenoxy)-pyrimidin-4-yl]-piperidine-4-carboxylic acid ethyl ester; 1-[6-[4-(3-oxo-butyl)-phenoxy]-5-(2,2,2-trifluoro-acetylamino)-pyrimidin-4-yl]-piperidine-4-carboxylic acid ethyl ester; 1-[6-(2-Benzoyl-5-methoxy-phenoxy)-5-nitro-pyrimidin-4-yl]piperidine-4-carboxylic acid ethyl ester; 3'-Nitro-4'-[4-(3-oxo-butyl)-phenoxy]-3,4,5, 6-tetrahydro-2H-[1,2']bipyridinyl-4-carboxylic acid ethyl ester; 1-[6-(4-Dimethyl sulfamoyl-phenylamino)-5-nitro-pyrimidin-4-yl]-piperidine-4-carboxylic acid ethyl ester; 1-{6-[4-(4,5-Dichloro-imidazol-1-yl)-phenylamino]-5-nitro-pyrimidin-4-yl}-piperidine-4-carboxylic acid ethyl ester; Benzo[1,3]dioxol-5-yl-{5-nitro-6-[4-(pyridin-2-ylsulfanyl)-piperidin-1-yl]-pyrimidin-4-yl}-amine; (4-Fluoro-phenyl)-{1-[6-(2-fluoro-phenylamino)-5-nitro-pyrimidin-4-yl]-piperidin-4-yl}-methanone; (2,5-Difluoro-phenyl)-{5-nitro-6-[4-(pyridin-2-ylsulfanyl)-piperidin-1-yl]-pyrimidin-4-yl}-amine; 1-{5-Nitro-6-[4-(3-oxo-butyl)-phenoxy]-pyrimidin-4-yl}-piperidine-4-carboxylic acid ethyl ester; 4-[4-(3-Isopropyl-[1,2,4]oxadiazol-5-yl)-piperidin-1-yl]-6-(4-methanesulfonyl-phenoxy)-pyrimidine-5-carbonitrile; 5-[1,3]Dioxolan-2-yl-4-[4-(3-isopropyl-[1,2,4]oxadiazol-5-yl)-piperidin-1-yl]-6-(4-methanesulfonyl-phenoxy)-pyrimidine; 4-[4-(3-Isopropyl-[1,2,4]oxadiazol-5-yl)-piperidin-1-yl]-6-(4-methanesulfonyl-phenoxy)-pyrimidine-5-carbaldehyde; 5-[1,3]Dioxolan-2-yl-4-[4-(3-isopropyl-[1,2,4]oxadiazol-5-yl)-piperidin-1-yl]-6-(4-[1,2,3]thiadiazol-4-yl-phenoxy)-pyrimidine; 4-[4-(3-Isopropyl-[1,2,4]oxadiazol-5-yl)-piperidin-1-yl]-6-(4-[1,2,3]thiadiazol-4-yl-phenoxy)-pyrimidine-5-carbaldehyde; 4-[4-(3-Isopropyl-[1,2,4]oxadiazol-5-yl)-piperidin-1-yl]-6-(4-[1,2,3]thiadiazol-4-yl-phenoxy)-pyrimidine-5-carboxylic acid; [4-[4-(3-Isopropyl-[1,2,4]oxadiazol-5-yl)-piperidin-1-yl]-6-(4-[1,2,3]thiadiazol-4-yl-phenoxy)-pyrimidin-5-yl]-methanol; [4-[4-(3-Isopropyl-[1,2,4]oxadiazol-5-yl)-piperidin-1-yl]-6-(4-[1,2,3]thiadiazol-4-yl-phenoxy)-pyrimidin-5-ylmethyl]-dimethyl-amine; 4-[4-(3-Isopropyl-[1,2,4]oxadiazol-5-yl)-piperidin-1-yl]-6-(4-methylsulfanyl-phenylamino)-pyrimidine-5-carbonitrile; 4-[4-(3-Isopropyl-[1,2,4]oxadiazol-5-yl)-piperidin-1-yl]-6-(4-methanesulfinyl-phenylamino)-pyrimidine-5-carbonitrile; (4-Methanesulfonyl-phenyl)-{5-nitro-6-[4-(4-trifluoromethoxy-phenoxy)-piperidin-1-yl]-pyrimidin-4-yl}-amine; 4-[4-(3-Isopropyl-[1,2,4]oxadiazol-5-yl)-piperidin-1-yl]-6-(4-methanesulfonyl-phenylamino)-pyrimidine-5-carbonitrile; 1-{1-[6-(2-Fluoro-4-methanesulfonyl-phenylamino)-5-nitro-pyrimidin-4-yl]-piperidin-4-yl}-hexan-1-one; 1-{1-[6-(4-Methanesulfonyl-phenylamino)-5-nitro-pyrimidin-4-yl]-piperidin-4-yl}-hexan-1-one; {6-[4-(3-tert-Butyl-[1,2,4]oxadiazol-5-yl)-piperidin-1-yl]-5-nitro-pyrimidin-4-yl}-(2-fluoro-4-methanesulfonyl-phenyl)-amine; {6-[4-(3-tert-Butyl-[1,2,4]oxadiazol-5-yl)-piperidin-1-yl]-5-nitro-pyrimidin-4-yl}-(4-methanesulfonyl-phenyl)-amine; [6-(4-Benzofuran-2-yl-piperidin-1-yl)-5-nitro-pyrimidin-4-yl]-(4-methanesulfonyl-phenyl)-amine and 5-Nitro-4-(5-phenyl-[1,3,4]oxadiazol-2-ylsulfanyl)-6-[4-(pyridin-2-ylsulfanyl)-piperidin-1-yl]-pyrimidine.

Examples of GPR119 agonists are described in International Application No. PCT/US2004/005555 (published as WO 04/076413), the disclosure of which is herein incorporated by reference in its entirety. Disclosed in International Application No. PCT/US2004/005555 as a GPR119 agonist is a compound of Formula (II):

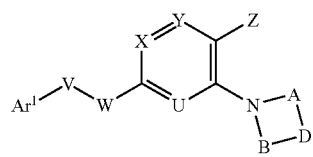

(II)

wherein:
A and B are independently $C_{1-3}$ alkylene optionally substituted with 1 to 4 methyl groups;
U is N or $CR_1$;
D is O, S, S(O), S(O)$_2$, $CR_2R_3$ or $NR_2$;
V is selected from the group consisting of $C_{1-3}$ alkylene, ethynylene and $C_{1-2}$ heteroalkylene optionally substituted with 1 to 4 substituents selected from the group consisting of $C_{1-3}$ alkyl, $C_{1-4}$ alkoxy, carboxy, cyano, $C_{1-3}$ haloalkyl and halogen; or V is absent;
W is —S(O)$_2$NR$_4$—, —NR$_4$—, —O—, —S—, —S(O)$_2$—; or W is absent;
X is N or $CR_5$;
Y is N or $CR_6$;
Z is selected from the group consisting of H, $C_{1-5}$ acyl, $C_{1-5}$ acyloxy, $C_{1-4}$ alkoxy, $C_{1-6}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{4-8}$ diacylamino, $C_{1-4}$ dialkylcarboxamide, $C_{1-4}$ dialkylthiocarboxamide, $C_{2-6}$ dialkylsulfonamide, $C_{1-4}$ dialkylsulfonylamino, formyl, $C_{1-4}$ haloalkoxy, $C_{1-4}$ haloalkyl, $C_{1-4}$ haloalkylcarboxamide, $C_{1-4}$ haloalkylsulfinyl, $C_{1-4}$ haloalkylsulfonyl, $C_{1-4}$ haloalkylthio, halogen, aryl, heteroaryl, hydroxyl, hydroxylamino, nitro and tetrazolyl; or
Z is a group of Formula (IIA):

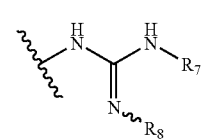

(IIA)

wherein:
$R_7$ is H, $C_{1-6}$ alkyl or $C_{3-6}$ cycloalkyl; and
$R_8$ is H, nitro or cyano;
$Ar_1$ is aryl or heteroaryl optionally substituted with $R_9$, $R_{10}$, $R_{11}$, $R_{12}$ and $R_{13}$;
$R_1$, $R_5$ and $R_6$ are independently selected from the group consisting of H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-6}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro;
$R_2$ is selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, cyano, $C_{3-6}$-cycloalkyl, $C_{2-6}$ dialkylcarboxamide, $C_{1-4}$ haloalkoxy, $C_{1-4}$ haloalkyl, halogen, heteroaryl, hydroxyl and phenyl; and wherein $C_{1-8}$ alkyl, heteroaryl and phenyl are optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; or $R_2$ is —$Ar_2$—$Ar_3$ wherein $Ar_2$ and $Ar_3$ are independently aryl or heteroaryl optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, cyano, $C_{3-6}$-cycloalkyl, $C_{2-6}$ dialkylcarboxamide, $C_{1-4}$ haloalkoxy, $C_{1-4}$ haloalkyl, halogen, hydroxyl and nitro; or $R_2$ is a group of Formula (IIB):

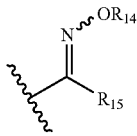

(IIB)

wherein:
$R_{14}$ is $C_{1-8}$ alkyl or $C_{3-6}$ cycloalkyl; and $R_{15}$ is F, Cl, Br or CN; or $R_2$ is a group of Formula (IIC):

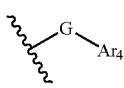

(IIC)

wherein:
G is C=O, $CR_{16}R_{17}$, O, S, S(O), S(O)$_2$; where $R_{16}$ and $R_{17}$ are independently H or $C_{1-8}$ alkyl; and
$Ar_4$ is phenyl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, hydroxyl, hydroxylamino and nitro;

$R_3$ is H, $C_{1-8}$ alkyl, $C_{1-4}$ alkoxy or hydroxyl;

$R_4$ is H or $C_{1-8}$ alkyl;

$R_9$ is selected from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, arylsulfonyl, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclicsulfonyl, heteroaryl, hydroxyl, nitro, $C_{4-7}$ oxo-cycloalkyl, phenoxy, phenyl, sulfonamide and sulfonic acid, and wherein $C_{1-5}$ acyl, $C_{1-4}$ alkoxy, $C_{1-8}$ alkyl, $C_{1-4}$ alkylsulfonamide, alkylsulfonyl, arylsulfonyl, heteroaryl, phenoxy and phenyl are optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro and phenyl; or $R_9$ is a group of Formula (IID):

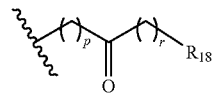

(IID)

wherein:
"p" and "r" are independently 0, 1, 2 or 3; and
$R_{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-6}$ cycloalkyl, $C_{2-6}$ dialkylcarboxamide, halogen, heteroaryl or phenyl, and wherein the heteroaryl or phenyl optionally substituted with 1 to 5 substituents selected independently from the group consisting of $C_{1-4}$ alkoxy, $C_{1-8}$ alkyl, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl; and $R_{10}$-$R_{13}$ are independently selected form the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro; or two adjacent $R_{10}$-$R_{11}$ groups form a 5, 6 or 7 membered cycloalkyl, cycloalkenyl or heterocyclic group with $Ar_1$ wherein the 5, 6 or 7 membered group is optionally substituted with halogen.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/US2004/005555 include the following compounds according to Formula (II) (referred to herein as Group B1): 6'-[4-(2-Methoxycarbonyl-acetyl)-phenoxy]-3'-nitro-3,4,5,6-tetrahydro-2H-[1,2']bipyridinyl-4-carboxyli c acid ethyl ester; 1-[4-(4-Acetyl-3'-nitro-3,4,5,6-tetrahydro-2H-[1,2']bipyridinyl-6'-yloxy)-phenyl]ethanone; 6'-[4-(4-Hydroxy-benzenesulfonyl)-phenoxy]-3'-nitro-3,4, 5,6-tetrahydro-2H-[1,2']bipyridinyl-4-carboxylic acid ethyl ester; 6'-(4-Imidazol-1-yl-phenoxy)-3'-nitro-3,4,5,6-tetrahydro-2H-[1,2']bipyridinyl-4-carboxylic acid ethyl ester; 6'-(4-

Benzoyl-phenoxy)-3'-nitro-3,4,5,6-tetrahydro-2H-[1,2']bipyridinyl-4-carboxylic acid ethyl ester; 6'-[4-(2-Methoxyethyl)-phenoxy]-3'-nitro-3,4,5,6-tetrahydro-2H-[1,2']bipyridinyl-4-carboxylic acid ethyl ester; 6'-(4-Cyclopentyl-phenoxy)-3'-nitro-3,4,5,6-tetrahydro-2H-[1,2']bipyridinyl-4-carboxylic acid ethyl ester; 6'-(4'-Cyano-biphenyl-4-yloxy)-3'-nitro-3,4,5,6-tetrahydro-2H-[1,2']bipyridinyl-4-carboxylic acid ethyl ester; 3'-Nitro-6'-(4-sulfo-phenoxy)-3,4,5,6-tetrahydro-2H-[1,2']bipyridinyl-4-carboxylic acid ethyl ester; 3'-Nitro-6'-(4-pyrrol-1-yl-phenoxy)-3,4,5,6-tetrahydro-2H-[1,2']bipyridinyl-4-carboxylic acid ethyl ester; 6'-(4-Carbamoyl-phenoxy)-3'-nitro-3,4,5,6-tetrahydro-2H-[1,2]bipyridinyl-4-carboxylic acid ethyl ester; 3'-Nitro-6'-(4-[1,2,4]triazol-1-yl-phenoxy)-3,4,5,6-tetrahydro-2H-[1,2']bipyridinyl-4-carboxylic acid ethyl ester; 6'-(2-Amino-4-ethanesulfonyl-phenoxy)-3'-nitro-3,4,5,6-tetrahydro-2H-[1,2]bipyridinyl-4-carboxylic acid ethyl ester; 3'-Nitro-6'-[4-(4-oxo-cyclohexyl)-phenoxy]-3,4,5,6-tetrahydro-2H-[1,2']bipyridinyl-4-carboxylic acid ethyl ester; 6'-(4'-Methoxy-biphenyl-4-yloxy)-3'-nitro-3,4,5,6-tetrahydro-2H-[1,2']bipyridinyl-4-carboxylic acid ethyl ester; 3'-Nitro-6'-(4-[1,2,3]thiadiazol-4-yl-phenoxy)-3,4,5,6-tetrahydro-2H-[1,2']bipyridinyl-4-carboxylic acid ethyl ester; 6'-[4-(1,3-Dioxo-1,3-dihydro-isoindol-2-yl)-phenoxy]-3'-nitro-3,4,5,6-tetrahydro-2H-[1,2']bipyridinyl-4-carboxylic acid ethyl ester; 6'-[4-(2,5-Dioxo-imidazolidin-4-yl)-phenoxy]-3'-nitro-3,4,5,6-tetrahydro-2H-[1,2']bipyridinyl-4-carboxylic acid ethyl ester; 3'-Nitro-6'-[4-(3-oxo-butyl)-phenoxy]-3,4,5,6-tetrahydro-2H-[1,2']bipyridinyl-4-carboxylic acid ethyl ester; 3-[4-(3'-Nitro-4-propyl-3,4,5,6-tetrahydro-2H-[1,2']bipyridinyl-6'-yloxy)-phenyl]-3-oxo-propionic acid methyl ester; 4-[4-(3'-Nitro-4-propyl-3,4,5,6-tetrahydro-2H-[1,2']bipyridinyl-6'-yloxy)-phenyl]-butan-2-one; 4-{7-[3'-Nitro-4-(pyridin-2-ylsulfanyl)-3,4,5,6-tetrahydro-2H-[1,2']bipyridinyl-6'-yloxy]-phenyl}-butan-2-one; and 3'-Nitro-4-(pyridin-2-ylsulfanyl)-6'-(4-[1,2,4]triazol-1-yl-phenoxy)-3,4,5,6-tetrahydro-2H-[1,2']bipyridinyl.

Specific examples of GPR119 agonists disclosed in International Application No. PCT/US2004/005555 include the following compounds according to Formula (II) (referred to herein as Group B2): 1-[5-(4-Benzoyl-phenoxy)-2-nitro-phenyl]-piperidine-4-carboxylic acid ethyl ester; 1-{5-[4-(2-Methoxycarbonyl-acetyl)-phenoxy]-2-nitro-phenyl}-piperidine-4-carboxylic acid ethyl ester; 1-[5-(2-Amino-4-ethanesulfonyl-phenoxy)-2-nitro-phenyl]piperidine-4-carboxylic acid ethyl ester; 1-{2-Nitro-5-[4-(3-oxo-butyl)-phenoxy]-phenyl}-piperidine-4-carboxylic acid ethyl ester; 4-{4-[4-Nitro-3-(4-propyl-piperidin-1-yl)-phenoxy]-phenyl}-butan-2-one; 1-{4-[4-Nitro-3-(4-propyl-piperidin-1-yl)-phenoxy]-phenyl}-ethanone; 3-{4-[4-Nitro-3-(4-propyl-piperidin-1-yl)-phenoxy]-phenyl}-3-oxo-propionic acid methyl ester; 5-Ethanesulfonyl-2-[4-nitro-3-(4-propyl-piperidin-1-yl)-phenoxy]-phenylamine; {4-[4-Nitro-3-(4-propyl-piperidin-1-yl)-phenoxy]-phenyl}-phenyl-methanone; 1-{4-Nitro-3-[4-(3-oxo-butyl)-phenoxy]-phenyl}-piperidine-4-carboxylic acid ethyl ester; 4-{4-[2-Nitro-5-(4-propyl-piperidin-1-yl)-phenoxy]-phenyl}-butan-2-one; 1-[3-(4-Benzoyl-phenoxy)-4-nitro-phenyl]-piperidine-4-carboxylic acid ethyl ester; {4-[2-Nitro-5-(4-propyl-piperidin-1-yl)-phenoxy]-phenyl}-phenyl-methanone; 1-{5-[4-(2-Carboxy-ethyl)-phenoxy]-2-nitro-phenyl}-piperidine-4-carboxylic acid ethyl ester; 1-{5-[4-(2-Carboxy-2-oxo-ethyl)-phenoxy]-2-nitro-phenyl}-piperidine-4-carboxylic acid ethyl ester; 1-[2-Nitro-5-(4-vinyl-phenoxy)-phenyl]-piperidine-4-carboxylic acid ethyl ester; 3-{4-[4-Nitro-3-(4-propyl-piperidin-1-yl)-phenoxy]-phenyl}-propionic acid; 3-{4-[4-Nitro-3-(4-propyl-piperidin-1-yl)-phenoxy]-phenyl}-2-oxo-propionic acid; 1-[2-Nitro-5-(4-vinyl-phenoxy)-phenyl]-4-propyl-piperidine; 1-{4-[4-Nitro-3-(4-propyl-piperidin-1-yl)-phenoxy]-phenyl}-butan-1-one; 1-{4-[4-Nitro-3-(4-propyl-piperidin-1-yl)-phenoxy]-phenyl}-pentan-1-one; 1-{4-[4-Nitro-3-(4-propyl-piperidin-1-yl)-phenoxy]-phenyl}-hexan-1-one; 4-{4-[3-(4-Methoxymethyl-piperidin-1-yl)-4-nitro-phenoxy]-phenyl}-butan-2-one; 1-{4-[3-(4-Methoxymethyl-piperidin-1-yl)-4-nitro-phenoxy]-phenyl}-ethanone; {4-[3-(4-Methoxymethyl-piperidin-1-yl)-4-nitro-phenoxy]-phenyl}-phenyl-methanone; 2-(3-Methyl-[1,2,4]oxadiazol-5-yl)-1-{4-[4-nitro-3-(4-propyl-piperidin-1-yl)-phenoxy]-phenyl}-ethanone; 4-(4-{3-[4-(3-Methyl-[1,2,4]oxadiazol-5-yl)-piperidin-1-yl]-4-nitro-phenoxy}-phenyl)-butan-2-one; 4-(4-{4-Nitro-3-[4-(pyridin-2-ylsulfanyl)-piperidin-1-yl]-phenoxy}-phenyl)-butan-2-one; 2-{1-[2-Nitro-5-(4-[1,2,4]triazol-1-yl-phenoxy)-phenyl]-piperidin-4-ylsulfanyl}-pyridine; 2-Methyl-5-{4-[4-nitro-3-(4-propyl-piperidin-1-yl)-phenoxy]-phenyl}-2H-pyrazol-3-ol; 2-[4-Nitro-3-(4-propyl-piperidin-1-yl)-phenoxy]-5-trifluoromethyl-pyridine; 5-Bromo-2-[4-nitro-3-(4-propyl-piperidin-1-yl)-phenoxy]-pyridine; 1-(4-{4-Nitro-3-[4-(pyridin-2-ylsulfanyl)-piperidin-1-yl]-phenoxy}-phenyl)-ethanone; 2-{1-[5-(4-Methanesulfonyl-phenoxy)-2-nitro-phenyl]-piperidin-4-ylsulfanyl}-pyridine; 1-{5-[4-(5-Methyl-[1,3,4]oxadiazol-2-yl)-phenoxy]-2-nitro-phenyl}-4-propyl-piperidine; 1-{5-[3-(3-Methyl-[1,2,4]oxadiazol-5-yl)-phenoxy]-2-nitro-phenyl}-4-propyl-piperidine.

Specific examples of GPR119 agonists disclosed in International Application No. PCT/US2004/005555 include the following compound according to Formula (II) (referred to herein as Group B3): 5-Bromo-1-[4-nitro-3-(4-propyl-piperidin-1-yl)-phenyl]-1H-pyridin-2-one.

Specific examples of GPR119 agonists disclosed in International Application No. PCT/US2004/005555 include the following compounds according to Formula (II) (referred to herein as Group B4): 6'-Benzenesulfonylamino-3'-nitro-3,4,5,6-tetrahydro-2H-[1,2']bipyridinyl-4-carboxylic acid ethyl ester; 6'-(Benzenesulfonyl-methyl-amino)-3'-nitro-3,4,5,6-tetrahydro-2H-[1,2']bipyridinyl-4-carboxylic acid ethyl ester; 6'-(Benzenesulfonyl-butyl-amino)-3'-nitro-3,4,5,6-tetrahydro-2H-[1,2']bipyridinyl-4-carboxylic acid ethyl ester; 6'-(5-Ethanesulfonyl-2-hydroxy-phenylamino)-3'-nitro-3,4,5,6-tetrahydro-2H-[1,2']bipyridinyl-4-carboxylic acid ethyl ester; 6'-(2-Bromo-4-trifluoromethyl-benzenesulfonylamino)-3'-nitro-3,4,5,6-tetrahydro-2H-[1,2']bipyridinyl-4-carboxylic acid ethyl ester; {4-[3'-Nitro-4-(pyridin-2-ylsulfanyl)-3,4,5,6-tetrahydro-2H-[1,2']bipyridinyl-6'-ylamino]-phenyl}-phenyl-methanone and [3'-Nitro-4-(pyridin-2-ylsulfanyl)-3,4,5,6-tetrahydro-2H-[1,2']bipyridinyl-6'-yl]-(4-[1,2,4]triazol-1-yl-phenyl)-amine.

Specific examples of GPR119 agonists disclosed in International Application No. PCT/US2004/005555 include the following compound according to Formula (II) (referred to herein as Group B5): 1-[5-(4-Benzoyl-phenylamino)-2-nitro-phenyl]-piperidine-4-carboxylic acid ethyl ester and {4-[4-Nitro-3-(4-propyl-piperidin-1-yl)-phenylamino]-phenyl}-phenyl-methanone.

Examples of GPR119 agonists are described in International Application No. PCT/US2004/022327 (published as WO 05/007647), the disclosure of which is herein incorporated by reference in its entirety. Disclosed in International Application No. PCT/US2004/022327 as a GPR119 agonist is a compound of Formula (III):

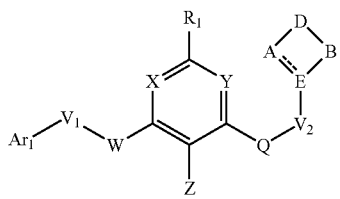
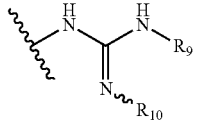

(III)

wherein:

A and B are each independently $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl and halogen;

D is O, S, S(O), S(O)$_2$, CR$_2$R$_3$ or N—R$_2$;

E is N, C or CR$_4$;

⁓ is a single bond when E is N or CR$_4$, or a double bond when E is C;

V$_1$ is selected from the group consisting of $C_{1-3}$ alkylene, ethynylene and $C_{1-2}$ heteroalkylene optionally substituted with 1 to 4 substituents selected from the group consisting of $C_{1-3}$ alkyl, $C_{1-4}$ alkoxy, carboxy, cyano, $C_{1-3}$ haloalkyl and halogen; or V$_1$ is a bond;

V$_2$ is $C_{3-6}$ cycloalkylene or $C_{1-3}$ alkylene wherein each are optionally substituted with 1 to 4 substituents selected from the group consisting of $C_{1-3}$ alkyl, $C_{1-4}$ alkoxy, carboxy, cyano, $C_{1-3}$ haloalkyl and halogen; or V$_2$ is a bond;

W is NR$_5$, O, S, S(O) or S(O)$_2$; or W is absent;

Q is NR$_8$, O, S, S(O) or S(O)$_2$;

X is N or CR$_7$;

Y is N or CR$_8$;

Z is selected from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, $C_{1-2}$ alkylamino, $C_{2-4}$ dialkylamino, carbamimidoyl, carbo-$C_{1-6}$-alkoxy, carboxamide, carboxy, cyano, $C_{3-7}$ cycloalkyl, $C_{4-8}$ diacylamino, $C_{2-6}$ dialkylcarboxamide, $C_{2-6}$ dialkylthiocarboxamide, $C_{2-6}$ dialkylsulfonamide, $C_{2-6}$ dialkylsulfonylamino, formyl, $C_{1-4}$ haloalkoxy, $C_{1-4}$ haloalkyl, $C_{1-4}$ haloalkylcarboxamide, $C_{1-4}$ haloalkylsulfinyl, $C_{1-4}$ haloalkylsulfonyl, $C_{1-4}$ haloalkylthio, halogen, aryl, heterocyclic, heteroaryl, hydroxyl, hydroxycarbamimidoyl, hydroxylamino, nitro and tetrazolyl, wherein $C_{1-8}$ alkyl, $C_{3-7}$ cycloalkyl, and heterocyclic are each optionally substituted with 1, 2, 3 or 4 groups selected from the group consisting of $C_{1-5}$ acyl, $C_{1-5}$ acyloxy, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-2}$ alkylamino, $C_{2-4}$ dialkylamino, carbo-$C_{1-6}$-alkoxy, carboxamide, carboxy, cyano, formyl, $C_{1-4}$ haloalkoxy, $C_{1-4}$ haloalkylsulfinyl, $C_{1-4}$ haloalkylsulfonyl, $C_{1-4}$ haloalkylthio, halogen, hydroxyl, hydroxylamino and nitro, and wherein said $C_{1-7}$ alkyl is optionally substituted with amino; or Z is a group of Formula (IIIA):

(IIIA)

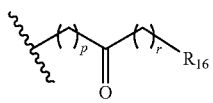

wherein:

R$_9$ is H, $C_{1-8}$ alkyl or $C_{3-7}$ cycloalkyl; and

R$_{10}$ is H, nitro or nitrile;

Ar$_1$ is aryl or heteroaryl each optionally substituted with R$_{11}$, R$_{12}$, R$_{13}$, R$_{14}$, and R$_{15}$; wherein R$_{11}$ is selected from the group consisting of $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, and thiol, and wherein $C_{1-5}$ acyl, $C_{1-6}$ acylsulfonamide, $C_{1-4}$ alkoxy, $C_{1-8}$ alkyl, $C_{1-4}$ alkylamino, $C_{1-6}$ alkylsulfonamide, $C_{1-4}$ alkylsulfonyl, $C_{1-4}$ alkylthio, arylsulfonyl, carbamimidoyl, $C_{2-6}$ dialkylamino, heterocyclic, heterocyclic-carbonyl, heteroaryl, phenoxy and phenyl are optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro, phenyl, and phosphonooxy, wherein said $C_{1-7}$ alkyl and $C_{1-4}$ alkylcarboxamide are each optionally substituted with 1 to 5 substituents selected from the group consisting of $C_{1-4}$ alkoxy and hydroxy; or R$_{11}$ is a group of Formula (IIIB):

(IIIB)

wherein:

"p" and "r" are each independently 0, 1, 2 or 3; and R$_{16}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein the heteroaryl or phenyl optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl; and $R_{12}$, $R_{13}$, $R_{14}$, and $R_{15}$ are each independently selected form the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro; or two adjacent groups selected from the group consisting of $R_{12}$, $R_{13}$, $R_{14}$ and $R_{15}$ together with the atoms to which they are attached form a 5-, 6- or 7-membered cycloalkyl, cycloalkenyl or heterocyclic group fused with $Ar_1$, wherein the 5-, 6- or 7-membered group is optionally substituted with halogen;

$R_1$, $R_7$ and $R_8$ are each independently selected from the group consisting of H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-7}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio and hydroxyl;

$R_2$ is selected from the group consisting of $C_{1-8}$ alkyl, amino, aryl, carboxamide, carboxy, cyano, $C_{3-6}$-cycloalkyl, $C_{1-4}$ haloalkoxy, $C_{1-4}$ haloalkyl, halogen, heteroaryl and hydroxyl; and wherein $C_{1-8}$ alkyl, aryl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; or $R_2$ is —$Ar_2$—$Ar_3$ wherein $Ar_2$ and $Ar_3$ are each independently aryl or heteroaryl optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, $C_{1-4}$ alkylamino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{1-4}$ haloalkoxy, $C_{1-4}$ haloalkyl, halogen, hydroxyl and nitro; or $R_2$ is a group of Formula (IIIC):

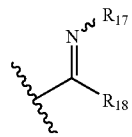

(IIIC)

wherein:

$R_{17}$ is H, $C_{1-8}$ alkyl, $C_{3-7}$ cycloalkyl, aryl, heteroaryl or $OR_{19}$; and $R_{18}$ is F, Cl, Br, CN or $NR_{20}R_{21}$; where $R_{19}$ is H, $C_{1-8}$ alkyl or $C_{3-7}$ cycloalkyl, and $R_{20}$ and $R_{21}$ are each independently H, $C_{1-8}$ alkyl, $C_{3-7}$ cycloalkyl, aryl or heteroaryl; or $R_2$ is a group of Formula (IIID):

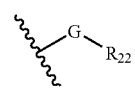

(IIID)

wherein:

G is:

i) —C(O)—, —C(O)$NR_{23}$—, —C(O)O—, —OC(O)$NR_{23}$—, —$NR_{23}$C(O)O—, —OC(O)—, —C(S)—, —C(S)$NR_{23}$—, —C(S)O—, —OC(S)—, —$CR_{23}R_{24}$—, —O—, —S—, —S(O)— or —S(O)$_2$— when D is $CR_2R_3$, or ii) —$CR_{23}R_{24}$C(O)—, —C(O)—, —$CR_{23}R_{24}$C(O)$NR_{25}$—, —C(O)$NR_{23}$—, —C(O)O—, —C(S)—, —C(S)$NR_{23}$—, —C(S)O—, —$CR_{23}R_{24}$—, —S(O)$_2$—, or a bond when D is $NR_2$, wherein $R_{23}$, $R_{24}$ and $R_{25}$ are each independently H or $C_{1-8}$ alkyl; and $R_{22}$ is H, $C_{1-8}$ alkyl, $C_{2-6}$ alkynyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-7}$ alkyl, heteroaryl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, and nitro;

$R_3$ is H, $C_{1-8}$ alkyl, $C_{1-4}$ alkoxy or hydroxyl; and $R_4$, $R_5$ and $R_6$ are each independently H, $C_{1-8}$ alkyl or $C_{3-7}$ cycloalkyl, wherein said $C_{1-8}$ alkyl is optionally substituted with $C_{1-4}$ alkoxy, $C_{3-7}$ cycloalkyl, or heteroaryl.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/US2004/022327 include the following compounds according to Formula (III) (referred to herein as Group C1): 3-[6-(4-Methanesulfonyl-phenylamino)-5-nitro-pyrimidin-4-yloxymethyl]-pyrrolidine-1-carboxylic acid tert-butyl ester; 4-[5-Cyano-6-(6-methylsulfanyl-pyridin-3-ylamino)-pyrimidin-4-yloxy]-piperidine-1-carboxylic acid tert-butyl ester; 4-[5-Cyano-6-(6-methanesulfonyl-pyridin-3-ylamino)-pyrimidin-4-yloxy]-piperidine-1-carboxylic acid tert-butyl ester; [6-(1-Hexyl-piperidin-4-yloxy)-5-nitro-pyrimidin-4-yl]-(4-methanesulfonyl-phenyl)-amine; [6-(1-Cyclopropylmethyl-piperidin-4-yloxy)-5-nitro-pyrimidin-4-yl]-(4-methanesulfonyl-phenyl)-amine; 4-[6-(4-Methanesulfonyl-phenylamino)-5-nitro-pyrimidin-4-yloxy]-piperidine-1-carboxylic acid isopropyl ester; 4-[6-(4-Methanesulfonyl-phenylamino)-5-nitro-pyrimidin-4-yloxy]-piperidine-1-carboxylic acid 2-isopropyl-5-methyl-cyclohexyl ester; {4-[6-(4-Methanesulfonyl-phenylamino)-5-nitro-pyrimidin-4-yloxy]-piperidin-1-yl}-pyridin-3-yl-methanone; (2-Chloro-pyridin-3-yl)-{4-[6-(4-methanesulfonyl-phenylamino)-5-nitro-pyrimidin-4-yloxy]-piperidin-1-yl}-methanone; {4-[6-(4-Methanesulfonyl-phenylamino)-5-nitro-pyrimidin-4-yloxy]-piperidin-1-yl}-pyridin-2-yl-methanone; (4-Methanesulfonyl-phenyl)-[6-(1-methanesulfonyl-piperidin-4-yloxy)-5-nitro-pyrimidin-4-yl]-amine; (4-Methanesulfonyl-phenyl)-{5-nitro-6-[1-(propane-1-sulfonyl)-piperidin-4-yloxy]-pyrimidin-4-yl}-amine; {6-[1-(Butane-1-sulfonyl)-piperidin-4-yloxy]-5-nitro-pyrimidin-4-yl}-(4-methanesulfonyl-phenyl)-amine; (4-Methanesulfonyl-phenyl)-{5-nitro-6-[1-(thiophene-2-sulfonyl)-piperidin-4-yloxy]-pyrimidin-4-yl}-amine; (4-Methanesulfonyl-phenyl)-{6-[1-(1-methyl-1H-imidazole-4-sulfonyl)-piperidin-4-yloxy]-5-nitro-pyrimidin-4-yl}-amine; {6-[1-(2,4-Dimethyl-thiazole-5-sulfonyl)-piperidin-4-yloxy]-5-nitro-pyrimidin-4-yl}-(4-methanesulfonyl-phenyl)-amine; 4-[5-Cyano-6-(3-fluoro-4-methanesulfonyl-phenylamino)-pyrimidin-4-yloxy]-piperidine-1-carboxylic acid tert-butyl ester; 4-[6-(2-Fluoro-4-methanesulfonyl-phenylamino)-5-nitro-pyrimidin-4-yloxy]-piperidine-1-carboxylic acid tert-butyl ester; 4-[5-Cyano-6-(4-methanesulfonyl-phenylamino)-pyrimidin-4-yloxy]-piperidine-1-carboxylic acid tert-butyl ester; 4-[6-(6-Methanesulfonyl-pyridin-3-ylamino)-5-nitro-pyrimidin-4-yloxy]-piperidine-1-carboxylic acid tert-butyl ester; 4-[5-Acetyl-6-(6-methanesulfonyl-pyridin-3-ylamino)-pyrimidin-4-yloxy]-piperidine-1-carboxylic acid tert-butyl ester; 4-[5-Amino-6-(2-fluoro-4-methanesulfonyl-phenylamino)-pyrimidin-4-yloxy]-piperidine-1-carboxylic acid tert-butyl ester; 4-[5-Cyano-6-(4-methanesulfonyl-phenylamino)-pyrimidin-4-yloxy]-piperidine-1-carboxylic acid isopropyl ester; 4-[5-Cyano-6-(4-methanesulfonyl-phenylamino)-pyrimidin-4-yloxy]-piperidine-1-carboxylic acid ethyl ester; 4-[5-Cyano-6-(4-methanesulfonyl-phenylamino)-pyrimidin-4-yloxy]-piperidine-1-carboxylic acid isobutyl ester; 4-(4-Methanesulfonyl-phenylamino)-6-[1-(tetrahydro-furan-2-carbonyl)-piperidin-4-yloxy]-pyrimidine-5-carbonitrile; 4-[1-(3,3-Dimethyl-2-oxo-butyl)-piperidin-4-yloxy]-6-(4-methanesulfonyl-phenylamino)-pyrimidine-5-carbonitrile; 4-(4-Methanesulfonyl-phenylamino)-6-[1-(pyridine-3-carbonyl)-piperidin-4-yloxy]-pyrimidine-5-carbonitrile; 4-(1-Formyl-piperidin-4-yloxy)-6-(4-methanesulfonyl-phenylamino)-pyrimidine-5-carbonitrile and 4-(4-Methanesulfonyl-phenylamino)-6-[1-(pyridine-2-carbonyl)-piperidin-4-yloxy]-pyrimidine-5-carbonitrile.

Specific examples of GPR119 agonists disclosed in International Application No. PCT/US2004/022327 include the following compounds according to Formula (III) (referred to herein as Group C2): 4-[6-(4-Methanesulfonyl-phenylamino)-5-nitro-pyrimidin-4-yloxy]-piperidine-1-carboxylic acid tert-butyl ester; (4-Methanesulfonyl-phenyl)-[5-nitro-6-(piperidin-4-yloxy)-pyrimidin-4-yl]-amine; 1-{4-[6-(4-Methanesulfonyl-phenylamino)-5-nitro-pyrimidin-4-yloxy]-piperidin-1-yl}-3,3-dimethyl-butan-1-one; (4-Methanesulfonyl-phenyl)-[5-nitro-6-(1-pyridin-2-ylmethyl-piperidin-4-yloxy)-pyrimidin-4-yl]-amine; (4-Methanesulfonyl-phenyl)-[5-nitro-6-(1-pyridin-3-ylmethyl-piperidin-4-yloxy)-pyrimidin-4-yl]-amine; {6-[1-(3,3-Dimethyl-butyl)-piperidin-4-yloxy]-5-nitro-pyrimidin-4-yl}-(4-methanesulfonyl-phenyl)-amine; (4-Methanesulfonyl-phenyl)-{6-[1-(3-methyl-butyl)-piperidin-4-yloxy]-5-nitro-pyrimidin-4-yl}-amine; (4-Methanesulfonyl-phenyl)-[5-nitro-6-(3,4,5,6-tetrahydro-2H-[1,2']bipyridinyl-4-yloxy)-pyrimidin-4-yl]-amine; 4-[6-(4-Methanesulfonyl-phenylamino)-5-nitro-pyrimidin-4-yloxy]-piperidine-1-carboxylic acid ethyl ester; 1-{4-[6-(4-Methanesulfonyl-phenylamino)-5-nitro-pyrimidin-4-yloxy]-piperidin-1-yl}-3,3-dimethyl-butan-2-one; {6-[1-(2-Ethoxy-ethyl)-piperidin-4-yloxy]-5-nitro-pyrimidin-4-yl}-(4-methanesulfonyl-phenyl)-amine; 4-[6-(4-Methanesulfonyl-phenylamino)-5-nitro-pyrimidin-4-yloxymethyl]-piperidine-1-carboxylic acid tert-butyl ester; 4-{2-[6-(4-Methanesulfonyl-phenylamino)-5-nitro-pyrimidin-4-yloxy]-ethyl}-piperidine-1-carboxylic acid tert-butyl ester; 3-[6-(4-Methanesulfonyl-phenylamino)-5-nitro-pyrimidin-4-yloxy]-pyrrolidine-1-carboxylic acid tert-butyl ester and 3-[6-(4-Methanesulfonyl-phenylamino)-5-nitro-pyrimidin-4-yloxymethyl]-pyrrolidine-1-carboxylic acid tert-butyl ester.

Specific examples of GPR119 agonists disclosed in International Application No. PCT/US2004/022327 include the following compounds according to Formula (III) (referred to herein as Group C3): 4-[6-(4-Methanesulfonyl-phenylamino)-5-nitro-pyrimidin-4-ylamino]-piperidine-1-carboxylic acid tert-butyl ester; N-(4-Methanesulfonyl-phenyl)-5-nitro-N'-piperidin-4-yl-pyrimidine-4,6-diamine; 1-{4-[6-(4-Methanesulfonyl-phenylamino)-5-nitro-pyrimidin-4-ylamino]-piperidin-1-yl}-ethanone and 1-{4-[6-(4-Methanesulfonyl-phenylamino)-5-nitro-pyrimidin-4-ylamino]-piperidin-1-yl}-2,2-dimethyl-propan-1-one.

Specific examples of GPR119 agonists disclosed in International Application No. PCT/US2004/022327 include the following compounds according to Formula (III) (referred to herein as Group C4): 4-[6-(4-Cyano-2-fluoro-phenylamino)-5-ethynyl-pyrimidin-4-yloxy]-piperidine-1-carboxylic acid isopropyl ester; 4-[5-Ethynyl-6-(2-fluoro-4-[1,2,4]triazol-1-yl-phenylamino)-pyrimidin-4-yloxy]-piperidine-1-carboxylic acid isopropyl ester; 4-{5-Ethynyl-6-[1-(3-isopropyl-[1,2,4]oxadiazol-5-yl)-piperidin-4-yloxy]-pyrimidin-4-ylamino}-3-fluoro-benzonitrile; {5-Ethynyl-6-[1-(3-isopropyl-[1,2,4]oxadiazol-5-yl)-piperidin-4-yloxy]-pyrimidin-4-yl}-(2-fluoro-4-methanesulfonyl-phenyl)-amine; 4-{6-[2,5-Difluoro-4-(2-methanesulfonyl-ethyl)-phenylamino]-5-methyl-pyrimidin-4-yloxy}-piperidine-1-carboxylic acid isopropyl ester; 4-{6-[2-Fluoro-4-(2-sulfamoyl-ethyl)-phenylamino]-5-methyl-pyrimidin-4-yloxy}-piperidine-1-carboxylic acid isopropyl ester; 4-{6-[6-(2-Fluoro-ethyl)-2-methyl-pyridin-3-ylamino]-5-methyl-pyrimidin-4-yloxy}-piperidine-1-carboxylic acid isopropyl ester; 4-{2-[4-Fluoro-6-(2-isopropoxy-ethyl)-pyridin-3-ylamino]-3-methyl-pyridin-4-yloxy}-piperidine-1-carboxylic acid isopropyl ester; 4-{6-[2,5-Difluoro-4-(2-[1,2,4]triazol-1-yl-ethyl)-phenylamino]-5-methyl-pyrimidin-4-yloxy}-piperidine-1-carboxylic acid isopropyl ester; 4-{5-Ethynyl-6-[2-fluoro-4-(4-methoxy-pyridin-2-yl)-phenylamino]-pyrimidin-4-yloxy}-piperidine-1-carboxylic acid isopropyl ester; 4-{6-[2-Fluoro-4-(2-propionylsulfamoyl-ethyl)-phenylamino]-5-methyl-pyrimidin-4-yloxy}-piperidine-1-carboxylic acid isopropyl ester; 4-{6-[2-Fluoro-4-(2-methanesulfonyl-ethyl)-phenylamino]-5-methyl-pyrimidin-4-yloxy}-piperidine-1-carboxylic acid isopropyl ester; and 4-{6-[2,3-Difluoro-4-(2-methanesulfonyl-ethyl)-phenylamino]-5-methyl-pyrimidin-4-yloxy}-piperidine-1-carboxylic acid isopropyl ester.

Specific examples of GPR119 agonists disclosed in International Application No. PCT/US2004/022327 include the following compounds according to Formula (III) (referred to herein as Group C5): 4-[5-Acetyl-6-(6-methanesulfonyl-pyridin-3-ylamino)-pyrimidin-4-yloxy]-piperidine-1-carboxylic acid isobutyl ester; 1-[4-(1-Benzyl-azetidin-3-yloxy)-6-(6-methanesulfonyl-pyridin-3-ylamino)-pyrimidin-5-yl]-ethanone; 4-[5-Cyano-6-(6-propylamino-pyridin-3-ylamino)-pyrimidin-4-yloxy]-piperidine-1-carboxylic acid isopropyl ester; 4-[5-Cyano-6-(2-fluoro-4-isopropylamino-phenylamino)-pyrimidin-4-yloxy]-piperidine-1-carboxylic acid isopropyl ester; 4-[5-Cyano-6-(2-fluoro-4-propylamino-phenylamino)-pyrimidin-4-yloxy]-piperidine-1-carboxylic acid isopropyl ester; 4-[5-Cyano-6-(2-fluoro-4-propoxy-phenylamino)-pyrimidin-4-yloxy]-piperidine-1-carboxylic acid isopropyl ester; 4-[5-Cyano-6-(6-propyl-pyridin-3-ylamino)-pyrimidin-4-yloxy]-piperidine-1-carboxylic acid isopropyl ester; 4-{5-Cyano-6-[4-(2-dimethylamino-ethylsulfanyl)-2-fluoro-phenylamino]-pyrimidin-4-yloxy}-piperidine-1-carboxylic acid isopropyl ester; 4-{5-Cyano-6-[4-(2-dimethylamino-ethanesulfonyl)-2-fluoro-phenylamino]-3-oxy-pyrimidin-4-yloxy}-piperidine-1-carboxylic acid isopropyl ester; 4-{5-Cyano-6-[2-fluoro-4-(4-methyl-piperazin-1-yl)-phenylamino]-pyrimidin-4-yloxy}-piperidine-1-carboxylic acid isopropyl ester; 4-{5-Cyano-6-[2-fluoro-4-(3-methyl-butylamino)-phenylamino]-pyrimidin-4-yloxy}-piperidine-1-carboxylic acid isopropyl ester; 4-[5-Cyano-6-(2-fluoro-4-morpholin-4-yl-phenylamino)pyrimidin-4-yloxy]-piperidine-1-carboxylic acid isopropyl ester; 4-{5-Cyano-6-[4-(2-dimethylamino-ethylamino)-2-fluoro-phenylamino]-pyrimidin-4-yloxy}-piperidine-1-carboxylic acid isopropyl ester; 4-[5-Cyano-6-(4-dimethylamino-2-fluoro-phenylamino)-pyrimidin-4-yloxy]-piperidine-1-carboxylic acid isopropyl ester; 4-{5-Cyano-6-[2-fluoro-4-(2-pyrrolidin-1-yl-ethylamino)-phenylamino]-pyrimidin-4-yloxy}-piperidine-1-carboxylic acid isopropyl ester; 4-[6-(2-Fluoro-4-methanesulfonyl-phenylamino)-5-methyl-pyrimidin-4-yloxy]-piperidine-1-carboxylic acid isopropyl ester; 4-{5-Cyano-6-[2-fluoro-4-(2-morpholin-4-yl-ethylamino)-phenylamino]-pyrimidin-4-yloxy}-piperidine-1-carboxylic acid isopropyl ester; 4-[6-(2-Fluoro-4-iodo-phenylamino)-5-methyl-pyrimidin-4-yloxy]-piperidine-1-carboxylic acid isopropyl ester; 4-[5-Cyano-6-(2-fluoro-4-methanesulfonyl-phenylamino)-pyrimidin-4-yloxy]-piperidine-1-carboxylic acid isopropyl ester; 4-[6-(2-Fluoro-4-morpholin-4-yl-phenylamino)-5-methyl-pyrimidin-4-yloxy]-piperidine-1-carboxylic acid isopropyl ester; 4-[6-(2,5-Difluoro-4-propoxy-phenylamino)-5-methyl-pyrimidin-4-yloxy]-piperidine-1-carboxylic acid isopropyl ester; 4-[6-(2-Fluoro-4-propylamino-phenylamino)-5-methyl-pyrimidin-4-yloxy]-piperidine-1-carboxylic acid isopropyl ester; 4-{6-[2-Fluoro-4-(2-methoxy-ethylamino)-phenylamino]-5-methyl-pyrimidin-4-yloxy}-piperidine-1-carboxylic acid isopropyl ester; 4-(6-{2-Fluoro-4-[(tetrahydro-furan-2-ylmethyl)-amino]-phenylamino}-5-methyl-pyrimidin-4-yloxy)-piperidine-1-carboxylic acid isopropyl ester; 4-{6-[2-Fluoro-4-(2-methanesulfonyl-ethylamino)-phenylamino]-5-methyl-pyrimidin-4-yloxy}-piperidine-1-carboxylic acid isopropyl ester; 4-(6-{2-Fluoro-4-[(2-methanesulfonyl-ethyl)-methyl-amino]-phenylamino}-5-methyl-pyrimidin-4-yloxy)-piperidine-1-carboxylic acid isopropyl ester; 4-[6-(4-Bromo-2,5-difluoro-phenylamino)-5-methyl-pyrimidin-4-yloxy]-piperidine-1-carboxylic acid isopropyl ester; 4-[6-(4-Cyano-2-fluoro-phenylamino)-5-methyl-pyrimidin-4-yloxy]-piperidine-1-carboxylic acid isopropyl ester; 4-[6-(4-Cyano-2,5-difluoro-phenylamino)-5-methyl-pyrimidin-4-yloxy]-piperidine-1-carboxylic acid isopropyl ester; 4-[6-(2,5-Difluoro-4-morpholin-4-yl-phenylamino)-5-methyl-pyrimidin-4-yloxy]-piperidine-1-carboxylic acid isopropyl ester; 4-[6-(6-Chloro-2-methyl-pyridin-3-ylamino)-5-methyl-pyrimidin-4-yloxy]-piperidine-1-carboxylic acid isopropyl ester; 4-[5-Methyl-6-(2-methyl-6-morpholin-4-yl-pyridin-3-ylamino)-pyrimidin-4-yloxy]-piperidine-1-carboxylic acid isopropyl ester; 4-[5-(4,5-Dihydro-1H-imidazol-2-yl)-6-(2-fluoro-4-methanesulfonyl-phenylamino)-pyrimidin-4-yloxy]-piperidine-1-carboxylic acid isopropyl ester; (2-Fluoro-4-methanesulfonyl-phenyl)-{6-[1-(3-isopropyl-[1,2,4]oxadiazol-5-yl)-piperidin-4-yloxy]-5-methyl-pyrimidin-4-yl}-amine; 4-[6-(2-Fluoro-4-propoxy-phenylamino)-5-methyl-pyrimidin-4-yloxy]-piperidine-1-carboxylic acid isopropyl ester; 4-{6-[2-Fluoro-4-(2-methanesulfonyl-ethoxy)-phenylamino]-5-methyl-pyrimidin-4-yloxy}-piperidine-1-carboxylic acid isopropyl ester; 4-{6-[2-Fluoro-4-(2-methoxy-ethoxy)-phenylamino]-5-methyl-pyrimidin-4-yloxy}-piperidine-1-carboxylic acid isopropyl ester; 4-{6-[2-Fluoro-4-(2-isopropoxy-ethoxy)-phenylamino]-5-methyl-pyrimidin-4-yloxy}-piperidine-1-carboxylic acid isopropyl ester; 4-[6-(6-Chloro-4-methyl-pyridin-3-ylamino)-5-methyl-pyrimidin-4-yloxy]-piperidine-1-carboxylic acid isopropyl ester; 4-[6-(2-Fluoro-4-methanesulfonyl-phenylamino)-5-(N-hydroxycarbamimidoyl)-pyrimidin-4-yloxy]-piperidine-1-carboxylic acid isopropyl ester; 4-[5-Carbamimidoyl-6-(2-fluoro-4-methanesulfonyl-phenylamino)-pyrimidin-4-yloxy]-piperidine-1-carboxylic acid isopropyl ester; 4-{6-[2-Fluoro-4-(tetrahydro-furan-2-ylmethoxy)-phenylamino]-5-methyl-pyrimidin-4-yloxy}-piperidine-1-carboxylic acid isopropyl ester; 4-[5-Methyl-6-(4-methyl-6-morpholin-4-yl-pyridin-3-ylamino)-pyrimidin-4-yloxy]-piperidine-1-carboxylic acid isopropyl ester; 4-{6-[6-(2-Methoxy-ethoxy)-2-methyl-pyridin-3-ylamino]-5-methyl-pyrimidin-4-yloxy}-piperidine-1-carboxylic acid isopropyl ester; 4-{6-[6-(2-Methoxy-ethoxy)-4-methyl-pyridin-3-ylamino]-5-methyl-pyrimidin-4-yloxy}-piperidine-1-carboxylic acid isopropyl ester; 4-{6-[2,5-Difluoro-4-(2-methoxy-ethoxy)-phenylamino]-5-methyl-pyrimidin-4-yloxy}-piperidine-1-carboxylic acid isopropyl ester; 4-{6-[2-Fluoro-4-(2-isopropoxy-ethylsulfamoyl)-phenylamino]-5-methyl-pyrimidin-4-yloxy}-piperidine-1-carboxylic acid isopropyl ester; 4-{6-[2,5-Difluoro-4-(N-hydroxycarbamimidoyl)-phenylamino]-5-methyl-pyrimidin-4-yloxy}-piperidine-1-carboxylic acid isopropyl ester; 4-[6-(4-Carbamoyl-2,5-difluoro-phenylamino)-5-methyl-pyrimidin-4-yloxy]-piperidine-1-carboxylic acid isopropyl ester; 4-{6-[(2-Fluoro-4-methanesulfonyl-phenyl)-(2-methoxy-ethyl)-amino]-5-methyl-pyrimidin-4-yloxy}-piperidine-1-carboxylic acid isopropyl ester; 4-[6-(4-Carbamimidoyl-2,5-difluoro-phenylamino)-5-methyl-pyrimidin-4-yloxy]-piperidine-1-carboxylic acid isopropyl ester; 4-{6-[4-(2-Ethoxy-ethoxy)-2-fluoro-phenylamino]-5-methyl-pyrimidin-4-yloxy}-piperidine-1-carboxylic acid isopropyl ester; 4-{6-[2-Fluoro-4-(tetrahydro-pyran-4-yloxy)-phenylamino]-5-methyl-pyrimidin-4- yloxy}-piperidine-1-carboxylic acid isopropyl ester; 4-{6-[2-Fluoro-4-(2-hydroxy-ethoxy)-phenylamino]-5-methyl-pyrimidin-4-yloxy}-piperidine-1-carboxylic acid isopropyl ester; 1-{4-[6-(2-Fluoro-4-methanesulfonyl-phenylamino)-5-methyl-pyrimidin-4-yloxy]-piperidin-1-yl}-butan-1-one; 1-{4-[6-(2-Fluoro-4-methanesulfonyl-phenylamino)-5-methyl-pyrimidin-4-yloxy]-piperidin-1-yl}-pentan-1-one; 1-{4-[6-(2-Fluoro-4-methanesulfonyl-phenylamino)-5-methyl-pyrimidin-4-yloxy]-piperidin-1-yl}-3-methyl-butan-1-one; 4-{6-[2-Fluoro-4-(pyridin-2-ylmethoxy)-phenylamino]-5-methyl-pyrimidin-4-yloxy}-piperidine-1-carboxylic acid isopropyl ester; 4-[2-(2-Fluoro-4-methanesulfonyl-phenylamino)-3-methyl-pyridin-4-yloxy]-piperidine-1-carboxylic acid isopropyl ester; 4-[6-(6-Chloro-4-fluoro-pyridin-3-ylamino)-5-cyano-pyrimidin-4-yloxy]-piperidine-1-carboxylic acid isopropyl ester; and 4-[5-Amino-6-(2-fluoro-4-methanesulfonyl-phenylamino)-pyrimidin-4-yloxy]-piperidine-1-carboxylic acid isopropyl ester.

Specific examples of GPR119 agonists disclosed in International Application No. PCT/US2004/022327 include the following compound according to Formula (III) (referred to herein as Group C6): 4-({[6-(2-Fluoro-4-methanesulfonyl-phenylamino)-5-methyl-pyrimidin-4-yl]-isopropyl-amino}-methyl)-piperidine-1-carboxylic acid tert-butyl ester.

Specific examples of GPR119 agonists disclosed in International Application No. PCT/US2004/022327 include the following compounds according to Formula (III) (referred to herein as Group C7): 4-(2-Fluoro-4-methanesulfonyl-phenoxy)-6-[1-(3-methoxy-propyl)-piperidin-4-yloxy]-5-methyl-pyrimidine; 1-{4-[6-(2-Fluoro-4-methanesulfonyl-phenoxy)-5-methyl-pyrimidin-4-yloxy]-piperidin-1-yl}-3-methoxy-propan-2-ol; 4-{6-[2-Fluoro-4-(5-isopropoxymethyl-[1,2,4]oxadiazol-3-yl)-phenoxy]-5-methyl-pyrimidin-4-yloxy}-piperidine-1-carboxylic acid isopropyl ester; 4-{6-[2-Fluoro-4-(5-methoxy-pyridin-2-yl)-phenoxy]-5-methyl-pyrimidin-4-yloxy}-piperidine-1-carboxylic acid isopropyl ester; 4-{6-[6-(2-Cyclopropoxy-ethylamino)-2-methyl-pyridin-3-yloxy]-5-methyl-pyrimidin-4-yloxy}-piperidine-1-carboxylic acid isopropyl ester; 4-{6-[2-Fluoro-4-(pyridine-2-carbonyl)-phenoxy]-5-methyl-pyrimidin-4-yloxy}-piperidine-1-carboxylic acid isopropyl ester; 4-[6-(2-Fluoro-4-methanesulfonyl-phenoxy)-5-methanesulfonylamino-pyrimidin-4-yloxy]-piperidine-1-carboxylic acid isopropyl ester; 4-[6-(4-Methoxy-6'-methyl-3,4,5,6-tetrahydro-2H-[1,2']bipyridinyl-5'-yloxy)-5-methyl-pyrimidin-4-yloxy]-piperidine-1-carboxylic acid isopropyl ester; 1-{4-[6-(2-Fluoro-4-methanesulfonyl-phenoxy)-5-methyl-pyrimidin-4-yloxy]-piperidin-1-yl}-2-(4-trifluoromethoxy-phenoxy)-propan-1-one; 1-{4-[6-(2-Fluoro-4-methanesulfonyl-phenoxy)-5-methyl-pyrimidin-4-yloxy]-piperidin-1-yl}-2-(4-trifluoromethoxy-phenoxy)-ethanone; N-(4-Chloro-phenyl)-2-{4-[6-(2-fluoro-4-methanesulfonyl-phenoxy)-5-methyl-pyrimidin-4-yloxy]-piperidin-1-yl}-acetamide; N-(3-Chloro-phenyl)-2-{4-[6-(2-fluoro-4-methanesulfonyl-phenoxy)-5-methyl-pyrimidin-4-yloxy]-piperidin-1-yl}-acetamide; N-(3,5-Dichloro-phenyl)-2-{4-[6-(2-fluoro-4-methanesulfonyl-phenoxy)-5-methyl-pyrimidin-4-yloxy]-piperidin-1-yl}-acetamide; 2-{4-[6-(2-Fluoro-4-methanesulfonyl-phenoxy)-5-methyl-pyrimidin-4-yloxy]-piperidin-1-yl}-N-(4-trifluoromethyl-phenyl)-acetamide; 2-{4-[6-(2-Fluoro-4-methanesulfonyl-phenoxy)-5-methyl-pyrimidin-4-yloxy]-piperidin-1-yl}-N-phenyl-acetamide; 2-{4-[6-(2-Fluoro-4-methanesulfonyl-phenoxy)-5-methyl-pyrimidin-4-yloxy]-piperidin-1-yl}-N-(4-isopropyl-phenyl)-acetamide; 2-{4-[6-(2-Fluoro-4-methanesulfonyl-phenoxy)-5-methyl-pyrimidin-4-yloxy]-piperidin-1-yl}-N-(4-methoxy-phenyl)-acetamide; 2-{4-[6-(2-Fluoro-4-methanesulfonyl-phenoxy)-5-methyl-pyrimidin-4-yloxy]-piperidin-1-yl}-N-(3-trifluoromethyl-phenyl)-acetamide; 4-{6-[2-Fluoro-4-(3-methoxy-propane-1-sulfonyl)-phenoxy]-5-methyl-pyrimidin-4-yloxy}-piperidine-1-carboxylic acid isopropyl ester; 4-{6-[6-(2-Isopropoxy-ethyl)-2-methyl-pyridin-3-yloxy]-5-methyl-pyrimidin-4-yloxy}-piperidine-1-carboxylic acid isopropyl ester; 4-{5-Methyl-6-[2-methyl-6-(2-pyridin-2-yl-ethoxy)-pyridin-3-yloxy]-pyrimidin-4-yloxy}-piperidine-1-carboxylic acid isopropyl ester; 4-{6-[2-Fluoro-4-(thiophene-2-carbonyl)-phenoxy]-5-methyl-pyrimidin-4-yloxy}-piperidine-1-carboxylic acid isopropyl ester; 4-(6-{6-[(2-Isopropoxy-ethyl)-methyl-amino]-2-methyl-pyridin-3-yloxy}-5-methyl-pyrimidin-4-yloxy)-piperidine-1-carboxylic acid isopropyl ester; 4-{6-[6-(2-Isopropoxy-ethanesulfonyl)-2-methyl-pyridin-3-yloxy]-5-methyl-pyrimidin-4-yloxy}-piperidine-1-carboxylic acid isopropyl ester; 4-{6-[6-(2-Hydroxy-ethanesulfonyl)-2-methyl-pyridin-3-yloxy]-5-methyl-pyrimidin-4-yloxy}-piperidine-1-carboxylic acid isopropyl ester; 4-[6-(6-Amino-2-methyl-pyridin-3-yloxy)-5-methyl-pyrimidin-4-yloxy]-piperidine-1-carboxylic acid isopropyl ester; 4-(2-Fluoro-4-methanesulfonyl-phenoxy)-5-methyl-6-[1-(3-methyl-butyl)-piperidin-4-yloxy]-pyrimidine; 2-{4-[6-(2-Fluoro-4-methanesulfonyl-phenoxy)-5-methyl-pyrimidin-4-yloxy]-piperidin-1-yl}-1-morpholin-4-yl-ethanone; 1-(3,4-Dichloro-phenyl)-2-{4-[6-(2-fluoro-4-methanesulfonyl-phenoxy)-5-methyl-pyrimidin-4-yloxy]-piperidin-1-yl}-ethanone; 1-(3-Chloro-phenyl)-2-{4-[6-(2-fluoro-4-methanesulfonyl-phenoxy)-5-methyl-pyrimidin-4-yloxy]-piperidin-1-yl}-ethanone; 2-{4-[6-(2-Fluoro-4-methanesulfonyl-phenoxy)-5-methyl-pyrimidin-4-yloxy]-piperidin-1-yl}-1-thiophen-3-yl-ethanone; 2-{4-[6-(2-Fluoro-4-methanesulfonyl-phenoxy)-5-methyl-pyrimidin-4-yloxy]-piperidin-1-yl}-1-phenyl-ethanone; 1-(2,4-Dimethoxy-phenyl)-2-{4-[6-(2-fluoro-4-methanesulfonyl-phenoxy)-5-methyl-pyrimidin-4-yloxy]-piperidin-1-yl}-ethanone; 4-(2-Fluoro-4-methanesulfonyl-phenoxy)-5-methyl-6-[1-(4-methyl-pentyl)-piperidin-4-yloxy]-pyrimidine; 1-{4-[6-(2-Fluoro-4-methanesulfonyl-phenoxy)-5-methyl-pyrimidin-4-yloxy]-piperidin-1-yl}-3-isopropoxy-propan-1-one; 1-{4-[6-(2-Fluoro-4-methanesulfonyl-phenoxy)-5-methyl-pyrimidin-4-yloxy]-piperidin-1-yl}-4-isopropoxy-butan-1-one; 1-{4-[6-(2-Fluoro-4-methanesulfonyl-phenoxy)-5-methyl-pyrimidin-4-yloxy]-piperidin-1-yl}-3-hydroxy-propan-1-one; 2-{4-[6-(2-Fluoro-4-methanesulfonyl-phenoxy)-5-methyl-pyrimidin-4-yloxy]-piperidin-1-yl}-1-(5-pyridin-2-yl-thiophen-2-yl)-ethanone; 4-(2-Fluoro-4-methanesulfonyl-phenoxy)-5-methyl-6-[1-(5-methyl-hexyl)-piperidin-4-yloxy]-pyrimidine; 3-{4-[6-(2-Fluoro-4-methanesulfonyl-phenoxy)-5-methyl-pyrimidin-4-yloxy]-piperidin-1-yl}-3-oxo-propane-1-sulfonic acid; 2-{4-[6-(2-Fluoro-4-methanesulfonyl-phenoxy)-5-methyl-pyrimidin-4-yloxy]-piperidin-1-yl}-1-thiophen-2-yl-ethanone; 4-(2-Fluoro-4-methanesulfonyl-phenoxy)-5-methyl-6-(1-pentyl-piperidin-4-yloxy)-pyrimidine; 4-(1-Butyl-piperidin-4-yloxy)-6-(2-fluoro-4-methanesulfonyl-phenoxy)-5-methyl-pyrimidine; 4-{4-[6-(2-Fluoro-4-methanesulfonyl-phenoxy)-5-methyl-pyrimidin-4-yloxy]-piperidin-1-yl}-cyclohexanecarboxylic acid; 1-(4-Diethylamino-phenyl)-2-{4-[6-(2-fluoro-4-methanesulfonyl-phenoxy)-5-methyl-pyrimidin-4-yloxy]-piperidin-1-yl}-ethanone; 2-{4-[6-(2-Fluoro-4-methanesulfonyl-phenoxy)-5-methyl-pyrimidin-4-yloxy]-piperidin-1-yl}-1-(2-methyl-4-phenyl-furan-3-yl)-ethanone; 4-(2-Fluoro-4-methanesulfonyl-phenoxy)-6-(1-hexyl-piperidin-4-yloxy)-5-methyl-pyrimidine; 4-{4-[6-(2-Fluoro-4- methanesulfonyl-phenoxy)-5-methyl-pyrimidin-4-yloxy]-piperidin-1-yl}-butyric acid; 1-{4-[6-(2-Fluoro-4-methanesulfonyl-phenoxy)-5-methyl-pyrimidin-4-yloxy]-piperidin-1-yl}-pentan-2-one; 1-{4-[6-(2-Fluoro-4-methanesulfonyl-phenoxy)-5-methyl-pyrimidin-4-yloxy]-piperidin-1-yl}-hexan-2-one; 1-{4-[6-(2-Fluoro-4-methanesulfonyl-phenoxy)-5-methyl-pyrimidin-4-yloxy]-piperidin-1-yl}-4-hexan-2-one; 1-{4-[6-(2-Fluoro-4-methanesulfonyl-phenoxy)-5-methyl-pyrimidin-4-yloxy]-piperidin-1-yl}-4-methyl-pentan-2-one; 1-{4-[6-(2-Fluoro-4-methanesulfonyl-phenoxy)-5-methyl-pyrimidin-4-yloxy]-piperidin-1-yl}-5-methyl-hexan-2-one; 1-{4-[6-(2-Fluoro-4-methanesulfonyl-phenoxy)-5-methyl-pyrimidin-4-yloxy]-piperidin-1-yl}-6-methyl-heptan-2-one; 5-{4-[6-(2-Fluoro-4-methanesulfonyl-phenoxy)-5-methyl-pyrimidin-4-yloxy]-piperidin-1-yl}-4-oxo-pentanoic acid; 5-{4-[6-(2-Fluoro-4-methanesulfonyl-phenoxy)-5-methyl-pyrimidin-4-yloxy]-piperidin-1-yl}-4-oxo-pentanenitrile; 1-{4-[6-(2-Fluoro-4-methanesulfonyl-phenoxy)-5-methyl-pyrimidin-4-yloxy]-piperidin-1-yl}-2-pyridin-2-yl-ethanone; 2-{4-[6-(2-Fluoro-4-methanesulfonyl-phenoxy)-5-methyl-pyrimidin-4-yloxy]-piperidin-1-yl}-1-pyridin-4-yl-ethanone; 2-{4-[6-(2-Fluoro-4-methanesulfonyl-phenoxy)-5-methyl-pyrimidin-4-yloxy]-piperidin-1-ylmethyl}-acrylic acid; 1-[1,4]Dioxan-2-yl-2-{4-[6-(2-fluoro-4-methanesulfonyl-phenoxy)-5-methyl-pyrimidin-4-yloxy]-piperidin-1-yl}-ethanone; 1-(2,3-Dihydro-[1,4]dioxin-2-yl)-2-{4-[6-(2-fluoro-4-methanesulfonyl-phenoxy)-5-methyl-pyrimidin-4-yloxy]-piperidin-1-yl}-ethanone; 2-{4-[6-(2-Fluoro-4-methanesulfonyl-phenoxy)-5-methyl-pyrimidin-4-yloxy]-piperidin-1-yl}-1-p-tolyl-ethanone; 2-{4-[6-(2-Fluoro-4-methanesulfonyl-phenoxy)-5-methyl-pyrimidin-4-yloxy]-piperidin-1-yl}-1-(4-methoxy-phenyl)-ethanone; 1-(2-Chloro-phenyl)-2-{4-[6-(2-fluoro-4-methanesulfonyl-phenoxy)-5-methyl-pyrimidin-4-yloxy]-piperidin-1-yl}-ethanone; 3-(2-{4-[6-(2-Fluoro-4-methanesulfonyl-phenoxy)-5-methyl-pyrimidin-4-yloxy]-piperidin-1-yl}-acetyl)-benzonitrile; 1-(2,4-Dimethyl-phenyl)-2-{4-[6-(2-fluoro-4-methanesulfonyl-phenoxy)-5-methyl-pyrimidin-4-yloxy]-piperidin-1-yl}-ethanone; 1-(4-Chloro-3-methyl-phenyl)-2-{4-[6-(2-fluoro-4-methanesulfonyl-phenoxy)-5-methyl-pyrimidin-4-yloxy]-piperidin-1-yl}-ethanone; 1-(4-Difluoromethoxy-phenyl)-2-{4-[6-(2-fluoro-4-methanesulfonyl-phenoxy)-5-methyl-pyrimidin-4-yloxy]-piperidin-1-yl}-ethanone; 1-(2,3-Dihydro-benzo[1,4]dioxin-6-yl)-2-{4-[6-(2-fluoro-4-methanesulfonyl-phenoxy)-5-methyl-pyrimidin-4-yloxy]-piperidin-1-yl}-ethanone; 2-{4-[6-(2-Fluoro-4-methanesulfonyl-phenoxy)-5-methyl-pyrimidin-4-yloxy]-piperidin-1-yl}-1-(5-phenyl-thiophen-2-yl)-ethanone; 2-{4-[6-(2-Fluoro-4-methanesulfonyl-phenoxy)-5-methyl-pyrimidin-4-yloxy]-piperidin-1-yl}-1-thiophen-2-yl-ethanone; {4-[6-(2-Fluoro-4-methanesulfonyl-phenoxy)-5-methyl-pyrimidin-4-yloxy]-piperidin-1-yl}-acetic acid ethyl ester; 1-{4-[6-(2-Fluoro-4-methanesulfonyl-phenoxy)-5-methyl-pyrimidin-4-yloxy]-piperidin-1-yl}-3-methoxy-propan-2-ol; 4-(2-Fluoro-4-methanesulfonyl-phenoxy)-6-[1-(4-methoxy-cyclohexyl)-piperidin-4-yloxy]-5-methyl-pyrimidine; 1-{4-[6-(2-Fluoro-4-methanesulfonyl-phenoxy)-5-methyl-pyrimidin-4-yloxy]-piperidin-1-yl}-hexan-1-one; 4-{6-[2-Fluoro-4-(2-isobutoxy-ethoxy)-phenoxy]-5-methyl-pyrimidin-4-yloxy}-piperidine-1-carboxylic acid isopropyl ester; 4-{6-[4-(2-Cyclopropoxy-ethoxy)-2-fluoro-phenoxy]-5-methyl-pyrimidin-4-yloxy}-piperidine-1-carboxylic acid isopropyl ester; 4-{6-[4-(2-Ethoxy-ethoxy)-2-fluoro-phenoxy]-5-methyl-pyrimidin-4-yloxy}-piperidine-1-carboxylic acid isopropyl ester; 4-{6-[2-Fluoro-4-(3-methoxy-propoxy)-phenoxy]-5-methyl-pyrimidin-4-yloxy}-piperidine-1-carboxylic acid isopropyl ester; 4-{6-[2-Fluoro-4-(2-pyridin-2-yl-ethoxy)-phenoxy]-5-methyl-pyrimidin-4-yloxy}-piperidine-1-carboxylic acid isopropyl ester; 4-{6-[2-Fluoro-4-(tetrahydro-pyran-4-yloxy)-phenoxy]-5-methyl-pyrimidin-4-yloxy}-piperidine-1-carboxylic acid isopropyl ester; 4-{6-[4-(2-tert-Butoxy-ethoxy)-2-fluoro-phenoxy]-5-methyl-pyrimidin-4-yloxy}-piperidine-1-carboxylic acid isopropyl ester; 4-[6-(2-Fluoro-4-sulfo-phenoxy)-5-methyl-pyrimidin-4-yloxy]-piperidine-1-carboxylic acid isopropyl ester; 4-[6-(2,5-Difluoro-4-trifluoromethoxy-phenoxy)-5-ethynyl-pyrimidin-4-yloxy]-piperidine-1-carboxylic acid isopropyl ester; 4-[6-(2,5-Difluoro-4-trifluoromethoxy-phenoxy)-5-prop-1-ynyl-pyrimidin-4-yloxy]-piperidine-1-carboxylic acid isopropyl ester; 4-[5-Ethynyl-6-(2-fluoro-4-methoxy-phenoxy)-pyrimidin-4-yloxy]-piperidine-1-carboxylic acid isopropyl ester; 4-[5-Ethynyl-6-(6-methoxy-4-methyl-pyridin-3-yloxy)-pyrimidin-4-yloxy]-piperidine-1-carboxylic acid isopropyl ester; 4-{5-Ethynyl-6-[6-(2-isopropoxy-ethyl)-2-methyl-pyridin-3-yloxy]-pyrimidin-4-yloxy}-piperidine-1-carboxylic acid isopropyl ester; 4-[6-(4-Cyano-2-fluoro-phenoxy)-5-ethynyl-pyrimidin-4-yloxy]-piperidine-1-carboxylic acid isopropyl ester; 4-[5-Ethynyl-6-(2-fluoro-4-[1,2,4]triazol-4-yl-phenoxy)-pyrimidin-4-yloxy]-piperidine-1-carboxylic acid isopropyl ester; 4-[5-Ethynyl-6-(2-fluoro-4-[1,2,4]triazol-1-yl-phenoxy)-pyrimidin-4-yloxy]-piperidine-1-carboxylic acid isopropyl ester; 1-{4-[5-Ethynyl-6-(2-fluoro-4-[1,2,4]triazol-1-yl-phenoxy)-pyrimidin-4-yloxy]-piperidin-1-yl}-3-pyridin-2-yl-propan-1-one; 4-{5-Ethynyl-6-[1-(3-isopropyl-[1,2,4]oxadiazol-5-yl)-piperidin-4-yloxy]-pyrimidin-4-yloxy}-3-fluoro-benzonitrile; 5-Ethynyl-4-(2-fluoro-4-methanesulfonyl-phenoxy)-6-[1-(3-isopropyl-[1,2,4]oxadiazol-5-yl)-piperidin-4-yloxy]-pyrimidine; 4-[1-(3-Ethyl-[1,2,4]oxadiazol-5-yl)-piperidin-4-yloxy]-5-ethynyl-6-(2-fluoro-4-methanesulfonyl-phenoxy)-pyrimidine; 4-[1-(3-Ethyl-[1,2,4]oxadiazol-5-yl)-piperidin-4-yloxy]-6-(2-fluoro-4-methanesulfonyl-phenoxy)-5-methyl-pyrimidine; 4-(2-Fluoro-4-methanesulfonyl-phenoxy)-5-methyl-6-[1-(3-methyl-[1,2,4]oxadiazol-5-yl)-piperidin-4-yloxy]-pyrimidine; 4-[6-(2-Fluoro-4-methanesulfonylamino-phenoxy)-5-methyl-pyrimidin-4-yloxy]-piperidine-1-carboxylic acid isopropyl ester; cis-{4-[6-(2-Fluoro-4-methanesulfonyl-phenoxy)-5-methyl-pyrimidin-4-yloxy]-cyclohexyl}-carbamic acid isopropyl ester; trans-{4-[6-(2-Fluoro-4-methanesulfonyl-phenoxy)-5-methyl-pyrimidin-4-yloxy]-cyclohexyl}-carbamic acid isopropyl ester; N-{4-[6-(2-Fluoro-4-methanesulfonyl-phenoxy)-5-methyl-pyrimidin-4-yloxy]-cyclohexyl}-3-methyl-butyramide; N-{4-[6-(2-Fluoro-4-methanesulfonyl-phenoxy)-5-methyl-pyrimidin-4-yloxy]-cyclohexyl}-isobutyramide; 4-{6-[2,5-Difluoro-4-(2-methanesulfonyl-ethyl)-phenoxy]-5-methyl-pyrimidin-4-yloxy}-piperidine-1-carboxylic acid isopropyl ester; 4-{6-[4-Fluoro-6-(2-methanesulfonyl-ethyl)-pyridin-3-yloxy]-5-methyl-pyrimidin-4-yloxy}-piperidine-1-carboxylic acid isopropyl ester; 4-{5-Cyclopropyl-6-[2,5-difluoro-4-(2-hydroxy-ethyl)-phenoxy]-pyrimidin-4-yloxy}-piperidine-1-carboxylic acid isopropyl ester; 4-(5-Cyclopropyl-6-{2,5-difluoro-4-[2-(4-methoxy-piperidin-1-yl)-ethyl]-phenoxy}-pyrimidin-4-yloxy)-piperidine-1-carboxylic acid isopropyl ester; 4-{6-[2,5-Difluoro-4-(2-morpholin-4-yl-ethyl)-phenoxy]-5-methyl-pyrimidin-4-yloxy}-piperidine-1-carboxylic acid isopropyl ester; 4-(6-{2-Fluoro-4-[2-(4-methoxy-piperidin-1-yl)-ethyl]-phenoxy}-5-methyl-pyrimidin-4-yloxy)-piperidine-1-carboxylic acid isopropyl ester; 4-{6-[6-(2-Fluoro-ethyl)-2-methyl-pyridin-3-yloxy]-5-methyl-pyrimidin-4-yloxy}-piperidine-1-carboxylic acid isopropyl ester; 4-{6-[2-Fluoro-4-(1-hydroxy-cyclopropylmethyl)-phenoxy]-5-methyl-pyrimidin-4-yloxy}-piperidine-1-carboxylic acid isopropyl ester; 4-{2-[2,5-Difluoro-4-(2-methanesulfonyl-ethyl)-phenoxy]-3-methyl-pyridin-4-yloxy}-piperidine-1-carboxylic acid isopropyl ester; (R)-4-(6-{2-Fluoro-4-[2-(3-methoxy-piperidin-1-yl)-ethyl]-phenoxy}-5-methyl-pyrimidin-4-yloxy)-piperidine-1-carboxylic acid isopropyl ester; (S)-4-(6-{2-Fluoro-4-[2-(3-methoxy-piperidin-1-yl)-ethyl]-phenoxy}-5-methyl-pyrimidin-4-yloxy)-piperidine-1-carboxylic acid isopropyl ester; (R)-4-(5-Ethynyl-6-{2-fluoro-4-[2-(2-methoxy-piperidin-1-yl)-ethyl]-phenoxy}-pyrimidin-4-yloxy)-piperidine-1-carboxylic acid isopropyl ester; (S)-4-(2-{2-Fluoro-4-[2-(2-methoxy-piperidin-1-yl)-ethyl]-phenoxy}-3-methyl-pyridin-4-yloxy)-piperidine-1-carboxylic acid isopropyl ester; 4-{6-[4-Fluoro-6-(2-morpholin-4-yl-ethyl)-pyridin-3-yloxy]-5-methyl-pyrimidin-4-yloxy}-piperidine-1-carboxylic acid isopropyl ester; 4-{5-Ethynyl-6-[4-fluoro-6-(2-methanesulfonyl-ethyl)-pyridin-3-yloxy]-pyrimidin-4-yloxy}-piperidine-1-carboxylic acid isopropyl ester; 4-{2-[2,5-Difluoro-4-(2-isopropoxy-ethyl)-phenoxy]-3-methyl-pyridin-4-yloxy}-piperidine-1-carboxylic acid isopropyl ester; 4-{6-[2-Fluoro-4-(2-propionylsulfamoyl-ethyl)-phenoxy]-5-methyl-pyrimidin-4-yloxy}-piperidine-1-carboxylic acid isopropyl ester; 4-{6-[2-Fluoro-4-(2-sulfamoyl-ethyl)-phenoxy]-5-methyl-pyrimidin-4-yloxy}-piperidine-1-carboxylic acid isopropyl ester; 4-{6-[2,5-Difluoro-4-(2-sulfamoyl-ethyl)-phenoxy]-5-ethynyl-pyrimidin-4-yloxy}-piperidine-1-carboxylic acid isopropyl ester; 4-{6-[2,5-Difluoro-4-(2-[1,2,4]triazol-1-yl-ethyl)-phenoxy]-5-methyl-pyrimidin-4-yloxy}-piperidine-1-carboxylic acid isopropyl ester; 4-{6-[2,3-Difluoro-4-(2-methanesulfonyl-ethyl)-phenoxy]-5-methyl-pyrimidin-4-yloxy}-piperidine-1-carboxylic acid isopropyl ester; 4-(2-{2-Fluoro-4-[2-(6-methoxy-pyridin-2-yl)-ethyl]-phenoxy}-3-methyl-pyridin-4-yloxy)-piperidine-1-carboxylic acid isopropyl ester; 4-(6-{2-Fluoro-4-[2-(3-methoxy-pyridin-2-yl)-ethyl]-phenoxy}-5-methyl-pyrimidin-4-yloxy)-piperidine-1-carboxylic acid isopropyl ester; 4-[6-(3-Fluoro-1-oxy-pyridin-4-yloxy)-5-methyl-pyrimidin-4-yloxy]-piperidine-1-carboxylic acid isopropyl ester; 4-[6-(5'-Methoxy-6-methyl-[2,2']bipyridinyl-5-yloxy)-5-methyl-pyrimidin-4-yloxy]-piperidine-1-carboxylic acid isopropyl ester; 4-{5-Ethynyl-6-[2-fluoro-4-(4-methoxy-pyridin-2-yl)-phenoxy]-pyrimidin-4-yloxy}-piperidine-1-carboxylic acid isopropyl ester; 4-{6-[2-Fluoro-4-(3-methoxy-pyridin-2-yl)-phenoxy]-5-methyl-pyrimidin-4-yloxy}-piperidine-1-carboxylic acid isopropyl ester; 4-(6-{2,5-Difluoro-4-[2-(3-methoxy-piperidin-1-yl)-ethyl]-phenoxy}-5-methyl-pyrimidin-4-yloxy)-piperidine-1-carboxylic acid isopropyl ester; and 4-(6-{2,5-Difluoro-4-[2-(3-methoxy-piperidin-1-yl)-ethyl]-phenoxy}-5-ethynyl-pyrimidin-4-yloxy)-piperidine-1-carboxylic acid isopropyl ester.

Specific examples of GPR119 agonists disclosed in International Application No. PCT/US2004/022327 include the following compounds according to Formula (III) (referred to herein as Group C8): 4-[6-(2-Fluoro-4-morpholin-4-yl-phenoxy)-5-methyl-pyrimidin-4-yloxy]-piperidine-1-carboxylic acid isopropyl ester; {4-[6-(2-Fluoro-4-methanesulfonyl-phenoxy)-5-methyl-pyrimidin-4-yloxy]-piperidin-1-yl}-[6-(2-pyrrolidin-1-yl-ethyl)-pyridin-3-yl]-methanone; (6-Amino-pyridin-3-yl)-{4-[6-(2-fluoro-4-methanesulfonyl-phenoxy)-5-methyl-pyrimidin-4-yloxy]-piperidin-1-yl}-methanone; 4-[5-Ethyl-6-(2-fluoro-4-methanesulfonyl-phenoxy)-pyrimidin-4-yloxy]-piperidine-1-carboxylic acid isopropyl ester; 4-[6-(2-Fluoro-phenoxy)-5-methyl-pyrimidin-4-yloxy]-piperidine-1-carboxylic acid isopropyl ester; 4-{6-[6-(2-Isopropoxy-ethylamino)-2-methyl-pyridin-3-yloxy]-5-methyl-pyrimidin-4-yloxy}-piperidine-1-carboxylic acid isopropyl ester; 4-{6-[6-(2-Hydroxy-ethylsulfanyl)-2-methyl-pyridin-3-yloxy]-5-methyl-pyrimidin-4-yloxy}-piperidine-1-carboxylic acid isopropyl ester; 4-[5-Methyl-6-(2-methyl-6-pentyl-pyridin-3-yloxy)-pyrimidin-4-yloxy]-piperidine-1-carboxylic acid isopropyl ester; 2-{4-[6-(2-Fluoro-4-methanesulfonyl-phenoxy)-5-methyl-pyrimidin-4-yloxy]-piperidin-1-yl}-1-(3-fluoro-phenyl)-ethanone; 4-(2-Fluoro-4-methanesulfonyl-phenoxy)-5-methyl-6-[1-(2-pyridin-3-yl-ethyl)-piperidin-4-yloxy]-pyrimidine; 2-{4-[6-(2-Fluoro-4-methanesulfonyl-phenoxy)-5-methyl-pyrimidin-4-yloxy]-piperidin-1-yl}-1-(4-trifluoromethoxy-phenyl)-ethanone; 2-{4-[6-(2-Fluoro-4-methanesulfonyl-phenoxy)-5-methyl-pyrimidin-4-yloxy]-piperidin-1-yl}-1-pyridin-2-yl-ethanone; 4-{6-[6-(2-Methoxy-ethanesulfonyl)-2-methyl-pyridin-3-yloxy]-5-methyl-pyrimidin-4-yloxy}-piperidine-1-carboxylic acid isopropyl ester; 4-(2-Fluoro-4-methanesulfonyl-phenoxy)-6-[1-(3-isopropyl-[1,2,4]oxadiazol-5-yl)-piperidin-4-yloxy]-5-methyl-pyrimidine; 4-(6-{2-Fluoro-4-[(2-hydroxy-ethylcarbamoyl)-methyl]-phenoxy}-5-methyl-pyrimidin-4-yloxy)-piperidine-1-carboxylic acid isopropyl ester; 4-[6-(5-Iodo-pyridin-2-yloxy)-5-methyl-pyrimidin-4-yloxy]-piperidine-1-carboxylic acid isopropyl ester; 4-(6-{2-Fluoro-4-[N-(2-isopropoxy-ethyl)-carbamimidoyl]-phenoxy}-5-methyl-pyrimidin-4-yloxy)-piperidine-1-carboxylic acid isopropyl ester; 4-[6-(4-Carboxy-2-fluoro-phenoxy)-5-methyl-pyrimidin-4-yloxy]-piperidine-1-carboxylic acid isopropyl ester; 4-(4-Bromo-2-fluoro-phenoxy)-6-[1-(3-isopropyl-[1,2,4]oxadiazol-5-yl)-piperidin-4-yloxy]-5-methyl-pyrimidine; 4-[6-(5-Methanesulfonyl-pyridin-2-yloxy)-5-methyl-pyrimidin-4-yloxy]-piperidine-1-carboxylic acid isopropyl ester; 4-{6-[6-(2-Hydroxy-ethylamino)-2-methyl-pyridin-3-yloxy]-5-methyl-pyrimidin-4-yloxy}-piperidine-1-carboxylic acid isopropyl ester; 4-[5-Cyclopropyl-6-(2-fluoro-4-methanesulfonyl-phenoxy)-pyrimidin-4-yloxy]-piperidine-1-carboxylic acid isopropyl ester; 4-{6-[6-(2-Methanesulfonyl-ethylamino)-2-methyl-pyridin-3-yloxy]-5-methyl-pyrimidin-4-yloxy}-piperidine-1-carboxylic acid isopropyl ester; 4-{4-[6-(2-Fluoro-4-methanesulfonyl-phenoxy)-5-methyl-pyrimidin-4-yloxy]-piperidin-1-yl}-4-oxo-butyric acid; 2-{4-[6-(2-Fluoro-4-methanesulfonyl-phenoxy)-5-methyl-pyrimidin-4-yloxy]-piperidin-1-yl}-1-(3-trifluoromethyl-phenyl)-ethanone; 4-{6-[6-(2-Methoxy-ethylsulfanyl)-2-methyl-pyridin-3-yloxy]-5-methyl-pyrimidin-4-yloxy}-piperidine-1-carboxylic acid isopropyl ester; 1-(2,5-Dimethoxy-phenyl)-2-{4-[6-(2-fluoro-4-methanesulfonyl-phenoxy)-5-methyl-pyrimidin-4-yloxy]-piperidin-1-yl}-ethanone; 2-{4-[6-(2-Fluoro-4-methanesulfonyl-phenoxy)-5-methyl-pyrimidin-4-yloxy]-piperidin-1-yl}-1-pyridin-2-yl-ethanone; 4-[6-(6-Chloro-2-methyl-pyridin-3-yloxy)-5-methyl-pyrimidin-4-yloxy]-piperidine-1-carboxylic acid isopropyl ester; 2-{4-[6-(2-Fluoro-4-methanesulfonyl-phenoxy)-5-methyl-pyrimidin-4-yloxy]-piperidin-1-yl}-1-(4-fluoro-phenyl)-ethanone; 2-{4-[6-(2-Fluoro-4-methanesulfonyl-phenoxy)-5-methyl-pyrimidin-4-yloxy]-piperidin-1-yl}-1-(4-trifluoromethyl-phenyl)-ethanone; 1-{4-[6-(2-Fluoro-4-methanesulfonyl-phenoxy)-5-methyl-pyrimidin-4-yloxy]-piperidin-1-yl}-3,3-dimethyl-butan-2-one; 2-{4-[6-(2-Fluoro-4-methanesulfonyl-phenoxy)-5-methyl-pyrimidin-4-yloxy]-piperidin-1-yl}-1-pyridin-3-yl-ethanone; 1-{4-[6-(2-Fluoro-4-methanesulfonyl-phenoxy)-5-methyl-pyrimidin-4-yloxy]-piperidin-1-yl}-butan-2-one; 4-(6-{2-Fluoro-4-[(2-isopropoxy-ethylcarbamoyl)-methyl]-phenoxy}-5-methyl-pyrimidin-4-yloxy)-piperidine-1-carboxylic acid isopropyl ester; 2-{4-[6-(2-Fluoro-4-methanesulfonyl-phenoxy)-5- methyl-pyrimidin-4-yloxy]-piperidin-1-yl}-1-(4-methanesulfonyl-phenyl)-ethanone; 1-(4-Chloro-phenyl)-2-{4-[6-(2-fluoro-4-methanesulfonyl-phenoxy)-5-methyl-pyrimidin-4-yloxy]-piperidin-1-yl}-ethanone; 4-(2-{4-[6-(2-Fluoro-4-methanesulfonyl-phenoxy)-5-methyl-pyrimidin-4-yloxy]-piperidin-1-yl}-acetyl)-benzonitrile; 1-(3,4-Difluoro-phenyl)-2-{4-[6-(2-fluoro-4-methanesulfonyl-phenoxy)-5-methyl-pyrimidin-4-yloxy]-piperidin-1-yl}-ethanone; 4-{6-[2-Fluoro-4-(2-isopropoxy-ethylcarbamoyl)-phenoxy]-5-methyl-pyrimidin-4-yloxy}-piperidine-1-carboxylic acid isopropyl ester; 1-{4-[6-(2-Fluoro-4-methanesulfonyl-phenoxy)-5-methyl-pyrimidin-4-yloxy]-piperidin-1-yl}-butan-1-one; 1-{4-[6-(2-Fluoro-4-methanesulfonyl-phenoxy)-5-methyl-pyrimidin-4-yloxy]-piperidin-1-yl}-pentan-1-one; 4-[6-(2,4-Difluoro-phenoxy)-5-methyl-pyrimidin-4-yloxy]-piperidine-1-carboxylic acid isopropyl ester; 1-{4-[6-(2-Fluoro-4-methanesulfonyl-phenoxy)-5-methyl-pyrimidin-4-yloxy]-piperidin-1-yl}-3-methyl-butan-1-one; 1-{4-[6-(2-Fluoro-4-methanesulfonyl-phenoxy)-5-methyl-pyrimidin-4-yloxy]-piperidin-1-yl}-4-methyl-pentan-1-one; 1-{4-[6-(2-Fluoro-4-methanesulfonyl-phenoxy)-5-methyl-pyrimidin-4-yloxy]-piperidin-1-yl}-5-methyl-hexan-1-one; 4-{6-[2-Fluoro-4-(2-methoxy-ethylcarbamoyl)-phenoxy]-5-methyl-pyrimidin-4-yloxy}-piperidine-1-carboxylic acid isopropyl ester; 4-[6-(2-Fluoro-4-methanesulfonyl-phenoxy)-5-methyl-pyrimidin-4-yloxy]-piperidine-1-carboxylic acid isopropyl ester; 4-[6-(4-Bromo-2-fluoro-phenoxy)-5-methyl-pyrimidin-4-yloxy]-piperidine-1-carboxylic acid isopropyl ester; 4-{6-[2-Fluoro-4-(methoxy-methyl-carbamoyl)-phenoxy]-5-methyl-pyrimidin-4-yloxy}-piperidine-1-carboxylic acid isopropyl ester; 1-{4-[6-(2-Fluoro-4-methanesulfonyl-phenoxy)-5-methyl-pyrimidin-4-yloxy]-piperidin-1-yl}-3-methoxy-propan-1-one; 4-[6-(4-Cyano-2-fluoro-phenoxy)-5-methyl-pyrimidin-4-yloxy]-piperidine-1-carboxylic acid isopropyl ester; 4-[5-(5-Aminomethyl-4,5-dihydro-oxazol-2-yl)-6-(2-fluoro-4-methanesulfonyl-phenoxy)-pyrimidin-4-yloxy]-piperidine-1-carboxylic acid isopropyl ester; 4-{6-[6-(2-Methoxy-ethylamino)-2-methyl-pyridin-3-yloxy]-5-methyl-pyrimidin-4-yloxy}-piperidine-1-carboxylic acid isopropyl ester; 4-{6-[6-(3-Methanesulfonyl-pyrrolidin-1-yl)-2-methyl-pyridin-3-yloxy]-5-methyl-pyrimidin-4-yloxy}-piperidine-1-carboxylic acid isopropyl ester; 4-[6-(6-Benzylamino-2-methyl-pyridin-3-yloxy)-5-methyl-pyrimidin-4-yloxy]-piperidine-1-carboxylic acid isopropyl ester; 4-[6-(4-Carbamoyl-2-fluoro-phenoxy)-5-methyl-pyrimidin-4-yloxy]-piperidine-1-carboxylic acid isopropyl ester; 4-{6-[2-Fluoro-4-(2-isopropoxy-ethylamino)-phenoxy]-5-methyl-pyrimidin-4-yloxy}-piperidine-1-carboxylic acid isopropyl ester; 4-(6-{2-Fluoro-4-[(tetrahydro-furan-2-ylmethyl)-amino]-phenoxy}-5-methyl-pyrimidin-4-yloxy)-piperidine-1-carboxylic acid isopropyl ester; 4-(6-{6-[(2-Methanesulfonyl-ethyl)-methyl-amino]-2-methyl-pyridin-3-yloxy}-5-methyl-pyrimidin-4-yloxy)-piperidine-1-carboxylic acid isopropyl ester; 4-[6-(2-Fluoro-4-hydroxycarbamoyl-phenoxy)-5-methyl-pyrimidin-4-yloxy]-piperidine-1-carboxylic acid isopropyl ester; 4-{6-[2-Fluoro-4-(2-pyrrolidin-1-yl-ethylcarbamoyl)-phenoxy]-5-methyl-pyrimidin-4-yloxy}-piperidine-1-carboxylic acid isopropyl ester; 4-{6-[2-Fluoro-4-(4-isopropyl-piperazine-1-carbonyl)-phenoxy]-5-methyl-pyrimidin-4-yloxy}-piperidine-1-carboxylic acid isopropyl ester; 4-{6-[2-Fluoro-4-(2-morpholin-4-yl-ethyl)-phenoxy]-5-methyl-pyrimidin-4-yloxy}-piperidine-1-carboxylic acid isopropyl ester; 4-{6-[2-Fluoro-4-(2-methanesulfonyl-ethyl)-phenoxy]-5-methyl-pyrimidin-4-yloxy}-piperidine-1-carboxylic acid isopropyl ester; 4-{6-[2-Fluoro-4-(2-hydroxy-ethyl)-phenoxy]-5-methyl-pyrimidin-4-yloxy}-piperidine-1-carboxylic acid isopropyl ester; 4-[6-(4-Carboxymethyl-2-fluoro-phenoxy)-5-methyl-pyrimidin-4-yloxy]-piperidine-1-carboxylic acid isopropyl ester; 4-[6-(4-Dimethylcarbamoylmethyl-2-fluoro-phenoxy)-5-methyl-pyrimidin-4-yloxy]-piperidine-1-carboxylic acid isopropyl ester; 4-[6-(2-Fluoro-4-sulfamoyl-phenoxy)-5-methyl-pyrimidin-4-yloxy]-piperidine-1-carboxylic acid isopropyl ester; 4-[6-(2-Fluoro-4-propionylsulfamoyl-phenoxy)-5-methyl-pyrimidin-4-yloxy]-piperidine-1-carboxylic acid isopropyl ester; 4-[5-Ethynyl-6-(2-fluoro-4-methanesulfonyl-phenoxy)-pyrimidin-4-yloxy]-piperidine-1-carboxylic acid isopropyl ester; 4-{6-[2-Fluoro-4-(2-phosphonooxy-ethyl)-phenoxy]-5-methyl-pyrimidin-4-yloxy}-piperidine-1-carboxylic acid isopropyl ester; 4-[5-Bromo-6-(2-fluoro-4-methanesulfonyl-phenoxy)-pyrimidin-4-yloxy]-piperidine-1-carboxylic acid isopropyl ester; 4-(6-{2-Fluoro-4-[2-(2-methanesulfonyl-pyrrolidin-1-yl)-2-oxo-ethyl]-phenoxy}-5-methyl-pyrimidin-4-yloxy)-piperidine-1-carboxylic acid isopropyl ester; 4-[6-(4-Carbamoylmethyl-2-fluoro-phenoxy)-5-methyl-pyrimidin-4-yloxy]-piperidine-1-carboxylic acid isopropyl ester; 4-[6-(2-Fluoro-4-{[(tetrahydro-furan-2-ylmethyl)-carbamoyl]-methyl}-phenoxy)-5-methyl-pyrimidin-4-yloxy]-piperidine-1-carboxylic acid isopropyl ester; 4-[6-(2-Fluoro-3-sulfamoyl-phenoxy)-5-methyl-pyrimidin-4-yloxy]-piperidine-1-carboxylic acid isopropyl ester; C-{4-[6-(2-Fluoro-4-methanesulfonyl-phenoxy)-5-methyl-pyrimidin-4-yloxy]-piperidin-1-yl}-C-(4-fluoro-phenyl)-methyleneamine; 3-tert-Butoxy-1-{4-[6-(2-fluoro-4-methanesulfonyl-phenoxy)-5-methyl-pyrimidin-4-yloxy]-piperidin-1-yl}-propan-1-one; 2-Ethoxy-1-{4-[6-(2-fluoro-4-methanesulfonyl-phenoxy)-5-methyl-pyrimidin-4-yloxy]-piperidin-1-yl}-ethanone; {4-[6-(2-Fluoro-4-methanesulfonyl-phenoxy)-5-methyl-pyrimidin-4-yloxy]-piperidin-1-yl}-(tetrahydro-furan-2-yl)-methanone; (S)-1-{4-[6-(2-Fluoro-4-methanesulfonyl-phenoxy)-5-methyl-pyrimidin-4-yloxy]-piperidin-1-yl}-3-methyl-2-methylamino-butan-1-one; 4-(6-{2-Fluoro-4-[2-(3-hydroxy-piperidin-1-yl)-2-oxo-ethyl]-phenoxy}-5-methyl-pyrimidin-4-yloxy)-piperidine-1-carboxylic acid isopropyl ester; 4-{6-[2-Fluoro-4-(2-morpholin-4-yl-2-oxo-ethyl)-phenoxy]-5-methyl-pyrimidin-4-yloxy}-piperidine-1-carboxylic acid isopropyl ester; 4-{6-[2-Fluoro-4-(2-imidazol-1-yl-ethyl)-phenoxy]-5-methyl-pyrimidin-4-yloxy}-piperidine-1-carboxylic acid isopropyl ester; 4-{6-[2-Fluoro-4-(2-[1,2,3]triazol-1-yl-ethyl)-phenoxy]-5-methyl-pyrimidin-4-yloxy}-piperidine-1-carboxylic acid isopropyl ester; (R)-1-{4-[6-(2-Fluoro-4-methanesulfonyl-phenoxy)-5-methyl-pyrimidin-4-yloxy]-piperidin-1-yl}-3-methyl-2-methylamino-butan-1-one; (S)-1-{4-[6-(2-Fluoro-4-methanesulfonyl-phenoxy)-5-methyl-pyrimidin-4-yloxy]-piperidin-1-yl}-3-hydroxy-butan-1-one; (R)—N-(1-{4-[6-(2-Fluoro-4-methanesulfonyl-phenoxy)-5-methyl-pyrimidin-4-yloxy]-piperidine-1-carbonyl}-2-methyl-propyl)-acetamide; (S)—N-(1-{4-[6-(2-Fluoro-4-methanesulfonyl-phenoxy)-5-methyl-pyrimidin-4-yloxy]-piperidine-1-carbonyl}-2-methyl-propyl)-acetamide; (R)—N-(2-{4-[6-(2-Fluoro-4-methanesulfonyl-phenoxy)-5-methyl-pyrimidin-4-yloxy]-piperidin-1-yl}-1-methyl-2-oxo-ethyl)-acetamide; (S)—N-(2-{4-[6-(2-Fluoro-4-methanesulfonyl-phenoxy)-5-methyl-pyrimidin-4-yloxy]-piperidin-1-yl}-1-methyl-2-oxo-ethyl)-acetamide; 4-[6-(2-Fluoro-4-methanesulfonyl-phenoxy)-5-methyl-pyrimidin-4-yloxy]-piperidine-1-carboxylic acid (S)-tetrahydro-furan-3-yl ester; 4-[6-(2-Fluoro-4-methanesulfonyl-phenoxy)-5-methyl-pyrimidin-4-yloxy]-piperidine-1-carboxylic acid (R)-tetrahydro-furan-3-yl ester; 4-[6-(2-Amino-4-ethanesulfonyl-phenoxy)-5-methyl-pyrimidin-4-yloxy]-piperidine-1-carboxylic acid isopropyl ester; 4-[6-(4-Methanesulfonyl-phenoxy)-5-methyl-pyrimidin-4-yloxy]-piperidine-1-carboxylic acid isopropyl ester; (1-{4-[6-(2-Fluoro-4-methanesulfonyl-phenoxy)-5-methyl-pyrimidin-4-yloxy]-piperidine-1-carbonyl}-2-methyl-propyl)-carbamic acid tert-butyl ester; 4-{6-[2-Fluoro-4-(6-methoxy-pyridin-3-yl)-phenoxy]-5-methyl-pyrimidin-4-yloxy}-piperidine-1-carboxylic acid isopropyl ester; 3-Amino-1-{4-[6-(2-fluoro-4-methanesulfonyl-phenoxy)-5-methyl-pyrimidin-4-yloxy]-piperidin-1-yl}-4-methyl-pentan-1-one; 2-Amino-1-{4-[6-(2-fluoro-4-methanesulfonyl-phenoxy)-5-methyl-pyrimidin-4-yloxy]-piperidin-1-yl}-3-methyl-butan-1-one; 4-{6-[2-Fluoro-4-(2-isopropoxy-ethoxy)-phenoxy]-5-methyl-pyrimidin-4-yloxy}-piperidine-1-carboxylic acid isopropyl ester; and 4-[5-Methyl-6-(4-sulfo-phenoxy)-pyrimidin-4-yloxy]-piperidine-1-carboxylic acid isopropyl ester.

Specific examples of GPR119 agonists disclosed in International Application No. PCT/US2004/022327 include the following compounds according to Formula (III) (referred to herein as Group C9): 4-({Cyclopropyl-[6-(2-fluoro-4-methanesulfonyl-phenoxy)-5-methyl-pyrimidin-4-yl]-amino}-methyl)-piperidine-1-carboxylic acid tert-butyl ester; 4-({Cyclopropyl-[6-(2-fluoro-4-methanesulfonyl-phenoxy)-5-methyl-pyrimidin-4-yl]-amino}-methyl)-piperidine-1-carboxylic acid isopropyl ester; 4-({[6-(2-Fluoro-4-methanesulfonyl-phenoxy)-5-methyl-pyrimidin-4-yl]-isopropyl-amino}-methyl)-piperidine-1-carboxylic acid isopropyl ester; and 4-({Cyclopropylmethyl-[6-(2-fluoro-4-methanesulfonyl-phenoxy)-5-methyl-pyrimidin-4-yl]-amino}-methyl)-piperidine-1-carboxylic acid isopropyl ester.

Specific examples of GPR119 agonists disclosed in International Application No. PCT/US2004/022327 include the following compound according to Formula (III) (referred to herein as Group C10): 4-[6-(2-Fluoro-4-methanesulfonyl-phenylamino)-5-methyl-pyrimidin-4-ylsulfanyl]-piperidine-1-carboxylic acid isopropyl ester.

Examples of GPR119 agonists are described in International Application No. PCT/US2004/022417 (published as WO 05/007658), the disclosure of each of which is herein incorporated by reference in its entirety. Disclosed in International Application No. PCT/US2004/022417 as a GPR119 agonist is a compound of Formula (IV):

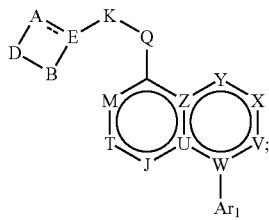

(IV)

wherein:
A and B are each independently $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl and halogen;
D is O, S, S(O), S(O)$_2$, CR$_1$R$_2$ or N—R$_2$, wherein R$_1$ is selected from the group consisting of H, $C_{1-8}$ alkyl, $C_{1-4}$ alkoxy, halogen and hydroxyl;
E is N, C or CR$_3$, wherein R$_3$ is H or $C_{1-8}$ alkyl;
----- is a single bond when E is N or CR$_3$, or a double bond when E is C;
K is a $C_{3-6}$ cycloalkylene or $C_{1-3}$ alkylene wherein each are optionally substituted with 1 to 4 substituents selected from the group consisting of $C_{1-3}$ alkyl, $C_{1-4}$ alkoxy, carboxy, cyano, $C_{1-3}$ haloalkyl and halogen; or K is a bond;
Q is NR$_4$, O, S, S(O) or S(O)$_2$, wherein R$_4$ is H or $C_{1-8}$ alkyl and the $C_{1-8}$ alkyl is optionally substituted with $C_{2-8}$ dialkylamine;
T is N or CR$_5$;
M is N or CR$_6$;
J is N or CR$_7$;
U is C or N;
V is N, CR$_1$ or V is a bond;
W is N or C;
X is O, S, N, CR$_9$ or NR$_{11}$;
Y is O, S, N, CR$_{10}$ or NR$_{12}$;
Z is C or N;
R$_5$, R$_6$, R$_7$, R$_8$, R$_9$ and R$_{10}$ are each independently selected from the group consisting of H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-6}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, hydroxylamino and nitro; wherein said $C_{2-6}$ alkenyl, $C_{1-8}$ alkyl, $C_{2-6}$ alkynyl and $C_{3-6}$ cycloalkyl are optionally substituted with 1, 2, 3 or 4 substituents selected from the group consisting of $C_{1-5}$ acyl, $C_{1-5}$ acyloxy, $C_{1-4}$ alkoxy, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro;
R$_{11}$ and R$_{12}$ are each independently selected from $C_{2-6}$ alkenyl, $C_{1-8}$ alkyl, $C_{2-6}$ alkynyl or $C_{3-6}$ cycloalkyl each optionally substituted with 1, 2, 3 or 4 substituents selected from the group consisting of $C_{1-5}$ acyl, $C_{1-5}$ acyloxy, $C_{1-4}$ alkoxy, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro;
Ar$_1$ is aryl or heteroaryl each optionally substituted with R$_{13}$, R$_{14}$, R$_{15}$, R$_{16}$, and R$_{17}$; wherein R$_{13}$ is selected from the group consisting of $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, and thiol, and wherein said $C_{1-5}$ acyl, $C_{1-6}$ acylsulfonamide, $C_{1-4}$ alkoxy, $C_{1-8}$ alkyl, $C_{1-4}$ alkylamino, $C_{1-6}$ alkylsulfonamide, $C_{1-4}$ alkylsulfonyl, $C_{1-4}$ alkylthio, arylsulfonyl, carbamimidoyl, $C_{2-6}$ dialkylamino, heterocyclic, heterocyclic-carbonyl, heteroaryl, phenoxy and phenyl are optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro, phenyl, and phosphonooxy, and wherein said $C_{1-7}$ alkyl and $C_{1-4}$ alkylcarboxamide are each optionally substituted with 1 to 5 substituents selected from the group consisting of $C_{1-4}$ alkoxy and hydroxy; or $R_{13}$ is a group of Formula (IVA):

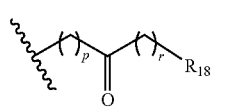

(IVA)

wherein:
"p" and "r" are independently 0, 1, 2 or 3; and
$R_{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, wherein said heteroaryl or phenyl optionally substituted with 1 to 5 substituents selected independently from the group consisting of $C_{1-4}$ alkoxy, amino, $C_{1-4}$ alkylamino, $C_{2-4}$ alkynyl, $C_{2-8}$ dialkylamino, halogen, $C_{1-4}$ haloalkoxy, $C_{1-4}$ haloalkyl and hydroxyl;

$R_{14}$, $R_{15}$, $R_{16}$, and $R_{17}$ are each independently selected form the group consisting of H, $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro; or two adjacent $R_{14}$, $R_{15}$, $R_{16}$ and $R_{17}$ together with the atoms to which they are attached form a 5, 6 or 7 member cycloalkyl, cycloalkenyl or heterocyclic group fused with $Ar_1$ wherein the 5, 6 or 7 member group is optionally substituted with halogen; and $R_2$ is selected from the group consisting of $C_{1-8}$ alkyl, $C_{2-6}$ alkynyl, amino, aryl, carboxamide, carboxy, cyano, $C_{3-6}$-cycloalkyl, $C_{1-4}$ haloalkoxy, $C_{1-4}$ haloalkyl, halogen, heteroaryl and hydroxyl; and wherein said $C_{1-8}$ alkyl, aryl and heteroaryl are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; or $R_2$ is —$Ar_2$—$Ar_3$ wherein $Ar_2$ and $Ar_3$ are each independently aryl or heteroaryl each optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, $C_{1-4}$ alkylamino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{1-4}$ haloalkoxy, $C_{1-4}$ haloalkyl, halogen, hydroxyl and nitro; or $R_2$ is a group of Formula (IVB):

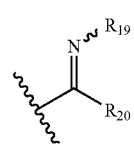

(IVB)

wherein:
$R_{19}$ is H, $C_{1-8}$ alkyl, $C_{3-7}$ cycloalkyl, aryl, heteroaryl or $OR_{21}$; and $R_{20}$ is F, Cl, Br, CN or $NR_{22}R_{23}$; where $R_{21}$ is H, $C_{1-8}$ alkyl or $C_{3-7}$ cycloalkyl, and $R_{22}$ and $R_{23}$ are independently H, $C_{1-8}$ alkyl, $C_{3-7}$ cycloalkyl, aryl or heteroaryl;

or $R_2$ is a group of Formula (IVC):

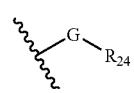

(IVC)

wherein:
G is:
i) —C(O)—, —C(O)$NR_{25}$—, —$NR_{25}$C(O)—, —$NR_{25}$—, —$NR_{25}$C(O)O—, —OC(O)$NR_{25}$—, —$CR_{25}R_{26}NR_{27}$C(O)—, —$CR_{25}R_{26}$C(O)$NR_{27}$—, —C(O)O—, —OC(O)—, —C(S)—, —C(S)$NR_{25}$—, —C(S)O—, —OC(S)—, —$CR_{25}R_{26}$—, —O—, —S—, —S(O)—, —S(O)$_2$— or a bond when D is $CR_2R_3$; or
ii) —$CR_{25}R_{26}$C(O)—, —C(O)—, —$CR_{25}R_{26}$C(O)$NR_{27}$—, —C(O)$NR_{25}$—, —C(O)O—, —C(S)—, —C(S)$NR_{25}$—, —C(S)O—, —$CR_{25}R_{26}$—, —S(O)$_2$—, or a bond when D is $NR_2$;

wherein $R_{25}$, $R_{26}$ and $R_{27}$ are each independently H or $C_{1-8}$ alkyl; and $R_{24}$ is H, $C_{1-8}$ alkyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-4}$ alkoxy, $C_{1-7}$ alkyl, $C_{1-4}$ alkylamino, heteroaryl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, nitro, and phenyl;

provided that Z and U are not both N.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/US2004/022417 include the following compounds according to Formula (IV) (referred to herein as Group D1): 4-[1-(4-Methanesulfonyl-phenyl)-1H-pyrazolo[3,4-d]pyrimidin-4-yloxy]-piperidine-1-carboxylic acid tert-butyl ester; 4-[1-(4-Methanesulfonyl-phenyl)-3-methyl-1H-pyrazolo[3,4-d]pyrimidin-4-yloxy]-piperidine-1-carboxylic acid tert-butyl ester; 4-[1-(4-Methanesulfonyl-phenyl)-3,6-dimethyl-1H-pyrazolo[3,4-d]pyrimidin-4-yloxy]-piperidine-1-carboxylic acid tert-butyl ester; 4-[1-(4-Methanesulfonyl-phenyl)-1H-pyrazolo[3,4-d]pyrimidin-4-yloxy]-piperidine-1-carboxylic acid isobutyl ester; 4-[1-(4-Methanesulfonyl-phenyl)-1H-pyrazolo[3,4-d]pyrimidin-4-yloxy]-piperidine-1-carboxylic acid isopropyl ester; 1-(4-Methanesulfonyl-phenyl)-4-(piperidin-4-yloxy)-1H-pyrazolo[3,4-d]pyrimidine; {4-[1-(4-Methanesulfonyl-phenyl)-1H-pyrazolo[3,4-d]pyrimidin-4-yloxy]-piperidin-1-yl}-pyridin-3-yl-methanone; (3-Fluoro-phenyl)-{4-[1-(4-methanesulfonyl-phenyl)-1H-pyrazolo[3,4-d]pyrimidin-4-yloxy]-piperidin-1-yl}-methanone; (1-tert-Butyl-5-methyl-1H-pyrazol-4-yl)-{4-[1-(4-methanesulfonyl-phenyl)-1H-pyrazolo[3,4-d]pyrimidin-4-yloxy]-piperidin-1-yl}-methanone; (5-tert-Butyl-2-methyl-2H-pyrazol-3-yl)-{4-[1-(4-methanesulfonyl-phenyl)-1H-pyrazolo[3,4-d]pyrimidin-4-yloxy]-piperidin-1-yl}-methanone; 4-[1-(4-Methanesulfonyl-phenyl)-1H-pyrazolo[3,4-d]pyrimidin-4-ylamino]-piperidine-1-carboxylic acid tert-butyl ester; 4-[1-(4-Methanesulfonyl-phenyl)-1H-pyrazolo[3,4-d]pyrimidin-4-ylamino]-piperidine-1-carboxylic acid isopropyl ester; 4-[1-(4-Methanesulfonyl-phenyl)-1H-pyrazolo[3,4-d]pyrimidin-4-ylamino]-piperidine-1-carboxylic acid isobutyl ester; Furan-2-yl-{4-[1-(4-methanesulfonyl-phenyl)-1H-pyrazolo[3,4-d]pyrimidin-4-yloxy]-piperidin-1-yl}-methanone; {4-[1-(4-Methanesulfonyl-phenyl)-1H-pyrazolo[3,4-d]pyrimidin-4-yloxy]-piperidin-1-yl}-(1-methyl-1H-pyrrol-2-yl)-methanone; 2-{4-[1-(4-Methanesulfonyl-phenyl)-1H-pyrazolo[3,4-d]pyrimidin-4-yloxy]-piperidin-1-yl}-1-pyridin-3-yl-ethanone; 2-{4-[1-(4-Methanesulfonyl-phenyl)-1H-pyrazolo[3,4-d]pyrimidin-4-yloxy]-piperidin-1-yl}-1-pyridin-2-yl-ethanone; {4-[1-(4-Methanesulfonyl-phenyl)-1H-pyrazolo[3,4-d]pyrimidin-4-yloxy]-piperidin-1-yl}-(5-methyl-pyridin-3-yl)-methanone; {4-[1-(4-Methanesulfonyl-phenyl)-1H-pyrazolo[3,4-d]pyrimidin-4-yloxy]-piperidin-1-yl}-(2-methyl-pyridin-3-yl)-methanone; {4-[1-(4-Methanesulfonyl-phenyl)-1H-pyrazolo[3,4-d]pyrimidin-4-yloxy]-piperidin-1-yl}-(6-methyl-pyridin-3-yl)-methanone; {4-[1-(4-Methanesulfonyl-phenyl)-1H-pyrazolo[3,4-d]pyrimidin-4-yloxy]-piperidin-1-yl}-(5-methyl-isoxazol-3-yl)-methanone; 2-{4-[1-(4-Methanesulfonyl-phenyl)-1H-pyrazolo[3,4-d]pyrimidin-4-yloxy]-piperidin-1-yl}-1-thiophen-2-yl-ethanone; 4-(1-Benzyl-azetidin-3-yloxy)-1-(4-methanesulfonyl-phenyl)-1H-pyrazolo[3,4-d]pyrimidine; 3-[1-(4-Methanesulfonyl-phenyl)-1H-pyrazolo[3,4-d]pyrimidin-4-ylamino]-piperidine-1-carboxylic acid tert-butyl ester; 1-{4-[1-(4-Methanesulfonyl-phenyl)-1H-pyrazolo[3,4-d]pyrimidin-4-yloxy]-piperidin-1-yl}-3,3-dimethyl-butan-2-one; {4-[1-(4-Methanesulfonyl-phenyl)-1H-pyrazolo[3,4-d]pyrimidin-4-yloxy]-piperidin-1-yl}-pyrazin-2-yl-methanone; {4-[1-(4-Methanesulfonyl-phenyl)-1H-pyrazolo[3,4-d]pyrimidin-4-yloxy]-piperidin-1-yl}-(5-methyl-pyrazin-2-yl)-methanone; {4-[1-(4-Methanesulfonyl-phenyl)-1H-pyrazolo[3,4-d]pyrimidin-4-yloxy]-piperidin-1-yl}-pyrimidin-5-yl-methanone; {4-[1-(4-Methanesulfonyl-phenyl)-1H-pyrazolo[3,4-d]pyrimidin-4-yloxy]-piperidin-1-yl}-pyridazin-4-yl-methanone; {4-[1-(4-Methanesulfonyl-phenyl)-1H-pyrazolo[3,4-d]pyrimidin-4-yloxy]-piperidin-1-yl}-thiophen-2-yl-methanone; (3,4-Dimethyl-isoxazol-5-yl)-{4-[1-(4-methanesulfonyl-phenyl)-1H-pyrazolo[3,4-d]pyrimidin-4-yloxy]-piperidin-1-yl}-methanone; 3-tert-Butoxy-1-{4-[1-(4-methanesulfonyl-phenyl)-1H-pyrazolo[3,4-d]pyrimidin-4-yloxy]-piperidin-1-yl}-propan-1-one; (3-{4-[1-(4-Methanesulfonyl-phenyl)-1H-pyrazolo[3,4-d]pyrimidin-4-yloxy]-piperidin-1-yl}-3-oxo-propyl)-methyl-carbamic acid tert-butyl ester; {4-[1-(4-Methanesulfonyl-phenyl)-1H-pyrazolo[3,4-d]pyrimidin-4-yloxy]-piperidin-1-yl}-(6-trifluoromethyl-pyridin-3-yl)-methanone; {4-[1-(4-Methanesulfonyl-phenyl)-1H-pyrazolo[3,4-d]pyrimidin-4-ylamino]-cyclohexyl}-carbamic acid tert-butyl ester; N-[1-(4-Methanesulfonyl-phenyl)-1H-pyrazolo[3,4-d]pyrimidin-4-yl]-cyclohexane-1,4-diamine; {4-[1-(4-Methanesulfonyl-phenyl)-1H-pyrazolo[3,4-d]pyrimidin-4-yloxy]-piperidin-1-yl}-(4-methyl-[1,2,3]thiadiazol-5-yl)-methanone; (3,5-Dimethyl-isoxazol-4-yl)-{4-[1-(4-methanesulfonyl-phenyl)-1H-pyrazolo[3,4-d]pyrimidin-4-yloxy]-piperidin-1-yl}-methanone; (2,5-Dimethyl-2H-pyrazol-3-yl)-{4-[1-(4-methanesulfonyl-phenyl)-1H-pyrazolo[3,4-d]pyrimidin-4-yloxy]-piperidin-1-yl}-methanone; {4-[1-(4-Methanesulfonyl-phenyl)-1H-pyrazolo[3,4-d]pyrimidin-4-yloxy]-piperidin-1-yl}-(3-methyl-isoxazol-5-yl)-methanone; 4-[1-(4-Methanesulfonyl-phenyl)-1H-pyrazolo[3,4-d]pyrimidin-4-yloxy]-piperidine-1-carbothioic acid pyridin-4-ylamide; N-{4-[1-(4-Methanesulfonyl-phenyl)-1H-pyrazolo[3,4-d]pyrimidin-4-ylamino]-cyclohexyl}-nicotinamide; 3-tert-Butoxy-N-{4-[1-(4-methanesulfonyl-phenyl)-1H-pyrazolo[3,4-d]pyrimidin-4-ylamino]-cyclohexyl}-propionamide; {4-[1-(4-Methanesulfonyl-phenyl)-1H-pyrazolo[3,4-d]pyrimidin-4-ylamino]-cyclohexyl}-carbamic acid tert-butyl ester; (3,5-

Dimethyl-isoxazol-4-yl)-{4-[1-(4-methanesulfonyl-phenyl)-1H-pyrazolo[3,4-d]pyrimidin-4-yloxy]-piperidin-1-yl}-methanone; 4-[1-(3,5-Bis-trifluoromethyl-phenyl)-1H-pyrazolo[3,4-d]pyrimidin-4-yloxy]-piperidine-1-carboxylic acid tert-butyl ester; 3-[1-(4-Methanesulfonyl-phenyl)-1H-pyrazolo[3,4-d]pyrimidin-4-yloxy]-azetidine-1-carboxylic acid isopropyl ester; 4-[1-(4-Methanesulfonyl-phenyl)-1H-pyrazolo[3,4-d]pyrimidin-4-yloxy]-piperidine-1-carboxylic acid butyl ester; 4-[1-(4-Methanesulfonyl-phenyl)-1H-pyrazolo[3,4-d]pyrimidin-4-yloxy]-piperidine-1-carboxylic acid propyl ester; 4-[1-(3-Fluoro-phenyl)-1H-pyrazolo[3,4-d]pyrimidin-4-yloxy]-piperidine-1-carboxylic acid tert-butyl ester; 4-[1-(2,4-Difluoro-phenyl)-1H-pyrazolo[3,4-d]pyrimidin-4-yloxy]-piperidine-1-carboxylic acid tert-butyl ester; {4-[1-(2,4-Difluoro-phenyl)-1H-pyrazolo[3,4-d]pyrimidin-4-ylamino]-cyclohexyl}-carbamic acid tert-butyl ester; {4-[1-(3-Fluoro-phenyl)-1H-pyrazolo[3,4-d]pyrimidin-4-ylamino]-cyclohexyl}-carbamic acid tert-butyl ester; N-[1-(4-Methanesulfonyl-phenyl)-1H-pyrazolo[3,4-d]pyrimidin-4-yl]-cyclohexane-1,4-diamine; {3-[1-(4-Methanesulfonyl-phenyl)-1H-pyrazolo[3,4-d]pyrimidin-4-ylamino]-piperidin-1-yl}-(6-methyl-pyridin-3-yl)-methanone; {3-[1-(4-Methanesulfonyl-phenyl)-1H-pyrazolo[3,4-d]pyrimidin-4-ylamino]-piperidin-1-yl}-(2-methyl-pyridin-3-yl)-methanone; {3-[1-(4-Methanesulfonyl-phenyl)-1H-pyrazolo[3,4-d]pyrimidin-4-ylamino]-piperidin-1-yl}-(5-methyl-pyridin-3-yl)-methanone; {3-[1-(4-Methanesulfonyl-phenyl)-1H-pyrazolo[3,4-d]pyrimidin-4-ylamino]-piperidin-1-yl}-pyridin-3-yl-methanone; {3-[1-(4-Methanesulfonyl-phenyl)-1H-pyrazolo[3,4-d]pyrimidin-4-ylamino]-piperidin-1-yl}-(1-methyl-1H-pyrrol-3-yl)-methanone; {4-[1-(4-Methanesulfonyl-phenyl)-1H-pyrazolo[3,4-d]pyrimidin-4-yloxy]-cyclohexyl}-carbamic acid tert-butyl ester; N-[1-(2,4-Difluoro-phenyl)-1H-pyrazolo[3,4-d]pyrimidin-4-yl]-cyclohexane-1,4-diamine; {4-[1-(4-Methanesulfonyl-phenyl)-1H-pyrazolo[3,4-d]pyrimidin-4-yloxy]-piperidin-1-yl}-(4-trifluoromethyl-pyridin-3-yl)-methanone; 4-[1-(4-Methanesulfonyl-phenyl)-1H-pyrazolo[3,4-d]pyrimidin-4-yloxy]-piperidine-1-carboxylic acid cyclohexyl ester; 4-[1-(4-Methanesulfonyl-phenyl)-1H-pyrazolo[3,4-d]pyrimidin-4-yloxy]-piperidine-1-carboxylic acid tetrahydro-pyran-4-yl ester; 4-[1-(4-Methanesulfonyl-phenyl)-1H-pyrazolo[3,4-d]pyrimidin-4-yloxy]-piperidine-1-carboxylic acid cyclopentyl ester; 4-[1-(4-Methanesulfonyl-phenyl)-1H-pyrazolo[3,4-d]pyrimidin-4-yloxy]-piperidine-1-carboxylic acid tetrahydro-furan-3-yl ester; 4-[1-(4-Methanesulfonyl-phenyl)-1H-pyrazolo[3,4-d]pyrimidin-4-yloxy]-piperidine-1-carboxylic acid tetrahydro-furan-3-yl ester; 4-[1-(4-Methanesulfonyl-phenyl)-1H-pyrazolo[3,4-d]pyrimidin-4-yloxy]-piperidine-1-carboxylic acid tetrahydro-thiopyran-4-yl ester; 4-[1-(4-Methanesulfonyl-phenyl)-1H-pyrazolo[3,4-d]pyrimidin-4-yloxy]-piperidine-1-carboxylic acid cyclobutyl ester; (6-tert-Butyl-pyridin-3-yl)-{4-[1-(4-methanesulfonyl-phenyl)-1H-pyrazolo[3,4-d]pyrimidin-4-yloxy]-piperidin-1-yl}-methanone; (4-{[1-(4-Methanesulfonyl-phenyl)-1H-pyrazolo[3,4-d]pyrimidin-4-ylamino]-methyl}-cyclohexyl)-carbamic acid tert-butyl ester; N-{4-[1-(4-Methanesulfonyl-phenyl)-1H-pyrazolo[3,4-d]pyrimidin-4-ylamino]-cyclohexylmethyl}-nicotinamide; N-{4-[1-(4-Methanesulfonyl-phenyl)-1H-pyrazolo[3,4-d]pyrimidin-4-ylamino]-cyclohexylmethyl}-6-methyl-nicotinamide; 4-[1-(2-Fluoro-4-methanesulfonyl-phenyl)-1H-pyrazolo[3,4-d]pyrimidin-4-yloxy]-piperidine-1-carboxylic acid tert-butyl ester; 4-({[1-(4-Methanesulfonyl-phenyl)-1H-pyrazolo[3,4-d]pyrimidin-4-yl]-methyl-amino}-methyl)-piperidine-1-carboxylic acid tert-butyl ester; 4-{[1-(4-Methanesulfonyl-phenyl)-1H-pyrazolo[3,4-d]pyrimidin-4-ylamino]-methyl}-piperidine-1-carboxylic acid tert-butyl ester; 3-{[1-(4-Methanesulfonyl-phenyl)-1H-pyrazolo[3,4-d]pyrimidin-4-ylamino]-methyl}-piperidine-1-carboxylic acid tert-butyl ester; 4-({Ethyl-[1-(4-methanesulfonyl-phenyl)-1H-pyrazolo[3,4-d]pyrimidin-4-yl]-amino}-methyl)-piperidine-1-carboxylic acid tert-butyl ester; 4-{1-[2-(2-Dimethylamino-ethoxy)-4-methanesulfonyl-phenyl]-1H-pyrazolo[3,4-d]pyrimidin-4-yloxy}-piperidine-1-carboxylic acid tert-butyl ester; 3-[1-(2-Fluoro-4-methanesulfonyl-phenyl)-1H-pyrazolo[3,4-d]pyrimidin-4-ylamino]-piperidine-1-carboxylic acid tert-butyl ester; 4-[1-(4-Methanesulfonyl-phenyl)-1H-pyrazolo[3,4-d]pyrimidin-4-yloxy]-piperidine-1-carboxylic acid pyridin-3-ylmethyl esteracid tert-butyl ester; 4-[1-(4-Methanesulfonyl-phenyl)-1H-pyrazolo[3,4-d]pyrimidin-4-yloxy]-piperidine-1-carboxylic acid 2-pyridin-3-yl-ethyl ester; 4-[1-(4-Methanesulfonyl-phenyl)-1H-pyrazolo[3,4-d]pyrimidin-4-yloxy]-piperidine-1-carboxylic acid 3-pyridin-3-yl-propyl ester; 4-[1-(4-Methanesulfonyl-phenyl)-1H-pyrazolo[3,4-d]pyrimidin-4-yloxy]-piperidine-1-carboxylic acid 2-dimethylamino-ethyl ester; 4-{[1-(4-Methanesulfonyl-phenyl)-1H-pyrazolo[3,4-d]pyrimidin-4-yl]-methyl-amino}-piperidine-1-carboxylic acid tert-butyl ester; 4-[1-(2,4-Difluoro-phenyl)-1H-pyrazolo[3,4-d]pyrimidin-4-yloxy]-piperidine-1-carboxylic acid tert-butyl ester; 4-({Ethyl-[1-(2-fluoro-4-methanesulfonyl-phenyl)-1H-pyrazolo[3,4-d]pyrimidin-4-yl]-amino}-methyl)-piperidine-1-carboxylic acid isopropyl ester; 4-({Ethyl-[1-(2-fluoro-4-methanesulfonyl-phenyl)-1H-pyrazolo[3,4-d]pyrimidin-4-yl]-amino}-methyl)-piperidine-1-carboxylic acid tert-butyl ester; 4-[6-Dimethylamino-1-(4-methanesulfonyl-phenyl)-1H-pyrazolo[3,4-d]pyrimidin-4-yloxy]-piperidine-1-carboxylic acid tert-butyl ester; 1-(4-{[1-(4-Methanesulfonyl-phenyl)-1H-pyrazolo[3,4-d]pyrimidin-4-yl]-methyl-amino}-piperidin-1-yl)-3,3-dimethyl-butan-2-one; 4-{[1-(4-Methanesulfonyl-phenyl)-1H-pyrazolo[3,4-d]pyrimidin-4-yl]-methyl-amino}-piperidine-1-carboxylic acid cyclobutyl ester; and 4-[({1-[4-(2-Methanesulfonyl-ethyl)-phenyl]-1H-pyrazolo[3,4-d]pyrimidin-4-yl}-methyl-amino)-methyl]-piperidine-1-carboxylic acid tert-butyl ester.

Specific examples of GPR119 agonists disclosed in International Application No. PCT/US2004/022417 include the following compounds according to Formula (IV) (referred to herein as Group D2): 4-({[1-(2,5-Difluoro-phenyl)-1H-pyrazolo[3,4-d]pyrimidin-4-yl]-methyl-amino}-methyl)-piperidine-1-carboxylic acid tert-butyl ester; 2-{4-[1-(2-Fluoro-4-methanesulfonyl-phenyl)-1H-pyrazolo[3,4-d]pyrimidin-4-yloxy]-piperidin-1-yl}-1-(4-trifluoromethoxy-phenyl)-ethanone; 2-{4-[1-(2-Fluoro-4-methanesulfonyl-phenyl)-1H-pyrazolo[3,4-d]pyrimidin-4-yloxy]-piperidin-1-yl}-1-(3-fluoro-phenyl)-ethanone; 2-{4-[1-(2-Fluoro-4-methanesulfonyl-phenyl)-1H-pyrazolo[3,4-d]pyrimidin-4-yloxy]-piperidin-1-yl}-1-pyridin-2-yl-ethanone; (2,5-Dimethyl-furan-3-yl)-{4-[1-(4-methanesulfonyl-phenyl)-1H-pyrazolo[3,4-d]pyrimidin-4-yloxy]-piperidin-1-yl}-methanone; 4-({(2-Dimethylamino-ethyl)-[1-(4-methanesulfonyl-phenyl)-1H-pyrazolo[3,4-d]pyrimidin-4-yl]-amino}-methyl)-piperidine-1-carboxylic acid tert-butyl ester; 4-({(2-Dimethylamino-ethyl)-[1-(2-fluoro-4-methanesulfonyl-phenyl)-1H-pyrazolo[3,4-d]pyrimidin-4-yl]-amino}-methyl)-piperidine-1-carboxylic acid tert-butyl ester; 4-[1-(2-Dimethylamino-4-methanesulfonyl-phenyl)-1H-pyrazolo[3,4-d]pyrimidin-4-yloxy]-piperidine-1-carboxylic acid tert-butyl ester; 4-(2-{Ethyl-[1-(4-methanesulfonyl-phenyl)-1H-pyrazolo[3,4-d]pyrimidin-4-yl]-amino}-ethyl)-piperazine-1-carboxylic acid tert-butyl ester; 4-[1-(4-Methanesulfonyl-phenyl)-1H-pyrazolo[3,4-d]pyrimidin-4-ylsulfanyl]-piperidine-1-carboxylic acid tert-butyl ester; 4-{2-[1-(4-Methanesulfonyl-phenyl)-1H-pyrazolo[3,4-d]pyrimidin-4-yloxy]-ethyl}-piperazine-1-carboxylic acid ethyl ester; 4-{2-[1-(4-Methanesulfonyl-phenyl)-1H-pyrazolo[3,4-d]pyrimidin-4-yloxy]-propyl}-piperazine-1-carboxylic acid ethyl ester; 4-[1-(4-Methanesulfonyl-phenyl)-1H-pyrazolo[3,4-d]pyrimidine-4-sulfinyl]-piperidine-1-carboxylic acid tert-butyl ester; 4-[1-(4-Methanesulfonyl-phenyl)-1H-pyrazolo[3,4-d]pyrimidine-4-sulfonyl]-piperidine-1-carboxylic acid tert-butyl ester; 4-[1-(2-Fluoro-4-methanesulfonyl-phenyl)-1H-pyrazolo[3,4-d]pyrimidin-4-ylsulfanyl]-piperidine-1-carboxylic acid tert-butyl ester; 4-[1-(2-Fluoro-4-methanesulfonyl-phenyl)-1H-pyrazolo[3,4-d]pyrimidin-4-ylsulfanyl]-piperidine-1-carboxylic acid butyl ester; 4-[1-(2-Fluoro-4-methanesulfonyl-phenyl)-1H-pyrazolo[3,4-d]pyrimidin-4-ylsulfanyl]-piperidine-1-carboxylic acid 2-methoxy-ethyl ester; 4-[1-(2-Fluoro-4-methanesulfonyl-phenyl)-1H-pyrazolo[3,4-d]pyrimidin-4-ylsulfanyl]-piperidine-1-carboxylic acid 3,3-dimethyl-butyl ester; 4-[1-(2-Fluoro-4-methanesulfonyl-phenyl)-1H-pyrazolo[3,4-d]pyrimidin-4-ylsulfanyl]-piperidine-1-carboxylic acid 4-methyl-pentyl ester; 4-[1-(2-Fluoro-4-methanesulfonyl-phenyl)-1H-pyrazolo[3,4-d]pyrimidin-4-ylsulfanyl]-piperidine-1-carboxylic acid cyclopropylmethyl ester; 4-[1-(2-Fluoro-4-methanesulfonyl-phenyl)-1H-pyrazolo[3,4-d]pyrimidin-4-ylsulfanyl]-piperidine-1-carboxylic acid cyclobutylmethyl ester; 4-[1-(2-Fluoro-4-methanesulfonyl-phenyl)-1H-pyrazolo[3,4-d]pyrimidin-4-ylsulfanyl]-piperidine-1-carboxylic acid 2-cyclopropyl-ethyl ester; (5-Bromo-furan-2-yl)-{4-[1-(2-fluoro-4-methanesulfonyl-phenyl)-1H-pyrazolo[3,4-d]pyrimidin-4-ylsulfanyl]-piperidin-1-yl}-methanone; {4-[1-(4-Methanesulfonyl-phenyl)-1H-pyrazolo[3,4-d]pyrimidin-4-yloxy]-piperidin-1-yl}-(5-morpholin-4-ylmethyl-furan-2-yl)-methanone; 4-[1-(4-Methanesulfonyl-phenyl)-1H-pyrazolo[3,4-d]pyrimidin-4-yloxy]-piperidine-1-carboxylic acid pentyl ester; 4-[1-(4-Methanesulfonyl-phenyl)-1H-pyrazolo[3,4-d]pyrimidin-4-yloxy]-piperidine-1-carboxylic acid 1-ethyl-propyl ester; 4-[1-(4-Methanesulfonyl-phenyl)-1H-pyrazolo[3,4-d]pyrimidin-4-yloxy]-piperidine-1-carboxylic acid 2-ethyl-butyl ester; 4-[1-(4-Methanesulfonyl-phenyl)-1H-pyrazolo[3,4-d]pyrimidin-4-yloxy]-piperidine-1-carboxylic acid cyclopentylmethyl ester; 4-[1-(4-Methanesulfonyl-phenyl)-1H-pyrazolo[3,4-d]pyrimidin-4-yloxy]-piperidine-1-carboxylic acid 2-pyrrolidin-1-yl-ethyl ester; 4-[1-(4-Methanesulfonyl-phenyl)-1H-pyrazolo[3,4-d]pyrimidin-4-yloxy]-piperidine-1-carboxylic acid 2-morpholin-4-yl-ethyl ester; 4-[1-(4-Methanesulfonyl-phenyl)-1H-pyrazolo[3,4-d]pyrimidin-4-yloxy]-piperidine-1-carboxylic acid ethyl ester; 4-[1-(4-Methanesulfonyl-phenyl)-1H-pyrazolo[3,4-d]pyrimidin-4-yloxy]-piperidine-1-carboxylic acid 2,2-dimethyl-propyl ester; (5-Butyl-pyridin-2-yl)-{4-[1-(4-methanesulfonyl-phenyl)-1H-pyrazolo[3,4-d]pyrimidin-4-yloxy]-piperidin-1-yl}-methanone; Ethyl-[1-(2-fluoro-4-methanesulfonyl-phenyl)-1H-pyrazolo[3,4-d]pyrimidin-4-yl]-(3,4,5,6-tetrahydro-2H-[1,2']bipyridinyl-4-ylmethyl)-amine; Ethyl-[1-(2-fluoro-4-methanesulfonyl-phenyl)-1H-pyrazolo[3,4-d]pyrimidin-4-yl]-(5'-trifluoromethyl-3,4,5,6-tetrahydro-2H-[1,2']bipyridinyl-4-ylmethyl)-amine; [1-(4-Methanesulfonyl-phenyl)-1H-pyrazolo[3,4-d]pyrimidin-4-yl]-(5'-trifluoromethyl-3,4,5,6-tetrahydro-2H-[1,2']bipyridinyl-4-yl)-amine; 4-[1-(2-Fluoro-4-methanesulfonyl-phenyl)-1H-pyrazolo[3,4-d]pyrimidin-4-yloxy]-piperidine-1-carboxylic acid isopropyl ester; 5'-Fluoro-4-[1-(4-methanesulfonyl-phenyl)-1H-pyrazolo[3,4-d]pyrimidin-4-yloxy]-3,4,5,6-tetrahydro-2H-[1,2']bipyridinyl; 4-[1-(4-Methanesulfonyl-phenyl)-1H-pyrazolo[3,4-d]pyrimidin-4-yloxy]-5'-methyl-3,4,5,6-tetrahydro-2H-[1,2']bipyridinyl; 4-[1-(4-Methanesulfonyl-phenyl)-H-pyrazolo[3,4-d]pyrimidin-4-yloxy]-6'-trifluoromethyl-3,4,5,6-tetrahydro-2H-[1,2']bipyridinyl; [1-(2-Fluoro-4-methanesulfonyl-phenyl)-1H-pyrazolo[3,4-d]pyrimidin-4-yl]-[1-(3-isopropyl-[1,2,4]oxadiazol-5-ylmethyl)-pyrrolidin-3-yl]-amine; [1-(2-Fluoro-4-methanesulfonyl-phenyl)-1H-pyrazolo[3,4-d]pyrimidin-4-yl]-[1-(3-isopropyl-[1,2,4]oxadiazol-5-ylmethyl)-pyrrolidin-3-yl]-amine; (4-Ethyl-pyridin-2-yl)-{4-[1-(2-fluoro-4-methanesulfonyl-phenyl)-1H-pyrazolo[3,4-d]pyrimidin-4-yloxy]-piperidin-1-yl}-methanone; 1-(2-Fluoro-4-methanesulfonyl-phenyl)-4-[1-(3-isopropyl-[1,2,4]oxadiazol-5-ylmethyl)-pyrrolidin-3-yloxy]-1H-pyrazolo[3,4-d]pyrimidine; 1-(2-Fluoro-4-methanesulfonyl-phenyl)-4-[1-(3-isopropyl-[1,2,4]oxadiazol-5-ylmethyl)-piperidin-4-yloxy]-1H-pyrazolo[3,4-d]pyrimidine; (5'-Fluoro-3,4,5,6-tetrahydro-2H-[1,2']bipyridinyl; -4-yl)-[1-(4-methanesulfonyl-phenyl)-1H-pyrazolo[3,4-d]pyrimidin-4-yl]-amine; (5-Bromo-pyridin-3-yl)-{4-[1-(2-fluoro-4-methanesulfonyl-phenyl)-1H-pyrazolo[3,4-d]pyrimidin-4-yloxy]-piperidin-1-yl}-methanone; 3-[1-(2-Fluoro-4-methanesulfonyl-phenyl)-1H-pyrazolo[3,4-d]pyrimidin-4-yloxy]-pyrrolidine-1-carboxylic acid tert-butyl ester; 3-[1-(4-Methanesulfonyl-phenyl)-1H-pyrazolo[3,4-d]pyrimidin-4-ylamino]-pyrrolidine-1-carboxylic acid tert-butyl ester; 3-[1-(2-Fluoro-4-methanesulfonyl-phenyl)-1H-pyrazolo[3,4-d]pyrimidin-4-ylamino]-pyrrolidine-1-carboxylic acid isopropyl ester; (6-Chloro-pyridin-3-yl)-{4-[1-(4-methanesulfonyl-phenyl)-1H-pyrazolo[3,4-d]pyrimidin-4-yloxy]-piperidin-1-yl}-methanone; (5-Chloro-pyridin-3-yl)-{4-[1-(4-methanesulfonyl-phenyl)-1H-pyrazolo[3,4-d]pyrimidin-4-yloxy]-piperidin-1-yl}-methanone; {4-[1-(4-Methanesulfonyl-phenyl)-1H-pyrazolo[3,4-d]pyrimidin-4-yloxy]-piperidin-1-yl}-(1-methyl-3-trifluoromethyl-1H-pyrazol-4-yl)-methanone; (2-Chloro-pyridin-4-yl)-{4-[1-(4-methanesulfonyl-phenyl)-1H-pyrazolo[3,4-d]pyrimidin-4-yloxy]-piperidin-1-yl}-methanone; (4-Hydroxy-3-methoxy-phenyl)-{4-[1-(4-methanesulfonyl-phenyl)-1H-pyrazolo[3,4-d]pyrimidin-4-yloxy]-piperidin-1-yl}-methanone; (4-Chloro-3-nitro-phenyl)-{4-[1-(4-methanesulfonyl-phenyl)-1H-pyrazolo[3,4-d]pyrimidin-4-yloxy]-piperidin-1-yl}-methanone; 1-{4-[1-(4-Methanesulfonyl-phenyl)-1H-pyrazolo[3,4-d]pyrimidin-4-yloxy]-piperidin-1-yl}-3-methyl-butan-1-one; {4-[1-(4-Methanesulfonyl-phenyl)-1H-pyrazolo[3,4-d]pyrimidin-4-yloxy]-piperidin-1-yl}-(6-pyrazol-1-yl-pyridin-3-yl)-methanone; (2-Hydroxy-pyridin-3-yl)-{4-[1-(4-methanesulfonyl-phenyl)-1H-pyrazolo[3,4-d]pyrimidin-4-yloxy]-piperidin-1-yl}-methanone; (5,6-Dichloro-pyridin-3-yl)-{4-[1-(4-methanesulfonyl-phenyl)-1H-pyrazolo[3,4-d]pyrimidin-4-yloxy]-piperidin-1-yl}-methanone; (5-Bromo-pyridin-3-yl)-{4-[1-(4-methanesulfonyl-phenyl)-1H-pyrazolo[3,4-d]pyrimidin-4-yloxy]-piperidin-1-yl}-methanone; 5-{4-[1-(4-Methanesulfonyl-phenyl)-1H-pyrazolo[3,4-d]pyrimidin-4-yloxy]-piperidine-1-carbonyl}-nicotinic acid; (1H-Imidazol-4-yl)-{4-[1-(4-methanesulfonyl-phenyl)-1H-pyrazolo[3,4-d]pyrimidin-4-yloxy]-piperidin-1-yl}-methanone; 3-[1-(4-Methanesulfonyl-phenyl)-1H-pyrazolo[3,4-d]pyrimidin-4-yloxy]-pyrrolidine-1-carboxylic acid tert-butyl ester; {4-[1-(4-Methanesulfonyl-phenyl)-1H-pyrazolo[3,4-d]pyrimidin-4-yloxy]-piperidin-1-yl}-(6-pyrrolidin-1-yl-pyridin-3-yl)-methanone; (6-Isobutylamino-pyridin-3-yl)-{4-[1-(4-methanesulfonyl-phenyl)-1H-pyrazolo[3,4-d]pyrimidin-4-yloxy]-piperidin-1-yl}-methanone; (6-Ethylamino-pyridin-3-yl)-{4-[1-(4-methanesulfonyl-phenyl)-1H-pyrazolo[3,4-d]pyrimidin-4-yloxy]-piperidin-1-yl}-methanone; (6-Cyclobutylamino-pyridin-3-yl)-{4-[1-(4-methanesulfonyl-phenyl)-1H-pyrazolo[3,4-d]pyrimidin-4-yloxy]-piperidin-1-yl}-methanone; (6-Isopropylamino-pyridin-3-yl)-{4-[1-(4-methanesulfonyl-phenyl)-1H-pyrazolo[3,4-d]pyrimidin-4-yloxy]-piperidin-1-yl}-methanone; [6-(1-Ethyl-propylamino)-pyridin-3-yl]-{4-[1-(4-methanesulfonyl-phenyl)-1H-pyrazolo[3,4-d]pyrimidin-4-yloxy]-piperidin-1-yl}-methanone; {4-[1-(4-Methanesulfonyl-phenyl)-1H-pyrazolo[3,4-d]pyrimidin-4-yloxy]-piperidin-1-yl}-[6-(1-propyl-butylamino)-pyridin-3-yl]-methanone; 5-Benzyloxy-2-{4-[1-(4-methanesulfonyl-phenyl)-1H-pyrazolo[3,4-d]pyrimidin-4-yloxy]-piperidine-1-carbonyl}-pyran-4-one; Benzo[c]isoxazol-3-yl-{4-[1-(4-methanesulfonyl-phenyl)-1H-pyrazolo[3,4-d]pyrimidin-4-yloxy]-piperidin-1-yl}-methanone; (4-Chloro-pyridin-2-yl)-{4-[1-(4-methanesulfonyl-phenyl)-1H-pyrazolo[3,4-d]pyrimidin-4-yloxy]-piperidin-1-yl}-methanone; (4-Iodo-pyridin-2-yl)-{4-[1-(4-methanesulfonyl-phenyl)-1H-pyrazolo[3,4-d]pyrimidin-4-yloxy]-piperidin-1-yl}-methanone; 1-{4-[1-(4-Methanesulfonyl-phenyl)-1H-pyrazolo[3,4-d]pyrimidin-4-yloxy]-piperidin-1-yl}-butan-2-one; 2-(5-Bromo-pyridin-3-yl)-1-{4-[1-(4-methanesulfonyl-phenyl)-1H-pyrazolo[3,4-d]pyrimidin-4-yloxy]-piperidin-1-yl}-ethanone; (6-Fluoro-pyridin-2-yl)-{4-[1-(4-methanesulfonyl-phenyl)-1H-pyrazolo[3,4-d]pyrimidin-4-yloxy]-piperidin-1-yl}-methanone; (5-Fluoro-pyridin-2-yl)-{4-[1-(4-methanesulfonyl-phenyl)-1H-pyrazolo[3,4-d]pyrimidin-4-yloxy]-piperidin-1-yl}-methanone; (6-Chloro-pyridin-2-yl)-{4-[1-(4-methanesulfonyl-phenyl)-1H-pyrazolo[3,4-d]pyrimidin-4-yloxy]-piperidin-1-yl}-methanone; (2-Chloro-5-fluoro-pyridin-3-yl)-{4-[1-(4-methanesulfonyl-phenyl)-1H-pyrazolo[3,4-d]pyrimidin-4-yloxy]-piperidin-1-yl}-methanone; {4-[1-(4-Methanesulfonyl-phenyl)-1H-pyrazolo[3,4-d]pyrimidin-4-yloxy]-piperidin-1-yl}-[5-(2-methyl-pyrrolidin-1-ylmethyl)-pyridin-3-yl]-methanone; {4-[1-(4-Methanesulfonyl-phenyl)-1H-pyrazolo[3,4-d]pyrimidin-4-yloxy]-piperidin-1-yl}-(6-methyl-pyridin-2-yl)-methanone; 5-{4-[1-(4-Methanesulfonyl-phenyl)-1H-pyrazolo[3,4-d]pyrimidin-4-yloxy]-piperidine-1-carbonyl}-nicotinonitrile; {4-[1-(4-Methanesulfonyl-phenyl)-1H-pyrazolo[3,4-d]pyrimidin-4-yloxy]-piperidin-1-yl}-(4-methoxy-pyridin-2-yl)-methanone; (2-Fluoro-pyridin-4-yl)-{4-[1-(4-methanesulfonyl-phenyl)-1H-pyrazolo[3,4-d]pyrimidin-4-yloxy]-piperidin-1-yl}-methanone; (2-Fluoro-pyridin-3-yl)-{4-[1-(4-methanesulfonyl-phenyl)-1H-pyrazolo[3,4-d]pyrimidin-4-yloxy]-piperidin-1-yl}-methanone; (6-Fluoro-pyridin-3-yl)-{4-[1-(4-methanesulfonyl-phenyl)-1H-pyrazolo[3,4-d]pyrimidin-4-yloxy]-piperidin-1-yl}-methanone; {4-[1-(4-Methanesulfonyl-phenyl)-1H-pyrazolo[3,4-d]pyrimidin-4-yloxy]-piperidin-1-yl}-(4-methoxy-thiophen-3-yl)-methanone; 2-{4-[1-(4-Methanesulfonyl-phenyl)-1H-pyrazolo[3,4-d]pyrimidin-4-yloxy]-piperidine-1-carbonyl}-pyran-4-one; (5-Ethyl-pyridin-2-yl)-{4-[1-(2-fluoro-4-methanesulfonyl-phenyl)-1H-pyrazolo[3,4-d]pyrimidin-4-yloxy]-piperidin-1-yl}-methanone; (4-Ethoxy-phenyl)-{4-[1-(2-fluoro-4-methanesulfonyl-phenyl)-1H-pyrazolo[3,4-d]pyrimidin-4-yloxy]-piperidin-1-yl}-methanone; {4-[1-(4-Methanesulfonyl-phenyl)-1H-pyrazolo[3,4-d]pyrimidin-4-yloxy]-piperidin-1-yl}-(5-pyridin-2-yl-thiophen-2-yl)-methanone; (5-Amino-pyridin-2-yl)-{4-[1-(4-methanesulfonyl-phenyl)-1H-pyrazolo[3,4-d]pyrimidin-4-yloxy]-piperidin-1-yl}-methanone; (5-Amino-pyridin-2-yl)-{4-[1-(2-fluoro-4-methanesulfonyl-phenyl)-1H-pyrazolo[3,4-d]pyrimidin-4-yloxy]-piperidin-1-yl}-methanone; {4-[1-(2-Fluoro-4-methanesulfonyl-phenyl)-1H-pyrazolo[3,4-d]pyrimidin-4-yloxy]-piperidin-1-yl}-[5-(3-methyl-butylamino)-pyridin-2-yl]-methanone; {4-[1-(2-Fluoro-4-methanesulfonyl-phenyl)-1H-pyrazolo[3,4-d]pyrimidin-4-yloxy]-piperidin-1-yl}-(4-trifluoromethoxy-phenyl)-methanone; (5-Butyl-pyridin-2-yl)-{4-[1-(2-fluoro-4-methanesulfonyl-phenyl)-1H-pyrazolo[3,4-d]pyrimidin-4-yloxy]-piperidin-1-yl}-methanone; (5-Ethylamino-pyridin-2-yl)-{4-[1-(2-fluoro-4-methanesulfonyl-phenyl)-1H-pyrazolo[3,4-d]pyrimidin-4-yloxy]-piperidin-1-yl}-methanone; {4-[1-(2-Fluoro-4-methanesulfonyl-phenyl)-1H-pyrazolo[3,4-d]pyrimidin-4-yloxy]-piperidin-1-yl}-(5-isopropoxymethyl-pyridin-2-yl)-methanone; (4-Difluoromethoxy-phenyl)-{4-[1-(2-fluoro-4-methanesulfonyl-phenyl)-1H-pyrazolo[3,4-d]pyrimidin-4-yloxy]-piperidin-1-yl}-methanone; {4-[1-(2-Fluoro-4-methanesulfonyl-phenyl)-1H-pyrazolo[3,4-d]pyrimidin-4-yloxy]-piperidin-1-yl}-(5-isopropoxy-pyridin-2-yl)-methanone; 5-{4-[1-(4-Methanesulfonyl-phenyl)-1H-pyrazolo[3,4-d]pyrimidin-4-yloxy]-piperidine-1-carbonyl}-pyridine-2-carboxylic acid methyl ester; {4-[1-(4-Methanesulfonyl-phenyl)-1H-pyrazolo[3,4-d]pyrimidin-4-yloxy]-piperidin-1-yl}-acetic acid ethyl ester; {4-[1-(2-Fluoro-4-methanesulfonyl-phenyl)-1H-pyrazolo[3,4-d]pyrimidin-4-yloxy]-piperidin-1-yl}-(3-trifluoromethoxy-phenyl)-methanone; 1-(2-Fluoro-4-methanesulfonyl-phenyl)-4-[1-(3-isopropyl-[1,2,4]oxadiazol-5-yl)-piperidin-4-yloxy]-1H-pyrazolo[3,4-d]pyrimidine; 1-(4-Chloro-phenyl)-2-{4-[1-(4-methanesulfonyl-phenyl)-1H-pyrazolo[3,4-d]pyrimidin-4-yloxy]-piperidin-1-yl}-ethanone; 2-{4-[1-(4-Methanesulfonyl-phenyl)-1H-pyrazolo[3,4-d]pyrimidin-4-yloxy]-piperidin-1-yl}-1-(3-trifluoromethyl-phenyl)-ethanone; 4-[1-(2-Fluoro-4-methanesulfonyl-phenyl)-1H-pyrazolo[3,4-d]pyrimidin-4-yloxy]-5'-isopropoxy-3,4,5,6-tetrahydro-2H-[1,2']bipyridinyl; 1-(4-Methanesulfonyl-phenyl)-4-[1-(4-trifluoromethoxy-phenyl)-piperidin-4-yloxy]-1H-pyrazolo[3,4-d]pyrimidine; 1-(2-Fluoro-4-methanesulfonyl-phenyl)-4-[1-(4-trifluoromethoxy-phenyl)-piperidin-4-yloxy]-1H-pyrazolo[3,4-d]pyrimidine; 1-(4-Chloro-3-methyl-phenyl)-2-{4-[1-(4-methanesulfonyl-phenyl)-1H-pyrazolo[3,4-d]pyrimidin-4-yloxy]-piperidin-1-yl}-ethanone; 1-(3,4-Dichloro-phenyl)-2-{4-[1-(4-methanesulfonyl-phenyl)-1H-pyrazolo[3,4-d]pyrimidin-4-yloxy]-piperidin-1-yl}-ethanone; 5'-Bromo-4-[1-(4-methanesulfonyl-phenyl)-1H-pyrazolo[3,4-d]pyrimidin-4-yloxy]-3,4,5,6-tetrahydro-2H-[1,2']bipyridinyl; 1-(2-Fluoro-4-methanesulfonyl-phenyl)-4-[1-(3-trifluoromethoxy-phenyl)-piperidin-4-yloxy]-1H-pyrazolo[3,4-d]pyrimidine; 4-[1-(4-Methanesulfonyl-phenyl)-1H-pyrazolo[3,4-d]pyrimidin-4-yloxy]-5'-trifluoromethyl-3,4,5,6-tetrahydro-2H-[1,2']bipyridinyl; 1-(2,4-Dimethoxy-phenyl)-2-{4-[1-(4-methanesulfonyl-phenyl)-1H-pyrazolo[3,4-d]pyrimidin-4-yloxy]-piperidin-1-yl}-ethanone; 1-(4-Difluoromethoxy-phenyl)-2-{4-[1-(4-methanesulfonyl-phenyl)-1H-pyrazolo[3,4-d]pyrimidin-4-yloxy]-piperidin-1-yl}-ethanone; 1-(4-Diethylamino-phenyl)-2-{4-[1-(4-methanesulfonyl-phenyl)-1H-pyrazolo[3,4-d]pyrimidin-4-yloxy]-piperidin-1-yl}-ethanone; (2-{4-[1-(2-Fluoro-4-methanesulfonyl-phenyl)-1H-pyrazolo[3,4-d]pyrimidin-4-yloxy]-piperidin-1-yl}-5-methyl-pyrimidin-4-yl)-dimethyl-amine; 1-(2-Fluoro-4-methanesulfonyl-phenyl)-4-[1-(5-methyl-4-pyrrolidin-1-yl-pyrimidin-2-yl)-piperidin-4-yloxy]-1H-pyrazolo[3,4-d]pyrimidine; 4-[1-(2-Fluoro-4-methanesulfonyl-phenyl)-1H-pyrazolo[3,4-d]pyrimidin-4-ylsulfanyl]-piperidine-1-carboxylic acid isopropyl ester; 4-[1-(2-Methyl-4-propylamino-phenyl)-1H-pyrazolo[3,4-d]pyrimidin-4-yloxy]-piperidine-1-carboxylic acid isopropyl ester; 4-[1-(4-Isopropylamino-2-methyl-phenyl)-1H-pyrazolo[3,4-d]pyrimidin-4-yloxy]-piperidine-1-carboxylic acid isopropyl ester; 4-[1-(2-Methyl-4-morpholin-4-yl-phenyl)-1H-pyrazolo[3,4-d]pyrimidin-4-yloxy]-piperidine-1-carboxylic acid isopropyl ester; 4-{1-[4-(2-Methoxy-ethylamino)-2-methyl-phenyl]-1H-pyrazolo[3,4-d]pyrimidin-4-yloxy}-piperidine-1-carboxylic acid isopropyl ester; 4-(1-{4-[(2-Methanesulfonyl-ethyl)-methyl-amino]-2-methyl-phenyl}-1H-pyrazolo[3,4-d]pyrimidin-4-yloxy)-piperidine-1-carboxylic acid isopropyl ester; 4-[1-(4-Bromo-phenyl)-1H-pyrazolo[3,4-d]pyrimidin-4-yloxy]-piperidine-1-carboxylic acid isopropyl ester; 4-[1-(4-Propylamino-phenyl)-1H-pyrazolo[3,4-d]pyrimidin-4-yloxy]-piperidine-1-carboxylic acid isopropyl ester; 4-[1-(4-Isopropylamino-phenyl)-1H-pyrazolo[3,4-d]pyrimidin-4-yloxy]-piperidine-1-carboxylic acid isopropyl ester; 4-(1-{4-[4-(2-Methanesulfonyl-ethyl)-piperazin-1-yl]-2-methyl-phenyl}-1H-pyrazolo[3,4-d]pyrimidin-4-yloxy)-piperidine-1-carboxylic acid isopropyl ester; 4-(1-{2-Methyl-4-[(tetrahydro-furan-2-ylmethyl)-amino]-phenyl}-1H-pyrazolo[3,4-d]pyrimidin-4-yloxy)-piperidine-1-carboxylic acid isopropyl ester; 4-[1-(4-Cyclopropylamino-2-methyl-phenyl)-1H-pyrazolo[3,4-d]pyrimidin-4-yloxy]-piperidine-1-carboxylic acid isopropyl ester; 4-{1-[4-(2-Dimethylamino-ethylamino)-2-methyl-phenyl]-1H-pyrazolo[3,4-d]pyrimidin-4-yloxy}-piperidine-1-carboxylic acid isopropyl ester; 4-[1-(4-Morpholin-4-yl-phenyl)-1H-pyrazolo[3,4-d]pyrimidin-4-yloxy]-piperidine-1-carboxylic acid isopropyl ester; 4-({[1-(2-Fluoro-4-methanesulfonyl-phenyl)-1H-pyrazolo[3,4-d]pyrimidin-4-yl]-isopropyl-amino}-methyl)-piperidine-1-carboxylic acid tert-butyl ester; 4-[1-(2-Fluoro-4-morpholin-4-yl-phenyl)-1H-pyrazolo[3,4-d]pyrimidin-4-yloxy]-piperidine-1-carboxylic acid isopropyl ester; 4-[1-(2-Fluoro-4-isopropylamino-phenyl)-1H-pyrazolo[3,4-d]pyrimidin-4-yloxy]-piperidine-1-carboxylic acid isopropyl ester; 4-(1-{4-[(2-Methanesulfonyl-ethyl)-methyl-amino]-phenyl}-1H-pyrazolo[3,4-d]pyrimidin-4-yloxy)-piperidine-1-carboxylic acid isopropyl ester; 4-{1-[4-(2-Methoxy-ethylamino)-phenyl]-1H-pyrazolo[3,4-d]pyrimidin-4-yloxy}-piperidine-1-carboxylic acid isopropyl ester; 4-(1-{4-[(Tetrahydro-furan-2-ylmethyl)-amino]-phenyl}-1H-pyrazolo[3,4-d]pyrimidin-4-yloxy)-piperidine-1-carboxylic acid isopropyl ester; 4-(1-{4-[4-(2-Methanesulfonyl-ethyl)-piperazin-1-yl]-phenyl}-1H-pyrazolo[3,4-d]pyrimidin-4-yloxy)-piperidine-1-carboxylic acid isopropyl ester; 4-[1-(4-Amino-phenyl)-1H-pyrazolo[3,4-d]pyrimidin-4-yloxy]-piperidine-1-carboxylic acid isopropyl ester; 4-({[1-(2-Fluoro-4-methanesulfonyl-phenyl)-1H-pyrazolo[3,4-d]pyrimidin-4-yl]-isopropyl-amino}-methyl)-piperidine-1-carboxylic acid isopropyl ester; 4-[1-(5-Ethyl-pyrimidin-2-yl)-piperidin-4-ylsulfanyl]-1-(2-fluoro-4-methanesulfonyl-phenyl)-1H-pyrazolo[3,4-d]pyrimidine; 4-[1-(2-Fluoro-4-sulfamoyl-phenyl)-1H-pyrazolo[3,4-d]pyrimidin-4-yloxy]-piperidine-1-carboxylic acid isopropyl ester; 4-[1-(2-Fluoro-4-propionylsulfamoyl-phenyl)-1H-pyrazolo[3,4-d]pyrimidin-4-yloxy]-piperidine-1-carboxylic acid isopropyl ester; 4-[1-(4-Cyano-2-fluoro-phenyl)-1H-pyrazolo[3,4-d]pyrimidin-4-yloxy]-piperidine-1-carboxylic acid isopropyl ester; 1-(2,5-Difluoro-4-methoxy-phenyl)-4-[4-(3-isopropyl-[1,2,4]oxadiazol-5-yl)-cyclohexyloxy]-1H-pyrazolo[3,4-d]pyrimidine; 4-[1-(2,5-Difluoro-4-methanesulfonyl-phenyl)-1H-pyrazolo[3,4-d]pyrimidin-4-yloxy]-piperidine-1-carboxylic acid isopropyl ester; 4-[1-(4-Fluoro-6-methoxy-pyridin-3-yl)-1H-pyrazolo[3,4-d]pyrimidin-4-yloxy]-piperidine-1-carboxylic acid isopropyl ester; 4-[1-(6-Methoxy-2-methyl-pyridin-3-yl)-1H-pyrazolo[3,4-d]pyrimidin-4-yloxy]-piperidine-1-carboxylic acid isopropyl ester; 4-[1-(2,5-Difluoro-4-sulfamoyl-phenyl)-1H-pyrazolo[3,4-d]pyrimidin-4-yloxy]-piperidine-1-carboxylic acid isopropyl ester; 4-[1-(2-Fluoro-4-hydroxy-phenyl)-1H-pyrazolo[3,4-d]pyrimidin-4-yloxy]-piperidine-1-carboxylic acid isopropyl ester; 3-Fluoro-4-{4-[1-(3-isopropyl-[1,2,4]oxadiazol-5-yl)-piperidin-4-yloxy]-pyrazolo[3,4-d]pyrimidin-1-yl}-N-propionyl-benzenesulfonamide; 3-Fluoro-4-{4-[1-(3-isopropyl-[1,2,4]oxadiazol-5-yl)-piperidin-4-yloxy]-pyrazolo[3,4-d]pyrimidin-1-yl}-benzonitrile; 3-Fluoro-4-{4-[1-(3-isopropyl-[1,2,4]oxadiazol-5-yl)-piperidin-4-yloxy]-pyrazolo[3,4-d]pyrimidin-1-yl}-benzenesulfonamide; 1-(2,5-Difluoro-4-methanesulfonyl-phenyl)-4-[1-(3-isopropyl-[1,2,4]oxadiazol-5-yl)-piperidin-4-yloxy]-1H-pyrazolo[3,4-d]pyrimidine; 1-(4-Fluoro-6-methoxy-pyridin-3-yl)-4-[1-(3-isopropyl-[1,2,4]oxadiazol-5-yl)-piperidin-4-yloxy]-1H-pyrazolo[3,4-d]pyrimidine; 4-[1-(3-Isopropyl-[1,2,4]oxadiazol-5-yl)-piperidin-4-yloxy]-1-(6-methoxy-2-methyl-pyridin-3-yl)-1H-pyrazolo[3,4-d]pyrimidine; 2,5-Difluoro-4-{4-[1-(3-isopropyl-[1,2,4]oxadiazol-5-yl)-piperidin-4-yloxy]-pyrazolo[3,4-d]pyrimidin-1-yl}-benzenesulfonamide; 1-(2-Fluoro-4-methanesulfonyl-phenyl)-4-[4-(3-isopropyl-[1,2,4]oxadiazol-5-yl)-cyclohexyloxy]-1H-pyrazolo[3,4-d]pyrimidine; 3-Fluoro-4-{4-[4-(3-isopropyl-[1,2,4]oxadiazol-5-yl)-cyclohexyloxy]-pyrazolo[3,4-d]pyrimidin-1-yl}-N-propionyl-benzenesulfonamide; 3-Fluoro-4-{4-[4-(3-isopropyl-[1,2,4]oxadiazol-5-yl)-cyclohexyloxy]-pyrazolo[3,4-d]pyrimidin-1-yl}-benzonitrile; 3-Fluoro-4-{4-[4-(3-isopropyl-[1,2,4]oxadiazol-5-yl)-cyclohexyloxy]-pyrazolo[3,4-d]pyrimidin-1-yl}-benzenesulfonamide; 1-(2,5-Difluoro-4-methanesulfonyl-phenyl)-4-[4-(3-isopropyl-[1,2,4]oxadiazol-5-yl)-cyclohexyloxy]-1H-pyrazolo[3,4-d]pyrimidine; 1-(4-Fluoro-6-methoxy-pyridin-3-yl)-4-[4-(3-isopropyl-[1,2,4]oxadiazol-5-yl)-cyclohexyloxy]-1H-pyrazolo[3,4-d]pyrimidine; 4-[4-(3-Isopropyl-[1,2,4]oxadiazol-5-yl)-cyclohexyloxy]-1-(6-methoxy-2-methyl-pyridin-3-yl)-1H-pyrazolo[3,4-d]pyrimidine; 2,5-Difluoro-4-{4-[4-(3-isopropyl-[1,2,4]oxadiazol-5-yl)-cyclohexyloxy]-pyrazolo[3,4-d]pyrimidin-1-yl}-benzenesulfonamide; 4-[1-(2-Fluoro-4-methoxy-phenyl)-1H-pyrazolo[3,4-d]pyrimidin-4-yloxy]-piperidine-1-carboxylic acid isopropyl ester; 4-[1-(4-Difluoromethoxy-2-fluoro-phenyl)-1H-pyrazolo[3,4-d]pyrimidin-4-yloxy]-piperidine-1-carboxylic acid isopropyl ester; 4-[1-(2-Fluoro-4-trifluoromethoxy-phenyl)-1H-pyrazolo[3,4-d]pyrimidin-4-yloxy]-piperidine-1-carboxylic acid isopropyl ester; 4-[1-(2,5-Difluoro-4-methoxy-phenyl)-1H-pyrazolo[3,4-d]pyrimidin-4-yloxy]-piperidine-1-carboxylic acid isopropyl ester; 3-Fluoro-4-{4-[1-(3-isopropyl-[1,2,4]oxadiazol-5-yl)-piperidin-4-yloxy]-pyrazolo[3,4-d]pyrimidin-1-yl}-phenol; 1-(2-Fluoro-4-methoxy-phenyl)-4-[1-(3-isopropyl-[1,2,4]oxadiazol-5-yl)-piperidin-4-yloxy]-1H-pyrazolo[3,4-d]pyrimidine; 1-(4-Difluoromethoxy-2-fluoro-phenyl)-4-[1-(3-isopropyl-[1,2,4]oxadiazol-5-yl)-piperidin-4-yloxy]-1H-pyrazolo[3,4-d]pyrimidine; 1-(2-Fluoro-4-trifluoromethoxy-phenyl)-4-[1-(3-isopropyl-[1,2,4]oxadiazol-5-yl)-piperidin-4-yloxy]-1H-pyrazolo[3,4-d]pyrimidine; 1-(2,5-Difluoro-4-methoxy-phenyl)-4-[1-(3-isopropyl-[1,2,4]oxadiazol-5-yl)-piperidin-4-yloxy]-1H-pyrazolo[3,4-d]pyrimidine; 3-Fluoro-4-{4-[4-(3-isopropyl-[1,2,4]oxadiazol-5-yl)-cyclohexyloxy]-pyrazolo[3,4-d]pyrimidin-1-yl}-phenol; 1-(2-Fluoro-4-methoxy-phenyl)-4-[4-(3-isopropyl-[1,2,4]oxadiazol-5-yl)-cyclohexyloxy]-1H-pyrazolo[3,4-d]pyrimidine; 1-(4-Difluoromethoxy-2-fluoro-phenyl)-4-[4-(3-isopropyl-[1,2,4]oxadiazol-5-yl)-cyclohexyloxy]-1H-pyrazolo[3,4-d]pyrimidine; and 1-(2-Fluoro-4-trifluoromethoxy-phenyl)-4-[4-(3-isopropyl-[1,2,4]oxadiazol-5-yl)-cyclohexyloxy]-1H-pyrazolo[3,4-d]pyrimidine.

Specific examples of GPR119 agonists disclosed in International Application No. PCT/US2004/022417 include the following compounds according to Formula (IV) (referred to herein as Group D3): 4-[9-(6-Methanesulfonyl-pyridin-3-yl)-9H-purin-6-yloxy]-piperidine-1-carboxylic acid isobutyl ester; {4-[9-(6-Methanesulfonyl-pyridin-3-yl)-9H-purin-6-yloxy]-piperidin-1-yl}-pyridin-3-yl-methanone; 4-[9-(4-Methanesulfonyl-phenyl)-9H-purin-6-yloxy]-piperidine-1-carboxylic acid tert-butyl ester; 4-[9-(6-Methanesulfonyl-pyridin-3-yl)-9H-purin-6-yloxy]-piperidine-1-carboxylic acid tert-butyl ester and 4-[9-(2-Fluoro-4-methanesulfonyl-phenyl)-9H-purin-6-yloxy]-piperidine-1-carboxylic acid tert-butyl ester.

Specific examples of GPR119 agonists disclosed in International Application No. PCT/US2004/022417 include the following compounds according to Formula (IV) (referred to herein as Group D4): 4-[9-(2-Fluoro-4-propionylsulfamoyl-phenyl)-9H-purin-6-yloxy]-piperidine-1-carboxylic acid isopropyl ester; 4-[9-(4-Cyano-2-fluoro-phenyl)-9H-purin-6-yloxy]-piperidine-1-carboxylic acid isopropyl ester; 4-[9-(2-Fluoro-4-sulfamoyl-phenyl)-9H-purin-6-yloxy]-piperidine-1-carboxylic acid isopropyl ester; 9-(2-Fluoro-4-methanesulfonyl-phenyl)-6-[1-(3-isopropyl-[1,2,4]oxadiazol-5-yl)-piperidin-4-yloxy]-9H-purine; 3-Fluoro-4-{6-[1-(3-isopropyl-[1,2,4]oxadiazol-5-yl)-piperidin-4-yloxy]-purin-9-yl}-N-propionyl-benzenesulfonamide; 3-Fluoro-4-{6-[1-(3-isopropyl-[1,2,4]oxadiazol-5-yl)-piperidin-4-yloxy]-purin-9-yl}-benzonitrile; 3-Fluoro-4-{6-[1-(3-isopropyl-[1,2,4]oxadiazol-5-yl)-piperidin-4-yloxy]-purin-9-yl}-benzenesulfonamide; 4-[9-(2,5-Difluoro-4-methanesulfonyl-phenyl)-9H-purin-6-yloxy]-piperidine-1-carboxylic acid isopropyl ester; 4-[9-(4-Fluoro-6-methoxy-pyridin-3-yl)-9H-purin-6-yloxy]-piperidine-1-carboxylic acid isopropyl ester; 4-[9-(6-Methoxy-2-methyl-pyridin-3-yl)-9H-purin-6-yloxy]-piperidine-1-carboxylic acid isopropyl ester; 4-[9-(2,5-Difluoro-4-sulfamoyl-phenyl)-9H-purin-6-yloxy]-piperidine-1-carboxylic acid isopropyl ester; 9-(2,5-Difluoro-4-methanesulfonyl-phenyl)-6-[1-(3-isopropyl-[1,2,4]oxadiazol-5-yl)-piperidin-4-yloxy]-9H-purine; 9-(4-Fluoro-6-methoxy-pyridin-3-yl)-6-[1-(3-isopropyl-[1,2,4]oxadiazol-5-yl)-piperidin-4-yloxy]-9H-purine; 6-[1-(3-Isopropyl-[1,2,4]oxadiazol-5-yl)-piperidin-4-yloxy]-9-(6-methoxy-2-methyl-pyridin-3-yl)-9H-purine; 2,5-Difluoro-4-{6-[1-(3-isopropyl-[1,2,4]oxadiazol-5-yl)-piperidin-4-yloxy]-purin-9-yl}-benzenesulfonamide; 9-(2-Fluoro-4-methanesulfonyl-phenyl)-6-[4-(3-isopropyl-[1,2,4]oxadiazol-5-yl)-cyclohexyloxy]-9H-purine; 3-Fluoro-4-{6-[4-(3-isopropyl-[1,2,4]oxadiazol-5-yl)-cyclohexyloxy]-purin-9-yl}-N-propionyl-benzenesulfonamide; 3-Fluoro-4-{6-[4-(3-isopropyl-[1,2,4]oxadiazol-5-yl)-cyclohexyloxy]-purin-9-yl}-benzonitrile; 3-Fluoro-4-{6-[4-(3-isopropyl-[1,2,4]oxadiazol-5-yl)-cyclohexyloxy]-purin-9-yl}-benzenesulfonamide; 9-(2,5-Difluoro-4-methanesulfonyl-phenyl)-6-[4-(3-isopropyl-[1,2,4]oxadiazol-5-yl)-cyclohexyloxy]-9H-purine; 9-(4-Fluoro-6-methoxy-pyridin-3-yl)-6-[4-(3-isopropyl-[1,2,4]oxadiazol-5-yl)-cyclohexyloxy]-9H-purine; 6-[4-(3-Isopropyl-[1,2,4]oxadiazol-5-yl)-cyclohexyloxy]-9-(6-methoxy-2-methyl-pyridin-3-yl)-9H-purine; and 2,5-Difluoro-4-{6-[4-(3-isopropyl-[1,2,4]oxadiazol-5-yl)-cyclohexyloxy]-purin-9-yl}-benzenesulfonamide.

Specific examples of GPR119 agonists disclosed in International Application No. PCT/US2004/022417 include the following compound according to Formula (IV) (referred to herein as Group D5): 4-[3-(4-Methanesulfonyl-phenyl)-3H-[1,2,3]triazolo[4,5-d]pyrimidin-7-yloxy]-piperidine-1-carboxylic acid tert-butyl ester.

Specific examples of GPR119 agonists disclosed in International Application No. PCT/US2004/022417 include the following compounds according to Formula (IV) (referred to herein as Group D6): 3-(2-Fluoro-4-methanesulfonyl-phenyl)-7-[1-(3-isopropyl-[1,2,4]oxadiazol-5-yl)-piperidin-4-yloxy]-3H-[1,2,3]triazolo[4,5-d]pyrimidine; 3-Fluoro-4-{7-[1-(3-isopropyl-[1,2,4]oxadiazol-5-yl)-piperidin-4-yloxy]-[1,2,3]triazolo[4,5-d]pyrimidin-3-yl}-N-propionyl-benzenesulfonamide; 3-Fluoro-4-{7-[1-(3-isopropyl-[1,2,4]oxadiazol-5-yl)-piperidin-4-yloxy]-[1,2,3]triazolo[4,5-d]pyrimidin-3-yl}-benzonitrile; 3-Fluoro-4-{7-[1-(3-isopropyl-[1,2,4]oxadiazol-5-yl)-piperidin-4-yloxy]-[1,2,3]triazolo[4,5-d]pyrimidin-3-yl}-benzenesulfonamide; 3-(2-Fluoro-4-methanesulfonyl-phenyl)-7-[4-(3-isopropyl-[1,2,4]oxadiazol-5-yl)-cyclohexyloxy]-3H-[1,2,3]triazolo[4,5-d]pyrimidine; 3-Fluoro-4-{7-[4-(3-isopropyl-[1,2,4]oxadiazol-5-yl)-cyclohexyloxy]-[1,2,3]triazolo[4,5-d]pyrimidin-3-yl}-N-propionyl-benzenesulfonamide; 3-Fluoro-4-{7-[4-(3-isopropyl-[1,2,4]oxadiazol-5-yl)-cyclohexyloxy]-[1,2,3]triazolo[4,5-d]pyrimidin-3-yl}-benzonitrile; 3-Fluoro-4-{7-[4-(3-isopropyl-[1,2,4]oxadiazol-5-yl)-cyclohexyloxy]-[1,2,3]triazolo[4,5-d]pyrimidin-3-yl}-benzenesulfonamide; 3-(2,5-Difluoro-4-methanesulfonyl-phenyl)-7-[4-(3-isopropyl-[1,2,4]oxadiazol-5-yl)-cyclohexyloxy]-3H-[1,2,3]triazolo[4,5-d]pyrimidine; 3-(4-Fluoro-6-methoxy-pyridin-3-yl)-7-[4-(3-isopropyl-[1,2,4]oxadiazol-5-yl)-cyclohexyloxy]-3H-[1,2,3]triazolo[4,5-d]pyrimidine; 7-[4-(3-Isopropyl-[1,2,4]oxadiazol-5-yl)-cyclohexyloxy]-3-(6-methoxy-2-methyl-pyridin-3-yl)-3H-[1,2,3]triazolo[4,5-d]pyrimidine; 2,5-Difluoro-4-{7-[4-(3-isopropyl-[1,2,4]oxadiazol-5-yl)-cyclohexyloxy]-[1,2,3]triazolo[4,5-d]pyrimidin-3-yl}-benzenesulfonamide; 4-[3-(2-Fluoro-4-methanesulfonyl-phenyl)-3H-[1,2,3]triazolo[4,5-d]pyrimidin-7-yloxy]-piperidine-1-carboxylic acid isopropyl ester; 4-[3-(2-Fluoro-4-propionylsulfamoyl-phenyl)-3H-[1,2,3]triazolo[4,5-d]pyrimidin-7-yloxy]-piperidine-1-carboxylic acid isopropyl ester; 4-[3-(4-Cyano-2-fluoro-phenyl)-3H-[1,2,3]triazolo[4,5-d]pyrimidin-7-yloxy]-piperidine-1-carboxylic acid isopropyl ester; 4-[3-(2-Fluoro-4-sulfamoyl-phenyl)-3H-[1,2,3]triazolo[4,5-d]pyrimidin-7-yloxy]-piperidine-1-carboxylic acid isopropyl ester; 4-[3-(2,5-Difluoro-4-methanesulfonyl-phenyl)-3H-[1,2,3]triazolo[4,5-d]pyrimidin-7-yloxy]-piperidine-1-carboxylic acid isopropyl ester; 4-[3-(4-Fluoro-6-methoxy-pyridin-3-yl)-3H-[1,2,3]triazolo[4,5-d]pyrimidin-7-yloxy]-piperidine-1-carboxylic acid isopropyl ester; 4-[3-(6-Methoxy-2-methyl-pyridin-3-yl)-3H-[1,2,3]triazolo[4,5-d]pyrimidin-7-yloxy]-piperidine-1-carboxylic acid isopropyl ester; 4-[3-(2,5-Difluoro-4-sulfamoyl-phenyl)-3H-[1,2,3]triazolo[4,5-d]pyrimidin-7-yloxy]-piperidine-1-carboxylic acid isopropyl ester; 3-(2,5-Difluoro-4-methanesulfonyl-phenyl)-7-[1-(3-isopropyl-[1,2,4]oxadiazol-5-yl)-piperidin-4-yloxy]-3H-[1,2,3]triazolo[4,5-d]pyrimidine; 3-(4-Fluoro-6-methoxy-pyridin-3-yl)-7-[1-(3-isopropyl-[1,2,4]oxadiazol-5-yl)-piperidin-4-yloxy]-3H-[1,2,3]triazolo[4,5-d]pyrimidine; 7-[1-(3-Isopropyl-[1,2,4]oxadiazol-5-yl)-piperidin-4-yloxy]-3-(6-methoxy-2-methyl-pyridin-3-yl)-3H-[1,2,3]triazolo[4,5-d]pyrimidine; and 2,5-Difluoro-4-{7-[1-(3-isopropyl-[1,2,4]oxadiazol-5-yl)-piperidin-4-yloxy]-[1,2,3]triazolo[4,5-d]pyrimidin-3-yl}-benzenesulfonamide.

Specific examples of GPR119 agonists disclosed in International Application No. PCT/US2004/022417 include the following compound according to Formula (IV) (referred to herein as Group D7): 4-[3-(4-Methanesulfonyl-phenyl)-isoxazolo[4,5-d]pyrimidin-7-yloxy]-piperidine-1-carboxylic acid tert-butyl ester.

Specific examples of GPR119 agonists disclosed in International Application No. PCT/US2004/022417 include the following compounds according to Formula (IV) (referred to herein as Group D8): 4-({Ethyl-[3-(4-methanesulfonyl-phenyl)-isoxazolo[4,5-d]pyrimidin-7-yl]-amino}-methyl)-piperidine-1-carboxylic acid tert-butyl ester; 4-[3-(4-Methanesulfonyl-phenyl)-isoxazolo[4,5-d]pyrimidin-7-ylsulfanyl]-piperidine-1-carboxylic acid tert-butyl ester; and 4-[3-(4-Methanesulfonyl-phenyl)-isoxazolo[4,5-d]pyrimidin-7-yloxy]-piperidine-1-carboxylic acid isopropyl ester.

Specific examples of GPR119 agonists disclosed in International Application No. PCT/US2004/022417 include the following compound according to Formula (IV) (referred to herein as Group D9): 4-[8-(2-Fluoro-4-methanesulfonyl-phenyl)-[1,7]naphthyridin-4-yloxy]-piperidine-1-carboxylic acid isopropyl ester.

Specific examples of GPR119 agonists disclosed in International Application No. PCT/US2004/022417 include the following compounds according to Formula (IV) (referred to herein as Group D10): 4-[8-(2-Fluoro-4-methanesulfonyl-phenyl)-quinolin-4-yloxy]-piperidine-1-carboxylic acid isopropyl ester; 4-[8-(4-Methylsulfanyl-phenyl)-quinolin-4-yloxy]-piperidine-1-carboxylic acid isopropyl ester; 4-[8-(4-Methanesulfonyl-phenyl)-quinolin-4-yloxy]-piperidine-1-carboxylic acid isopropyl ester; 4-[8-(4-Isopropoxy-phenyl)-quinolin-4-yloxy]-piperidine-1-carboxylic acid isopropyl ester; 4-[8-(4-Bromo-2-fluoro-phenyl)-quinolin-4-yloxy]-piperidine-1-carboxylic acid isopropyl ester; 4-[8-(2-Fluoro-4-propionylsulfamoyl-phenyl)-quinolin-4-yloxy]-piperidine-1-carboxylic acid isopropyl ester; 4-[8-(4-Cyano-2-fluoro-phenyl)-quinolin-4-yloxy]-piperidine-1-carboxylic acid isopropyl ester; 4-[8-(2-Fluoro-4-sulfamoyl-phenyl)-quinolin-4-yloxy]-piperidine-1-carboxylic acid isopropyl ester; 4-[8-(2,5-Difluoro-4-methanesulfonyl-phenyl)-quinolin-4-yloxy]-piperidine-1-carboxylic acid isopropyl ester; 4-[8-(4-Fluoro-6-methoxy-pyridin-3-yl)-quinolin-4-yloxy]-piperidine-1-carboxylic acid isopropyl ester; 4-[8-(6-Methoxy-2-methyl-pyridin-3-yl)-quinolin-4-yloxy]-piperidine-1-carboxylic acid isopropyl ester; 4-[8-(2,5-Difluoro-4-sulfamoyl-phenyl)-quinolin-4-yloxy]-piperidine-1-carboxylic acid isopropyl ester; 2,5-Difluoro-4-{4-[1-(3-isopropyl-[1,2,4]oxadiazol-5-yl)-piperidin-4-yloxy]-quinolin-8-yl}-benzenesulfonamide; 4-[1-(3-Isopropyl-[1,2,4]oxadiazol-5-yl)-piperidin-4-yloxy]-8-(6-methoxy-2-methyl-pyridin-3-yl)-quinoline; 8-(4-Fluoro-6-methoxy-pyridin-3-yl)-4-[1-(3-isopropyl-[1,2,4]oxadiazol-5-yl)-piperidin-4-yloxy]-quinoline; 8-(2,5-Difluoro-4-methanesulfonyl-phenyl)-4-[1-(3-isopropyl-[1,2,4]oxadiazol-5-yl)-piperidin-4-yloxy]-quinoline; 3-Fluoro-4-{4-[1-(3-isopropyl-[1,2,4]oxadiazol-5-yl)-piperidin-4-yloxy]-quinolin-8-yl}-benzenesulfonamide; 3-Fluoro-4-{4-[1-(3-isopropyl-[1,2,4]oxadiazol-5-yl)-piperidin-4-yloxy]-quinolin-8-yl}-benzonitrile; 3-Fluoro-4-{4-[1-(3-isopropyl-[1,2,4]oxadiazol-5-yl)-piperidin-4-yloxy]-quinolin-8-yl}-N-propionyl-benzenesulfonamide; 8-(2-Fluoro-4-methanesulfonyl-phenyl)-4-[1-(3-isopropyl-[1,2,4]oxadiazol-5-yl)-piperidin-4-yloxy]-quinoline; 2,5-Difluoro-4-{4-[4-(3-isopropyl-[1,2,4]oxadiazol-5-yl)-cyclohexyloxy]-quinolin-8-yl}-benzenesulfonamide; 4-[4-(3-Isopropyl-[1,2,4]oxadiazol-5-yl)-cyclohexyloxy]-8-(6-methoxy-2-methyl-pyridin-3-yl)-quinoline; 8-(4-Fluoro-6-methoxy-pyridin-3-yl)-4-[4-(3-isopropyl-[1,2,4]oxadiazol-5-yl)-cyclohexyloxy]-quinoline; 8-(2,5-Difluoro-4-methanesulfonyl-phenyl)-4-[4-(3-isopropyl-[1,2,4]oxadiazol-5-yl)-cyclohexyloxy]-quinoline; 3-Fluoro-4-{4-[4-(3-isopropyl-[1,2,4]oxadiazol-5-yl)-cyclohexyloxy]-quinolin-8-yl}-benzenesulfonamide; 3-Fluoro-4-{4-[4-(3-isopropyl-[1,2,4]oxadiazol-5-yl)-cyclohexyloxy]-quinolin-8-yl}-benzonitrile; 3-Fluoro-4-{4-[4-(3-isopropyl-[1,2,4]oxadiazol-5-yl)-cyclohexyloxy]-quinolin-8-yl}-N-propionyl-benzenesulfonamide; and 8-(2-Fluoro-4-methanesulfonyl-phenyl)-4-[4-(3-isopropyl-[1,2,4]oxadiazol-5-yl)-cyclohexyloxy]-quinoline.

Specific examples of GPR119 agonists disclosed in International Application No. PCT/US2004/022417 include the following compounds according to Formula (IV) (referred to herein as Group D11): 4-[8-(2-Fluoro-4-methanesulfonyl-phenyl)-pyrido[3,4-d]pyrimidin-4-yloxy]-piperidine-1-carboxylic acid isopropyl ester; 4-[8-(2-Fluoro-4-propionylsulfamoyl-phenyl)-pyrido[3,4-d]pyrimidin-4-yloxy]-piperidine-1-carboxylic acid isopropyl ester; 4-[8-(4-Cyano-2-fluoro-phenyl)-pyrido[3,4-d]pyrimidin-4-yloxy]-piperidine-1-carboxylic acid isopropyl ester; 4-[8-(2-Fluoro-4-sulfamoyl-phenyl)-pyrido[3,4-d]pyrimidin-4-yloxy]-piperidine-1-carboxylic acid isopropyl ester; 4-[8-(2,5-Difluoro-4-methanesulfonyl-phenyl)-pyrido[3,4-d]pyrimidin-4-yloxy]-piperidine-1-carboxylic acid isopropyl ester; 4-[8-(4-Fluoro-6-methoxy-pyridin-3-yl)-pyrido[3,4-d]pyrimidin-4-yloxy]-piperidine-1-carboxylic acid isopropyl ester; 4-[8-(6-Methoxy-2-methyl-pyridin-3-yl)-pyrido[3,4-d]pyrimidin-4-yloxy]-piperidine-1-carboxylic acid isopropyl ester; 4-[8-(2,5-Difluoro-4-sulfamoyl-phenyl)-pyrido[3,4-d]pyrimidin-4-yloxy]-piperidine-1-carboxylic acid isopropyl ester; 8-(2-Fluoro-4-methanesulfonyl-phenyl)-4-[1-(3-isopropyl-[1,2,4]oxadiazol-5-yl)-piperidin-4-yloxy]-pyrido[3,4-d]pyrimidine; 3-Fluoro-4-{4-[1-(3-isopropyl-[1,2,4]oxadiazol-5-yl)-piperidin-4-yloxy]-pyrido[3,4-d]pyrimidin-8-yl}-N-propionyl-benzenesulfonamide; 3-Fluoro-4-{4-[1-(3-isopropyl-[1,2,4]oxadiazol-5-yl)-piperidin-4-yloxy]-pyrido[3,4-d]pyrimidin-8-yl}-benzonitrile; 3-Fluoro-4-{4-[1-(3-isopropyl-[1,2,4]oxadiazol-5-yl)-piperidin-4-yloxy]-pyrido[3,4-d]pyrimidin-8-yl}-benzenesulfonamide; 8-(2,5-Difluoro-4-methanesulfonyl-phenyl)-4-[1-(3-isopropyl-[1,2,4]oxadiazol-5-yl)-piperidin-4-yloxy]-pyrido[3,4-d]pyrimidine; 8-(4-Fluoro-6-methoxy-pyridin-3-yl)-4-[1-(3-isopropyl-[1,2,4]oxadiazol-5-yl)-piperidin-4-yloxy]-pyrido[3,4-d]pyrimidine; 4-[1-(3-Isopropyl-[1,2,4]oxadiazol-5-yl)-piperidin-4-yloxy]-8-(6-methoxy-2-methyl-pyridin-3-yl)-pyrido[3,4-d]pyrimidine; 2,5-Difluoro-4-{4-[1-(3-isopropyl-[1,2,4]oxadiazol-5-yl)-piperidin-4-yloxy]-pyrido[3,4-d]pyrimidin-8-yl}-benzenesulfonamide; 8-(2-Fluoro-4-methanesulfonyl-phenyl)-4-[4-(3-isopropyl-[1,2,4]oxadiazol-5-yl)-cyclohexyloxy]-pyrido[3,4-d]pyrimidine; 3-Fluoro-4-{4-[4-(3-isopropyl-[1,2,4]oxadiazol-5-yl)-cyclohexyloxy]-pyrido[3,4-d]pyrimidin-8-yl}-N-propionyl-benzenesulfonamide; 3-Fluoro-4-{4-[4-(3-isopropyl-[1,2,4]oxadiazol-5-yl)-cyclohexyloxy]-pyrido[3,4-d]pyrimidin-8-yl}-benzonitrile; 3-Fluoro-4-{4-[4-(3-isopropyl-[1,2,4]oxadiazol-5-yl)-cyclohexyloxy]-pyrido[3,4-d]pyrimidin-8-yl}-benzenesulfonamide; 8-(2,5-Difluoro-4-methanesulfonyl-phenyl)-4-[4-(3-isopropyl-[1,2,4]oxadiazol-5-yl)-cyclohexyloxy]-pyrido[3,4-d]pyrimidine; 8-(4-Fluoro-6-methoxy-pyridin-3-yl)-4-[4-(3-isopropyl-[1,2,4]oxadiazol-5-yl)-cyclohexyloxy]-pyrido[3,4-d]pyrimidine; 4-[4-(3-Isopropyl-[1,2,4]oxadiazol-5-yl)-cyclohexyloxy]-8-(6-methoxy-2-methyl-pyridin-3-yl)-pyrido[3,4-d]pyrimidine; and 2,5-Difluoro-4-{4-[4-(3-isopropyl-[1,2,4]oxadiazol-5-yl)-cyclohexyloxy]-pyrido[3,4-d]pyrimidin-8-yl}-benzenesulfonamide.

Specific examples of GPR119 agonists disclosed in International Application No. PCT/US2004/022417 include the following compounds according to Formula (IV) (referred to herein as Group D12): 3-(2-Fluoro-4-methanesulfonyl-phenyl)-7-[4-(3-isopropyl-[1,2,4]oxadiazol-5-yl)-cyclohexyloxy]-pyrazolo[1,5-a]pyrimidine; 3-Fluoro-4-{7-[4-(3-isopropyl-[1,2,4]oxadiazol-5-yl)-cyclohexyloxy]-pyrazolo[1,5-a]pyrimidin-3-yl}-N-propionyl-benzenesulfonamide;

3-Fluoro-4-{7-[4-(3-isopropyl-[1,2,4]oxadiazol-5-yl)-cyclohexyloxy]-pyrazolo[1,5-a]pyrimidin-3-yl}-benzonitrile; 3-Fluoro-4-{7-[4-(3-isopropyl-[1,2,4]oxadiazol-5-yl)-cyclohexyloxy]-pyrazolo[1,5-a]pyrimidin-3-yl}-benzenesulfonamide; 3-(2,5-Difluoro-4-methanesulfonyl-phenyl)-7-[4-(3-isopropyl-[1,2,4]oxadiazol-5-yl)-cyclohexyloxy]-pyrazolo[1,5-a]pyrimidine; 3-(4-Fluoro-6-methoxy-pyridin-3-yl)-7-[4-(3-isopropyl-[1,2,4]oxadiazol-5-yl)-cyclohexyloxy]-pyrazolo[1,5-a]pyrimidine; 7-[4-(3-Isopropyl-[1,2,4]oxadiazol-5-yl)-cyclohexyloxy]-3-(6-methoxy-2-methyl-pyridin-3-yl)-pyrazolo[1,5-a]pyrimidine; 2,5-Difluoro-4-{7-[4-(3-isopropyl-[1,2,4]oxadiazol-5-yl)-cyclohexyloxy]-pyrazolo[1,5-a]pyrimidin-3-yl}-benzenesulfonamide; 4-[3-(2-Fluoro-4-methanesulfonyl-phenyl)-pyrazolo[1,5-a]pyrimidin-7-yloxy]-piperidine-1-carboxylic acid isopropyl ester; 4-[3-(2-Fluoro-4-propionylsulfamoyl-phenyl)-pyrazolo[1,5-a]pyrimidin-7-yloxy]-piperidine-1-carboxylic acid isopropyl ester; 4-[3-(4-Cyano-2-fluoro-phenyl)-pyrazolo[1,5-a]pyrimidin-7-yloxy]-piperidine-1-carboxylic acid isopropyl ester; 4-[3-(2-Fluoro-4-sulfamoyl-phenyl)-pyrazolo[1,5-a]pyrimidin-7-yloxy]-piperidine-1-carboxylic acid isopropyl ester; 4-[3-(2,5-Difluoro-4-methanesulfonyl-phenyl)-pyrazolo[1,5-a]pyrimidin-7-yloxy]-piperidine-1-carboxylic acid isopropyl ester; 4-[3-(4-Fluoro-6-methoxy-pyridin-3-yl)-pyrazolo[1,5-a]pyrimidin-7-yloxy]-piperidine-1-carboxylic acid isopropyl ester; 4-[3-(6-Methoxy-2-methyl-pyridin-3-yl)-pyrazolo[1,5-a]pyrimidin-7-yloxy]-piperidine-1-carboxylic acid isopropyl ester; 4-[3-(2,5-Difluoro-4-sulfamoyl-phenyl)-pyrazolo[1,5-a]pyrimidin-7-yloxy]-piperidine-1-carboxylic acid isopropyl ester; 3-(2-Fluoro-4-methanesulfonyl-phenyl)-7-[1-(3-isopropyl-[1,2,4]oxadiazol-5-yl)-piperidin-4-yloxy]-pyrazolo[1,5-a]pyrimidine; 3-Fluoro-4-{7-[1-(3-isopropyl-[1,2,4]oxadiazol-5-yl)-piperidin-4-yloxy]-pyrazolo[1,5-a]pyrimidin-3-yl}-N-propionyl-benzenesulfonamide; 3-Fluoro-4-{7-[1-(3-isopropyl-[1,2,4]oxadiazol-5-yl)-piperidin-4-yloxy]-pyrazolo[1,5-a]pyrimidin-3-yl}-benzonitrile; 3-Fluoro-4-{7-[1-(3-isopropyl-[1,2,4]oxadiazol-5-yl)-piperidin-4-yloxy]-pyrazolo[1,5-a]pyrimidin-3-yl}-benzenesulfonamide; 3-(2,5-Difluoro-4-methanesulfonyl-phenyl)-7-[1-(3-isopropyl-[1,2,4]oxadiazol-5-yl)-piperidin-4-yloxy]-pyrazolo[1,5-a]pyrimidine; 3-(4-Fluoro-6-methoxy-pyridin-3-yl)-7-[1-(3-isopropyl-[1,2,4]oxadiazol-5-yl)-piperidin-4-yloxy]-pyrazolo[1,5-a]pyrimidine; 7-[1-(3-Isopropyl-[1,2,4]oxadiazol-5-yl)-piperidin-4-yloxy]-3-(6-methoxy-2-methyl-pyridin-3-yl)-pyrazolo[1,5-a]pyrimidine; 2,5-Difluoro-4-{7-[1-(3-isopropyl-[1,2,4]oxadiazol-5-yl)-piperidin-4-yloxy]-pyrazolo[1,5-a]pyrimidin-3-yl}-benzenesulfonamide; 4-[3-(2-Fluoro-4-methanesulfonyl-phenyl)-2-methyl-pyrazolo[1,5-a]pyrimidin-7-yloxy]-piperidine-1-carboxylic acid isopropyl ester; 4-[3-(2-Fluoro-4-propionylsulfamoyl-phenyl)-2-methyl-pyrazolo[1,5-a]pyrimidin-7-yloxy]-piperidine-1-carboxylic acid isopropyl ester; 4-[3-(4-Cyano-2-fluoro-phenyl)-2-methyl-pyrazolo[1,5-a]pyrimidin-7-yloxy]-piperidine-1-carboxylic acid isopropyl ester; 4-[3-(2-Fluoro-4-sulfamoyl-phenyl)-2-methyl-pyrazolo[1,5-a]pyrimidin-7-yloxy]-piperidine-1-carboxylic acid isopropyl ester; 4-[3-(2,5-Difluoro-4-methanesulfonyl-phenyl)-2-methyl-pyrazolo[1,5-a]pyrimidin-7-yloxy]-piperidine-1-carboxylic acid isopropyl ester; 4-[3-(4-Fluoro-6-methoxy-pyridin-3-yl)-2-methyl-pyrazolo[1,5-a]pyrimidin-7-yloxy]-piperidine-1-carboxylic acid isopropyl ester; 4-[3-(6-Methoxy-2-methyl-pyridin-3-yl)-2-methyl-pyrazolo[1,5-a]pyrimidin-7-yloxy]-piperidine-1-carboxylic acid isopropyl ester; 4-[3-(2,5-Difluoro-4-sulfamoyl-phenyl)-2-methyl-pyrazolo[1,5-a]pyrimidin-7-yloxy]-piperidine-1-carboxylic acid isopropyl ester; 2,5-Difluoro-4-{7-[1-(3-isopropyl-[1,2,4]oxadiazol-5-yl)-piperidin-4-yloxy]-2-methyl-pyrazolo[1,5-a]pyrimidin-3-yl}-benzenesulfonamide; 7-[1-(3-Isopropyl-[1,2,4]oxadiazol-5-yl)-piperidin-4-yloxy]-3-(6-methoxy-2-methyl-pyridin-3-yl)-2-methyl-pyrazolo[1,5-a]pyrimidine; 3-(4-Fluoro-6-methoxy-pyridin-3-yl)-7-[1-(3-isopropyl-[1,2,4]oxadiazol-5-yl)-piperidin-4-yloxy]-2-methyl-pyrazolo[1,5-a]pyrimidine; 3-(2,5-Difluoro-4-methanesulfonyl-phenyl)-7-[1-(3-isopropyl-[1,2,4]oxadiazol-5-yl)-piperidin-4-yloxy]-2-methyl-pyrazolo[1,5-a]pyrimidine; 3-Fluoro-4-{7-[1-(3-isopropyl-[1,2,4]oxadiazol-5-yl)-piperidin-4-yloxy]-2-methyl-pyrazolo[1,5-a]pyrimidin-3-yl}-benzenesulfonamide; 3-Fluoro-4-{7-[1-(3-isopropyl-[1,2,4]oxadiazol-5-yl)-piperidin-4-yloxy]-2-methyl-pyrazolo[1,5-a]pyrimidin-3-yl}-benzonitrile; 3-Fluoro-4-{7-[1-(3-isopropyl-[1,2,4]oxadiazol-5-yl)-piperidin-4-yloxy]-2-methyl-pyrazolo[1,5-a]pyrimidin-3-yl}-N-propionyl-benzenesulfonamide; 3-(2-Fluoro-4-methanesulfonyl-phenyl)-7-[1-(3-isopropyl-[1,2,4]oxadiazol-5-yl)-piperidin-4-yloxy]-2-methyl-pyrazolo[1,5-a]pyrimidine; 3-(2-Fluoro-4-methanesulfonyl-phenyl)-7-[4-(3-isopropyl-[1,2,4]oxadiazol-5-yl)-cyclohexyloxy]-2-methyl-pyrazolo[1,5-a]pyrimidine; 3-Fluoro-4-{7-[4-(3-isopropyl-[1,2,4]oxadiazol-5-yl)-cyclohexyloxy]-2-methyl-pyrazolo[1,5-a]pyrimidin-3-yl}-N-propionyl-benzenesulfonamide; 3-Fluoro-4-{7-[4-(3-isopropyl-[1,2,4]oxadiazol-5-yl)-cyclohexyloxy]-2-methyl-pyrazolo[1,5-a]pyrimidin-3-yl}-benzonitrile; 3-Fluoro-4-{7-[4-(3-isopropyl-[1,2,4]oxadiazol-5-yl)-cyclohexyloxy]-2-methyl-pyrazolo[1,5-a]pyrimidin-3-yl}-benzenesulfonamide; 3-(2,5-Difluoro-4-methanesulfonyl-phenyl)-7-[4-(3-isopropyl-[1,2,4]oxadiazol-5-yl)-cyclohexyloxy]-2-methyl-pyrazolo[1,5-a]pyrimidine; 3-(4-Fluoro-6-methoxy-pyridin-3-yl)-7-[4-(3-isopropyl-[1,2,4]oxadiazol-5-yl)-cyclohexyloxy]-2-methyl-pyrazolo[1,5-a]pyrimidine; 7-[4-(3-Isopropyl-[1,2,4]oxadiazol-5-yl)-cyclohexyloxy]-3-(6-methoxy-2-methyl-pyridin-3-yl)-2-methyl-pyrazolo[1,5-a]pyrimidine; and 2,5-Difluoro-4-{7-[4-(3-isopropyl-[1,2,4]oxadiazol-5-yl)-cyclohexyloxy]-2-methyl-pyrazolo[1,5-a]pyrimidin-3-yl}-benzenesulfonamide.

Specific examples of GPR119 agonists disclosed in International Application No. PCT/US2004/022417 include the following compounds according to Formula (IV) (referred to herein as Group D13): 4-[3-(2-Fluoro-4-methanesulfonyl-phenyl)-1-methyl-1H-pyrazolo[4,3-d]pyrimidin-7-yloxy]-piperidine-1-carboxylic acid isopropyl ester; 4-[3-(2-Fluoro-4-propionylsulfamoyl-phenyl)-1-methyl-1H-pyrazolo[4,3-d]pyrimidin-7-yloxy]-piperidine-1-carboxylic acid isopropyl ester; 4-[3-(4-Cyano-2-fluoro-phenyl)-1-methyl-1H-pyrazolo[4,3-d]pyrimidin-7-yloxy]-piperidine-1-carboxylic acid isopropyl ester; 4-[3-(2-Fluoro-4-sulfamoyl-phenyl)-1-methyl-1H-pyrazolo[4,3-d]pyrimidin-7-yloxy]-piperidine-1-carboxylic acid isopropyl ester; 4-[3-(2,5-Difluoro-4-methanesulfonyl-phenyl)-1-methyl-1H-pyrazolo[4,3-d]pyrimidin-7-yloxy]-piperidine-1-carboxylic acid isopropyl ester; 4-[3-(4-Fluoro-6-methoxy-pyridin-3-yl)-1-methyl-1H-pyrazolo[4,3-d]pyrimidin-7-yloxy]-piperidine-1-carboxylic acid isopropyl ester; 4-[3-(6-Methoxy-2-methyl-pyridin-3-yl)-1-methyl-1H-pyrazolo[4,3-d]pyrimidin-7-yloxy]-piperidine-1-carboxylic acid isopropyl ester; 4-[3-(2,5-Difluoro-4-sulfamoyl-phenyl)-1-methyl-1H-pyrazolo[4,3-d]pyrimidin-7-yloxy]-piperidine-1-carboxylic acid isopropyl ester; 3-(2-Fluoro-4-methanesulfonyl-phenyl)-7-[1-(3-isopropyl-[1,2,4]oxadiazol-5-yl)-piperidin-4-yloxy]-1-methyl-1H-pyrazolo[4,3-d]pyrimidine; 3-Fluoro-4-{7-[1-(3-isopropyl-[1,2,4]oxadiazol-5-yl)-piperidin-4-yloxy]-1-methyl-1H-pyrazolo[4,3-d]pyrimidin-3-yl}-N-propionylbenzenesulfonamide; 3-Fluoro-4-{7-[1-(3-isopropyl-[1,2,4] oxadiazol-5-yl)-piperidin-4-yloxy]-1-methyl-1H-pyrazolo [4,3-d]pyrimidin-3-yl}-benzonitrile; 3-Fluoro-4-{7-[1-(3-isopropyl-[1,2,4]oxadiazol-5-yl)-piperidin-4-yloxy]-1-methyl-1H-pyrazolo[4,3-d]pyrimidin-3-yl}-benzenesulfonamide; 3-(2,5-Difluoro-4-methanesulfonyl-phenyl)-7-[1-(3-isopropyl-[1,2,4]oxadiazol-5-yl)-piperidin-4-yloxy]-1-methyl-1H-pyrazolo[4,3-d]pyrimidine; 3-(4-Fluoro-6-methoxy-pyridin-3-yl)-7-[1-(3-isopropyl-[1,2,4] oxadiazol-5-yl)-piperidin-4-yloxy]-1-methyl-1H-pyrazolo [4,3-d]pyrimidine; 7-[1-(3-Isopropyl-[1,2,4]oxadiazol-5-yl)-piperidin-4-yloxy]-3-(6-methoxy-2-methyl-pyridin-3-yl)-1-methyl-1H-pyrazolo[4,3-d]pyrimidine; 2,5-Difluoro-4-{7-[1-(3-isopropyl-[1,2,4]oxadiazol-5-yl)-piperidin-4-yloxy]-1-methyl-1H-pyrazolo[4,3-d]pyrimidin-3-yl}-benzenesulfonamide; 3-(2-Fluoro-4-methanesulfonyl-phenyl)-7-[4-(3-isopropyl-[1,2,4]oxadiazol-5-yl)-cyclohexyloxy]-1-methyl-1H-pyrazolo[4,3-d]pyrimidine; 3-Fluoro-4-{7-[4-(3-isopropyl-[1,2,4]oxadiazol-5-yl)-cyclohexyloxy]-1-methyl-1H-pyrazolo[4,3-d]pyrimidin-3-yl}-N-propionyl-benzenesulfonamide; 3-Fluoro-4-{7-[4-(3-isopropyl-[1,2,4]oxadiazol-5-yl)-cyclohexyloxy]-1-methyl-1H-pyrazolo[4,3-d]pyrimidin-3-yl}-benzonitrile; 3-Fluoro-4-{7-[4-(3-isopropyl-[1,2,4]oxadiazol-5-yl)-cyclohexyloxy]-1-methyl-1H-pyrazolo[4,3-d]pyrimidin-3-yl}-benzenesulfonamide; 3-(2,5-Difluoro-4-methanesulfonyl-phenyl)-7-[4-(3-isopropyl-[1,2,4] oxadiazol-5-yl)-cyclohexyloxy]-1-methyl-1H-pyrazolo[4,3-d]pyrimidine; 3-(4-Fluoro-6-methoxy-pyridin-3-yl)-7-[4-(3-isopropyl-[1,2,4]oxadiazol-5-yl)-cyclohexyloxy]-1-methyl-1H-pyrazolo[4,3-d]pyrimidine; 7-[4-(3-Isopropyl-[1,2,4] oxadiazol-5-yl)-cyclohexyloxy]-3-(6-methoxy-2-methyl-pyridin-3-yl)-1-methyl-1H-pyrazolo[4,3-d]pyrimidine; and 2,5-Difluoro-4-{7-[4-(3-isopropyl-[1,2,4]oxadiazol-5-yl)-cyclohexyloxy]-1-methyl-1H-pyrazolo[4,3-d]pyrimidin-3-yl}-benzenesulfonamide.

Specific examples of GPR119 agonists disclosed in International Application No. PCT/US2004/022417 include the following compounds according to Formula (IV) (referred to herein as Group D14): 4-[3-(2-Fluoro-4-methanesulfonyl-phenyl)-2-methyl-2H-pyrazolo[4,3-d]pyrimidin-7-yloxy]-piperidine-1-carboxylic acid isopropyl ester; 4-[3-(2-Fluoro-4-propionylsulfamoyl-phenyl)-2-methyl-2H-pyrazolo[4,3-d]pyrimidin-7-yloxy]-piperidine-1-carboxylic acid isopropyl ester; 4-[3-(4-Cyano-2-fluoro-phenyl)-2-methyl-2H-pyrazolo[4,3-d]pyrimidin-7-yloxy]-piperidine-1-carboxylic acid isopropyl ester; 4-[3-(2-Fluoro-4-sulfamoyl-phenyl)-2-methyl-2H-pyrazolo[4,3-d]pyrimidin-7-yloxy]-piperidine-1-carboxylic acid isopropyl ester; 4-[3-(2,5-Difluoro-4-methanesulfonyl-phenyl)-2-methyl-2H-pyrazolo [4,3-d]pyrimidin-7-yloxy]-piperidine-1-carboxylic acid isopropyl ester; 4-[3-(4-Fluoro-6-methoxy-pyridin-3-yl)-2-methyl-2H-pyrazolo[4,3-d]pyrimidin-7-yloxy]-piperidine-1-carboxylic acid isopropyl ester; 4-[3-(6-Methoxy-2-methyl-pyridin-3-yl)-2-methyl-2H-pyrazolo[4,3-d]pyrimidin-7-yloxy]-piperidine-1-carboxylic acid isopropyl ester; 4-[3-(2,5-Difluoro-4-sulfamoyl-phenyl)-2-methyl-2H-pyrazolo [4,3-d]pyrimidin-7-yloxy]-piperidine-1-carboxylic acid isopropyl ester; 3-(2-Fluoro-4-methanesulfonyl-phenyl)-7-[1-(3-isopropyl-[1,2,4]oxadiazol-5-yl)-piperidin-4-yloxy]-2-methyl-2H-pyrazolo[4,3-d]pyrimidine; 3-Fluoro-4-{7-[1-(3-isopropyl-[1,2,4]oxadiazol-5-yl)-piperidin-4-yloxy]-2-methyl-2H-pyrazolo[4,3-d]pyrimidin-3-yl}-N-propionyl-benzenesulfonamide; 3-Fluoro-4-{7-[1-(3-isopropyl-[1,2,4] oxadiazol-5-yl)-piperidin-4-yloxy]-2-methyl-2H-pyrazolo [4,3-d]pyrimidin-3-yl}-benzonitrile; 3-Fluoro-4-{7-[1-(3-isopropyl-[1,2,4]oxadiazol-5-yl)-piperidin-4-yloxy]-2-methyl-2H-pyrazolo[4,3-d]pyrimidin-3-yl}-benzenesulfonamide; 3-(2,5-Difluoro-4-methanesulfonyl-phenyl)-7-[1-(3-isopropyl-[1,2,4]oxadiazol-5-yl)-piperidin-4-yloxy]-2-methyl-2H-pyrazolo[4,3-d]pyrimidine; 3-(4-Fluoro-6-methoxy-pyridin-3-yl)-7-[1-(3-isopropyl-[1,2,4]oxadiazol-5-yl)-piperidin-4-yloxy]-2-methyl-2H-pyrazolo[4,3-d] pyrimidine; 7-[1-(3-Isopropyl-[1,2,4]oxadiazol-5-yl)-piperidin-4-yloxy]-3-(6-methoxy-2-methyl-pyridin-3-yl)-2-methyl-2H-pyrazolo[4,3-d]pyrimidine; 2,5-Difluoro-4-{7-[1-(3-isopropyl-[1,2,4]oxadiazol-5-yl)-piperidin-4-yloxy]-2-methyl-2H-pyrazolo[4,3-d]pyrimidin-3-yl}-benzenesulfonamide; 3-(2-Fluoro-4-methanesulfonyl-phenyl)-7-[4-(3-isopropyl-[1,2,4]oxadiazol-5-yl)-cyclohexyloxy]-2-methyl-2H-pyrazolo[4,3-d]pyrimidine; 3-Fluoro-4-{7-[4-(3-isopropyl-[1,2,4]oxadiazol-5-yl)-cyclohexyloxy]-2-methyl-2H-pyrazolo[4,3-d]pyrimidin-3-yl}-N-propionyl-benzenesulfonamide; 3-Fluoro-4-{7-[4-(3-isopropyl-[1,2,4]oxadiazol-5-yl)-cyclohexyloxy]-2-methyl-2H-pyrazolo[4,3-d]pyrimidin-3-yl}-benzonitrile; 3-Fluoro-4-{7-[4-(3-isopropyl-[1,2,4]oxadiazol-5-yl)-cyclohexyloxy]-2-methyl-2H-pyrazolo[4,3-d]pyrimidin-3-yl}-benzenesulfonamide; 3-(2,5-Difluoro-4-methanesulfonyl-phenyl)-7-[4-(3-isopropyl-[1,2,4] oxadiazol-5-yl)-cyclohexyloxy]-2-methyl-2H-pyrazolo[4,3-d]pyrimidine; 3-(4-Fluoro-6-methoxy-pyridin-3-yl)-7-[4-(3-isopropyl-[1,2,4]oxadiazol-5-yl)-cyclohexyloxy]-2-methyl-2H-pyrazolo[4,3-d]pyrimidine; 7-[4-(3-isopropyl-[1,2,4] oxadiazol-5-yl)-cyclohexyloxy]-3-(6-methoxy-2-methyl-pyridin-3-yl)-2-methyl-2H-pyrazolo[4,3-d]pyrimidine; and 2,5-Difluoro-4-{7-[4-(3-isopropyl-[1,2,4]oxadiazol-5-yl)-cyclohexyloxy]-2-methyl-2H-pyrazolo[4,3-d]pyrimidin-3-yl}-benzenesulfonamide.

Examples of GPR119 agonists are described in U.S. Patent Application No. 60/577,354, the disclosure of which is herein incorporated by reference in its entirety. Disclosed in U.S. Patent Application No. 60/577,354 as a GPR119 agonist is a compound of Formula (V):

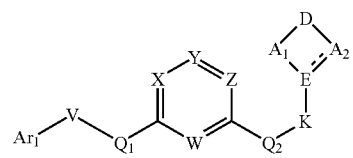

(V)

or N-oxide thereof;
wherein:
$A_1$ and $A_2$ are independently $C_{1-3}$ alkylene optionally substituted with one or more substituents selected independently from the group consisting of $C_{1-6}$ alkyl, $C_{1-6}$ alkoxy, and carboxy;

D is $CR_1R_2$ or $NR_2$, wherein $R_1$ is selected from the group consisting of H, $C_{1-6}$ alkyl, $C_{1-6}$ alkoxy, halogen and hydroxyl;

E is N, C or $CR_3$, wherein $R_3$ is H or $C_{1-6}$ alkyl;

----- is a single bond when E is N or $CR_3$, or a double bond when E is C;

K is absent, $C_{3-6}$ cycloalkylene, or $C_{1-3}$ alkylene group optionally substituted with one or more substituents selected independently from the group consisting of $C_{1-6}$ alkyl, $C_{1-6}$ alkoxy, carboxy, cyano, and halogen;

$Q_1$ is $NR_4$, O, S, S(O) or $S(O)_2$, wherein $R_4$ is H, $C_{1-6}$ acyl, $C_{1-6}$ alkyl, $C_{2-6}$ alkenyl, $C_{2-6}$ alkynyl, $C_{3-7}$ cycloalkyl, or $C_{3-7}$-cycloalkyl-$C_{1-3}$-alkylene, wherein said $C_{1-6}$ alkyl is optionally substituted with one or more substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, $C_{1-6}$ alkylureyl, amino, di-$C_{1-6}$-alkylamino, $C_{1-6}$ alkoxycarbonyl, carboxamide, carboxy, cyano, $C_{3-6}$ cycloalkyl, di-$C_{1-6}$-alkylcarboxamide, di-$C_{1-6}$-alkylsulfonamide, di-$C_{1-6}$-alkylthiocarboxamido, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-6}$ haloalkylthio, hydroxyl, hydroxylamino and nitro;

$Q_2$ is absent, $NR_5$, or O, wherein $R_5$ is H, $C_{1-6}$ acyl, $C_{1-6}$ alkyl, $C_{2-6}$ alkenyl, $C_{2-6}$ alkynyl, $C_{3-7}$ cycloalkyl, or $C_{3-7}$-cycloalkyl-$C_{1-3}$-alkylene, wherein said $C_{1-6}$ alkyl is optionally substituted with one or more substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, $C_{1-6}$ alkylureyl, amino, di-$C_{1-6}$-alkylamino, $C_{1-6}$ alkoxycarbonyl, carboxamide, carboxy, cyano, $C_{3-6}$ cycloalkyl, di-$C_{1-6}$-alkylcarboxamide, di-$C_{1-6}$-alkylsulfonamide, di-$C_{1-6}$-alkylthiocarboxamido, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-4}$ haloalkylthio, hydroxyl, hydroxylamino and nitro;

W is N or CH;

X is N or $CR_6$;

Y is N or $CR_7$;

Z is N or $CR_8$;

V is absent, $C_{1-3}$ heteroalkylene, or $C_{1-3}$ alkylene wherein each are optionally substituted with one or more substituents selected independently from the group consisting of $C_{1-3}$ alkyl, $C_{1-6}$ alkoxy, carboxy, cyano, $C_{1-3}$ haloalkyl, and halogen;

$R_6$, $R_7$, and $R_8$ are each independently selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, $C_{1-6}$ alkylureyl, amino, di-$C_{1-6}$-alkylamino, $C_{1-6}$ alkoxycarbonyl, carboxamide, carboxy, cyano, $C_{3-6}$ cycloalkyl, di-$C_{1-6}$-alkylcarboxamide, di-$C_{1-6}$-alkylsulfonamide, di-$C_{1-6}$-alkylthiocarboxamido, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-6}$ haloalkylthio, hydroxyl, hydroxylamino and nitro, wherein said $C_{2-6}$ alkenyl, $C_{1-6}$ alkyl, $C_{2-6}$ alkynyl and $C_{3-6}$ cycloalkyl are each optionally substituted with one or more substituents independently selected from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, $C_{1-6}$ alkylureyl, amino, di-$C_{1-6}$ alkylamino, $C_{1-6}$ alkoxycarbonyl, carboxamide, carboxy, cyano, $C_{3-6}$ cycloalkyl, di-$C_{1-6}$-alkylcarboxamide, di-$C_{1-6}$-alkylsulfonamide, di-$C_{1-6}$-alkylthiocarboxamido, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-6}$ haloalkylthio, hydroxyl, hydroxylamino and nitro;

Ar is aryl or heteroaryl optionally substituted with $R_9$-$R_{13}$;

$R_9$ is selected from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, $C_{1-6}$ alkylureyl, amino, aryl, arylcarbonyl, arylsulfonyl, di-$C_{1-6}$-alkylamino, carbamimidoyl, $C_{1-6}$ alkoxycarbonyl, carboxamide, carboxy, cyano, $C_{3-6}$ cycloalkyl, di-$C_{1-6}$-alkylcarboxamide, di-$C_{1-6}$-alkylsulfonamide, di-$C_{1-6}$-alkylthiocarboxamido, guanidine, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-6}$ haloalkylthio, heterocyclic, heterocyclicsulfonyl, heteroaryl, hydroxyl, hydroxylamino, nitro, $C_{3-6}$ oxo-cycloalkyl, phenoxy, sulfonamide, sulfonic acid and thiol; and wherein each available $R_9$ is optionally substituted with one or more substituents selected independently from the group consisting of $C_{1-6}$ acyl, $C_{1-6}$ acylsulfonamide, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, $C_{1-6}$ alkylureyl, amino, aryl, arylcarbonyl, arylsulfonyl, di-$C_{1-6}$-alkylamino, $C_{1-6}$ alkoxycarbonyl, carboxamide, carboxy, cyano, $C_{3-6}$ cycloalkyl, di-$C_{1-6}$-alkylcarboxamide, di-$C_{1-6}$-alkylsulfonamide, di-$C_{1-6}$-alkylthiocarboxamido, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-6}$ haloalkylthio, heteroaryl, heteroarylcarbonyl, heteroarylsulfonyl, heterocyclic, hydroxyl, hydroxylamino, and nitro;

$R_{10}$-$R_{13}$ are independently selected from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, $C_{1-6}$ alkylureyl, amino, di-$C_{1-6}$-alkylamino, $C_{1-6}$ alkoxycarbonyl, carboxamide, carboxy, cyano, $C_{3-6}$ cycloalkyl, di-$C_{1-6}$-alkylcarboxamide, di-$C_{1-6}$-alkylsulfonamide, di-$C_{1-6}$-alkylthiocarboxamido, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-6}$ haloalkylthio, hydroxyl, hydroxylamino, nitro, and thiol; or two adjacent groups together with the atoms to which they are bonded form a 5, 6 or 7 member cycloalkyl, cycloalkenyl or heterocyclic group wherein the 5, 6 or 7 member group is optionally substituted with halogen or oxo; and $R_2$ is selected from the group consisting of H, $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, $C_{1-6}$ alkylureyl, amino, aryl, arylcarbonyl, aryloxy, di-$C_{1-6}$-alkylamino, carbamimidoyl, $C_{1-6}$ alkoxycarbonyl, $C_{3-7}$-cycloalkoxycarbonyl, carboxamide, carboxy, cyano, $C_{3-6}$ cycloalkyl, di-$C_{1-6}$-alkylcarboxamide, di-$C_{1-6}$-alkylsulfonamide, di-$C_{1-6}$-alkylthiocarboxamido, guanidine, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-6}$ haloalkylthio, heteroaryl, heteroaryl-$C_{1-3}$-alkylene, heteroarylcarbonyl, heteroaryloxy, heterocycliccarboxamide, hydroxyl, hydroxylamino and nitro; wherein each available $R_2$ is optionally substituted with one or more substituents selected independently from the group consisting of $C_{1-6}$ acyl, $C_{1-6}$ acyloxy, $C_{2-6}$ alkenyl, $C_{1-6}$ alkoxy, $C_{1-6}$ alkyl, $C_{1-6}$ alkylamino, $C_{1-6}$ alkylcarboxamide, $C_{2-6}$ alkynyl, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylthiocarboxamide, $C_{1-6}$ alkylthioureyl, $C_{1-6}$ alkylureyl, amino, aryl, di-$C_{1-6}$-alkylamino, $C_{1-6}$ alkoxycarbonyl, carboxamide, carboxy, cyano, $C_{3-6}$ cycloalkyl, di-$C_{1-6}$-alkylcarboxamide, di-$C_{1-6}$-alkylsulfonamide, di-$C_{1-6}$-alkylthiocarboxamido, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-6}$ haloalkylthio, heterocyclic, heteroaryl, hydroxyl, hydroxylamino and nitro, and wherein $C_{1-6}$ alkyl is further optionally substituted with one or more substituents selected independently from the group consisting of $C_{1-6}$ acyl, $C_{1-6}$ alkoxy, $C_{1-6}$ alkylamino, $C_{1-6}$ alkylcarboxamide, $C_{1-6}$ alkylsulfonamide, $C_{1-6}$ alkylsulfinyl, $C_{1-6}$ alkylsulfonyl, $C_{1-6}$ alkylthio, $C_{1-6}$ alkylureyl, amino, di-$C_{1-6}$-alkylamino, $C_{1-6}$ alkoxycarbonyl, carboxamide, carboxy, cyano, $C_{3-6}$ cycloalkyl, di-$C_{1-6}$-alkylcarboxamide, di-$C_{1-6}$-alkylsulfonamide, $C_{1-6}$ haloalkoxy, $C_{1-6}$ haloalkyl, halogen, $C_{1-6}$ haloalkylsulfinyl, $C_{1-6}$ haloalkylsulfonyl, $C_{1-6}$ haloalkylthio, heterocyclic, hydroxyl, hydroxylamino and nitro.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in U.S. Patent Application No. 60/577,354 include the following compounds according to Formula (V) (referred to herein as Group E1): 4-[4-(3-Isopropyl-[1,2,4]oxadiazol-5-yl)-piperidin-1-yl]-6-(4-methanesulfonyl-phenoxy)-pyrimidine; {6-[4-(3-Isopropyl-[1,2,4]oxadiazol-5-yl)-piperidin-1-yl]-pyrimidin-4-yl}-(4-methanesulfonyl-phenyl)-amine; 4-{[6-(2-Fluoro-4-methanesulfonyl-phenylamino)-pyrimidin-4-yl]-methyl-amino}-piperidine-1-carboxylic acid tert-butyl ester; 4-({[6-(2-Fluoro-4-methanesulfonyl-phenylamino)-pyrimidin-4-yl]-methyl-amino}-methyl)-piperidine-1-carboxylic acid tert-butyl ester; 4-({[6-(4-Methanesulfonyl-phenylamino)-pyrimidin-4-yl]-methyl-amino}-methyl)-piperidine-1-carboxylic acid tert-butyl ester; 4-({[6-(2,5-Difluoro-benzylamino)-pyrimidin-4-yl]-methyl-amino}-methyl)-piperidine-1-carboxylic acid tert-butyl ester; 4-[({6-[(Benzo[1,3]dioxol-5-ylmethyl)-amino]-pyrimidin-4-yl}-methyl-amino)-methyl]-piperidine-1-carboxylic acid tert-butyl ester; (2-Fluoro-4-methanesulfonyl-phenyl)-{6-[4-(3-fluoro-phenoxy)-piperidin-1-yl]-pyrimidin-4-yl}-amine; 4-({Methyl-[6-(2-pyridin-4-yl-ethylamino)-pyrimidin-4-yl]-amino}-methyl)-piperidine-1-carboxylic acid tert-butyl ester; 4-({Methyl-[6-(2-pyridin-3-yl-ethylamino)-pyrimidin-4-yl]-amino}-methyl)-piperidine-1-carboxylic acid tert-butyl ester; 4-[(Methyl-{6-[(pyridin-3-ylmethyl)-amino]-pyrimidin-4-yl}-amino)-methyl]-piperidine-1-carboxylic acid tert-butyl ester; 4-[({6-[(2-Fluoro-4-methanesulfonyl-phenyl)-methyl-amino]-pyrimidin-4-yl}-methyl-amino)-methyl]-piperidine-1-carboxylic acid tert-butyl ester; 4-({[6-(2-Fluoro-4-methanesulfonyl-phenylamino)-pyrimidin-4-yl]-methyl-amino}-methyl)-piperidine-1-carboxylic acid isobutyl ester; 4-({[6-(4-Cyano-2-fluoro-phenylamino)-pyrimidin-4-yl]-methyl-amino}-methyl)-piperidine-1-carboxylic acid tert-butyl ester; 4-[({6-[4-(2-Methanesulfonyl-ethyl)-phenylamino]-pyrimidin-4-yl}-methyl-amino)-methyl]-piperidine-1-carboxylic acid tert-butyl ester; 4-({[6-(4-Ethylsulfanyl-phenylamino)-pyrimidin-4-yl]-methyl-amino}-methyl)-piperidine-1-carboxylic acid tert-butyl ester; 4-({[6-(4-Isopropylsulfanyl-phenylamino)-pyrimidin-4-yl]-methyl-amino}-methyl)-piperidine-1-carboxylic acid tert-butyl ester; 4-({[6-(4-Ethylsulfamoyl-phenylamino)-pyrimidin-4-yl]-methyl-amino}-methyl)-piperidine-1-carboxylic acid tert-butyl ester; 4-({Methyl-[6-(4-methylsulfamoyl-phenylamino)-pyrimidin-4-yl]-amino}-methyl)-piperidine-1-carboxylic acid tert-butyl ester; 4-({[6-(4-Dimethylsulfamoyl-phenylamino)-pyrimidin-4-yl]-methyl-amino}-methyl)-piperidine-1-carboxylic acid tert-butyl ester; 4-({Methyl-[6-(4-methylsulfamoylmethyl-phenylamino)-pyrimidin-4-yl]-amino}-methyl)-piperidine-1-carboxylic acid tert-butyl ester; 4-({Methyl-[6-(4-sulfamoyl-phenylamino)-pyrimidin-4-yl]-amino}-methyl)-piperidine-1-carboxylic acid tert-butyl ester; 4-({Methyl-[6-(4-[1,2,4]triazol-1-yl-phenylamino)-pyrimidin-4-yl]-amino}-methyl)-piperidine-1-carboxylic acid tert-butyl ester; 4-({Methyl-[6-(4-[1,2,4]triazol-1-ylmethyl-phenylamino)-pyrimidin-4-yl]-amino}-methyl)-piperidine-1-carboxylic acid tert-butyl ester; 4-[(Methyl-{6-[4-(2-[1,2,4]triazol-1-yl-ethyl)-phenylamino]-pyrimidin-4-yl}-amino)-methyl]-piperidine-1-carboxylic acid tert-butyl ester; 4-({[6-(Benzo[1,3]dioxol-5-ylamino)-pyrimidin-4-yl]-methyl-amino}-methyl)-piperidine-1-carboxylic acid tert-butyl ester; 4-({[6-(6-Methanesulfonyl-pyridin-3-ylamino)-pyrimidin-4-yl]-methyl-amino}-methyl)-piperidine-1-carboxylic acid tert-butyl ester; 4-({[6-(3,5-Dimethoxy-phenylamino)-pyrimidin-4-yl]-methyl-amino}-methyl)-piperidine-1-carboxylic acid tert-butyl ester; 4-[(Methyl-{6-[4-(2-oxo-oxazolidin-4-ylmethyl)-phenylamino]-pyrimidin-4-yl}-amino)-methyl]-piperidine-1-carboxylic acid tert-butyl ester; 4-[({6-[4-(1,1-Dioxo-1λ6-thiomorpholin-4-ylmethyl)-phenylamino]-pyrimidin-4-yl}-methyl-amino)-methyl]-piperidine-1-carboxylic acid tert-butyl ester; 4-({Methyl-[6-(4-pyrazol-1-yl-phenylamino)-pyrimidin-4-yl]-amino}-methyl)-piperidine-1-carboxylic acid tert-butyl ester; 4-({[6-(2,2-Difluoro-benzo[1,3]dioxol-5-ylamino)-pyrimidin-4-yl]-methyl-amino}-methyl)-piperidine-1-carboxylic acid tert-butyl ester; 4-({Methyl-[6-(4-trifluoromethanesulfonyl-phenylamino)-pyrimidin-4-yl]-amino}-methyl)-piperidine-1-carboxylic acid tert-butyl ester; 4-[(Methyl-{6-[4-(morpholine-4-sulfonyl)-phenylamino]-pyrimidin-4-yl}-amino)-methyl]-piperidine-1-carboxylic acid tert-butyl ester; 4-[(Methyl-{6-[2-(pyridine-2-carbonyl)-phenylamino]-pyrimidin-4-yl}-amino)-methyl]-piperidine-1-carboxylic acid tert-butyl ester; 4-({[6-(2-Fluoro-5-methanesulfonyl-phenylamino)-pyrimidin-4-yl]-methyl-amino}-methyl)-piperidine-1-carboxylic acid tert-butyl ester; N-Ethyl-3-fluoro-4-[6-(methyl-piperidin-4-ylmethyl-amino)-pyrimidin-4-ylamino]-benzenesulfonamide; 3-Fluoro-N-isopropyl-4-[6-(methyl-piperidin-4-ylmethyl-amino)-pyrimidin-4-ylamino]-benzenesulfonamide; 4-({[6-(3,4-Difluoro-phenylamino)-pyrimidin-4-yl]-methyl-amino}-methyl)-piperidine-1-carboxylic acid tert-butyl ester; 4-({[6-(2,6-Difluoro-phenylamino)-pyrimidin-4-yl]-methyl-amino}-methyl)-piperidine-1-carboxylic acid tert-butyl ester; 4-({[6-(2,5-Difluoro-phenylamino)-pyrimidin-4-yl]-methyl-amino}-methyl)-piperidine-1-carboxylic acid tert-butyl ester; 4-({[6-(2,3-Difluoro-phenylamino)-pyrimidin-4-yl]-methyl-amino}-methyl)-piperidine-1-carboxylic acid tert-butyl ester; 4-({Methyl-[6-(2,3,5-trifluoro-phenylamino)-pyrimidin-4-yl]-amino}-methyl)-piperidine-1-carboxylic acid tert-butyl ester; 4-({[6-(2-Fluoro-phenylamino)-pyrimidin-4-yl]-methyl-amino}-methyl)-piperidine-1-carboxylic acid tert-butyl ester; 4-({[6-(2-Fluoro-4-methyl-phenylamino)-pyrimidin-4-yl]-methyl-amino}-methyl)-piperidine-1-carboxylic acid tert-butyl ester; 4-({[6-(3-Chloro-2-fluoro-phenylamino)-pyrimidin-4-yl]-methyl-amino}-methyl)-piperidine-1-carboxylic acid tert-butyl ester; 4-({[6-(2,4-Difluoro-phenylamino)-pyrimidin-4-yl]-methyl-amino}-methyl)-piperidine-1-carboxylic acid tert-butyl ester; 4-[(Methyl-{6-[2-(1-oxy-pyridin-3-yl)-ethylamino]-pyrimidin-4-yl}-amino)-methyl]-piperidine-1-carboxylic acid tert-butyl ester; 4-[(Methyl-{6-[2-(1-oxy-pyridin-3-yl)-ethylamino]-pyrimidin-4-yl}-amino)-methyl]-piperidine-1-carboxylic acid isobutyl ester; 4-({[6-(2,5-Difluoro-phenylamino)-pyrimidin-4-yl]-methyl-amino}-methyl)-piperidine-1-carboxylic acid isobutyl ester; 4-({[6-(4-Cyano-2-fluoro-phenylamino)-pyrimidin-4-yl]-methyl-amino}-methyl)-piperidine-1-carboxylic acid isobutyl ester; 4-[({6-[2-(2-Fluoro-phenoxy)-ethylamino]-pyrimidin-4-yl}-methyl-amino)-methyl]-piperidine-1-carboxylic acid tert-butyl ester; 4-({[6-(2-Fluoro-phenoxy)-pyrimidin-4-yl]-methyl-amino}-methyl)-piperidine-1-carboxylic acid tert-butyl ester; 4-({[6-(2,5-Difluoro-phenoxy)-pyrimidin-4-yl]-methyl-amino}-methyl)-piperidine-1-carboxylic acid tert-butyl ester; 4-[({6-[2-(2-Chloro-phenoxy)-ethylamino]-pyrimidin-4-yl}-methyl-amino)-methyl]-piperidine-1-carboxylic acid tert-butyl ester; 4-({[6-(2-Chloro-phenoxy)-pyrimidin-4-yl]-methyl-amino}-methyl)-piperidine-1-carboxylic acid tert-butyl ester; 4-[({6-[2-(4-Fluoro-phenoxy)-propylamino]-pyrimidin-4-yl}-methyl-amino)-methyl]-piperidine-1-carboxylic acid tert-butyl ester; 4-({[6-(4-Ethylsulfamoyl-2-fluoro-phenylamino)-pyrimidin-4-yl]-methyl-amino}-methyl)-piperidine-1-carboxylic acid tert-butyl ester; 4-({[6-(2-Fluoro-4-isopropylsulfamoyl-phenylamino)-pyrimidin-4-yl]-methyl-amino}-methyl)-piperidine-1-carboxylic acid tert-butyl ester; 4-({[6-(4-Cyano-2,5-difluoro-phenylamino)-pyrimidin-4-yl]-methyl-amino}-methyl)-piperidine-1-carboxylic acid tert-butyl ester; 4-({[6-(4-Bromo-2,5-difluoro-phenylamino)-pyrimidin-4-yl]-methyl-amino}-methyl)-piperidine-1-carboxylic acid tert-butyl ester; 4-({[6-(5-Carboxy-2-fluoro-phenylamino)-pyrimidin-4-yl]-methyl-amino}-methyl)-piperidine-1-carboxylic acid tert-butyl ester; 4-({[6-(6-Methoxy-pyridin-3-ylamino)-pyrimidin-4-yl]-methyl-amino}-methyl)-piperidine-1-carboxylic acid tert-butyl ester; 4-({[6-(2,6-Dimethoxy-pyridin-3-ylamino)-pyrimidin-4-yl]-methyl-amino}-methyl)-piperidine-1-carboxylic acid tert-butyl ester; 6-{6-[(1-tert-Butoxycarbonyl-piperidin-4-ylmethyl)-methyl-amino]-pyrimidin-4-ylamino}-nicotinic acid; 4-({[6-(6-Acetylamino-pyridin-3-ylamino)-pyrimidin-4-yl]-methyl-amino}-methyl)-piperidine-1-carboxylic acid tert-butyl ester; 4-({[6-(5-Fluoro-pyridin-2-ylamino)-pyrimidin-4-yl]-methyl-amino}-methyl)-piperidine-1-carboxylic acid tert-butyl ester; 4-({[6-(4-Cyano-2-ethyl-phenylamino)-pyrimidin-4-yl]-methyl-amino}-methyl)-piperidine-1-carboxylic acid tert-butyl ester; 4-({[6-(4-Butyryl-phenylamino)-pyrimidin-4-yl]-methyl-amino}-methyl)-piperidine-1-carboxylic acid tert-butyl ester; 4-({[6-(5-Bromo-3-methyl-pyridin-2-ylamino)-pyrimidin-4-yl]-methyl-amino}-methyl)-piperidine-1-carboxylic acid tert-butyl ester; 4-({[6-(3-Bromo-5-methyl-pyridin-2-ylamino)-pyrimidin-4-yl]-methyl-amino}-methyl)-piperidine-1-carboxylic acid tert-butyl ester; 4-({Methyl-[6-(5-trifluoromethyl-pyridin-2-ylamino)-pyrimidin-4-yl]-amino}-methyl)-piperidine-1-carboxylic acid tert-butyl ester; 4-({[6-(4-Bromo-2-fluoro-phenylamino)-pyrimidin-4-yl]-methyl-amino}-methyl)-piperidine-1-carboxylic acid tert-butyl ester; 4-({[6-(3-Carboxy-4-fluoro-phenylamino)-pyrimidin-4-yl]-methyl-amino}-methyl)-piperidine-1-carboxylic acid tert-butyl ester; 4-({[6-(4-Ethoxycarbonyl-2-fluoro-phenylamino)-pyrimidin-4-yl]-methyl-amino}-methyl)-piperidine-1-carboxylic acid isobutyl ester; 4-({[6-(4-Carboxy-2-fluoro-phenylamino)-pyrimidin-4-yl]-methyl-amino}-methyl)-piperidine-1-carboxylic acid isobutyl ester; 4-({[6-(4-Cyano-2-fluoro-phenylamino)-pyrimidin-4-yl]-methyl-amino}-methyl)-piperidine-1-carboxylic acid isopropyl ester; 4-({[6-(4-Cyano-2-fluoro-phenylamino)-pyrimidin-4-yl]-methyl-amino}-methyl)-piperidine-1-carboxylic acid butyl ester; 4-({[6-(4-Cyano-2-fluoro-phenylamino)-pyrimidin-4-yl]-methyl-amino}-methyl)-piperidine-1-carboxylic acid cyclopropylmethyl ester; {4-[6-(2-Fluoro-4-methanesulfonyl-phenylamino)-pyrimidin-4-yl]-piperazin-1-yl}-acetic acid ethyl ester; (2-Fluoro-4-methanesulfonyl-phenyl)-{6-[4-(3-isopropyl-[1,2,4]oxadiazol-5-ylmethyl)-piperazin-1-yl]-pyrimidin-4-yl}-amine; 4-({[6-(2,5-Difluoro-4-hydroxy-phenylamino)-pyrimidin-4-yl]-methyl-amino}-methyl)-piperidine-1-carboxylic acid isobutyl ester; 4-({[6-(4-Ethylcarbamoyl-2-fluoro-phenylamino)-pyrimidin-4-yl]-methyl-amino}-methyl)-piperidine-1-carboxylic acid isobutyl ester; 4-[({6-[2-Fluoro-4-(N-hydroxycarbamimidoyl)-phenylamino]-pyrimidin-4-yl}-methyl-amino)-methyl]-piperidine-1-carboxylic acid isobutyl ester; 4-({[6-(2-Fluoro-4-methanesulfonyl-phenylamino)-pyrimidin-4-yl]-methyl-amino}-methyl)-piperidine-1-carboxylic acid 3-methyl-butyl ester; 4-({[6-(2,5-Difluoro-4-methanesulfonyl-phenylamino)-pyrimidin-4-yl]-methyl-amino}-methyl)-piperidine-1-carboxylic acid tert-butyl ester; 4-({[6-(2-Fluoro-4-methanesulfonyl-phenylamino)-pyrimidin-4-yl]-methyl-amino}-methyl)-piperidine-1-carboxylic acid isopropyl ester; (5-Butyl-pyridin-2-yl)-[4-({[6-(2-fluoro-4-methanesulfonyl-phenylamino)-pyrimidin-4-yl]-methyl-amino}-methyl)-piperidin-1-yl]-methanone; N-(2-Fluoro-4-methanesulfonyl-phenyl)-N'-(5'-fluoro-3,4,5,6-tetrahydro-2H-[1,2']bipyridinyl-4-ylmethyl)-N'-methyl-pyrimidine; -4,6-diamine; 4-({[6-(4-Carbamimidoyl-2-fluoro-phenylamino)-pyrimidin-4-yl]-methyl-amino}-methyl)-piperidine-1-carboxylic acid isobutyl ester; 4-({[6-(2-Fluoro-4-methanesulfonyl-phenylamino)-pyrimidin-4-yl]-methyl-amino}-methyl)-piperidine-1-carboxylic acid cyclobutyl ester; 4-[6-(2-Fluoro-4-methanesulfonyl-phenylamino)-pyrimidin-4-ylamino]-piperidine-1-carboxylic acid tert-butyl ester; N-(2-Fluoro-4-methanesulfonyl-phenyl)-N'-[1-(3-isopropyl-[1,2,4]oxadiazol-5-ylmethyl)-piperidin-4-ylmethyl]-N'-methyl-pyrimidine; -4,6-diamine; 4-({[6-(2-Fluoro-4-methanesulfonyl-phenylamino)-pyrimidin-4-yl]-methyl-amino}-methyl)-piperidine-1-carboxylic acid 1-ethyl-propyl ester; 4-({Ethyl-[6-(2-fluoro-4-methanesulfonyl-phenylamino)-pyrimidin-4-yl]-amino}-methyl)-piperidine-1-carboxylic acid tert-butyl ester; 4-({Ethyl-[6-(2-fluoro-4-methanesulfonyl-phenylamino)-pyrimidin-4-yl]-amino}-methyl)-piperidine-1-carboxylic acid isopropyl ester; 4-({[6-(4-Cyano-2,5-difluoro-phenylamino)-pyrimidin-4-yl]-ethyl-amino}-methyl)-piperidine-1-carboxylic acid isopropyl ester; 4-({[6-(4-Amino-2,5-difluoro-phenoxy)-pyrimidin-4-yl]-ethyl-amino}-methyl)-piperidine-1-carboxylic acid tert-butyl ester; 4-({[6-(2,5-Difluoro-4-methoxy-phenylamino)-pyrimidin-4-yl]-ethyl-amino}-methyl)-piperidine-1-carboxylic acid tert-butyl ester; 4-({[6-(2,5-Difluoro-4-methanesulfonyl-phenylamino)-pyrimidin-4-yl]-ethyl-amino}-methyl)-piperidine-1-carboxylic acid tert-butyl ester; 4-({Ethyl-[6-(2,4,5-trifluoro-phenylamino)-pyrimidin-4-yl]-amino}-methyl)-piperidine-1-carboxylic acid tert-butyl ester; (2-Fluoro-4-methanesulfonyl-phenyl)-{6-[4-(3-isopropyl-[1,2,4]oxadiazol-5-yl)-piperidin-1-yl]-pyrimidin-4-yl}-amine; 4-[(Ethyl-{6-[4-(N-ethylcarbamimidoyl)-2,5-difluoro-phenylamino]-pyrimidin-4-yl}-amino)-methyl]-piperidine-1-carboxylic acid isopropyl ester; 4-({[6-(4-Bromo-2,5-difluoro-phenylamino)-pyrimidin-4-yl]-ethyl-amino}-methyl)-piperidine-1-carboxylic acid tert-butyl ester; 4-[({6-[5-(2-Amino-ethylamino)-4-cyano-2-fluoro-phenylamino]-pyrimidin-4-yl}-ethyl-amino)-methyl]-piperidine-1-carboxylic acid isopropyl ester; {(1-[6-(2-Fluoro- 4-methanesulfonyl-phenylamino)-pyrimidin-4-yl]-piperidin-4-yl}-acetic acid methyl ester; 3-{4-[6-(2-Fluoro-4-methanesulfonyl-phenylamino)-pyrimidin-4-yl]-piperazin-1-yl}-propionic acid ethyl ester; (2-Fluoro-4-methanesulfonyl-phenyl)-{6-[4-(4-isobutyl-phenyl)-piperidin-1-yl]-pyrimidin-4-yl}-amine; (2-Fluoro-4-methanesulfonyl-phenyl)-{6-[4-(4-isopropyl-phenyl)-piperidin-1-yl]-pyrimidin-4-yl}-amine; {6-[4-(3-Cyclopropylmethyl-[1,2,4]oxadiazol-5-yl)-piperidin-1-yl]-pyrimidin-4-yl}-(2-fluoro-4-methanesulfonyl-phenyl)-amine; (2-Fluoro-4-methanesulfonyl-phenyl)-{6-[4-(3-isobutyl-[1,2,4]oxadiazol-5-yl)-piperidin-1-yl]-pyrimidin-4-yl}-amine; (2-Fluoro-4-methanesulfonyl-phenyl)-{6-[4-(4-isopropoxy-phenyl)-piperazin-1-yl]-pyrimidin-4-yl}-amine; (2-Fluoro-4-methanesulfonyl-phenyl)-{6-[4-(4-isopropoxy-phenyl)-piperidin-1-yl]-pyrimidin-4-yl}-amine; (2-Fluoro-4-methanesulfonyl-phenyl)-{6-[4-(5-isopropoxy-pyridin-2-yl)-piperazin-1-yl]-pyrimidin-4-yl}-amine; {6-[4-(3-Dimethylaminomethyl-[1,2,4]oxadiazol-5-yl)-piperidin-1-yl]-pyrimidin-4-yl}-(2-fluoro-4-methanesulfonyl-phenyl)-amine; (2-Fluoro-4-methanesulfonyl-phenyl)-(6-{4-[2-(3-isopropyl-[1,2,4]oxadiazol-5-yl)-ethyl]-piperazin-1-yl}-pyrimidin-4-yl)-amine; (2-Fluoro-4-methanesulfonyl-phenyl)-{6-[4-(5-isopropoxy-pyridin-2-yloxy)-piperidin-1-yl]-pyrimidin-4-yl}-amine; (2-Fluoro-4-methanesulfonyl-phenyl)-{6-[4-(3-pyridin-3-yl-[1,2,4]oxadiazol-5-yl)-piperidin-1-yl]-pyrimidin-4-yl}-amine; 2,5-Difluoro-4-{6-[4-(4-isopropoxy-phenyl)-piperazin-1-yl]-pyrimidin-4-ylamino}-benzonitrile; 4-{[6-(2-Fluoro-4-methanesulfonyl-phenylamino)-pyrimidin-4-ylamino]-methyl}-piperidine-1-carboxylic acid tert-butyl ester; 4-{[6-(2-Fluoro-4-methanesulfonyl-phenylamino)-pyrimidin-4-ylamino]-methyl}-piperidine-1-carboxylic acid isopropyl ester; 4-({[6-(2-Fluoro-4-methanesulfonyl-phenylamino)-pyrimidin-4-yl]-isopropyl-amino}-methyl)-piperidine-1-carboxylic acid tert-butyl ester; 4-({[4-(2-Fluoro-4-methanesulfonyl-phenylamino)-pyridin-2-yl]-methyl-amino}-methyl)-piperidine-1-carboxylic acid isobutyl ester; and 4-({[2-(2-Fluoro-4-methanesulfonyl-phenylamino)-pyridin-4-yl]-methyl-amino}-methyl)-piperidine-1-carboxylic acid isobutyl ester.

Specific examples of GPR119 agonists disclosed in U.S. Patent Application No. 60/577,354 include the following compounds according to Formula (V) (referred to herein as Group E2): 4-[6-(2-Fluoro-4-methanesulfonyl-phenylamino)-pyrimidin-4-yloxy]-piperidine-1-carboxylic acid tert-butyl ester; (2-Fluoro-4-methanesulfonyl-phenyl)-{6-[1-(3-isopropyl-[1,2,4]oxadiazol-5-ylmethyl)-piperidin-4-yloxy]-pyrimidin-4-yl}-amine; 4-[6-(2-Fluoro-4-methanesulfonyl-phenylamino)-pyrimidin-4-yloxy]-piperidine-1-carboxylic acid isopropyl ester; (6-Chloro-pyridin-2-yl)-{4-[6-(2-fluoro-4-methanesulfonyl-phenylamino)-pyrimidin-4-yloxy]-piperidin-1-yl}-methanone; (6-Bromo-pyridin-2-yl)-{4-[6-(2-fluoro-4-methanesulfonyl-phenylamino)-pyrimidin-4-yloxy]-piperidin-1-yl}-methanone; {4-[6-(2-Fluoro-4-methanesulfonyl-phenylamino)-pyrimidin-4-yloxy]-piperidin-1-yl}-(6-methyl-pyridin-2-yl)-methanone; {4-[6-(2-Fluoro-4-methanesulfonyl-phenylamino)-pyrimidin-4-yloxy]-piperidin-1-yl}-(6-fluoro-pyridin-2-yl)-methanone; {4-[6-(2-Fluoro-4-methanesulfonyl-phenylamino)-pyrimidin-4-yloxy]-piperidin-1-yl}-pyridin-2-yl-methanone; (5-Bromo-pyridin-3-yl)-{4-[6-(2-fluoro-4-methanesulfonyl-phenylamino)-pyrimidin-4-yloxy]-piperidin-1-yl}-methanone; {4-[6-(2-Fluoro-4-methanesulfonyl-phenylamino)-pyrimidin-4-yloxy]-piperidin-1-yl}-(5-methyl-pyridin-3-yl)-methanone; (5,6-Dichloro-pyridin-3-yl)-{4-[6-(2-fluoro-4-methanesulfonyl-phenylamino)-pyrimidin-4-yloxy]-piperidin-1-yl}-methanone; 4-[6-(4-Cyano-2,5-difluoro-phenylamino)-pyrimidin-4-yloxy]-piperidine-1-carboxylic acid tert-butyl ester; 4-[6-(2,5-Difluoro-4-methanesulfonyl-phenylamino)-pyrimidin-4-yloxy]-piperidine-1-carboxylic acid tert-butyl ester; 4-[6-(2,4,5-Trifluoro-phenylamino)-pyrimidin-4-yloxy]-piperidine-1-carboxylic acid tert-butyl ester; 4-[6-(4-Bromo-2,5-difluoro-phenylamino)-pyrimidin-4-yloxy]-piperidine-1-carboxylic acid tert-butyl ester; 4-[6-(3-Fluoro-4-methyl-phenylamino)-pyrimidin-4-yloxy]-piperidine-1-carboxylic acid tert-butyl ester; 4-[6-(3-Hydroxy-4-methoxy-phenylamino)-pyrimidin-4-yloxy]-piperidine-1-carboxylic acid tert-butyl ester; 4-[6-(6-Cyano-pyridin-3-ylamino)-pyrimidin-4-yloxy]-piperidine-1-carboxylic acid tert-butyl ester; 4-[6-(3-Chloro-4-cyano-phenylamino)-pyrimidin-4-yloxy]-piperidine-1-carboxylic acid tert-butyl ester; 4-[6-(6-Chloro-pyridin-3-ylamino)-pyrimidin-4-yloxy]-piperidine-1-carboxylic acid tert-butyl ester; 4-[6-(3-Fluoro-4-methoxy-phenylamino)-pyrimidin-4-yloxy]-piperidine-1-carboxylic acid tert-butyl ester; 4-[6-(3,4-Dimethoxy-phenylamino)-pyrimidin-4-yloxy]-piperidine-1-carboxylic acid tert-butyl ester; 4-[6-(2,3-Dihydro-benzo[1,4]dioxin-6-ylamino)-pyrimidin-4-yloxy]-piperidine-1-carboxylic acid tert-butyl ester; 4-[6-(4-Cyano-2,5-difluoro-phenylamino)-pyrimidin-4-yloxy]-piperidine-1-carboxylic acid isopropyl ester; 4-[6-(4-Cyano-5-ethylamino-2-fluoro-phenylamino)-pyrimidin-4-yloxy]-piperidine-1-carboxylic acid tert-butyl ester; 4-[6-(4-Ethoxy-2,5-difluoro-phenylamino)-pyrimidin-4-yloxy]-piperidine-1-carboxylic acid isopropyl ester; 4-[6-(4-Ethylsulfanyl-phenylamino)-pyrimidin-4-yloxy]-piperidine-1-carboxylic acid tert-butyl ester; 4-[6-(4-Isopropylsulfanyl-phenylamino)-pyrimidin-4-yloxy]-piperidine-1-carboxylic acid tert-butyl ester; (5-Butyl-pyridin-2-yl)-{4-[6-(2-fluoro-4-methanesulfonyl-phenylamino)-pyrimidin-4-yloxy]-piperidin-1-yl}-methanone; 4-[6-(5-Chloro-3-methyl-pyridin-2-ylamino)-pyrimidin-4-yloxy]-piperidine-1-carboxylic acid tert-butyl ester; 4-[6-(6-Acetylamino-4-methyl-pyridin-3-ylamino)-pyrimidin-4-yloxy]-piperidine-1-carboxylic acid tert-butyl ester; 4-[6-(5-Fluoro-4-methyl-pyridin-2-ylamino)-pyrimidin-4-yloxy]-piperidine-1-carboxylic acid tert-butyl ester; 4-[6-(6-Methoxy-5-methyl-pyridin-3-ylamino)-pyrimidin-4-yloxy]-piperidine-1-carboxylic acid tert-butyl ester; 4-[6-(6-Methoxy-2-methyl-pyridin-3-ylamino)-pyrimidin-4-yloxy]-piperidine-1-carboxylic acid tert-butyl ester; 4-[6-(6-Fluoro-5-methyl-pyridin-3-ylamino)-pyrimidin-4-yloxy]-piperidine-1-carboxylic acid tert-butyl ester; 4-[6-(2-Chloro-6-methyl-pyridin-3-ylamino)-pyrimidin-4-yloxy]-piperidine-1-carboxylic acid tert-butyl ester; 4-[6-(4-Methyl-pyridin-3-ylamino)-pyrimidin-4-yloxy]-piperidine-1-carboxylic acid tert-butyl ester; 4-[6-(2-Methyl-pyridin-3-ylamino)-pyrimidin-4-yloxy]-piperidine-1-carboxylic acid tert-butyl ester; 4-[6-(6-Chloro-2-methyl-pyridin-3-ylamino)-pyrimidin-4-yloxy]-piperidine-1-carboxylic acid tert-butyl ester; 4-[6-(6-Fluoro-pyridin-3-ylamino)-pyrimidin-4-yloxy]-piperidine-1-carboxylic acid tert-butyl ester; 4-[6-(2-Chloro-4-methyl-pyridin-3-ylamino)-pyrimidin-4-yloxy]-piperidine-1-carboxylic acid tert-butyl ester; 4-[6-(6-Methoxy-pyridin-3-ylamino)-pyrimidin-4-yloxy]-piperidine-1-carboxylic acid tert-butyl ester; 4-[6-(5-Fluoro-pyridin-2-ylamino)-pyrimidin-4-yloxy]-piperidine-1-carboxylic acid tert-butyl ester; 4-[6-(2-Fluoro-pyridin-3-ylamino)-pyrimidin-4-yloxy]-piperidine-1-carboxylic acid tert-butyl ester; 4-[6-(6-Chloro-5-methyl-pyridin-3-ylamino)-pyrimidin-4-yloxy]-piperidine-1-carboxylic acid tert-butyl ester; 4-[6-(2-Methyl-pyridin-4-ylamino)-pyrimidin-4-yloxy]-piperidine-1-carboxylic acid tert-butyl ester; 4-[6-(2-Methoxy-pyridin-3-ylamino)-pyrimidin-4-yloxy]- piperidine-1-carboxylic acid tert-butyl ester; 4-[6-(2,5-Difluoro-phenylamino)-pyrimidin-4-yloxy]-piperidine-1-carboxylic acid tert-butyl ester; 4-[6-(4-Chloro-2-fluoro-phenylamino)-pyrimidin-4-yloxy]-piperidine-1-carboxylic acid tert-butyl ester; 4-[6-(2,5-Difluoro-phenylamino)-pyrimidin-4-yloxy]-piperidine-1-carboxylic acid isopropyl ester; 4-[6-(6-Methoxy-pyridin-3-ylamino)-pyrimidin-4-yloxy]-piperidine-1-carboxylic acid isopropyl ester; 4-[6-(4-Cyano-3-methoxy-phenylamino)-pyrimidin-4-yloxy]-piperidine-1-carboxylic acid isopropyl ester; 4-[6-(3-Fluoro-4-hydroxy-phenylamino)-pyrimidin-4-yloxy]-piperidine-1-carboxylic acid isopropyl ester; 4-[6-(6-Ethoxy-pyridin-3-ylamino)-pyrimidin-4-yloxy]-piperidine-1-carboxylic acid isopropyl ester; 4-[6-(2,5-Difluoro-4-isopropoxy-phenylamino)-pyrimidin-4-yloxy]-piperidine-1-carboxylic acid isopropyl ester; (2-Fluoro-4-methanesulfonyl-phenyl)-[6-(5'-isopropoxy-3,4,5,6-tetrahydro-2H-[1,2']bipyridinyl-4-yloxy)-pyrimidin-4-yl]-amine; (2-Fluoro-4-methanesulfonyl-phenyl)-{6-[1-(3-isopropyl-[1,2,4]oxadiazol-5-yl)-piperidin-4-yloxy]-pyrimidin-4-yl}-amine; 4-[6-(4-Cyano-2-fluoro-phenylamino)-pyrimidin-4-yloxy]-piperidine-1-carboxylic acid isopropyl ester; 4-[6-(Pyridin-3-ylamino)-pyrimidin-4-yloxy]-piperidine-1-carboxylic acid isopropyl ester; 4-[6-(Pyridin-4-ylamino)-pyrimidin-4-yloxy]-piperidine-1-carboxylic acid isopropyl ester; 4-[6-(2,5-Difluoro-4-propoxy-phenylamino)-pyrimidin-4-yloxy]-piperidine-1-carboxylic acid isopropyl ester; 4-[6-(4-Ethylamino-2-fluoro-phenylamino)-pyrimidin-4-yloxy]-piperidine-1-carboxylic acid isopropyl ester; 4-[6-(4-Dimethylamino-2-fluoro-phenylamino)-pyrimidin-4-yloxy]-piperidine-1-carboxylic acid isopropyl ester; 4-[6-(2-Fluoro-4-propylamino-phenylamino)-pyrimidin-4-yloxy]-piperidine-1-carboxylic acid isopropyl ester; 4-[6-(2-Fluoro-4-isopropylamino-phenylamino)-pyrimidin-4-yloxy]-piperidine-1-carboxylic acid isopropyl ester; 4-[6-(2-Methyl-6-propylamino-pyridin-3-ylamino)-pyrimidin-4-yloxy]-piperidine-1-carboxylic acid isopropyl ester; 4-[6-(2-Methyl-pyridin-3-ylamino)-pyrimidin-4-yloxy]-piperidine-1-carboxylic acid isopropyl ester; 4-[6-(6-Isopropylamino-2-methyl-pyridin-3-ylamino)-pyrimidin-4-yloxy]-piperidine-1-carboxylic acid isopropyl ester; 4-[6-(2-Methyl-6-propoxy-pyridin-3-ylamino)-pyrimidin-4-yloxy]-piperidine-1-carboxylic acid isopropyl ester; 4-[6-(4-Iodo-2-methyl-phenylamino)-pyrimidin-4-yloxy]-piperidine-1-carboxylic acid isopropyl ester; 4-[6-(2-Fluoro-4-iodo-phenylamino)-pyrimidin-4-yloxy]-piperidine-1-carboxylic acid isopropyl ester; 4-{6-[Methyl-(2-methyl-4,5,6,7-tetrahydro-2H-indazol-3-yl)-amino]-pyrimidin-4-yloxy}-piperidine-1-carboxylic acid isopropyl ester; 4-[6-(2-Methyl-2H-pyrazol-3-ylamino)-pyrimidin-4-yloxy]-piperidine-1-carboxylic acid isopropyl ester; 4-[6-(2-Phenyl-2H-pyrazol-3-ylamino)-pyrimidin-4-yloxy]-piperidine-1-carboxylic acid isopropyl ester; 4-[6-(5-tert-Butyl-1H-pyrazol-3-ylamino)-pyrimidin-4-yloxy]-piperidine-1-carboxylic acid isopropyl ester; 4-[6-(5-p-Tolyl-1H-pyrazol-3-ylamino)-pyrimidin-4-yloxy]-piperidine-1-carboxylic acid isopropyl ester; 4-[6-(6-Methoxy-5-methyl-pyridin-3-ylamino)-pyrimidin-4-yloxy]-piperidine-1-carboxylic acid isopropyl ester; 4-[6-(4-Methyl-pyridin-3-ylamino)-pyrimidin-4-yloxy]-piperidine-1-carboxylic acid isopropyl ester; 4-[6-(4-Acetylamino-3-methyl-phenylamino)-pyrimidin-4-yloxy]-piperidine-1-carboxylic acid isopropyl ester; 4-[6-(3-Chloro-4-fluoro-phenylamino)-pyrimidin-4-yloxy]-piperidine-1-carboxylic acid isopropyl ester; 4-[6-(3,5-Dimethoxy-phenylamino)-pyrimidin-4-yloxy]-piperidine-1-carboxylic acid isopropyl ester; 4-[6-(6-Ethyl-pyridin-2-ylamino)-pyrimidin-4-yloxy]-piperidine-1-carboxylic acid isopropyl ester; 4-[6-(5-Methyl-pyridin-2-ylamino)-pyrimidin-4-yloxy]-piperidine-1-carboxylic acid isopropyl ester; 4-[6-(2-Methyl-quinolin-6-ylamino)-pyrimidin-4-yloxy]-piperidine-1-carboxylic acid isopropyl ester; 4-[6-(2-Methylsulfanyl-benzothiazol-6-ylamino)-pyrimidin-4-yloxy]-piperidine-1-carboxylic acid isopropyl ester; 4-[6-(6-Morpholin-4-yl-pyridin-3-ylamino)-pyrimidin-4-yloxy]-piperidine-1-carboxylic acid isopropyl ester; 4-[6-(4-Benzenesulfonyl-thiophen-3-ylamino)-pyrimidin-4-yloxy]-piperidine-1-carboxylic acid isopropyl ester; 4-[6-(4-Piperidin-1-yl-phenylamino)-pyrimidin-4-yloxy]-piperidine-1-carboxylic acid isopropyl ester; 4-[6-(3-Trifluoromethoxy-phenylamino)-pyrimidin-4-yloxy]-piperidine-1-carboxylic acid isopropyl ester; 4-[6-(5-Oxo-5,6,7,8-tetrahydro-naphthalen-2-ylamino)-pyrimidin-4-yloxy]-piperidine-1-carboxylic acid isopropyl ester; 4-[6-(6-Methyl-1H-pyrazolo[3,4-b]pyridin-3-ylamino)-pyrimidin-4-yloxy]-piperidine-1-carboxylic acid isopropyl ester; 4-[6-(5-Cyano-pyridin-2-ylamino)-pyrimidin-4-yloxy]-piperidine-1-carboxylic acid isopropyl ester; 4-[6-(4-Bromo-2,5-difluoro-phenylamino)-pyrimidin-4-yloxy]-piperidine-1-carboxylic acid isopropyl ester; 4-[6-(4-Trifluoromethyl-pyridin-2-ylamino)-pyrimidin-4-yloxy]-piperidine-1-carboxylic acid isopropyl ester; 4-[6-(5-Methyl-1H-pyrazol-3-ylamino)-pyrimidin-4-yloxy]-piperidine-1-carboxylic acid isopropyl ester; 4-[6-(5-Cyclopropyl-1H-pyrazol-3-ylamino)-pyrimidin-4-yloxy]-piperidine-1-carboxylic acid isopropyl ester; 4-[6-(2,6-Dimethyl-pyridin-3-ylamino)-pyrimidin-4-yloxy]-piperidine-1-carboxylic acid isopropyl ester; 4-[6-(4-Cyano-2-methyl-phenylamino)-pyrimidin-4-yloxy]-piperidine-1-carboxylic acid isopropyl ester; 4-[6-(4-Methoxy-2-methyl-phenylamino)-pyrimidin-4-yloxy]-piperidine-1-carboxylic acid isopropyl ester; 4-[6-(2,4-Dimethoxy-phenylamino)-pyrimidin-4-yloxy]-piperidine-1-carboxylic acid isopropyl ester; 4-{6-[Acetyl-(2-fluoro-4-methanesulfonyl-phenyl)-amino]-pyrimidin-4-yloxy}-piperidine-1-carboxylic acid isopropyl ester; 4-[6-(5-Carbamoyl-pyridin-2-ylamino)-pyrimidin-4-yloxy]-piperidine-1-carboxylic acid isopropyl ester; 4-{6-[4-(3,4-Difluoro-phenyl)-thiazol-2-ylamino]-pyrimidin-4-yloxy}-piperidine-1-carboxylic acid isopropyl ester; 4-[6-(5-Oxo-1-phenyl-4,5-dihydro-1H-pyrazol-3-ylamino)-pyrimidin-4-yloxy]-piperidine-1-carboxylic acid isopropyl ester; 4-[6-(3-Oxazol-5-yl-phenylamino)-pyrimidin-4-yloxy]-piperidine-1-carboxylic acid isopropyl ester; 4-[6-(5-Trifluoromethyl-pyridin-2-ylamino)-pyrimidin-4-yloxy]-piperidine-1-carboxylic acid isopropyl ester; 4-[6-(4-Chloro-2-trifluoromethoxy-phenylamino)-pyrimidin-4-yloxy]-piperidine-1-carboxylic acid isopropyl ester; 4-{6-[(5-Pyridin-2-yl-thiophen-2-ylmethyl)-amino]-pyrimidin-4-yloxy}-piperidine-1-carboxylic acid isopropyl ester; 4-{6-[5-(4-Chloro-phenyl)-2H-pyrazol-3-ylamino]-pyrimidin-4-yloxy}-piperidine-1-carboxylic acid isopropyl ester; 4-[6-(1-Oxo-indan-5-ylamino)-pyrimidin-4-yloxy]-piperidine-1-carboxylic acid isopropyl ester; 4-{6-[5-(1-Methyl-pyrrolidin-2-yl)-pyridin-2-ylamino]-pyrimidin-4-yloxy}-piperidine-1-carboxylic acid isopropyl ester; 4-[6-(6-Methoxy-2-methyl-pyridin-3-ylamino)-pyrimidin-4-yloxy]-piperidine-1-carboxylic acid isopropyl ester; 4-[6-(5-Bromo-3-methyl-pyridin-2-ylamino)-pyrimidin-4-yloxy]-piperidine-1-carboxylic acid isopropyl ester; 4-[6-(2-Chloro-6-methyl-pyridin-3-ylamino)-pyrimidin-4-yloxy]-piperidine-1-carboxylic acid isopropyl ester; 4-[6-(2-Ethynyl-phenylamino)-pyrimidin-4-yloxy]-piperidine-1-carboxylic acid isopropyl ester; 4-[6-(4-Bromo-2-trifluoromethoxy-phenylamino)-pyrimidin-4-yloxy]-piperidine-1-carboxylic acid isopropyl ester; 4-[6-(3-Iodo-4-methyl-phenylamino)-pyrimidin-4-yloxy]-piperidine-1- carboxylic acid isopropyl ester; 4-[6-(2-Fluoro-5-methyl-phenylamino)-pyrimidin-4-yloxy]-piperidine-1-carboxylic acid isopropyl ester; 4-{6-[5-(4-Methoxy-phenyl)-[1,3,4]thiadiazol-2-ylamino]-pyrimidin-4-yloxy}-piperidine-1-carboxylic acid isopropyl ester; 4-[6-(3,5-Dimethyl-isoxazol-4-ylamino)-pyrimidin-4-yloxy]-piperidine-1-carboxylic acid isopropyl ester; 4-[2-(2,5-Difluoro-4-propoxy-phenylamino)-pyridin-4-yloxy]-piperidine-1-carboxylic acid isopropyl ester; 4-[6-(2,5-Difluoro-4-propylamino-phenylamino)-pyrimidin-4-yloxy]-piperidine-1-carboxylic acid isopropyl ester; 4-[6-(2,5-Difluoro-4-morpholin-4-yl-phenylamino)-pyrimidin-4-yloxy]-piperidine-1-carboxylic acid isopropyl ester; 4-[6-(2-Methyl-4-propylamino-phenylamino)-pyrimidin-4-yloxy]-piperidine-1-carboxylic acid isopropyl ester; 4-{6-[2,5-Difluoro-4-(4-methyl-piperazin-1-yl)-phenylamino]-pyrimidin-4-yloxy}-piperidine-1-carboxylic acid isopropyl ester; 4-{6-[2,5-Difluoro-4-(2-pyrrolidin-1-yl-ethoxy)-phenylamino]-pyrimidin-4-yloxy}-piperidine-1-carboxylic acid isopropyl ester; 4-{6-[4-(2-Dimethylamino-ethoxy)-2,5-difluoro-phenylamino]-pyrimidin-4-yloxy}-piperidine-1-carboxylic acid isopropyl ester; 4-{6-[2,5-Difluoro-4-(2-morpholin-4-yl-ethoxy)-phenylamino]-pyrimidin-4-yloxy}-piperidine-1-carboxylic acid isopropyl ester; 4-[6-(2,4-Difluoro-phenylamino)-pyrimidin-4-yloxy]-piperidine-1-carboxylic acid isopropyl ester; 4-[6-(2,4,5-Trifluoro-phenylamino)-pyrimidin-4-yloxy]-piperidine-1-carboxylic acid isopropyl ester; 4-[6-(4-Methanesulfonyl-phenylamino)-pyrimidin-4-yloxy]-piperidine-1-carboxylic acid isopropyl ester; 4-{6-[Acetyl-(4-methanesulfonyl-phenyl)-amino]-pyrimidin-4-yloxy}-piperidine-1-carboxylic acid isopropyl ester; (2,5-Difluoro-4-propoxy-phenyl)-{6-[1-(5-isopropyl-[1,2,4]oxadiazol-3-yl)-piperidin-4-yloxy]-pyrimidin-4-yl}-amine; 4-{6-[2,5-Difluoro-4-(morpholin-4-ylamino)-phenylamino]-pyrimidin-4-yloxy}-piperidine-1-carboxylic acid isopropyl ester; 4-{6-[2,5-Difluoro-4-(2-methoxy-ethylamino)-phenylamino]-pyrimidin-4-yloxy}-piperidine-1-carboxylic acid isopropyl ester; 4-(6-{2,5-Difluoro-4-[(tetrahydro-furan-2-ylmethyl)-amino]-phenylamino}-pyrimidin-4-yloxy)-piperidine-1-carboxylic acid isopropyl ester; 4-[6-(4-Butylamino-2,5-difluoro-phenylamino)-pyrimidin-4-yloxy]-piperidine-1-carboxylic acid isopropyl ester; 4-{6-[2,5-Difluoro-4-(3-methyl-butylamino)-phenylamino]-pyrimidin-4-yloxy}-piperidine-1-carboxylic acid isopropyl ester; 4-[6-(2-Fluoro-4-methanesulfonyl-phenylamino)-2-methyl-pyrimidin-4-yloxy]-piperidine-1-carboxylic acid isopropyl ester; 4-{6-[2,5-Difluoro-4-(2-morpholin-4-yl-ethylamino)-phenylamino]-pyrimidin-4-yloxy}-piperidine-1-carboxylic acid isopropyl ester; 4-{6-[2-(2,5-Difluoro-phenoxy)-ethylamino]-pyrimidin-4-yloxy}-piperidine-1-carboxylic acid isopropyl ester; 4-[6-(2,5-Difluoro-phenoxy)-pyrimidin-4-yloxy]-piperidine-1-carboxylic acid isopropyl ester; 4-[6-(4-Bromo-2-fluoro-phenoxy)-pyrimidin-4-yloxy]-piperidine-1-carboxylic acid isopropyl ester; 4-[6-(2-Fluoro-4-morpholin-4-yl-phenoxy)-pyrimidin-4-yloxy]-piperidine-1-carboxylic acid isopropyl ester; 4-{6-[2,5-Difluoro-4-(tetrahydro-furan-2-ylmethoxy)-phenylamino]-pyrimidin-4-yloxy}-piperidine-1-carboxylic acid isopropyl ester; 4-[6-(2-Fluoro-4-methanesulfonyl-phenylamino)-pyridin-2-yloxy]-piperidine-1-carboxylic acid tert-butyl ester; 4-[5-(2-Fluoro-4-methanesulfonyl-phenylamino)-pyridin-3-yloxy]-piperidine-1-carboxylic acid tert-butyl ester; 4-[6-(2-Fluoro-4-methanesulfonyl-phenylamino)-pyridin-2-yloxy]-piperidine-1-carboxylic acid isopropyl ester; 4-[4-(2-Fluoro-4-methanesulfonyl-phenylamino)-pyridin-2-yloxy]-piperidine-1-carboxylic acid isopropyl ester; 4-[4-(2,5-Difluoro-4-propoxy-phenylamino)-pyridin-2-yloxy]-piperidine-1-carboxylic acid isopropyl ester; and 4-[2-(2-Fluoro-4-methanesulfonyl-phenylamino)-pyridin-4-yloxy]-piperidine-1-carboxylic acid isopropyl ester; 4-[2-(2,5-Difluoro-4-propoxy-phenylamino)-pyridin-4-yloxy]-piperidine-1-carboxylic acid isopropyl ester.

Examples of GPR119 agonists are described in International Application No. PCT/GB2004/050046 (published as WO 2005/061489), the disclosure of which is herein incorporated by reference in its entirety. Disclosed in International Application No. PCT/GB2004/050046 as a GPR119 agonist is a compound of Formula (VI):

$$R^1\text{-}A\text{-}V\text{—}B\text{—}R^2 \qquad (VI)$$

wherein:

V is a 5-membered heteroaryl ring containing up to four heteroatoms selected from O, N and S, optionally substituted by $C_{1-4}$ alkyl;

A is —CH=CH— or $(CH_2)_n$;

B is —CH=CH— or $(CH_2)_n$, where one of the $CH_2$ groups may be replaced by O, $NR^5$, $S(O)_m$, $C(O)$ or $C(O)NR^{12}$;

n is independently 0, 1, 2 or 3;

m is independently 0, 1 or 2;

$R^1$ is 3- or 4-pyridyl, 4- or 5-pyrimidinyl or 2-pyrazinyl, any of which may be optionally substituted by one or more substituents selected from halo, $C_{1-4}$ alkyl, $C_{1-4}$ fluoroalkyl, $C_{2-4}$ alkenyl, $C_{2-4}$ alkynyl, $C_{3-7}$ cycloalkyl, aryl, $OR^6$, CN, $NO_2$, $S(O)_mR^6$, $CON(R^6)_2$, $N(R^6)_2$, $NR^{10}COR^6$, $NR^{10}SO_2R^6$, $SO_2N(R^6)_2$, a 4- to 7-membered heterocyclyl group or a 5- or 6-membered heteroaryl group;

$R^2$ is 4- to 7-membered cycloalkyl substituted by $R^3$, $C(O)OR^3$, $C(O)R^3$ or $S(O)_2R^3$, or 4- to 7-membered heterocyclyl, containing one or two nitrogen atoms which is unsubstituted or substituted by $C(O)OR^4$, $C(O)R^3$, $S(O)_2 R^3$, $C(O)NHR^4$, $P(O)(OR^{11})_2$ or a 5- or 6-membered nitrogen containing heteroaryl group;

$R^3$ is $C_{3-8}$ alkyl, $C_{3-8}$ alkenyl or $C_{3-8}$ alkynyl, any of which may be optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be optionally substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^4$ is $C_{2-8}$ alkyl, $C_{2-8}$ alkenyl or $C_{2-8}$ alkynyl, any of which may be optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^5$ is hydrogen, $C(O)R^7$, $S(O)_2R^8$, $C_{3-7}$ cycloalkyl or $C_{1-4}$ alkyl optionally substituted by $OR^6$, $C_{3-7}$ cycloalkyl, aryl, heterocyclyl or heteroaryl, wherein the cyclic groups may be substituted with one or more substituents selected from halo, $C_{1-2}$ alkyl, $C_{1-2}$ fluoroalkyl, $OR^6$, CN, $N(R^6)_2$ and $NO_2$;

$R^6$ are independently hydrogen, $C_{1-4}$ alkyl, $C_{3-7}$ cycloalkyl, aryl, heterocyclyl or heteroaryl, wherein the cyclic groups may be substituted with one or more substituents selected from halo, $C_{1-4}$ alkyl, $C_{1-4}$ fluoroalkyl, $OR^9$, CN, $SO_2CH_3$, $N(R^{10})_2$ and $NO_2$; or a group $(N(R^{10})_2$ may form a 4- to 7-membered heterocyclic ring optionally containing a further heteroatom selected from O and NR$^{10}$;

R$^7$ is hydrogen, C$_{1-4}$ alkyl, OR$^6$, N(R$^6$)$_2$, aryl or heteroaryl;

R$^8$ is C$_{1-4}$ alkyl, C$_{1-4}$ fluoroalkyl, aryl or heteroaryl;

R$^9$ is hydrogen, C$_{1-2}$ alkyl or C$_{1-2}$ fluoroalkyl;

R$^{10}$ is hydrogen or C$_{1-4}$ alkyl;

R$^{11}$ is phenyl; and

R$^{12}$ is hydrogen, C$_{1-4}$ alkyl or C$_{3-7}$ cycloalkyl.

The present invention also encompasses diastereomers as well as optical isomers, e.g. mixtures of enantiomers including racemic mixtures, as well as individual enantiomers and diastereomers, which arise as a consequence of structural asymmetry in certain compounds of the invention. Separation of the individual isomers or selective synthesis of the individual isomers is accomplished by application of various methods which are well known to practitioners in the art.

Specific examples of GPR119 agonists disclosed in International Application No. PCT/GB2004/050046 include the following compounds according to Formula (VI) (referred to herein as Group F1): 4-(3-Pyridin-4-yl-[1,2,4]oxadiazol-5-ylmethoxy)piperidine-1-carboxylic acid tert-butyl ester; 4-(3-Pyridin-4-yl-[1,2,4]oxadiazol-5-yl)piperidine-1-carboxylic acid tert-butyl ester; 3-(3-Pyridin-4-yl-[1,2,4]oxadiazol-5-ylmethoxy)piperidine-1-carboxylic acid tert-butyl ester; 4-[5-(4-Pentylcyclohexylmethyl)-[1,2,4]oxadiazol-3-yl]pyridine; trans-2-Chloro-4-[5-(4-pentylcyclohexane)-[1,2,4]oxadiazol-3-yl]pyridine; trans-4-[5-(4-Pentylcyclohexane)-[1,2,4]oxadiazol-3-ylmethyl]pyridine; 4-(3-Pyridin-4-ylmethyl-[1,2,4]oxadiazol-5-yl)piperidine-1-carboxylic acid tert-butyl ester; trans-3-[5-(4-Pentylcyclohexyl)-[1,2,4]oxadiazol-3-ylmethyl]pyridine; 4-[5-(4-Butylcyclohexane)-[1,2,4]oxadiazol-3-yl]pyridine; 4-[5-(4-n-Propylcyclohexyl)-[1,2,4]oxadiazol-3-yl]pyridine; trans-4-[5-(4-Pentylcyclohexane)-[1,2,4]oxadiazol-3-yl]pyridine; 4-[2-(3-Pyridin-4-yl-[1,2,4]oxadiazol-5-yl)-ethyl]piperidine-1-carboxylic acid tert-butyl ester; 4-(3-Pyridin-4-yl-[1,2,4]oxadiazol-5-ylmethyl)piperidine-1-carboxylic acid tert-butyl ester; 3-[5-(4-Propylcyclohexyl)-[1,2,4]oxadiazol-3-yl]pyridine; 3-[5-(4-Butylcyclohexane)-[1,2,4]oxadiazol-3-yl]pyridine; trans-4-[3-(4-Pentylcyclohexyl)-[1,2,4]oxadiazol-5-yl]pyridine-2-carboxylic acid methylamide; trans-4-[5-(4-Pentylcyclohexyl)-[1,2,4]oxadiazol-3-yl]pyridine-2-carboxylic acid amide; trans-4-[3-(4-Pentylcyclohexyl)-[1,2,4]oxadiazol-5-yl]pyridine; trans-2-Chloro-4-[3-(4-pentylcyclohexyl)-[1,2,4]oxadiazol-5-yl]pyridine; trans-3-[3-(4-Pentylcyclohexyl)-[1,2,4]oxadiazol-5-yl]pyridine; trans-2-Methyl-3-[3-(4-pentylcyclohexyl)-[1,2,4]oxadiazol-5-yl]pyridine; trans-2-Chloro-6-methyl-4-[3-(4-pentylcyclohexyl)-[1,2,4]oxadiazol-5-yl]pyridine; trans-4-[3-(4-Pentylcyclohexyl)-[1,2,4]oxadiazol-5-yl]pyridine-2-carbonitrile; trans-2-Chloro-3-[3-(4-pentylcyclohexyl)-[1,2,4]oxadiazol-5-yl]pyridine; trans-2-Chloro-6-methyl-3-[3-(4-pentylcyclohexyl)-[1,2,4]oxadiazol-5-yl]pyridine; trans-2-Methyl-5-[3-(4-pentylcyclohexyl)-[1,2,4]oxadiazol-5-yl]pyridine; trans-3-Methyl-5-[3-(4-pentylcyclohexyl)-[1,2,4]oxadiazol-5-yl]pyridine; trans-2,6-Dichloro-4-[3-(4-pentylcyclohexyl)-[1,2,4]oxadiazol-5-yl]pyridine; trans-2-Chloro-6-methoxy-4-[3-(4-pentylcyclohexyl)-[1,2,4]oxadiazol-5-yl]pyridine; trans-5-[3-(4-Pentylcyclohexyl)-[1,2,4]oxadiazol-5-yl]-2-[1,2,4]triazol-1-ylpyridine; 2-[3-(4-Pentylcyclohexyl)-[1,2,4]oxadiazol-5-yl]pyrazine; 4-[3-(4-Pentylcyclohexyl)-[1,2,4]oxadiazol-5-yl]pyrimidine; trans-5-[3-(4-Pentylcyclohexyl)-[1,2,4]oxadiazol-5-yl]pyridine-2-carbonitrile; trans-5-Chloro-2-methylsulfanyl-4-[3-(4-pentylcyclohexyl)-[1,2,4]oxadiazol-5-yl]pyrimidine; trans-2-Fluoro-5-[3-(4-pentylcyclohexyl)-[1,2,4]oxadiazol-5-yl]pyridine; trans-2-Fluoro-4-[3-(4-pentylcyclohexyl)-[1,2,4]oxadiazol-5-yl]pyridine; trans-2-Imidazol-1-yl-5-[3-(4-pentylcyclohexyl)-[1,2,4]oxadiazol-5-yl]pyridine; trans-2-Methyl-4-[3-(4-pentylcyclohexyl)-[1,2,4]oxadiazol-5-yl]pyridine; trans-3-Methyl-4-[3-(4-pentylcyclohexyl)-[1,2,4]oxadiazol-5-yl]pyridine; trans-4-{2-[3-(4-Pentylcyclohexyl)-[1,2,4]oxadiazol-5-yl]vinyl}pyridine; 4-(5-Pyridin-4-yl-[1,2,4]oxadiazol-3-ylmethoxy)piperidine-1-carboxylic acid tert-butyl ester; 4-[5-(2-Cyanopyridin-4-yl)-[1,2,4]oxadiazol-3-ylmethoxy]piperidine-1-carboxylic acid tert-butyl ester; (E)-4-[5-(2-Pyridin-3-yl-vinyl)-[1,2,4]oxadiazol-3-ylmethoxy]piperidine-1-carboxylic acid tert-butyl ester; (E)-4-[5-(2-Pyridin-3-yl-vinyl)-[1,2,4]oxadiazol-3-yl]piperidine-1-carboxylic acid tert-butyl ester; (E)-4-[5-(2-Pyridin-3-yl-vinyl)-[1,2,4]oxadiazol-3-ylmethyl]piperidine-1-carboxylic acid tert-butyl ester; (E)-4-[5-(2-Pyridin-4-yl-vinyl)-[1,2,4]oxadiazol-3-yl]piperidine-1-carboxylic acid tert-butyl ester; 4-[5-(2-Pyridin-4-yl-ethyl)-[1,2,4]oxadiazol-3-yl]-piperidine-1-carboxylic acid tert-butyl ester; 4-{5-[2-(2-Cyanopyridin-4-yl)ethyl]-[1,2,4]oxadiazol-3-yl}piperidine-1-carboxylic acid tert-butyl ester; 4-{5-[2-(2-Cyanopyridin-4-yl)ethyl]-[1,2,4]oxadiazol-3-ylmethoxy}piperidine-1-carboxylic acid tert-butyl ester; 4-{5-[2-(2-Cyanopyridin-4-yl)ethyl]-[1,2,4]oxadiazol-3-ylmethyl}piperidine-1-carboxylic acid tert-butyl ester; 4-(5-Piperidin-4-yl-[1,2,4]oxadiazol-3-yl)pyridine; 4-(3-Pyridin-4-yl-[1,2,4]oxadiazol-5-yl)piperidine-1-carboxylic acid isobutyl ester; 4-(3-Pyridin-4-yl-[1,2,4]oxadiazol-5-yl)piperidine-1-carboxylic acid 2-methoxyethyl ester; 4-(3-Pyridin-4-yl-[1,2,4]oxadiazol-5-yl)piperidine-1-carboxylic acid ethyl ester; 3,3-Dimethyl-1-[4-(3-pyridin-4-yl-[1,2,4]oxadiazol-5-yl)piperidin-1-yl]butan-1-one; 2-Cyclopentyl-1-[4-(3-pyridin-4-yl-[1,2,4]oxadiazol-5-yl)piperidin-1-yl]ethanone; 4-{5-[1-(Butane-1-sulfonyl)piperidin-4-yl]-[1,2,4]oxadiazol-3-yl}pyridine; 4-(3-Pyridin-4-yl-[1,2,4]oxadiazol-5-yl)piperidine-1-carboxylic acid propylamide; 4-(3-Pyridin-4-yl-[1,2,4]oxadiazol-5-yl)piperidine-1-carboxylic acid tert-butylamide; 4-(3-Pyridin-4-yl-[1,2,4]oxadiazol-5-ylmethoxy)piperidine-1-carboxylic acid cyclopentyl ester; 4-(3-Pyridin-4-yl-[1,2,4]oxadiazol-5-ylmethoxy)piperidine-1-carboxylic acid benzyl ester; 4-(3-Pyridin-4-yl-[1,2,4]oxadiazol-5-ylmethoxy)piperidine-1-carboxylic acid isobutyl ester; 4-(3-Pyridin-4-yl-[1,2,4]oxadiazol-5-ylmethoxy)piperidine-1-carboxylic acid ethyl ester; 4-(3-Pyridin-4-yl-[1,2,4]oxadiazol-5-ylmethoxy)piperidine-1-carboxylic acid cycloheptyl ester; 4-(3-Pyridin-4-yl-[1,2,4]oxadiazol-5-ylmethoxy)piperidine-1-carboxylic acid methyl ester; 4-(3-Pyridin-4-yl-[1,2,4]oxadiazol-5-ylmethoxy)piperidine-1-carboxylic acid 2-methoxy-ethyl ester; 4-(3-Pyridin-4-yl-[1,2,4]oxadiazol-5-ylmethoxy)piperidine-1-carboxylic acid isopropyl ester; 4-(3-Pyridin-4-yl-[1,2,4]oxadiazol-5-ylmethoxy)piperidine-1-carboxylic acid 4-methoxy-phenyl ester; 4-(3-Pyridin-4-yl-[1,2,4]oxadiazol-5-ylmethoxy)piperidine-1-carboxylic acid 2,2,2-trichloroethyl ester; 4-(3-Pyridin-4-yl-[1,2,4]oxadiazol-5-ylmethoxy)piperidine-1-carboxylic acid 4-chloro-phenyl ester; 4-(3-Pyridin-4-yl-[1,2,4]oxadiazol-5-ylmethoxy)piperidine-1-carboxylic acid phenyl ester; 4-(3-Pyridin-4-yl-[1,2,4]oxadiazol-5-ylmethoxy)piperidine-1-carboxylic acid 2-ethyl-hexyl ester; 4-(3-Pyridin-4-yl-[1,2,4]oxadiazol-5-ylmethoxy)piperidine-1-carboxylic acid propyl ester; 4-(3-Pyridin-4-yl-[1,2,4]oxadiazol-5-ylmethoxy)piperidine-1-carboxylic acid hexyl ester; 4-(3-Pyridin-4-yl-[1,2,4]oxadiazol-5-ylmethoxy)piperidine-1-carboxylic acid (1R,2S,5R)-2-isopropyl-5-methylcyclohexyl ester; 4-(3-Pyridin-4-yl-[1,2,4]oxadiazol-5-ylmethoxy)piperidine-1-carboxylic acid (1S,2R,5S)-2-isopropyl-5-methylcyclohexyl ester; 4-(3-Pyridin- 4-yl-[1,2,4]oxadiazol-5-ylmethoxy)piperidine-1-carboxylic acid 2,2-dimethylpropyl ester; 4-(3-Pyridin-4-yl-[1,2,4]oxadiazol-5-ylmethoxy)piperidine-1-carboxylic acid naphthalen-1-yl ester; 4-(3-Pyridin-4-yl-[1,2,4]oxadiazol-5-ylmethoxy)piperidine-1-carboxylic acid 2-methoxy-phenyl ester; 4-(3-Pyridin-4-yl-[1,2,4]oxadiazol-5-ylmethoxy)piperidine-1-carboxylic acid 3-trifluoromethylphenyl ester; 4-(3-Pyridin-4-yl-[1,2,4]oxadiazol-5-ylmethoxy)piperidine-1-carboxylic acid prop-2-ynyl ester; 4-(3-Pyridin-4-yl-[1,2,4]oxadiazol-5-ylmethoxy)piperidine-1-carboxylic acid but-2-ynyl ester; 4-(3-Pyridin-4-yl-[1,2,4]oxadiazol-5-ylmethoxy)piperidine-1-carboxylic acid pentyl ester; 4-(3-Pyridin-4-yl-[1,2,4]oxadiazol-5-ylmethoxy)piperidine-1-carboxylic acid p-tolyl ester; 4-(3-Pyridin-4-yl-[1,2,4]oxadiazol-5-ylmethoxy)piperidine-1-carboxylic acid 2-chloro-phenyl ester; 4-(3-Pyridin-4-yl-[1,2,4]oxadiazol-5-ylmethoxy)piperidine-1-carboxylic acid naphthalen-2-yl ester; 4-(3-Pyridin-4-yl-[1,2,4]oxadiazol-5-ylmethoxy)piperidine-1-carboxylic acid butyl ester; 4-(3-Pyridin-4-yl-[1,2,4]oxadiazol-5-ylmethoxy)piperidine-1-carboxylic acid 4-methoxycarbonyl-phenyl ester; 4-(3-Pyridin-4-yl-[1,2,4]oxadiazol-5-ylmethoxy)piperidine-1-carboxylic acid 4-fluoro-phenyl ester; 3-Methyl-1-[4-(3-pyridin-4-yl-[1,2,4]oxadiazol-5-ylmethoxy)piperidin-1-yl]-butan-1-one; Phenyl-[4-(3-pyridin-4-yl-[1,2,4]oxadiazol-5-ylmethoxy)piperidin-1-yl]methanone; 1-[4-(3-Pyridin-4-yl-[1,2,4]oxadiazol-5-ylmethoxy)piperidin-1-yl]butan-1-one; 2,2-Dimethyl-1-[4-(3-pyridin-4-yl-[1,2,4]oxadiazol-5-ylmethoxy)piperidin-1-yl]propan-1-one; Cyclopentyl-[4-(3-pyridin-4-yl-[1,2,4]oxadiazol-5-ylmethoxy)piperidin-1-yl]methanone; [4-(3-Pyridin-4-yl-[1,2,4]oxadiazol-5-ylmethoxy)piperidin-1-yl]-p-tolylmethanone; 3,3-Dimethyl-1-[4-(3-pyridin-4-yl-[1,2,4]oxadiazol-5-ylmethoxy)piperidin-1-yl]butan-1-one; 4-{5-[1-(Butane-1-sulfonyl)piperidin-4-yloxymethyl]-[1,2,4]oxadiazol-3-yl}pyridine; 4-{5-[1-(Propane-1-sulfonyl)piperidin-4-yloxymethyl]-[1,2,4]oxadiazol-3-yl}pyridine; 4-(3-Pyridin-4-yl-[1,2,4]oxadiazol-5-ylmethoxy)piperidine-1-carboxylic acid tert-butylamide; 4-(3-Pyridin-4-yl-[1,2,4]oxadiazol-5-ylmethoxy)piperidine-1-carboxylic acid o-tolylamide; trans-4-(3-Pyridin-4-yl-[1,2,4]oxadiazol-5-yl)cyclohexanecarboxylic acid propyl ester; trans-4-(3-Pyridin-4-yl-[1,2,4]oxadiazol-5-yl)cyclohexanecarboxylic acid butyl ester; trans-4-(3-Pyridin-4-yl-[1,2,4]oxadiazol-5-yl)cyclohexanecarboxylic acid isobutyl ester; trans-4-[5-(4-Propoxymethylcyclohexyl)-[1,2,4]oxadiazol-3-yl]pyridine; trans-4-[5-(4-Butoxymethylcyclohexyl)-[1,2,4]oxadiazol-3-yl]pyridine; cis-4-[5-(3-Butoxymethylcyclopentyl)-[1,2,4]oxadiazol-3-yl]pyridine; cis-4-[5-(3-Propoxymethylcyclopentyl)-[1,2,4]oxadiazol-3-yl]pyridine; cis-4-[5-(3-Butoxymethylcyclohexyl)-[1,2,4]oxadiazol-3-yl]pyridine; 4-(3-Pyridin-4-yl-[1,2,4]oxadiazol-5-ylmethoxy)-3,4,5,6-tetrahydro-2H-[1,3']bipyridinyl; 2-[4-(3-Pyridin-4-yl-[1,2,4]oxadiazol-5-ylmethoxy)piperidin-1-yl]pyrazine; 2-[4-(3-Pyridin-4-yl-[1,2,4]oxadiazol-5-ylmethoxy)piperidin-1-yl]pyrimidine; (4-Pentylcyclohexyl)-(3-pyridin-4-yl-[1,2,4]oxadiazol-5-ylmethyl)amine; (4-Pentylcyclohexyl-methyl)-(3-pyridin-4-yl-[1,2,4]oxadiazol-5-ylmethyl)amine; 4-[(3-Pyridin-4-yl-[1,2,4]oxadiazol-5-ylmethyl)amino]piperidine-1-carboxylic acid tert-butyl ester; 4-{[3-Pyridin-4-yl-[1,2,4]oxadiazol-5-ylmethyl)amino]methyl}-piperidine-1-carboxylic acid tert-butyl ester; 4-{[5-(2-Cyanopyridin-4-yl)-[1,2,4]oxadiazol-3-ylmethyl]amino}-piperidine-1-carboxylic acid tert-butyl ester; Methyl-(4-pentylcyclohexyl)-(3-pyridin-4-yl-[1,2,4]oxadiazol-5-ylmethyl)amine; Methyl-(4-pentylcyclohexyl-methyl)-(3-pyridin-4-yl-[1,2,4]oxadiazol-5-ylmethyl)amine; 4-[Methyl-(3-pyridin-4-yl-[1,2,4]oxadiazol-5-ylmethyl)amino]piperidine-1-carboxylic acid tert-butyl ester; 4-[Ethyl-(3-pyridin-4-yl-[1,2,4]oxadiazol-5-ylmethyl)amino]piperidine-1-carboxylic acid tert-butyl ester; 4-[Propyl-(3-pyridin-4-yl-[1,2,4]oxadiazol-5-ylmethyl)amino]piperidine-1-carboxylic acid tert-butyl ester; 4-[Cyclopropylmethyl-(3-pyridin-4-yl-[1,2,4]oxadiazol-5-ylmethyl)amino]piperidine-1-carboxylic acid tert-butyl ester; 4-[Butyl-(3-pyridin-4-yl-[1,2,4]oxadiazol-5-ylmethyl)amino]piperidine-1-carboxylic acid tert-butyl ester; 4-{[Methyl-(3-pyridin-4-yl-[1,2,4]oxadiazol-5-ylmethyl)amino]methyl}-piperidine-1-carboxylic acid tert-butyl ester; 4-{[Ethyl-(3-pyridin-4-yl-[1,2,4]oxadiazol-5-ylmethyl)amino]methyl}-piperidine-1-carboxylic acid tert-butyl ester; 4-{[5-(2-Cyanopyridin-4-yl)-[1,2,4]oxadiazol-3-ylmethyl]ethylamino}-piperidine-1-carboxylic acid tert-butyl ester; 4-[Methyl-(3-pyridin-4-yl-[1,2,4]oxadiazol-5-ylmethyl)amino]piperidine-1-carboxylic acid cyclopentyl ester; 4-{[Methyl-(3-pyridin-4-yl-[1,2,4]oxadiazol-5-ylmethyl)amino]methyl}-piperidine-1-carboxylic acid 2,2,2-trichloroethyl ester; 4-(3-Pyridin-4-yl-[1,2,4]oxadiazol-5-ylmethoxymethyl)piperidine-1-carboxylic acid tert-butyl ester; 4-(3-Pyridin-4-yl-[1,2,4]oxadiazol-5-ylmethyl)piperazine-1-carboxylic acid tert-butyl ester; 4-(3-Pyridin-4-yl-[1,2,4]oxadiazol-5-ylmethylsulfanyl)piperidine-1-carboxylic acid tert-butyl ester; 4-(3-Pyridin-4-yl-[1,2,4]oxadiazol-5-ylmethanesulfonyl)piperidine-1-carboxylic acid tert-butyl ester; 4-(5-Pyridin-4-yl-[1,3,4]oxadiazol-2-ylmethoxy)piperidine-1-carboxylic acid tert-butyl ester; 3-Pyridin-4-yl-[1,2,4]oxadiazole-5-carboxylic acid (4-pentylcyclohexyl)amide; [4-(3-Pyridin-4-yl-[1,2,4]oxadiazol-5-ylmethoxy)piperidin-1-yl]phosphonic acid diphenyl ester; 4-(4-Pyridin-4-yl-thiazol-2-ylmethoxy)piperidine-1-carboxylic acid tert-butyl ester; 4-(2-Pyridin-4-yl-thiazol-4-ylmethyl)piperidine-1-carboxylic acid tert-butyl ester; trans-4-[5-(4-Pentyl-cyclohexyl)-[1,3,4]thiadiazol-2-yl]pyridine; 4-(5-Pyridin-4-yl-[1,3,4]thiadiazol-2-ylmethoxy)piperidine-1-carboxylic acid tert-butyl ester; 4-(5-Pyridin-4-yl-4H-[1,2,4]triazol-3-ylmethoxy)piperidine-1-carboxylic acid tert-butyl ester; 4-[2-(5-Pyridin-4-yl-isoxazol-3-yl)ethyl]piperidine-1-carboxylic acid tert-butyl ester; 4-(5-Pyridin-4-yl-isoxazol-3-ylmethoxy)piperidine-1-carboxylic acid tert-butyl ester; 4-(5-Pyridin-4-yl-isoxazol-3-ylmethyl)piperidine-1-carboxylic acid tert-butyl ester; 4-[2-(1-Methyl-5-pyridin-4-yl-1H-pyrazol-3-yl)ethyl]piperidine-1-carboxylic acid tert-butyl ester; 4-[2-(2-Methyl-5-pyridin-4-yl-2H-pyrazol-3-yl)ethyl]-piperidine-1-carboxylic acid tert-butyl ester; (E)-4-{5-[2-(2-Cyanopyridin-4-yl)vinyl]-[1,2,4]oxadiazol-3-yl}piperidine-1-carboxylic acid tert-butyl ester; 4-{5-[2-(2H-Tetrazol-5-yl)pyridine-4-yl]-[1,2,4]oxadiazol-3-ylmethoxy}-piperidine-1-carboxylic acid tert-butyl ester; 4-[5-(2-Cyanopyridin-4-yl)-[1,2,4]oxadiazol-3-ylmethoxy]piperidine-1-carboxylic acid isopropyl ester; and 4-[5-(2-Cyanopyridin-4-yl)-[1,2,4]oxadiazol-3-ylmethoxy]piperidine-1-carboxylic acid phenyl ester.

In one aspect of the present invention, the GPR119 agonist is a compound of Formula (I).

In one aspect of the present invention, the GPR119 agonist is a compound of Formula (II).

In one aspect of the present invention, the GPR119 agonist is a compound of Formula (III).

In one aspect of the present invention, the GPR119 agonist is a compound of Formula (IV).

In one aspect of the present invention, the GPR119 agonist is a compound of Formula (V).

In one aspect of the present invention, the GPR119 agonist is a compound of Formula (VI).

In one aspect of the present invention, the GPR119 agonist is a compound of Formula (VI), provided that the compound is not 4-(5-piperidin-4-yl-[1,2,4]oxadiazol-3-yl)pyridine, 4-(3-pyridin-4-yl-[1,2,4]oxadiazol-5-yl)piperidine-1-carboxylic acid butyl ester, 4-[5-(4-butylcyclohexyl)-[1,2,4]oxadiazol-3-yl]pyridine, 3-[5-(4-butylcyclohexyl)-[1,2,4]oxadiazol-3-yl]pyridine, or 3-[5-(4-propylcyclohexyl)-[1,2,4]oxadiazol-3-yl]pyridine.

In one aspect of the present invention, the GPR119 agonist is selected from Group A1, Group B1, Group B2, Group B3, Group B4, Group B5, Group C1, Group C2, Group C3, Group C4, Group C5, Group C6, Group C7, Group C8, Group C9, Group C10, Group D1, Group D2, Group D3, Group D4, Group D5, Group D6, Group D7, Group D8, Group D9, Group D10, Group D11, Group D12, Group D13, Group D14, Group E1, Group E2 or Group F1.

In one aspect, the GPR119 agonist is selected from the left column of Table B.

Specific examples of GPR119 agonists include 2-(pyridine-4-yl)ethyl thiobenzoate and L-α-lysophosphatidylcholine oleoyl, as disclosed in EP 1338651, the disclosure of which is herein incorporated by reference in its entirety.

Examples of GPR119 agonists may be found in International Application WO 03/026661, the disclosure of which is herein incorporated by reference in its entirety. GPR119 agonists disclosed in WO 03/026661 include but are not limited to the compounds in Table C.

TABLE C

| Cmpd No. | Chemical Structure | Chemical Name |
|---|---|---|
| 1C | 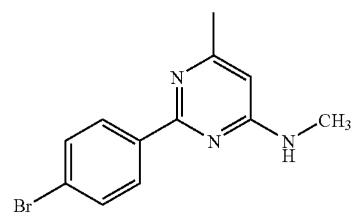 | [2-(4-Bromo-phenyl)-6-methyl-pyrimidin-4-yl]-methyl-amine |
| 2C | 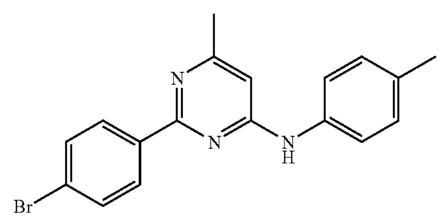 | [2-(4-Bromo-phenyl)-6-methyl-pyrimidin-4-yl]-p-tolyl-amine |
| 3C | 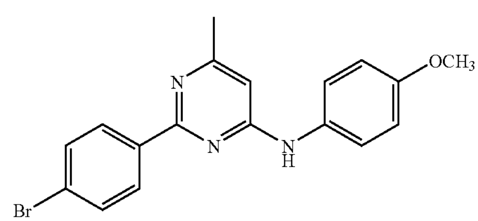 | [2-(4-Bromo-phenyl)-6-methyl-pyrimidin-4-yl]-(4-methoxy-phenyl)-amine |
| 4C | 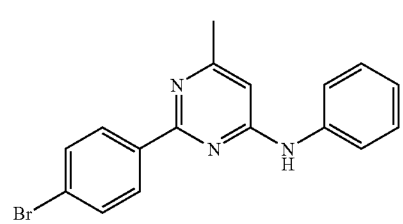 | [2-(4-Bromo-phenyl)-6-methyl-pyrimidin-4-yl]-phenyl-amine |
| 5C | 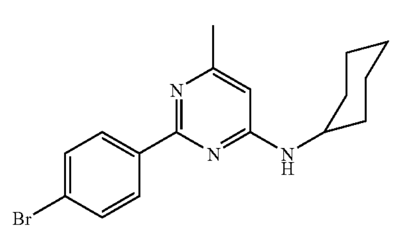 | [2-(4-Bromo-phenyl)-6-methyl-pyrimidin-4-yl]-cyclohexyl-amine |

TABLE C-continued

| Cmpd No. | Chemical Structure | Chemical Name |
|---|---|---|
| 6C | 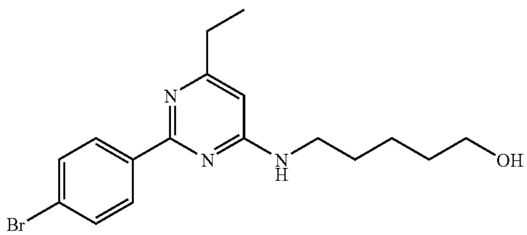 | 5-[2-(4-Bromo-phenyl)-6-ethyl-pyrimidin-4-ylamino]-pentan-1-ol |
| 7C | 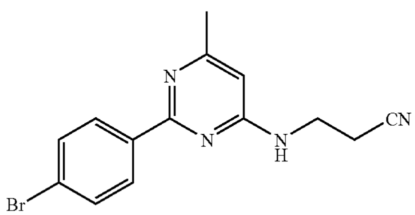 | 3-[2-(4-Bromo-phenyl)-6-methyl-pyrimidin-4-ylamino]-propionitrile |
| 8C | 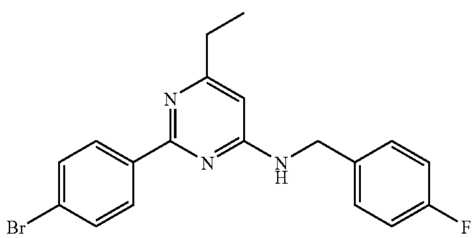 | [2-(4-Bromo-phenyl)-6-ethyl-pyrimidin-4-yl]-(4-fluoro-benzyl)-amine |
| 9C | 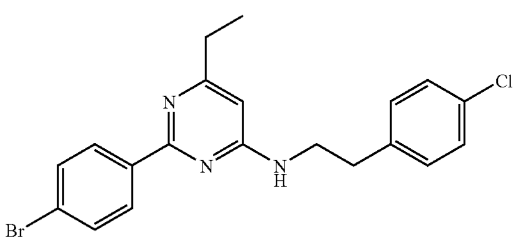 | [2-(4-Bromo-phenyl)-6-ethyl-pyrimidin-4-yl]-[2-(4-chloro-phenyl)-ethyl]-amine |
| 10C | 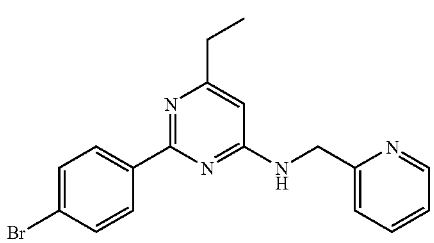 | [2-(4-Bromo-phenyl)-6-ethyl-pyrimidin-4-yl]-pyridin-2-ylmethyl-amine |
| 11C | 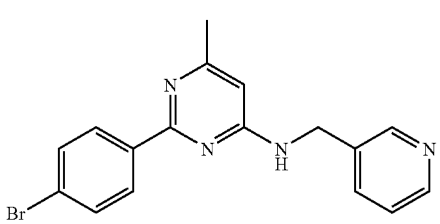 | [2-(4-Bromo-phenyl)-6-methyl-pyrimidin-4-yl]-pyridin-3-ylmethyl-amine |

TABLE C-continued

| Cmpd No. | Chemical Structure | Chemical Name |
|---|---|---|
| 12C | 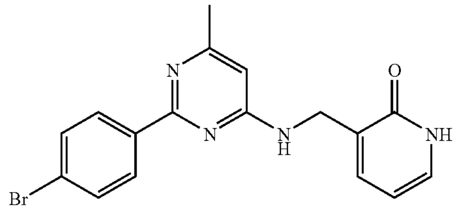 | 3-{[2-(4-Bromo-phenyl)-6-methyl-pyrimidin-4-ylamino]-methyl}-1H-pyridin-2-one |
| 13C | 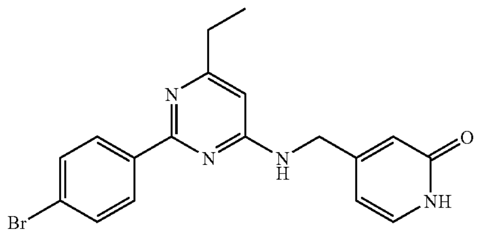 | 4-{[2-(4-Bromo-phenyl)-6-ethyl-pyrimidin-4-ylamino]-methyl}-1H-pyridin-2-one |
| 14C | 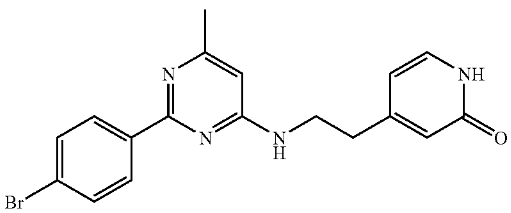 | 4-{2-[2-(4-Bromo-phenyl)-6-methyl-pyrimidin-4-ylamino]-ethyl}-1H-pyridin-2-one |
| 15C | 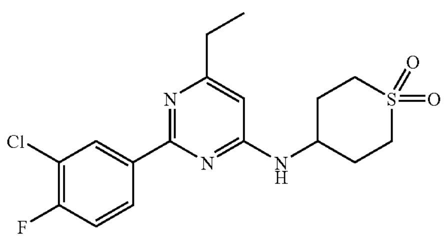 | [2-(3-Chloro-4-fluoro-phenyl)-6-ethyl-pyrimidin-4-yl]-(1,1-dioxo-hexahydro-1l6-thiopyran-4-yl)-amine |
| 16C | 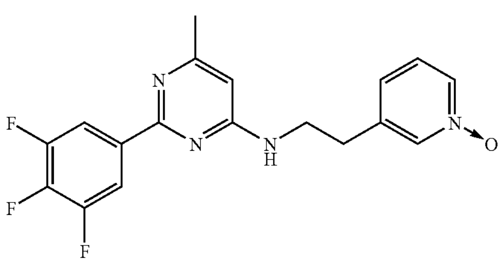 | [6-Methyl-2-(3,4,5-trifluoro-phenyl)-pyrimidin-4-yl]-[2-(1-oxy-pyridin-3-yl)-ethyl]-amine |
| 17C | 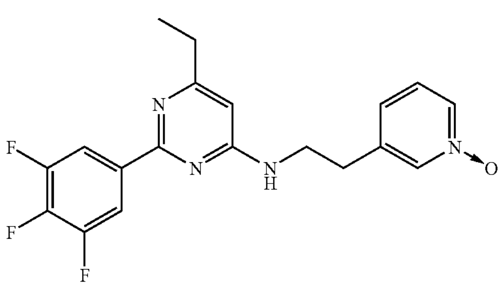 | [6-Ethyl-2-(3,4,5-trifluoro-phenyl)-pyrimidin-4-yl]-[2-(1-oxy-pyridin-3-yl)-ethyl]-amine |

TABLE C-continued

| Cmpd No. | Chemical Structure | Chemical Name |
|---|---|---|
| 18C | 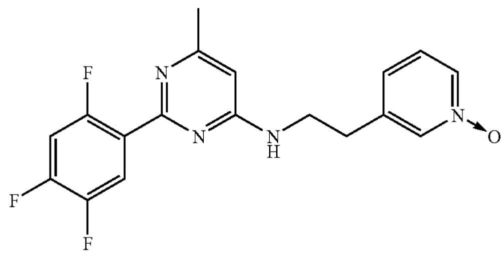 | [6-Methyl-2-(2,4,5-trifluoro-phenyl)-pyrimidin-4-yl]-[2-(1-oxy-pyridin-3-yl)-ethyl]-amine |
| 19C | 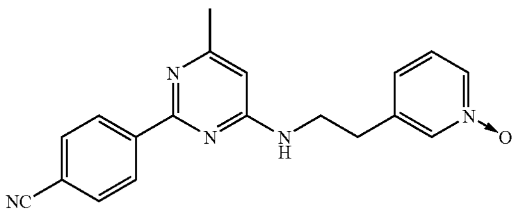 | 4-{4-Methyl-6-[2-(1-oxy-pyridin-3-yl)-ethylamino]-pyrimidin-2-yl}-benzonitrile |
| 20C | 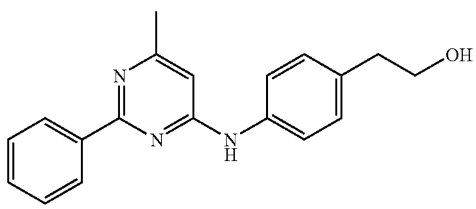 | 2-[4-(6-Methyl-2-phenyl-pyrimidin-4-ylamino)-phenyl]-ethanol |
| 21C | 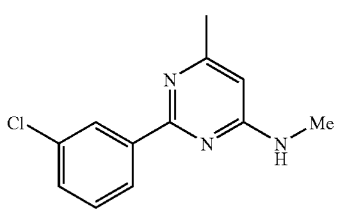 | [2-(3-Chloro-phenyl)-6-methyl-pyrimidin-4-yl]-methyl-amine |
| 22C | 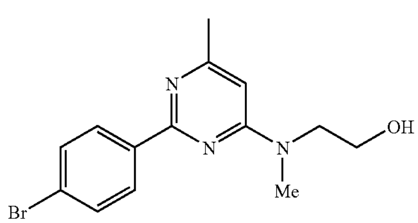 | 2-{[2-(4-Bromo-phenyl)-6-methyl-pyrimidin-4-yl]-methyl-amino}-ethanol; compound with methane |

Examples of GPR119 agonists may be found in International Application JP 2004269468, the disclosure of which is herein incorporated by reference in its entirety. GPR119 agonists disclosed in JP 2004269468 include but are not limited to the compounds in Table D.

TABLE D

| Cmpd No. | Chemical Structure | Chemical Name |
|---|---|---|
| 1D | 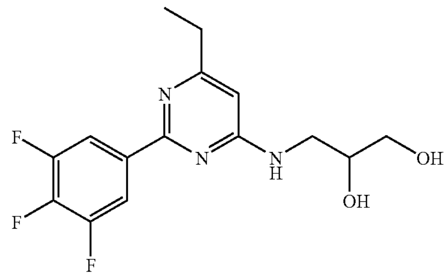 | 3-[6-Ethyl-2-(3,4,5-trifluoro-phenyl)-pyrimidin-4-ylamino]-propane-1,2-diol |
| 2D | 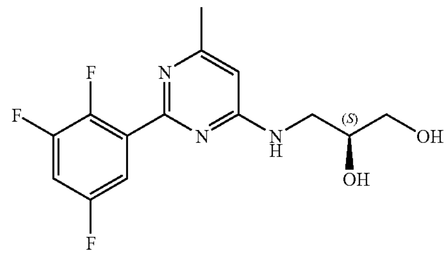 | (S)-3-[6-Methyl-2-(2,3,5-trifluoro-phenyl)-pyrimidin-4-ylamino]-propane-1,2-diol |
| 3D | 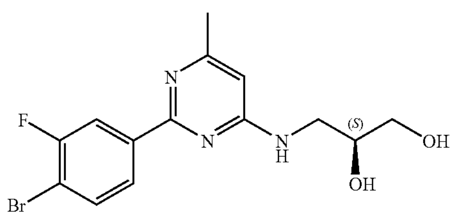 | (S)-3-[2-(4-Bromo-3-fluoro-phenyl)-6-methyl-pyrimidin-4-ylamino]-propane-1,2-diol |
| 4D | 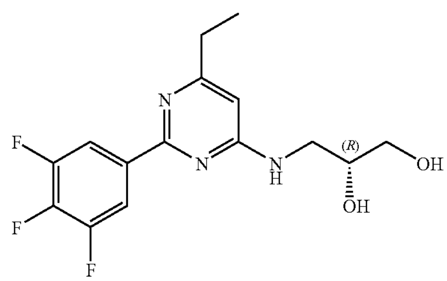 | (R)-3-[6-Ethyl-2-(3,4,5-trifluoro-phenyl)-pyrimidin-4-ylamino]-propane-1,2-diol |
| 5D | 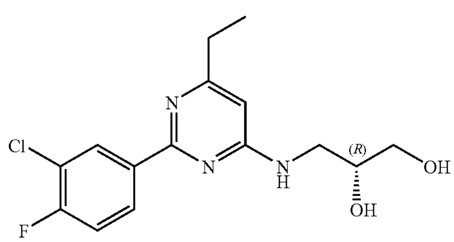 | (R)-3-[2-(3-Chloro-4-fluoro-phenyl)-6-ethyl-pyrimidin-4-ylamino]-propane-1,2-diol |
| 6D | 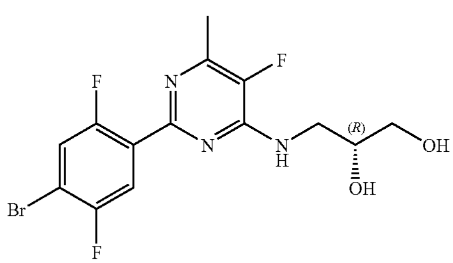 | (R)-3-[2-(4-Bromo-2,5-difluoro-phenyl)-5-fluoro-6-methyl-pyrimidin-4-ylamino]-propane-1,2-diol |

TABLE D-continued

| Cmpd No. | Chemical Structure | Chemical Name |
|---|---|---|
| 7D | 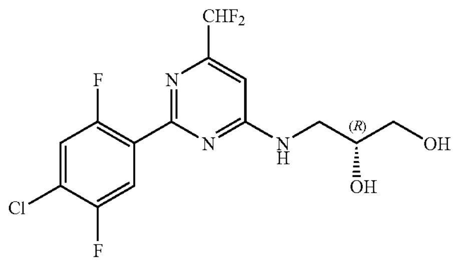 | (R)-3-[2-(4-Chloro-2,5-difluoro-phenyl)-6-difluoromethyl-pyrimidin-4-ylamino]-propane-1,2-diol |

Examples of GPR119 agonists may be found in International Application JP 2004269469, the disclosure of which is herein incorporated by reference in its entirety. GPR119 agonists disclosed in JP 2004269469 include but are not limited to the compounds in Table E.

TABLE E

| Cmpd No. | Chemical Structure | Chemical Name |
|---|---|---|
| 1E | 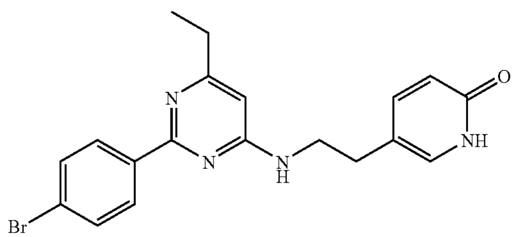 | 5-{2-[2-(4-Bromo-phenyl)-6-ethyl-pyrimidin-4-ylamino]-ethyl}-1H-pyridin-2-one |
| 2E | 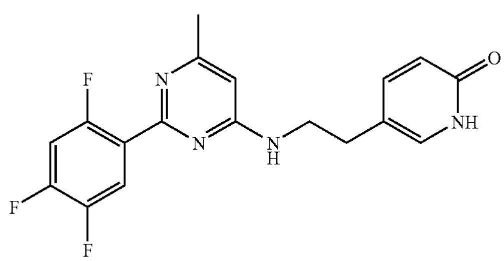 | 5-{2-[6-Methyl-2-(2,4,5-trifluoro-phenyl)-pyrimidin-4-ylaminol-ethyl}-1H-pyridin-2-one |
| 3E | 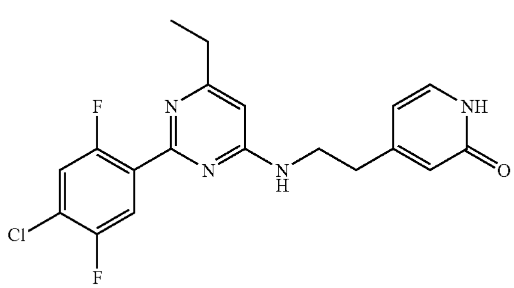 | 4-{2-[2-(4-Chloro-2,5-difluoro-phenyl)-6-ethyl-pyrimidin-4-ylamino]-ethyl}-1H-pyridin-2-one |

TABLE E-continued

| Cmpd No. | Chemical Structure | Chemical Name |
|---|---|---|
| 4E | 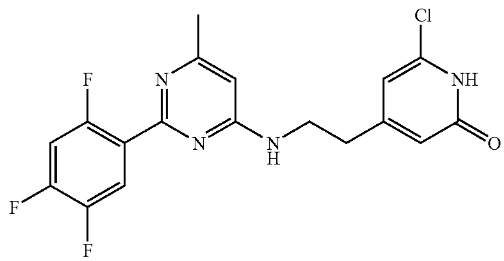 | 6-Chloro-4-{2-[6-methyl-2-(2,4,5-trifluoro-phenyl)-pyrimidin-4-ylamino]-ethyl}-1H-pyridin-2-one |
| 5E | 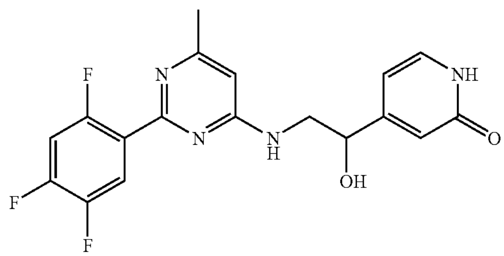 | 4-{1-Hydroxy-2-[6-methyl-2-(2,4,5-trifluoro-phenyl)-pyrimidin-4-ylamino]-ethyl}-1H-pyridin-2-one |
| 6E | 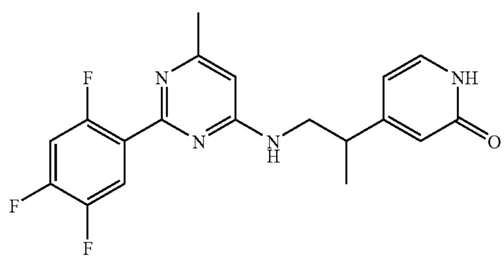 | 4-{1-Methyl-2-[6-methyl-2-(2,4,5-trifluoro-phenyl)-pyrimidin-4-ylamino]-ethyl}-1H-pyridin-2-one |

In one aspect of the present invention, the GPR119 agonist is a compound which comprises Group A1, Group B1, Group B2, Group B3, Group B4, Group B5, Group C1, Group C2, Group C3, Group C4, Group C5, Group C6, Group C7, Group C8, Group C9, Group C10, Group D1, Group D2, Group D3, Group D4, Group D5, Group D6, Group D7, Group D8, Group D9, Group D10, Group D11, Group D12, Group D13, Group D14, Group E1, Group E2 or Group F1.

In one aspect, the GPR119 agonist is not identical to a compound included in the left column of Table B.

In one aspect, the GPR119 agonist is not identical to a compound disclosed in International Application No. PCT/US2004/001267.

In one aspect, the GPR119 agonist is not identical to a compound disclosed in International Application No. PCT/GB2004/050046.

In one aspect, the GPR119 agonist is not identical to a compound of Formula (I).

In one aspect, the GPR119 agonist is not identical to a compound which comprises Group A1.

In one aspect, the GPR119 agonist is not identical to a compound disclosed in International Application No. PCT/US2004/005555.

In one aspect, the GPR119 agonist is not identical to a compound of Formula (II).

In one aspect, the GPR119 agonist is not identical to a compound which comprises Group B1, Group B2, Group B3, Group B4 or Group B5.

In one aspect, the GPR119 agonist is not identical to a compound, taken individually, which comprises any one of Group B1, Group B2, Group B3, Group B4 or Group B5 taken individually.

In one aspect, the GPR119 agonist is not identical to a compound which comprises Group B1.

In one aspect, the GPR119 agonist is not identical to a compound which comprises Group B2. In one aspect, the GPR119 agonist is not identical to a compound which comprises Group B3. In one aspect, the GPR119 agonist is not identical to a compound which comprises Group B4. In one aspect, the GPR119 agonist is not identical to a compound which comprises Group B5.

In one aspect, the GPR119 agonist is not identical to a compound disclosed in International Application No. PCT/US04/022327.

In one aspect, the GPR119 agonist is not identical to a compound of Formula (III).

In one aspect, the GPR119 agonist is not identical to a compound which comprises Group C1, Group C2, Group C3, Group C4, Group C5, Group C6, Group C7, Group C8, Group C9 or Group C10.

In one aspect, the GPR119 agonist is not identical to a compound, taken individually, which comprises any one of Group C1, Group C2, Group C3, Group C4, Group C5, Group C6, Group C7, Group C8, Group C9 or Group C10 taken individually.

In one aspect, the GPR119 agonist is not identical to a compound which comprises Group C1. In one aspect, the GPR119 agonist is not identical to a compound which comprises Group C2. In one aspect, the GPR119 agonist is not identical to a compound which comprises Group C3. In one aspect, the GPR119 agonist is not identical to a compound which comprises Group C4. In one aspect, the GPR119 agonist is not identical to a compound which comprises Group C5. In one aspect, the GPR119 agonist is not identical to a compound which comprises Group C6. In one aspect, the GPR119 agonist is not identical to a compound which comprises Group C7. In one aspect, the GPR119 agonist is not identical to a compound which comprises Group C8. In one aspect, the GPR119 agonist is not identical to a compound which comprises Group C9. In one aspect, the GPR119 agonist is not identical to a compound which comprises Group C10.

In one aspect, the GPR119 agonist is not identical to a compound disclosed in International Application No. PCT/US04/022417.

In one aspect, the GPR119 agonist is not identical to a compound of Formula (IV).

In one aspect, the GPR119 agonist is not identical to a compound which comprises Group D1, Group D2, Group D3, Group D4, Group D5, Group D6, Group D7, Group D8, Group D9, Group D10, Group D11, Group D12, Group D13 or Group D14.

In one aspect, the GPR119 agonist is not identical to a compound, taken individually, which comprises any one of Group D1, Group D2, Group D3, Group D4, Group D5, Group D6, Group D7, Group D8, Group D9, Group D10, Group D11, Group D12, Group D13 or Group D14 taken individually.

In one aspect, the GPR119 agonist is not identical to a compound which comprises Group D1. In one aspect, the GPR119 agonist is not identical to a compound which comprises Group D2. In one aspect, the GPR119 agonist is not identical to a compound which comprises Group D3. In one aspect, the GPR119 agonist is not identical to a compound which comprises Group D4. In one aspect, the GPR119 agonist is not identical to a compound which comprises Group D5. In one aspect, the GPR119 agonist is not identical to a compound which comprises Group D6. In one aspect, the GPR119 agonist is not identical to a compound which comprises Group D7. In one aspect, the GPR119 agonist is not identical to a compound which comprises Group D8. In one aspect, the GPR119 agonist is not identical to a compound which comprises Group D9. In one aspect, the GPR119 agonist is not identical to a compound which comprises Group D10. In one aspect, the GPR119 agonist is not identical to a compound which comprises Group D11. In one aspect, the GPR119 agonist is not identical to a compound which comprises Group D12. In one aspect, the GPR119 agonist is not identical to a compound which comprises Group D13. In one aspect, the GPR119 agonist is not identical to a compound which comprises Group D14.

In one aspect, the GPR119 agonist is not identical to a compound disclosed in U.S. Patent Application No. 60/577,354.

In one aspect, the GPR119 agonist is not identical to a compound of Formula (V).

In one aspect, the GPR119 agonist is not identical to a compound which comprises Group E1 or Group E2.

In one aspect, the GPR119 agonist is not identical to a compound which comprises Group E1.

In one aspect, the GPR119 agonist is not identical to a compound which comprises Group E2.

In one aspect, the GPR119 agonist is not identical to a compound of Formula (VI).

In one aspect, the GPR119 agonist is not identical to a compound which comprises Group F1.

In one aspect, the GPR119 agonist is not identical to a compound disclosed in EP 1338651.

In one aspect, the GPR119 agonist is not identical to 2-(pyridine-4-yl)ethyl thiobenzoate.

In one aspect, the GPR119 agonist is not identical to L-α-lysophosphatidylcholine oleoyl.

In one aspect, the GPR119 agonist is not identical to a compound disclosed in WO 03/026661.

In one aspect, the GPR119 agonist is not identical to a compound in Table C.

In one aspect, the GPR119 agonist is not identical to a compound disclosed in JP 2004269468.

In one aspect, the GPR119 agonist is not identical to a compound in Table D.

In one aspect, the GPR119 agonist is not identical to a compound disclosed in JP 2004269469.

In one aspect, the GPR119 agonist is not identical to a compound in Table E.

In one aspect, the GPR119 agonist is not identical to a compound disclosed in WO 2005/061489.

In one aspect, the GPR119 agonist is not identical to 4-(5-piperidin-4-yl-[1,2,4]oxadiazol-3-yl)pyridine. In one aspect, the GPR119 agonist is not identical to 4-(3-pyridin-4-yl-[1,2,4]oxadiazol-5-yl)piperidine-1-carboxylic acid butyl ester. In one aspect, the GPR119 agonist is not identical to 4-[5-(4-butylcyclohexyl)-[1,2,4]oxadiazol-3-yl]pyridine. In one aspect, the GPR119 agonist is not identical to 3-[5-(4-butylcyclohexyl)-[1,2,4]oxadiazol-3-yl]pyridine. In one aspect, the GPR119 agonist is not identical to 3-[5-(4-propylcyclohexyl)-[1,2,4]oxadiazol-3-yl]pyridine.

In one aspect of the present invention, any one or more GPR119 agonist can be excluded from any embodiment of the present invention.

In one aspect of the present invention, any one or more GPR119 agonist which comprises Group A1, Group B1, Group B2, Group B3, Group B4, Group B5, Group C1, Group C2, Group C3, Group C4, Group C5, Group C6, Group C7, Group C8, Group C9, Group C10, Group D1, Group D2, Group D3, Group D4, Group D5, Group D6, Group D7, Group D8, Group D9, Group D10, Group D11, Group D12, Group D13, Group D14, Group E1, Group E2 or Group F1 can be excluded from any embodiment of the present invention.

In one aspect of the present invention, the GPR119 agonist has an EC50 of less than about 10 μM, less than about 1 μM, less than about 100 nM, less than about 75 nM, less than about 50 nM, less than about 25 nM, less than about 20 nM, less than about 15 nM, less than about 10 nM, less than about 5 nM, less than about 4 nM, less than about 3 nM, less than about 2 nM, or less than about 1 nM. Preferably the GPR119 agonist has an EC50 of less than about 50 nM, less than about 25 nM, less than about 20 nM, less than about 15 nM, less than about 10 nM, less than about 5 nM, less than about 4 nM, less than about 3 nM, less than about 2 nM, or less than about 1 nM.

In one aspect of the present invention, the GPR119 agonist is a selective GPR119 agonist, wherein the selective GPR119 agonist has a selectivity for GPR119 over corticotrophin-releasing factor-1 (CRF-1) receptor of at least about 100-fold.

In one aspect of the present invention, the GPR19 agonist is orally active.

In one aspect of the present invention, the GPR119 agonist is an agonist of human GPR119.

DPP-IV Inhibitors

The class of DPP-IV inhibitors useful in the novel therapeutic combinations of the present invention include compounds which exhibit an acceptably high affinity for DPP-IV. The DPP-IV inhibitor or pharmaceutically acceptable salt may be any DPP-IV inhibitor, more preferably a selective dipeptidyl peptidase inhibitor, and most preferably a selective DPP-IV inhibitor.

Examples of DPP-IV inhibitors are described in Villhauer et al., J Med Chem (2003) 46:2774-2789, for LAF237; Ahren et al, J Clin Endocrinol Metab (2004) 89:2078-2084; Villhauer et al., J Med Chem (2002) 45:2362-2365 for NVP-DPP728; Ahren et al, Diabetes Care (2002) 25:869-875 for NVP-DPP728; Peters et al., Bioorg Med Chem Lett (2004) 14:1491-1493; Caldwell et al., Bioorg Med Chem Lett (2004) 14:1265-1268; Edmondson et al., Bioorg Med Chem Lett (2004) 14:5151-5155; and Abe et al., J Nat Prod (2004) 67:999-1004; the disclosure of each of which is herein incorporated by reference in its entirety.

Specific examples of DPP-IV inhibitors include, but are not limited to, dipeptide derivatives or dipeptide mimetics such as alanine-pyrrolidide, isoleucine-thiazolidide, and the pseudosubstrate N-valyl prolyl, O-benzoyl hydroxylamine, as described e.g. in U.S. Pat. No. 6,303,661, the disclosure of which is herein incorporated by reference in its entirety.

Examples of DPP-IV inhibitors may be found in U.S. Pat. Nos. 6,869,947, 6,867,205, 6,861,440, 6,849,622, 6,812,350, 6,803,357, 6,800,650, 6,727,261, 6,716,843, 6,710,040, 6,706,742, 6,645,995, 6,617,340, 6,699,871, 6,573,287, 6,432,969, 6,395,767, 6,380,398, 6,303,661, 6,242,422, 6,166,063, 6,100,234, 6,040,145, the disclosure of each of which is herein incorporated by reference in its entirety. Examples of DPP-IV inhibitors may be found in U.S. Pat. Appl. Nos. 2005059724, 2005059716, 2005043292, 2005038020, 2005032804, 2005004205, 2004259903, 2004259902, 2004259883, 2004254226, 2004242898, 2004229926, 2004180925, 2004176406, 2004138214, 2004116328, 2004110817, 2004106656, 2004097510, 2004087587, 2004082570, 2004077645, 2004072892, 2004063935, 2004034014, 2003232788, 2003225102, 2003216450, 2003216382, 2003199528, 2003195188, 2003162820, 2003149071, 2003134802, 2003130281, 2003130199, 2003125304, 2003119750, 2003119738, 2003105077, 2003100563, 2003087950, 2003078247, 2002198205, 2002183367, 2002103384, 2002049164, 2002006899, the disclosure of each of which is herein incorporated by reference in its entirety.

Examples of DPP-IV inhibitors may be found in International Applications WO 2005/087235, WO 2005/082348, WO 2005/082849, WO 2005/079795, WO 2005/075426, WO 2005/072530, WO 2005/063750, WO 2005/058849, WO 2005/049022, WO 2005/047297, WO 2005/044195, WO 2005/042488, WO 2005/040095, WO 2005/037828, WO 2005/037779, WO 2005/034940, WO 2005/033099, WO 2005/032590, WO 2005/030751, WO 2005/030127, WO 2005/026148, WO 2005/025554, WO 2005/023762, WO 2005/020920, WO 05/19168, WO 05/12312, WO 05/12308, WO 05/12249, WO 05/11581, WO 05/09956, WO 05/03135, WO 05/00848, WO 05/00846, WO 04/112701, WO 04/111051, WO 04/111041, WO 04/110436, WO 04/110375, WO 04/108730, WO 04/104216, WO 04/104215, WO 04/103993, WO 04/103276, WO 04/99134, WO 04/96806, WO 04/92128, WO 04/87650, WO 04/87053, WO 04/85661, WO 04/85378, WO 04/76434, WO 04/76433, WO 04/71454, WO 04/69162, WO 04/67509, WO 04/64778, WO 04/58266, WO 04/52362, WO 04/52850, WO 04/50022, WO 04/50658, WO 04/48379, WO 04/46106, WO 04/43940, WO 04/41820, WO 04/41795, WO 04/37169, WO 04/37181, WO 04/33455, WO 04/32836, WO 04/20407, WO 04/18469, WO 04/18468, WO 04/18467, WO 04/14860, WO 04/09544, WO 04/07468, WO 04/07446, WO 04/04661, WO 04/00327, WO 03/106456, WO 03/104229, WO 03/101958, WO 03/101448, WO 03/99279, WO 03/95425, WO 03/84940, WO 03/82817, WO 03/80633, WO 03/74500, WO 03/72556, WO 03/72528, WO 03/68757, WO 03/68748, WO 03/57666, WO 03/57144, WO 03/55881, WO 03/45228, WO 03/40174, WO 03/38123, WO 03/37327, WO 03/35067, WO 03/35057, WO 03/24965, WO 03/24942, WO 03/22871, WO 03/15775, WO 03/04498, WO 03/04496, WO 03/02530, WO 03/02596, WO 03/02595, WO 03/02593, WO 03/02553, WO 03/02531, WO 03/00181, WO 03/00180, WO 03/00250, WO 02/83109, WO 02/83128, WO 02/76450, WO 02/68420, WO 02/62764, WO 02/55088, WO 02/51836, WO 02/38541, WO 02/34900, WO 02/30891, WO 02/30890, WO 02/14271, WO 02/02560, WO 01/97808, WO 01/96295, WO 01/81337, WO 01/81304, WO 01/68603, WO 01/55105, WO 01/52825, WO 01/34594, WO 00/71135, WO 00/69868, WO 00/56297, WO 00/56296, WO 00/34241, WO 00/23421, WO 00/10549, WO 99/67278, WO 99/62914, WO 99/61431, WO 99/56753, WO 99/25719, WO 99/16864, WO 98/50066, WO 98/50046, WO 98/19998, WO 98/18763, WO 97/40832, WO 95/29691, WO 95/15309, WO 93/10127, WO 93/08259, WO 91/16339, EP 1517907, EP 1513808, EP 1492777, EP 1490335, EP 1489088, EP 1480961, EP 1476435, EP 1476429, EP 1469873, EP 1465891, EP 1463727, EP 1461337, EP 1450794, EP 1446116, EP 1442049, EP 1441719, EP 1426366, EP 1412357, EP 1406873, EP 1406872, EP 1406622, EP 1404675, EP 1399420, EP 1399471, EP 1399470, EP 1399469, EP 1399433, EP 1399154, EP 1385508, EP 1377288, EP 1355886, EP 1354882, EP 1338592, EP 1333025, EP 1304327, EP 1301187, EP 1296974, EP 1280797, EP 1282600, EP 1261586, EP 1258476, EP 1254113, EP 1248604, EP 1245568, EP 1215207, EP 1228061, EP 1137635, EP 1123272, EP 1104293, EP 1082314, EP 1050540, EP 1043328, EP 0995440, EP 0980249, EP 0975359, EP 0731789, EP 0641347, EP 0610317, EP 0528858, CA 2466870, CA 2433090, CA 2339537, CA 2289125, CA 2289124, CA 2123128, DD 296075, DE 19834591, DE 19828113, DE 19823831, DE 19616486, DE 10333935, DE 10327439, DE 10256264, DE 10251927, DE 10238477, DE 10238470, DE 10238243, DE 10143840, FR 2824825, FR 2822826, JP2005507261; JP 2005505531, JP 2005502624, JP 2005500321, JP 2005500308, JP2005023038, JP 2004536115, JP 2004535445, JP 2004535433, JP 2004534836, JP 2004534815, JP 2004532220, JP 2004530729, JP 2004525929, JP 2004525179, JP 2004522786, JP 2004521149, JP 2004503531, JP 2004315496, JP 2004244412, JP 2004043429, JP 2004035574, JP 2004026820, JP 2004026678, JP 2004002368, JP 2004002367, JP 2003535898, JP 2003535034, JP 2003531204, JP 2003531191, JP 2003531118, JP 2003524591, JP 2003520849, JP 2003327532, JP 2003300977, JP 2003238566, JP 2002531547, JP 2002527504, JP 2002517401, JP 2002516318, JP 2002363157, JP 2002356472, JP 2002356471, JP 2002265439, JP 2001510442, JP 2000511559, JP 2000327689, JP 2000191616, JP 1998182613, JP 1998081666, JP 1997509921, JP 1995501078, JP 1993508624, the disclosure of each of which is herein incorporated by reference in its entirety.

In one aspect of the present invention, the DPP-IV inhibitor is valine-pyrrolidide [Deacon et al, Diabetes (1998) 47:764769; the disclosure of which is herein incorporated by reference in its entirety].

In one aspect of the present invention, the DPP-IV inhibitor is 3-(L-Isoleucyl)thiazolidine (isoleucine-thiazolidide). Isoleucine-thiazolidide may be found in JP 2001510442, WO 97/40832, U.S. Pat. No. 6,303,661, and DE 19616486, the disclosure of each of which is herein incorporated by reference in its entirety. Isoleucine-thiazolidide is described as an orally active and selective DPP-IV inhibitor [Pederson et al, Diabetes (1998) 47:1253-1258; the disclosure of which is herein incorporated by reference in its entirety].

In one aspect of the present invention, the DPP-IV inhibitor is 1-[2-[5-cyanopyridin-2-yl)amino]ethylamino]acetyl-2-cyano-(S)-pyrrolidine (NVP-DPP728). NVP-DPP728 may be found in WO 98/19998 and JP 2000511559, the disclosure of each of which is herein incorporated by reference in its entirety. NVP-DPP728 is described as an orally active and selective DPP-IV inhibitor [Villhauer et al, J Med Chem (2002) 45:2362-2365].

In one aspect of the present invention, the DPP-IV inhibitor is 3(R)-Amino-1-[3-(trifluoromethyl)-5,6,7,8-tetrahydro[1, 2,4]triazolo[4,3-a]pyrazin-7-yl]-4-(2,4,5-trifluorophenyl) butan-1-one (MK-0431). MK-0431 may be found in EP 1412357, WO 03/04498, U.S. Pat. No. 6,699,871, and US 2003100563, the disclosure of each of which is herein incorporated by reference in its entirety. MK-0431 is described as an orally active and selective DPP-IV inhibitor [Weber et al, Diabetes (2004) 53(Suppl. 2):A151, 633-P (Abstract), the disclosure of which is herein incorporated by reference in its entirety].

In one aspect of the present invention, the DPP-IV inhibitor is (1-[[3-hydroxy-1-adamantyl)amino]acetyl]-2-cyano-(S)-pyrrolidine (LAF237). LAF237 may be found in U.S. Pat. No. 6,166,063, WO 00/34241, EP 1137635, and JP 2002531547, the disclosure of each of which is herein incorporated by reference in its entirety. LAF237 is described as an orally active and selective DPP-IV inhibitor [Villhauer et al, J Med Chem (2003) 46:2774-2789].

In one aspect of the present invention, the DPP-IV inhibitor is (1S,3S,5S)-2-[2(S)-Amino-2-(3-hydroxyadamantan-1-yl) acetyl]-2-azabicyclo[3.1.0]hexane-3-carbonitrile (BMS-477118).

In one aspect of the present invention, the DPP-IV inhibitor is [1-[2(S)-Amino-3-methylbutyryl]pyrrolidin-2(R)-yl]boronic acid (PT-100).

In one aspect of the present invention, the DPP-IV inhibitor is GSK-823093.

In one aspect of the present invention, the DPP-IV inhibitor is PSN-9301.

In one aspect of the present invention, the DPP-IV inhibitor is T-6666.

In one aspect of the present invention, the DPP-IV inhibitor is SYR-322.

In one aspect of the present invention, the DPP-IV inhibitor is SYR-619.

In one aspect of the present invention, the DPP-IV inhibitor is CR-14023.

In one aspect of the present invention, the DPP-IV inhibitor is CR-14025.

In one aspect of the present invention, the DPP-IV inhibitor is CR-14240.

In one aspect of the present invention, the DPP-IV inhibitor is CR-13651.

In one aspect of the present invention, the DPP-IV inhibitor is NNC-72-2138.

In one aspect of the present invention, the DPP-IV inhibitor is N,N-7201.

In one aspect of the present invention, the DPP-IV inhibitor is PHX-1149.

In one aspect of the present invention, the DPP-IV inhibitor is PHX-1004.

In one aspect of the present invention, the DPP-IV inhibitor is SNT-189379.

In one aspect of the present invention, the DPP-IV inhibitor is GRC-8087.

In one aspect of the present invention, the DPP-IV inhibitor is PT-630.

In one aspect of the present invention, the DPP-IV inhibitor is SK-0403.

In one aspect of the present invention, the DPP-IV inhibitor is GSK-825964.

In one aspect of the present invention, the DPP-IV inhibitor is TS-021.

In one aspect of the present invention, the DPP-IV inhibitor is GRC-8200.

In one aspect of the present invention, the DPP-IV inhibitor is GRC-8116.

In one aspect of the present invention, the DPP-IV inhibitor is FE107542.

In one aspect of the present invention, the DPP-IV inhibitor is selected from the right column of Table B.

In one aspect of the present invention, the DPP-IV inhibitor is not a dipeptide derivative.

In one aspect of the present invention, the DPP-IV inhibitor is not a dipeptide mimetic.

In one aspect of the present invention, the DPP-IV inhibitor is not identical to valine-pyrrolidide.

In one aspect of the present invention, the DPP-IV inhibitor is not identical to alanine-pyrrolidide.

In one aspect of the present invention, the DPP-IV inhibitor is not identical to 3-(L-Isoleucyl)thiazolidine (isoleucine-thiazolidide).

In one aspect of the present invention, the DPP-IV inhibitor is not identical to N-valyl propyl,O-benzoyl hydroxylamine.

In one aspect of the present invention, the DPP-IV inhibitor is not identical to 1-[2-[5-cyanopyridin-2-yl)amino]ethylamino]acetyl-2-cyano-(S)-pyrrolidine (NVP-DPP728).

In one aspect of the present invention, the DPP-IV inhibitor is not identical to 3(R)-Amino-1-[3-(trifluoromethyl)-5,6,7, 8-tetrahydro[1,2,4]triazolo[4,3-a]pyrazin-7-yl]-4-(2,4,5-trifluorophenyl)butan-1-one (MK-0431).

In one aspect of the present invention, the DPP-IV inhibitor is not identical to (1-[[3-hydroxy-1-adamantyl)amino] acetyl]-2-cyano-(S)-pyrrolidine (LAF237).

In one aspect of the present invention, the DPP-IV inhibitor is not identical to (1S,3S,5S)-2-[2(S)-Amino-2-(3-hydroxyadamantan-1-yl)acetyl]-2-azabicyclo[3.1.0]hexane-3-carbonitrile (BMS-477118).

In one aspect of the present invention, the DPP-IV inhibitor is not identical to [1-[2(S)-Amino-3-methylbutyryl]pyrrolidin-2(R)-yl]boronic acid (PT-100).

In one aspect of the present invention, the DPP-IV inhibitor is not identical to GSK-823093.

In one aspect of the present invention, the DPP-IV inhibitor is not identical to PSN-9301.

In one aspect of the present invention, the DPP-IV inhibitor is not identical to T-6666.

In one aspect of the present invention, the DPP-IV inhibitor is not identical to SYR-322.

In one aspect of the present invention, the DPP-IV inhibitor is not identical to SYR-619.

In one aspect of the present invention, the DPP-IV inhibitor is not identical to CR-14023.

In one aspect of the present invention, the DPP-IV inhibitor is not identical to CR-14025.

In one aspect of the present invention, the DPP-IV inhibitor is not identical to CR-14240.

In one aspect of the present invention, the DPP-IV inhibitor is not identical to CR-13651.

In one aspect of the present invention, the DPP-IV inhibitor is not identical to NNC-72-2138.

In one aspect of the present invention, the DPP-IV inhibitor is not identical to N,N-7201.

In one aspect of the present invention, the DPP-IV inhibitor is not identical to PHX-1149.

In one aspect of the present invention, the DPP-IV inhibitor is not identical to PHX-1004.

In one aspect of the present invention, the DPP-IV inhibitor is not identical to SNT-189379.

In one aspect of the present invention, the DPP-IV inhibitor is not identical to GRC-8087.

In one aspect of the present invention, the DPP-IV inhibitor is not identical to PT-630.

In one aspect of the present invention, the DPP-IV inhibitor is not identical to SK-0403.

In one aspect of the present invention, the DPP-IV inhibitor is not identical to GSK-825964.

In one aspect of the present invention, the DPP-IV inhibitor is not identical to TS-021.

In one aspect of the present invention, the DPP-IV inhibitor is not identical to GRC-8200.

In one aspect of the present invention, the DPP-IV inhibitor is not identical to GRC-8116.

In one aspect of the present invention, the DPP-IV inhibitor is not identical to FE107542.

In one aspect of the present invention, the DPP-IV inhibitor is not identical to a compound included in the right column of Table B.

In one aspect of the present invention, the DPP-IV inhibitor is not identical to a compound disclosed in a U.S. patent application having a U.S. Pat. Appln. No. selected from the group consisting of U.S. Pat. Nos. 6,869,947, 6,867,205, 6,861,440, 6,849,622, 6,812,350, 6,803,357, 6,800,650, 6,727,261, 6,716,843, 6,710,040, 6,706,742, 6,645,995, 6,617,340, 6,699,871, 6,573,287, 6,432,969, 6,395,767, 6,380,398, 6,303,661, 6,242,422, 6,166,063, 6,100,234, and 6,040,145.

In one aspect of the present invention, the DPP-IV inhibitor is not identical to a compound disclosed in a U.S. patent application having a U.S. Pat. Appln. No. selected from the group consisting of 2005059724, 2005059716, 2005043292, 2005038020, 2005032804, 2005004205, 2004259903, 2004259902, 2004259883, 2004254226, 2004242898, 2004229926, 2004180925, 2004176406, 2004138214, 2004116328, 2004110817, 2004106656, 2004097510, 2004087587, 2004082570, 2004077645, 2004072892, 2004063935, 2004034014, 2003232788, 2003225102, 2003216450, 2003216382, 2003199528, 2003195188, 2003162820, 2003149071, 2003134802, 2003130281, 2003130199, 2003125304, 2003119750, 2003119738, 2003105077, 2003100563, 2003087950, 2003078247, 2002198205, 2002183367, 2002103384, 2002049164, and 2002006899.

In one aspect of the present invention, the DPP-IV inhibitor is not identical to a compound disclosed in an International Application selected from the group consisting of WO 2005/087235, WO 2005/082348, WO 2005/082849, WO 2005/079795, WO 2005/075426, WO 2005/072530, WO 2005/063750, WO 2005/058849, WO 2005/049022, WO 2005/047297, WO 2005/044195, WO 2005/042488, WO 2005/040095, WO 2005/037828, WO 2005/037779, WO 2005/034940, WO 2005/033099, WO 2005/032590, WO 2005/030751, WO 2005/030127, WO 2005/026148, WO 2005/025554, WO 2005/023762, WO 2005/020920, WO 05/19168, WO 05/12312, WO 05/12308, WO 05/12249, WO 05/11581, WO 05/09956, WO 05/03135, WO 05/00848, WO 05/00846, WO 04/112701, WO 04/111051, WO 04/111041, WO 04/110436, WO 04/110375, WO 04/108730, WO 04/104216, WO 04/104215, WO 04/103993, WO 04/103276, WO 04/99134, WO 04/96806, WO 04/92128, WO 04/87650, WO 04/87053, WO 04/85661, WO 04/85378, WO 04/76434, WO 04/76433, WO 04/71454, WO 04/69162, WO 04/67509, WO 04/64778, WO 04/58266, WO 04/52362, WO 04/52850, WO 04/50022, WO 04/50658, WO 04/48379, WO 04/46106, WO 04/43940, WO 04/41820, WO 04/41795, WO 04/37169, WO 04/37181, WO 04/33455, WO 04/32836, WO 04/20407, WO 04/18469, WO 04/18468, WO 04/18467, WO 04/14860, WO 04/09544, WO 04/07468, WO 04/07446, WO 04/04661, WO 04/00327, WO 03/106456, WO 03/104229, WO 03/101958, WO 03/101448, WO 03/99279, WO 03/95425, WO 03/84940, WO 03/82817, WO 03/80633, WO 03/74500, WO 03/72556, WO 03/72528, WO 03/68757, WO 03/68748, WO 03/57666, WO 03/57144, WO 03/55881, WO 03/45228, WO 03/40174, WO 03/38123, WO 03/37327, WO 03/35067, WO 03/35057, WO 03/24965, WO 03/24942, WO 03/22871, WO 03/15775, WO 03/04498, WO 03/04496, WO 03/02530, WO 03/02596, WO 03/02595, WO 03/02593, WO 03/02553, WO 03/02531, WO 03/00181, WO 03/00180, WO 03/00250, WO 02/83109, WO 02/83128, WO 02/76450, WO 02/68420, WO 02/62764, WO 02/55088, WO 02/51836, WO 02/38541, WO 02/34900, WO 02/30891, WO 02/30890, WO 02/14271, WO 02/02560, WO 01/97808, WO 01/96295, WO 01/81337, WO 01/81304, WO 01/68603, WO 01/55105, WO 01/52825, WO 01/34594, WO 00/71135, WO 00/69868, WO 00/56297, WO 00/56296, WO 00/34241, WO 00/23421, WO 00/10549, WO 99/67278, WO 99/62914, WO 99/61431, WO 99/56753, WO 99/25719, WO 99/16864, WO 98/50066, WO 98/50046, WO 98/19998, WO 98/18763, WO 97/40832, WO 95/29691, WO 95/15309, WO 93/10127, WO 93/08259, WO 91/16339, EP 1517907, EP 1513808, EP 1492777, EP 1490335, EP 1489088, EP 1480961, EP 1476435, EP 1476429, EP 1469873, EP 1465891, EP 1463727, EP 1461337, EP 1450794, EP 1446116, EP 1442049, EP 1441719, EP 1426366, EP 1412357, EP 1406873, EP 1406872, EP 1406622, EP 1404675, EP 1399420, EP 1399471, EP 1399470, EP 1399469, EP 1399433, EP 1399154, EP 1385508, EP 1377288, EP 1355886, EP 1354882, EP 1338592, EP 1333025, EP 1304327, EP 1301187, EP 1296974, EP 1280797, EP 1282600, EP 1261586, EP 1258476, EP 1254113, EP 1248604, EP 1245568, EP 1215207, EP 1228061, EP 1137635, EP 1123272, EP 1104293, EP 1082314, EP 1050540, EP 1043328, EP 0995440, EP 0980249, EP 0975359, EP 0731789, EP 0641347, EP 0610317, EP 0528858, CA 2466870, CA 2433090, CA 2339537, CA 2289125, CA 2289124, CA 2123128, DD 296075, DE 19834591, DE 19828113, DE 19823831, DE 19616486, DE 10333935, DE 10327439, DE 10256264, DE 10251927, DE 10238477, DE 10238470, DE 10238243, DE 10143840, FR 2824825, FR 2822826, JP2005507261, JP 2005505531, JP 2005502624, JP 2005500321, JP 2005500308, JP2005023038, JP 2004536115, JP 2004535445, JP 2004535433, JP 2004534836, JP 2004534815, JP 2004532220, JP 2004530729, JP 2004525929, JP 2004525179, JP 2004522786, JP 2004521149, JP 2004503531, JP 2004315496, JP 2004244412, JP 2004043429, JP 2004035574, JP 2004026820, JP 2004026678, JP 2004002368, JP 2004002367, JP 2003535898, JP 2003535034, JP 2003531204, JP 2003531191, JP 2003531118, JP 2003524591, JP 2003520849, JP 2003327532, JP 2003300977, JP 2003238566, JP 2002531547, JP 2002527504, JP 2002517401, JP 2002516318, JP 2002363157, JP 2002356472, JP 2002356471, JP 2002265439, JP 2001510442, JP 2000511559, JP 2000327689, JP 2000191616, JP 1998182613, JP 1998081666, JP 1997509921, JP 1995501078, and JP 1993508624.

In one aspect of the present invention, any one or more DPP-IV inhibitor can be excluded from any embodiment of the present invention.

In one aspect of the present invention, the DPP-IV inhibitor has an IC50 of less than about 10 µM, less than about 1 µM, less than about 100 nM, less than about 75 nM, less than about 50 nM, less than about 25 nM, less than about 20 nM, less than about 15 nM, less than about 10 nM, less than about 5 nM, less than about 4 nM, less than about 3 nM, less than about 2 nM, or less than about 1 nM. Preferably the DPP-IV inhibitor has an IC50 of less than about 50 nM, less than about 25 nM, less than about 20 nM, less than about 15 nM, less than about 10 nM, less than about 5 nM, less than about 4 nM, less than about 3 nM, less than about 2 nM, or less than about 1 nM.

In one aspect of the present invention, the DPP-IV inhibitor a selective DPP-IV inhibitor, wherein the selective DPP-IV inhibitor has a selectivity for human plasma DPP-IV over one or more of PPCE, DPP-II, DPP-8 and DPP-9 of at least about 10-fold, more preferably of at least about 100-fold, and most preferably of at least about 1000-fold.

In one aspect of the present invention, the DPP-IV inhibitor is orally active.

In one aspect of the present invention, the DPP-IV inhibitor is an inhibitor of human DPP-IV.

Combination of GPR119 Agonist and DPP-IV Inhibitor

By way of illustration and not limitation, an exemplary combination of GPR119 agonist and DPP-IV inhibitor in accordance with the present invention is provided by selecting a GPR119 agonist from the left column of Table B and a DPP-IV inhibitor from the right column of Table B. It is expressly contemplated that each individual combination of GPR119 agonist and DPP-IV inhibitor provided by selecting a GPR119 agonist from the left column of Table B and a DPP-IV inhibitor from the right column of Table B is a separate embodiment within the scope of the present invention.

TABLE B

| GPR119 Agonist | DPP-IV Inhibitor |
|---|---|
| [6-(4-Benzenesulfonyl-piperidin-1-yl)-5-nitro-pyrimidin-4-yl]-(4-methanesulfonyl-phenyl)-amine | valine-pyrrolidide |
| {4-[6-(4-Methanesulfonyl-phenylamino)-5-nitro-pyrimidin-4-yl]-piperazin-1-yl}-acetic acid ethyl ester | 3-(L-Isoleucyl)thiazolidine (isoleucine-thiazolidide) |
| (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine | 1-[2-[5-cyanopyridin-2-yl)amino]ethylamino]acetyl-2-cyano-(S)-pyrrolidine (NVP-DPP728) |
| 6'-[4-(2-Methoxycarbonyl-acetyl)-phenoxy]-3'-nitro-3,4,5,6-tetrahydro-2H-[1,2']bipyridinyl-4-carboxylic acid ethyl ester | 3(R)-Amino-1-[3-(trifluoromethyl)-5,6,7,8-tetrahydro[1,2,4]triazolo[4,3-a]pyrazin-7-yl]-4-(2,4,5-trifluorophenyl)butan-1-one (MK-0431) |
| 1-[4-(4-Acetyl-3'-nitro-3,4,5,6-tetrahydro-2H-[1,2']bipyridinyl-6'-yloxy)-phenyl]-ethanone | (1-[[3-hydroxy-1-adamantyl)amino]acetyl]-2-cyano-(S)-pyrrolidine (LAF237) |
| 6'-[4-(4-Hydroxy-benzenesulfonyl)-phenoxy]-3'-nitro-3,4,5,6-tetrahydro-2H-[1,2']bipyridinyl-4-carboxylic acid ethyl ester | (1S,3S,5S)-2-[2(S)-Amino-2-(3-hydroxyadamantan-1-yl)acetyl]-2-azabicyclo[3.1.0]hexane-3-carbonitrile (BMS-477118) |
| 1-[5-(4-Benzoyl-phenoxy)-2-nitro-phenyl]-piperidine-4-carboxylic acid ethyl ester | [1-[2(S)-Amino-3-methylbutyryl]pyrrolidin-2(R)-yl]boronic acid (PT-100) |
| 1-{5-[4-(2-Methoxycarbonyl-acetyl)-phenoxy]-2-nitro-phenyl}-piperidine-4-carboxylic acid ethyl ester | GSK-823093 |
| 1-[5-(2-Amino-4-ethanesulfonyl-phenoxy)-2-nitro-phenyl]-piperidine-4-carboxylic acid ethyl ester | PSN-9301 |
| 5-Bromo-1-[4-nitro-3-(4-propyl-piperidin-1-yl)-phenyl]-1H-pyridin-2-one | T-6666 |
| 6'-Benzenesulfonylamino-3'-nitro-3,4,5,6-tetrahydro-2H-[1,2']bipyridinyl-4-carboxylic acid ethyl ester | SYR-322 |
| 6'-(Benzenesulfonyl-methyl-amino)-3'-nitro-3,4,5,6-tetrahydro-2H-[1,2']bipyridinyl-4-carboxylic acid ethyl ester | SYR-619 |
| 6'-(Benzenesulfonyl-butyl-amino)-3'-nitro-3,4,5,6-tetrahydro-2H-[1,2']bipyridinyl-4-carboxylic acid ethyl ester | CR-14023 |
| 1-[5-(4-Benzoyl-phenylamino)-2-nitro-phenyl]-piperidine-4-carboxylic acid ethyl ester | CR-14025 |
| {4-[4-Nitro-3-(4-propyl-piperidin-1-yl)-phenylamino]-phenyl}-phenyl-methanone | CR-14240 |
| 3-[6-(4-Methanesulfonyl-phenylamino)-5-nitro-pyrimidin-4-yloxymethyl]-pyrrolidine-1-carboxylic acid tert-butyl ester | CR-13651 |

TABLE B-continued

| GPR119 Agonist | DPP-IV Inhibitor |
| --- | --- |
| 4-[5-Cyano-6-(6-methylsulfanyl-pyridin-3-ylamino)-pyrimidin-4-yloxy]-piperidine-1-carboxylic acid tert-butyl ester | NNC-72-2138 |
| 4-[5-Cyano-6-(6-methanesulfonyl-pyridin-3-ylamino)-pyrimidin-4-yloxy]-piperidine-1-carboxylic acid tert-butyl ester | NN-7201 |
| 4-[6-(4-Methanesulfonyl-phenylamino)-5-nitro-pyrimidin-4-yloxy]-piperidine-1-carboxylic acid tert-butyl ester | PHX-1149 |
| (4-Methanesulfonyl-phenyl)-[5-nitro-6-(piperidin-4-yloxy)-pyrimidin-4-yl]-amine | PHX-1004 |
| 1-{4-[6-(4-Methanesulfonyl-phenylamino)-5-nitro-pyrimidin-4-yloxy]-piperidin-1-yl}-3,3-dimethyl-butan-1-one | SNT-189379 |
| 4-[6-(4-Methanesulfonyl-phenylamino)-5-nitro-pyrimidin-4-ylamino]-piperidine-1-carboxylic acid tert-butyl ester | GRC-8087 |
| N-(4-Methanesulfonyl-phenyl)-5-nitro-N'-piperidin-4-yl-pyrimidine-4,6-diamine | PT-630 |
| 1-{4-[6-(4-Methanesulfonyl-phenylamino)-5-nitro-pyrimidin-4-ylamino]-piperidin-1-yl}-ethanone | SK-0403 |
| 4-[6-(4-Cyano-2-fluoro-phenylamino)-5-ethynyl-pyrimidin-4-yloxy]-piperidine-1-carboxylic acid isopropyl ester | GSK-825964 |
| 4-[5-Ethynyl-6-(2-fluoro-4-[1,2,4]triazol-1-yl-phenylamino)-pyrimidin-4-yloxy]-piperidine-1-carboxylic acid isopropyl ester | 8-(3-Aminopiperidin-1-yl)-N2,7-dibenzyl-1-methylguanine trifluoroacetate |
| 4-{5-Ethynyl-6-[1-(3-isopropyl-[1,2,4]oxadiazol-5-yl)-piperidin-4-yloxy]-pyrimidin-4-ylamino}-3-fluoro-benzonitrile | N-[2-[2-[8-(3-Aminopiperidin-1-yl)-7-(2-butynyl)-3-methylxanthin-1-yl]acetyl]phenyl]formamide |
| 4-[5-Acetyl-6-(6-methanesulfonyl-pyridin-3-ylamino)-pyrimidin-4-yloxy]-piperidine-1-carboxylic acid isobutyl ester | 8-[3(R)-Aminopiperidin-1-yl]-7-(2-butynyl)-3-methyl-1-(quinazolin-2-ylmethyl)xanthine |
| 1-[4-(1-Benzyl-azetidin-3-yloxy)-6-(6-methanesulfonyl-pyridin-3-ylamino)-pyrimidin-5-yl]-ethanone | 8-(3-Aminopiperidin-1-yl)-1-(benzo[c]-1,8-naphthyridin-6-ylmethyl)-7-(2-butynyl)-3-methylxanthine |
| 4-[5-Cyano-6-(6-propylamino-pyridin-3-ylamino)-pyrimidin-4-yloxy]-piperidine-1-carboxylic acid isopropyl ester | 2-[8-[3(R)-Aminopiperidin-1-yl]-7-(2-butynyl)-3-methylxanthin-1-yl]-N-(2-pyridyl)acetamide |
| 4-({[6-(2-Fluoro-4-methanesulfonyl-phenylamino)-5-methyl-pyrimidin-4-yl]-isopropyl-amino}-methyl)-piperidine-1-carboxylic acid tert-butyl ester | 2-(3-Aminopiperidin-1-yl)-3-(2-butynyl)-5-(quinoxalin-6-ylmethyl)-4,5-dihydro-3H-imidazo[4,5-d]pyridazin-4-one |
| 4-(2-Fluoro-4-methanesulfonyl-phenoxy)-6-[1-(3-methoxy-propyl)-piperidin-4-yloxy]-5-methyl-pyrimidine | (1S,3S,5S)-2-[2(S)-Amino-4,4-dimethylpentanoyl]-2-azabicyclo[3.1.0]hexane-3(S)-carbonitrile trifluoroacetate |
| 1-{4-[6-(2-Fluoro-4-methanesulfonyl-phenoxy)-5-methyl-pyrimidin-4-yloxy]-piperidin-1-yl}-3-methoxy-propan-2-ol | N1-(1-Cyanoethyl)-N1,3-dimethyl-L-valinamide |
| 4-{6-[2-Fluoro-4-(5-isopropoxymethyl-[1,2,4]oxadiazol-3-yl)-phenoxy]-5-methyl-pyrimidin-4-yloxy}-piperidine-1-carboxylic acid isopropyl ester | (1S,3S,5S)-2-[2(S)-Amino-2-[1-(3,3-dimethylbutyryl)piperidin-4-yl]acetyl]-2-azabicyclo[3.1.0]hexane-3-carbonitrile |
| 4-[6-(2-Fluoro-4-morpholin-4-yl-phenoxy)-5-methyl-pyrimidin-4-yloxy]-piperidine-1-carboxylic acid isopropyl ester | 2-[7-(2-Butynyl)-1-(2-phenylethyl)-8-(1-piperazinyl)xanthin-3-yl]-N-(2-propynyl)acetamide hydrochloride |
| {4-[6-(2-Fluoro-4-methanesulfonyl-phenoxy)-5-methyl-pyrimidin-4-yloxy]-piperidin-1-yl}-[6-(2-pyrrolidin-1-yl-ethyl)-pyridin-3-yl]-methanone | 2-[7-(2-Butynyl)-1-(3-cyanobenzyl)-6-oxo-8-(1-piperazinyl)-6,7-dihydro-1H-purin-2-yloxy]-N-methylbenzamide trifluoroacetate |
| (6-Amino-pyridin-3-yl)-{4-[6-(2-fluoro-4-methanesulfonyl-phenoxy)-5-methyl-pyrimidin-4-yloxy]-piperidin-1-yl}-methanone | 2-[3-(2-Butynyl)-4-oxo-2-(1-piperazinyl)-4,5-dihydro-3H-imidazo[4,5-d]pyridazin-5-ylmethyl]benzonitrile trifluoroacetate |
| 4-({Cyclopropyl-[6-(2-fluoro-4-methanesulfonyl-phenoxy)-5-methyl-pyrimidin-4-yl]-amino}-methyl)-piperidine-1-carboxylic acid tert-butyl ester | N-[1(S)-[2(S)-Cyanopyrrolidin-1-ylcarbonyl]-4-(pyrazin-2-ylcarboxamido)butyl]carbamic acid 1-acetoxyethyl ester |
| 4-({Cyclopropyl-[6-(2-fluoro-4-methanesulfonyl-phenoxy)-5-methyl-pyrimidin-4-yl]-amino}-methyl)-piperidine-1-carboxylic acid isopropyl ester | 2(S),4-Diamino-1-(4-thiomorpholinyl)butan-1-one |
| 4-({[6-(2-Fluoro-4-methanesulfonyl-phenoxy)-5-methyl-pyrimidin-4-yl]-isopropyl-amino}-methyl)-piperidine-1-carboxylic acid isopropyl ester | 1-[Perhydroindol-2(S)-ylcarbonyl]azetidine-2(S)-carbonitrile |
| 4-[6-(2-Fluoro-4-methanesulfonyl-phenylamino)-5-methyl-pyrimidin-4-ylsulfanyl]-piperidine-1-carboxylic acid isopropyl ester | 1-(2-Benzothiazolyl)-1-[1-[(2S,3aS,7aS)-perhydroindol-2-ylcarbonyl]pyrrolidin-2(S)-yl]methanone hydrochloride |

TABLE B-continued

| GPR119 Agonist | DPP-IV Inhibitor |
|---|---|
| 4-[1-(4-Methanesulfonyl-phenyl)-1H-pyrazolo[3,4-d]pyrimidin-4-yloxy]-piperidine-1-carboxylic acid tert-butyl ester | 1-[2(S)-Amino-2-cyclohexylacetyl]-4-methylazetidine-2-carbonitrile hydrochloride |
| 4-[1-(4-Methanesulfonyl-phenyl)-3-methyl-1H-pyrazolo[3,4-d]pyrimidin-4-yloxy]-piperidine-1-carboxylic acid tert-butyl ester | 6-[2-[2-[5(S)-Cyano-4,5-dihydro-1H-pyrazol-1-yl]-2-oxoethylamino]ethylamino]pyridine-3-carbonitrile |
| 4-[1-(4-Methanesulfonyl-phenyl)-3,6-dimethyl-1H-pyrazolo[3,4-d]pyrimidin-4-yloxy]-piperidine-1-carboxylic acid tert-butyl ester | 6-[2-[2-[2(S)-Cyano-4(S)-fluoropyrrolidin-1-yl]-2-oxoethylamino]-2-methylpropylamino]-N,N-dimethylpyridine-3-sulfonamide |
| 4-({[1-(2,5-Difluoro-phenyl)-1H-pyrazolo[3,4-d]pyrimidin-4-yl]-methyl-amino}-methyl)-piperidine-1-carboxylic acid tert-butyl ester | trans-N-[4-[1(S)-Amino-2-[3(S)-fluoropyrrolidin-1-yl]-2-oxoethyl]cyclohexyl]-2,4-difluorobenzenesulfonamide |
| 2-{4-[1-(2-Fluoro-4-methanesulfonyl-phenyl)-1H-pyrazolo[3,4-d]pyrimidin-4-yloxy]-piperidin-1-yl}-1-(4-trifluoromethoxy-phenyl)-ethanone | 2(S)-Amino-1-(1-pyrrolidinyl)-2-[4-(thiazol-2-ylamino)cyclohexyl]ethanone trifluoroacetate |
| 2-{4-[1-(2-Fluoro-4-methanesulfonyl-phenyl)-1H-pyrazolo[3,4-d]pyrimidin-4-yloxy]-piperidin-1-yl}-1-(3-fluoro-phenyl)-ethanone | N-[(1R,3R)-3-[1(S)-Amino-2-oxo-2-(1-pyrrolidinyl)ethyl]cyclopentyl]-4-(methylsulfonyl)benzenesulfonamide |
| 4-[9-(6-Methanesulfonyl-pyridin-3-yl)-9H-purin-6-yloxy]-piperidine-1-carboxylic acid isobutyl ester | 3(R)-Amino-1-(6-benzyl-3-methyl-5,6,7,8-tetrahydroimidazo[1,2-a]pyrazin-7-yl)-4-(3,4-difluorophenyl)butan-1-one |
| {4-[9-(6-Methanesulfonyl-pyridin-3-yl)-9H-purin-6-yloxy]-piperidin-1-yl}-pyridin-3-yl-methanone | trans-N-[4-[1(S)-Amino-2-oxo-2-(1-pyrrolidinyl)ethyl]cyclohexyl]-2,4-difluorobenzenesulfonamide |
| 4-[9-(4-Methanesulfonyl-phenyl)-9H-purin-6-yloxy]-piperidine-1-carboxylic acid tert-butyl ester | 3(R)-Amino-4-(2,5-difluorophenyl)-1-[4-hydroxy-2-(trifluoromethyl)-5,6,7,8-tetrahydropyrido[3,4-d]pyrimidin-7-yl]butan-1-one |
| 4-[9-(2-Fluoro-4-propionylsulfamoyl-phenyl)-9H-purin-6-yloxy]-piperidine-1-carboxylic acid isopropyl ester | N-[(1R,3R)-3-[1(S)-Amino-2-oxo-2-(1-pyrrolidinyl)ethyl]cyclopentyl]-2-(methylsulfonamido)ethanesulfonamide |
| 4-[9-(4-Cyano-2-fluoro-phenyl)-9H-purin-6-yloxy]-piperidine-1-carboxylic acid isopropyl ester | 2-[4-[3(R)-Amino-4-(2-fluorophenyl)butyryl]-3(R)-benzylpiperazin-1-yl]-N-[3-(methylsulfonamido)phenyl]acetamide |
| 4-[9-(2-Fluoro-4-sulfamoyl-phenyl)-9H-purin-6-yloxy]-piperidine-1-carboxylic acid isopropyl ester | 3(R)-Amino-1-(3-thiazolidinyl)-4-(2,4,5-trifluorophenyl)butan-1-one |
| 4-[3-(4-Methanesulfonyl-phenyl)-3H-[1,2,3]triazolo[4,5-d]pyrimidin-7-yloxy]-piperidine-1-carboxylic acid tert-butyl ester | 4-[3(R)-Amino-4-(2,4,5-trifluorophenyl)butyryl]-3(R)-methyl-1,4-diazepan-2-one |
| 3-(2-Fluoro-4-methanesulfonyl-phenyl)-7-[1-(3-isopropyl-[1,2,4]oxadiazol-5-yl)-piperidin-4-yloxy]-3H-[1,2,3]triazolo[4,5-d]pyrimidine | 3(S)-Amino-4-(3,3-difluoropyrrolidin-1-yl)-N,N-dimethyl-4-oxo-2(S)-[4-([1,2,4]triazolo[1,5-a]pyridin-6-yl)phenyl]butyramide |
| 3-Fluoro-4-{7-[1-(3-isopropyl-[1,2,4]oxadiazol-5-yl)-piperidin-4-yloxy]-[1,2,3]triazolo[4,5-d]pyrimidin-3-yl}-N-propionyl-benzenesulfonamide | 3(R)-Amino-1-[2-(trifluoromethyl)-5,6,7,8-tetrahydro[1,2,4]triazolo[1,5-a]pyrazine-7-yl]-4-(2,4,5-trifluorophenyl)butanone hydrochloride |
| 3-Fluoro-4-{7-[1-(3-isopropyl-[1,2,4]oxadiazol-5-yl)-piperidin-4-yloxy]-[1,2,3]triazolo[4,5-d]pyrimidin-3-yl}-benzonitrile | 2(S)-Amino-3(S)-(4-fluorophenyl)-1-(3-thiazolidinyl)butan-1-one |
| 4-[3-(4-Methanesulfonyl-phenyl)-isoxazolo[4,5-d]pyrimidin-7-yloxy]-piperidine-1-carboxylic acid tert-butyl ester | 7-[3(R)-Amino-4-(2,5-difluorophenyl)butyryl]-5,6,7,8-tetrahydroimidazo[1,2-a]pyrazine-2-carboxylic acid ethyl ester |
| 4-({Ethyl-[3-(4-methanesulfonyl-phenyl)-isoxazolo[4,5-d]pyrimidin-7-yl]-amino}-methyl)-piperidine-1-carboxylic acid tert-butyl ester | 3(R)-Amino-1-(8-chloro-1,2,3,4-tetrahydropyrazino[1,2-a]benzimidazol-2-yl)-4-(2,5-difluorophenyl)butan-1-one trifluoroacetate |
| 4-[3-(4-Methanesulfonyl-phenyl)-isoxazolo[4,5-d]pyrimidin-7-ylsulfanyl]-piperidine-1-carboxylic acid tert-butyl ester | 3(R)-Amino-4-(2,5-difluorophenyl)-1-[2-(4-fluorophenyl)-4,5,6,7-tetrahydrothiazolo[4,5-c]pyridin-5-yl]butan-1-one |
| 4-[3-(4-Methanesulfonyl-phenyl)-isoxazolo[4,5-d]pyrimidin-7-yloxy]-piperidine-1-carboxylic acid isopropyl ester | 2-[4-[2-[3(R)-Amino-4-(2-fluorophenyl)butyryl]-1,2,3,4-tetrahydroisoquinolin-3-ylcarboxamidomethyl]phenyl]acetic acid |
| 4-[8-(2-Fluoro-4-methanesulfonyl-phenyl)-[1,7]naphthyridin-4-yloxy]-piperidine-1-carboxylic acid isopropyl ester | 3(S)-Amino-2-oxopiperidin-1-ylphosphonic diamide hydrochloride |
| 4-[8-(2-Fluoro-4-methanesulfonyl-phenyl)-quinolin-4-yloxy]-piperidine-1-carboxylic acid isopropyl ester | 2-[2-(5-Nitropyridin-2-ylamino)ethylamino]-1-(1-pyrrolidinyl)ethanone dihydrochloride |
| 4-[8-(4-Methylsulfanyl-phenyl)-quinolin-4-yloxy]-piperidine-1-carboxylic acid isopropyl ester | 2-[8-(3-Aminopiperidin-1-yl)-1,3-dimethylxanthin-7-ylmethyl]benzonitrile hemisuccinate |
| 4-[8-(4-Methanesulfonyl-phenyl)-quinolin-4-yloxy]-piperidine-1-carboxylic acid isopropyl ester | 2(S)-Amino-2-cyclohexyl-1-(3,3,4,4-tetrafluoropyrrolidin-1-yl)ethanone hydrochloride |
| 4-[8-(2-Fluoro-4-methanesulfonyl-phenyl)-pyrido[3,4-d]pyrimidin-4-yloxy]-piperidine-1-carboxylic acid isopropyl ester | 2(S)-Amino-2-cyclohexyl-1-(3-fluoropyrrolidin-1-yl)ethanone |

TABLE B-continued

| GPR119 Agonist | DPP-IV Inhibitor |
| --- | --- |
| 4-[8-(2-Fluoro-4-propionylsulfamoyl-phenyl)-pyrido[3,4-d]pyrimidin-4-yloxy]-piperidine-1-carboxylic acid isopropyl ester | 2-Amino-1-cyclopentyl-3-methylpentan-1-one hydrochloride |
| 4-[8-(4-Cyano-2-fluoro-phenyl)-pyrido[3,4-d]pyrimidin-4-yloxy]-piperidine-1-carboxylic acid isopropyl ester | 4-Amino-5-oxo-5-(1-pyrrolidinyl)pentanamide |
| 3-(2-Fluoro-4-methanesulfonyl-phenyl)-7-[4-(3-isopropyl-[1,2,4]oxadiazol-5-yl)-cyclohexyloxy]-pyrazolo[1,5-a]pyrimidine | 1-[2-[1,1-Dimethyl-2-(6-phenylpyridin-2-ylamino)ethylamino]acetyl]pyrrolidine-2(S)-carbonitrile hydrochloride |
| 3-Fluoro-4-{7-[4-(3-isopropyl-[1,2,4]oxadiazol-5-yl)-cyclohexyloxy]-pyrazolo[1,5-a]pyrimidin-3-yl}-N-propionyl-benzenesulfonamide | (7R*,8S*,13bS*)-7-Butyl-11,12-dimethoxy-,3,4,4a,6,7,8,9,9a,13b-decahydro-1H-pyrido[1,2-f]phenanthridin-8-amine |
| 3-Fluoro-4-{7-[4-(3-isopropyl-[1,2,4]oxadiazol-5-yl)-cyclohexyloxy]-pyrazolo[1,5-a]pyrimidin-3-yl}-benzonitrile | 5-(Aminomethyl)-6-(2,4-dichlorophenyl)-2-(3,5-dimethoxyphenyl)pyrimidin-4-amine |
| 4-[3-(2-Fluoro-4-methanesulfonyl-phenyl)-1-methyl-1H-pyrazolo[4,3-d]pyrimidin-7-yloxy]-piperidine-1-carboxylic acid isopropyl ester | 3-(Aminomethyl)-4-(2,4-dichlorophenyl)-7,8-dimethoxy-5H-indeno[1,2-b]pyridin-2-amine |
| 4-[3-(2-Fluoro-4-propionylsulfamoyl-phenyl)-1-methyl-1H-pyrazolo[4,3-d]pyrimidin-7-yloxy]-piperidine-1-carboxylic acid isopropyl ester | 5-(Aminomethyl)-6-(2,4-dichlorophenyl)-N2-(2-methoxyethyl)-N2-methylpyrimidine-2,4-diamine |
| 4-[3-(4-Cyano-2-fluoro-phenyl)-1-methyl-1H-pyrazolo[4,3-d]pyrimidin-7-yloxy]-piperidine-1-carboxylic acid isopropyl ester | 4,4-Difluoro-1-[2-[exo-8-(2-pyrimidinyl)-8-azabicyclo[3.2.1]oct-3-ylamino]acetyl]pyrrolidine-2(S)-carbonitrile |
| 4-[3-(2-Fluoro-4-methanesulfonyl-phenyl)-2-methyl-2H-pyrazolo[4,3-d]pyrimidin-7-yloxy]-piperidine-1-carboxylic acid isopropyl ester | exo-3-[2-[8-(2-Pyrimidinyl)-8-azabicyclo[3.2.1]oct-3-ylamino]acetyl]thiazolidine-4(R)-carbonitrile |
| 4-[3-(2-Fluoro-4-propionylsulfamoyl-phenyl)-2-methyl-2H-pyrazolo[4,3-d]pyrimidin-7-yloxy]-piperidine-1-carboxylic acid isopropyl ester | 1-[2-[3-(2,3-Dihydro-1H-isoindol-2-yl)-1,1-dimethyl-3-oxopropylamino]acetyl]pyrrolidine-2(S)-carbonitrile |
| 4-[3-(4-Cyano-2-fluoro-phenyl)-2-methyl-2H-pyrazolo[4,3-d]pyrimidin-7-yloxy]-piperidine-1-carboxylic acid isopropyl ester | 8-(3-Aminoperhydroazepin-1-yl)-3-methyl-7-(2-methylbenzyl)-2,3,6,7-tetrahydro-1H-purine-2,6-dione |
| 4-[4-(3-Isopropyl-[1,2,4]oxadiazol-5-yl)-piperidin-1-yl]-6-(4-methanesulfonyl-phenoxy)-pyrimidine | 8-[3(R)-Aminopiperidin-1-yl]-7-(5-fluoro-2-methylbenzyl)-1,3-dimethylxanthine |
| {6-[4-(3-Isopropyl-[1,2,4]oxadiazol-5-yl)-piperidin-1-yl]-pyrimidin-4-yl}-(4-methanesulfonyl-phenyl)-amine | 2-[2-(3-Aminopiperidin-1-yl)-6,7-dimethoxy-4-oxo-3,4-dihydroquinazolin-3-ylmethyl]benzonitrile |
| 4-{[6-(2-Fluoro-4-methanesulfonyl-phenylamino)-pyrimidin-4-yl]-methyl-amino}-piperidine-1-carboxylic acid tert-butyl ester | 1-[2(S)-Amino-3,3-dimethylbutyryl]-4(S)-fluoropyrrolidine-2(S)-carbonitrile hydrochloride |
| 4-[6-(2-Fluoro-4-methanesulfonyl-phenylamino)-pyrimidin-4-yloxy]-piperidine-1-carboxylic acid tert-butyl ester | 2-[3-(Aminomethyl)-4-butoxy-2-(2,2-dimethylpropyl)-1-oxo-1,2-dihydroisoquinolin-6-yloxy]acetamide hydrochloride |
| (2-Fluoro-4-methanesulfonyl-phenyl)-{6-[1-(3-isopropyl-[1,2,4]oxadiazol-5-ylmethyl)-piperidin-4-yloxy]-pyrimidin-4-yl}-amine; 4-[6-(2-Fluoro-4-methanesulfonyl-phenylamino)-pyrimidin-4-yloxy]-piperidine-1-carboxylic acid isopropyl ester | 3-(3-Chloroimidazo[1,2-a]pyridin-2-ylmethylsulfonyl)-N,N-dimethyl-1H-1,2,4-triazole-1-carboxamide |
| (6-Chloro-pyridin-2-yl)-{4-[6-(2-fluoro-4-methanesulfonyl-phenylamino)-pyrimidin-4-yloxy]-piperidin-1-yl}-methanone | 6-Chloro-2-isobutyl-4-phenylquinolin-3-ylmethylamine |
| [2-(4-Bromo-phenyl)-6-methyl-pyrimidin-4-yl]-methyl-amine | trans-1-[2-[4-(1,3-Dioxo-2,3-dihydro-1H-isoindol-2-yl)cyclohexylamino]acetyl]pyrrolidine-2(S)-carbonitrile hydrochloride |
| [2-(4-Bromo-phenyl)-6-methyl-pyrimidin-4-yl]-p-tolyl-amine | trans-4-[2-[4(R)-Cyanothiazolidin-3-yl]-2-oxoethylamino]-N,N-dimethylcyclohexanecarboxamide hydrochloride |
| [2-(4-Bromo-phenyl)-6-methyl-pyrimidin-4-yl]-(4-methoxy-phenyl)-amine | N-(5-Chloropyridin-2-yl)-2-[4-[1-[2-(4-cyanothiazolidin-3-yl)-2-oxoethyl]hydrazino]piperidin-1-yl]acetamide tris(trifluoroacetate) |
| [2-(4-Bromo-phenyl)-6-methyl-pyrimidin-4-yl]-phenyl-amine | 6-[2-[2-[2(S)-Cyanoazetidin-1-yl]-2-oxoethylamino]ethylamino]pyridine-3-carbonitrile dihydrochloride |
| [2-(4-Bromo-phenyl)-6-methyl-pyrimidin-4-yl]-cyclohexyl-amine | 4(S)-Fluoro-1-[2-[1-(2-hydroxyacetyl)-4-methylpiperidin-4-ylamino]acetyl]pyrrolidine-2(S)-carbonitrile fumarate |
| 5-[2-(4-Bromo-phenyl)-6-ethyl-pyrimidin-4-ylamino]-pentan-1-ol | TS-021 |
| 3-[2-(4-Bromo-phenyl)-6-methyl-pyrimidin-4-ylamino]-propionitrile | GRC-8200 |
| [2-(4-Bromo-phenyl)-6-ethyl-pyrimidin-4-yl]-(4-fluoro-benzyl)-amine | GRC-8116 |

TABLE B-continued

| GPR119 Agonist | DPP-IV Inhibitor |
|---|---|
| [2-(4-Bromo-phenyl)-6-ethyl-pyrimidin-4-yl]-[2-(4-chloro-phenyl)-ethyl]-amine | FE107542 |
| [2-(4-Bromo-phenyl)-6-ethyl-pyrimidin-4-yl]-pyridin-2-ylmethyl-amine | |
| [2-(4-Bromo-phenyl)-6-methyl-pyrimidin-4-yl]-pyridin-3-ylmethyl-amine | |
| 3-{[2-(4-Bromo-phenyl)-6-methyl-pyrimidin-4-ylamino]-methyl}-1H-pyridin-2-one | |
| 4-{[2-(4-Bromo-phenyl)-6-ethyl-pyrimidin-4-ylamino]-methyl}-1H-pyridin-2-one | |
| 4-{2-[2-(4-Bromo-phenyl)-6-methyl-pyrimidin-4-ylamino]-ethyl}-1H-pyridin-2-one | |
| [2-(3-Chloro-4-fluoro-phenyl)-6-ethyl-pyrimidin-4-yl]-(1,1-dioxo-hexahydro-116-thiopyran-4-yl)-amine | |
| [6-Methyl-2-(3,4,5-trifluoro-phenyl)-pyrimidin-4-yl]-[2-(1-oxy-pyridin-3-yl)-ethyl]-amine | |
| [6-Ethyl-2-(3,4,5-trifluoro-phenyl)-pyrimidin-4-yl]-[2-(1-oxy-pyridin-3-yl)-ethyl]-amine | |
| [6-Methyl-2-(2,4,5-trifluoro-phenyl)-pyrimidin-4-yl]-[2-(1-oxy-pyridin-3-yl)-ethyl]-amine | |
| 4-{4-Methyl-6-[2-(1-oxy-pyridin-3-yl)-ethylamino]-pyrimidin-2-yl}-benzonitrile | |
| 2-[4-(6-Methyl-2-phenyl-pyrimidin-4-ylamino)-phenyl]-ethanol | |
| [2-(3-Chloro-phenyl)-6-methyl-pyrimidin-4-yl]-methyl-amine | |
| 2-{[2-(4-Bromo-phenyl)-6-methyl-pyrimidin-4-yl]-methyl-amino}-ethanol; compound with methane | |
| 3-[6-Ethyl-2-(3,4,5-trifluoro-phenyl)-pyrimidin-4-ylamino]-propane-1,2-diol | |
| (S)-3-[6-Methyl-2-(2,3,5-trifluoro-phenyl)-pyrimidin-4-ylamino]-propane-1,2-diol | |
| (S)-3-[2-(4-Bromo-3-fluoro-phenyl)-6-methyl-pyrimidin-4-ylamino]-propane-1,2-diol | |
| (R)-3-[6-Ethyl-2-(3,4,5-trifluoro-phenyl)-pyrimidin-4-ylamino]-propane-1,2-diol | |
| (R)-3-[2-(3-Chloro-4-fluoro-phenyl)-6-ethyl-pyrimidin-4-ylamino]-propane-1,2-diol | |
| (R)-3-[2-(4-Bromo-2,5-difluoro-phenyl)-5-fluoro-6-methyl-pyrimidin-4-ylamino]-propane-1,2-diol | |
| (R)-3-[2-(4-Chloro-2,5-difluoro-phenyl)-6-difluoromethyl-pyrimidin-4-ylamino]-propane-1,2-diol | |
| 5-{2-[2-(4-Bromo-phenyl)-6-ethyl-pyrimidin-4-ylamino]-ethyl}-1H-pyridin-2-one | |
| 5-{2-[6-Methyl-2-(2,4,5-trifluoro-phenyl)-pyrimidin-4-ylamino]-ethyl}-1H-pyridin-2-one | |
| 4-{2-[2-(4-Chloro-2,5-difluoro-phenyl)-6-ethyl-pyrimidin-4-ylamino]-ethyl}-1H-pyridin-2-one | |
| 6-Chloro-4-{2-[6-methyl-2-(2,4,5-trifluoro-phenyl)-pyrimidin-4-ylamino]-ethyl}-1H-pyridin-2-one | |
| 4-{1-Hydroxy-2-[6-methyl-2-(2,4,5-trifluoro-phenyl)-pyrimidin-4-ylamino]-ethyl}-1H-pyridin-2-one | |
| 4-{1-Methyl-2-[6-methyl-2-(2,4,5-trifluoro-phenyl)-pyrimidin-4-ylamino]-ethyl}-1H-pyridin-2-one | |
| 4-(3-Pyridin-4-yl-[1,2,4]oxadiazol-5-ylmethoxy)piperidine-1-carboxylic acid tert-butyl ester | |
| 4-[5-(2-Cyanopyridin-4-yl)-[1,2,4]oxadiazol-3-ylmethoxy]piperidine-1-carboxylic acid tert-butyl ester | |
| 4-(3-Pyridin-4-yl-[1,2,4]oxadiazol-5-ylmethoxy)piperidine-1-carboxylic acid cyclopentyl ester | |
| 4-(3-Pyridin-4-yl-[1,2,4]oxadiazol-5-ylmethoxy)piperidine-1-carboxylic acid 2,2,2-trichloroethyl ester | |
| 4-[Ethyl-(3-pyridin-4-yl-[1,2,4]oxadiazol-5-ylmethyl)amino]piperidine-1-carboxylic acid tert-butyl ester | |
| 4-[Methyl-(3-pyridin-4-yl-[1,2,4]oxadiazol-5-ylmethyl)amino]piperidine-1-carboxylic acid cyclopentyl ester | |

TABLE B-continued

| GPR119 Agonist | DPP-IV Inhibitor |
|---|---|
| 4-{[Methyl-(3-pyridin-4-yl-[1,2,4]oxadiazol-5-ylmethyl)amino]methyl}piperidine-1-carboxylic acid 2,2,2-trichloroethyl ester | |

Additionally, compounds of the invention, including those illustrated in TABLE B, encompass all pharmaceutically acceptable salts, solvates, and hydrates thereof. See, e.g., Berge et al (1977), Journal of Pharmaceutical Sciences 66:1-19; and Polymorphism in Pharmaceutical Solids (1999) Brittain, ed., Marcel Dekker, Inc.; the disclosure of each of which is herein incorporated by reference in its entirety.

As relates to the combination therapy described above, the compounds according to the invention can be administered in any suitable way. Suitable routes of administration include oral, nasal, rectal, transmucosal, transdermal, or intestinal administration, parenteral delivery, including intramuscular, subcutaneous, intramedullary injections, as well as intrathecal, direct intraventricular, intravenous, intraperitoneal, intranasal, intrapulmonary (inhaled) or intraocular injections using methods known in the art. Other suitable routes of administration are aerosol and depot formulation. Sustained release formulations, particularly depot, of the invented medicaments are expressly contemplated. In certain preferred embodiments, the compounds according to the present invention are administered orally. The compounds according to the present invention can be made up in solid or liquid form, such as tablets, capsules, powders, syrups, elixirs and the like, aerosols, sterile solutions, suspensions or emulsions, and the like. In certain embodiments, one or both of the GPR119 agonist and the DPP-IV inhibitor are administered orally.

Formulations for oral administration may be in the form of aqueous solutions and suspensions, in addition to solid tablet and capsule formulations. The aqueous solutions and suspensions may be prepared from sterile powders or granules. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants are well and widely known in the art.

It will be appreciated that the GPR119 agonist and the DPP-IV inhibitor may be present as a combined preparation for simultaneous, separate or sequential use for the treatment or prevention of diabetes or a condition related thereto. Such combined preparations may be, for example, in the form of a twin pack.

It will therefore be further appreciated that the invention contemplates a product comprising or consisting essentially of a GPR119 agonist and a DPP-IV inhibitor as a combined preparation for simultaneous, separate or sequential use in the prevention or treatment of diabetes or a condition related thereto.

A combination of the present invention comprising or consisting essentially of a GPR119 agonist and a DPP-IV inhibitor can be prepared by mixing the GPR119 agonist and the DPP-IV inhibitor either all together or independently with a pharmaceutically acceptable carrier, excipient, binder, diluent, etc. as described herein, and administering the mixture or mixtures either orally or non-orally as a pharmaceutical composition(s).

It will therefore be further appreciated that the GPR119 agonist and the DPP-IV inhibitor or pharmaceutical composition can be administered in separate dosage forms or in a single dosage form.

It is further appreciated that when the GPR119 agonist and the DPP-IV inhibitor are in separate dosage forms, GPR119 agonist and DPP-IV inhibitor can be administered by different routes.

Pharmaceutical compositions of the GPR119 agonist and DPP-IV inhibitor, either individually or in combination, may be prepared by methods well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Suitable pharmaceutically acceptable carriers are available to those in the art [see, e.g., Remington: The Science and Practice of Pharmacy, (Gennaro et al., eds.), $20^{th}$ Edition, 2000, Lippincott Williams & Wilkins; and Handbook of Pharmaceutical Excipients (Rowe et al., eds), $4^{th}$ Edition, 2003, Pharmaceutical Press; the disclosure of each of which is herein incorporated by reference in its entirety]. Proper formulation is dependent upon the route of administration chosen. The term "carrier" material or "excipient" material herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improved appearance of the composition. Acceptable excipients include stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials, such as cellulose esters of alkanoic acids and cellulose alkyl esters, low melting wax cocoa butter or powder, polymers, such as polyvinyl-pyrrolidone, polyvinyl alcohol, and polytheylene glycols, and other pharmaceutically acceptable materials. The components of the pharmaceutical composition can be encapsulated or tableted for convenient administration.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When the GPR119 agonist and the DPP-IV inhibitor are in separate dosage forms, it is understood that a pharmaceutically acceptable carrier used for the GPR119 agonist formulation need not be identical to a pharmaceutically acceptable carrier used for the DPP-IV inhibitor formulation.

Dragee cores are provided with suitable coatings. For this purpose, concentrated sugar solutions may be used which may optionally contain gum Arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mon-, di- or triglycerides. Stabilizers may be added in these formulations, also.

Additionally, the GPR119 agonist and DPP-IV inhibitor may be delivered using a sustained-release system. Various sustained-release materials have been established and are well known to those skilled in the art. Sustained-release tablets or capsules are particularly preferred. For example, a time delay material such as glyceryl monostearate or glyceryl distearate may be employed. The dosage form may also be coated by the techniques described in the U.S. Pat. Nos. 4,256,108, 4,166,452, and 4,265,874 to form osmotic therapeutic tablets for controlled release.

It is expressly contemplated that a combination therapy of the present invention may be administered or provided alone or in combination with one or more other pharmaceutically or physiologically acceptable compound. In one aspect of the present invention, the other pharmaceutically or physiologically acceptable compound is not a GPR119 agonist and is not a DPP-IV inhibitor. In one aspect of the present invention, the other pharmaceutically or physiologically acceptable compound is a pharmaceutical agent selected from the group consisting of sulfonylurea (e.g., glibenclamide, glipizide, gliclazide, glimepiride), meglitinide (e.g., repaglinide, nateglinide), biguanide (e.g., metformin), alpha-glucosidase inhibitor (e.g., acarbose, epalrestat, miglitol, voglibose), thizaolidinedione (e.g., rosiglitazone, pioglitazone), insulin analog (e.g., insulin lispro, insulin aspart, insulin glargine), chromium picolinate/biotin, and biological agent (e.g., adiponectin or a fragment comprising the C-terminal globular domain thereof, or a multimer of adiponectin or said fragment thereof; or an agonist of adiponectin receptor AdipoR1 or AdipoR2, preferably wherein said agonist is orally active). In one aspect of the present invention, the pharmaceutical agent is metformin. In one aspect of the present invention, the pharmaceutical agent is an agonist to adiponectin receptor AdipoR1 or AdipoR2, preferably wherein the agonist is orally active.

In a combination therapy according to the present invention, the GPR119 agonist according to the present invention and the DPP-IV inhibitor according to the present invention can be administered simultaneously or at separate intervals. When administered simultaneously the GPR119 agonist and the DPP-IV inhibitor can be incorporated into a single pharmaceutical composition or into separate compositions, e.g., the GPR119 agonist in one composition and the DPP-IV inhibitor in another composition. Each of these compositions may be formulated with common excipients, diluents or carriers, and compressed into tablets, or formulated elixirs or solutions; and as sustained relief dosage forms and the like. The GPR119 agonist and DPP-IV inhibitor may be administered via different routes. For example, the GPR119 agonist may be administered orally via tablet and the DPP-IV inhibitor may be administered via inhalation.

When separately administered, therapeutically effective amounts of the GPR119 agonist and the DPP-IV inhibitor according to the present invention are administered on a different schedule. One may be administered before the other as long as the time between the two administrations falls within a therapeutically effective interval. A therapeutically effective interval is a period of time beginning when one of either (a) the GPR119 agonist or (b) the DPP-IV inhibitor is administered to a mammal and ending at the limit of the beneficial effect in the treatment of the combination of (a) and (b).

In one aspect, the present invention features a pharmaceutical composition comprising or consisting essentially of a combination of an amount of a GPR119 agonist according to the present invention and an amount of a DPP-IV inhibitor according to the present invention, together with at least one pharmaceutically acceptable carrier.

In one aspect, the present invention features a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the pharmaceutical composition wherein the GPR119 agonist and the DPP-IV inhibitor are in amounts sufficient to give an effect in lowering a blood glucose level in a subject. In certain embodiments, the blood glucose level is an elevated blood glucose level.

In one aspect, the present invention features a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the pharmaceutical composition wherein the GPR119 agonist and the DPP-IV inhibitor are in amounts sufficient to give an effect in lowering a blood glucose level in a subject, and wherein the amount of the GPR119 agonist alone and the amount of the DPP-IV inhibitor alone are therapeutically ineffective in lowering the blood glucose level in the subject. In certain embodiments, the blood glucose level is an elevated blood glucose level.

In one aspect, the present invention features a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the pharmaceutical composition wherein the GPR119 agonist and the DPP-IV inhibitor are in amounts sufficient to give an effect in lowering a blood glucose level in a subject, and wherein the effect is a synergistic effect. In certain embodiments, the blood glucose level is an elevated blood glucose level.

In one aspect, the present invention relates to a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the pharmaceutical composition wherein the GPR119 agonist and the DPP-IV inhibitor are in amounts sufficient to give an effect in lowering a blood glucose level in a subject, wherein the effect is a synergistic effect, and wherein the amount of the GPR119 agonist alone and the amount of the DPP-IV inhibitor alone are therapeutically ineffective in lowering the blood glucose level in the subject. In certain embodiments, the blood glucose level is an elevated blood glucose level.

In one aspect, the present invention features a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the pharmaceutical composition wherein the GPR119 agonist and the DPP-IV inhibitor are in amounts sufficient to give an effect in increasing a blood GLP-1 level in a subject.

In one aspect, the present invention features a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the pharmaceutical composition wherein the GPR119 agonist and the DPP-IV inhibitor are in amounts sufficient to give an effect in increasing a blood GLP-1 level in a subject, and wherein the amount of the GPR119 agonist alone and the amount of the DPP-IV inhibitor alone are therapeutically ineffective in increasing a blood GLP-1 level in the subject.

In one aspect, the present invention features a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the pharmaceutical composition wherein the GPR119 agonist and the DPP-IV inhibitor are in amounts sufficient to give an effect in increasing a blood GLP-1 level in a subject, and wherein the effect is a synergistic effect.

In one aspect, the present invention relates to a pharmaceutical composition comprising or consisting essentially of a combination of an amount of a GPR119 agonist according to the present invention and an amount of a DPP-IV inhibitor according to the present invention, together with at least one pharmaceutically acceptable carrier. The present invention also relates to a dosage form of the pharmaceutical composition wherein the GPR119 agonist and the DPP-IV inhibitor are in amounts sufficient to give an effect in increasing a blood GLP-1 level in a subject, wherein the effect is a synergistic effect, and wherein the amount of the GPR119 agonist alone and the amount of the DPP-IV inhibitor alone are therapeutically ineffective in increasing a blood GLP-1 level in the subject.

Pharmaceutical compositions suitable for use in the present invention include compositions wherein the active ingredients are contained in an amount to achieve their intended purpose. In some embodiments, a pharmaceutical composition of the present invention is understood to be useful for treating or preventing diabetes and conditions related thereto. Diabetes and conditions related thereto according to the present invention. In some embodiments, a pharmaceutical composition of the present invention is understood to be useful for treating or preventing a condition ameliorated by increasing a blood GLP-1 level. Conditions ameliorated by increasing a blood GLP-1 level are according to the present invention.

In certain embodiments of the combination therapy of the present invention, the amount of GPR119 agonist according to the present invention and the amount of DPP-IV inhibitor according to the present invention are provided in amounts to give a synergistic effect in lowering a blood glucose level in a subject. In certain embodiments, the blood glucose level is an elevated blood glucose level. Determination of the amounts of GPR119 agonist and DPP-IV inhibitor providing a synergistic effect in lowering blood glucose level in a subject is well within the capability of those skilled in the art, especially in light of the detailed disclosure provided herein. In one embodiment of the combination therapy of the present invention, the amount of GPR119 agonist according to the present invention and the amount of DPP-IV inhibitor according to the present invention are provided in amounts to give a synergistic effect in lowering a blood glucose level in a subject, wherein the amount of the GPR119 agonist alone and the amount of the DPP-IV inhibitor alone are therapeutically ineffective in lowering the blood glucose level in the subject. In certain embodiments, the blood glucose level is an elevated blood glucose level. Determination of the amounts of GPR119 agonist and DPP-IV inhibitor providing a synergistic effect in lowering blood glucose level in a subject, wherein the amount of the GPR119 agonist alone and the amount of the DPP-IV inhibitor alone are therapeutically ineffective in lowering blood glucose level in the subject, is well within the capability of those skilled in the art, especially in light of the detailed disclosure provided herein.

In certain embodiments of the combination therapy of the present invention, the amount of GPR119 agonist according to the present invention and the amount of DPP-IV inhibitor according to the present invention are provided in amounts to give a synergistic effect in increasing a blood GLP-1 level in a subject. Determination of the amounts of GPR119 agonist and DPP-IV inhibitor providing a synergistic effect in increasing a blood GLP-1 level in a subject is well within the capability of those skilled in the art, especially in light of the detailed disclosure provided herein. In one embodiment of the combination therapy of the present invention, the amount of GPR119 agonist according to the present invention and the amount of DPP-IV inhibitor according to the present invention are provided in amounts to give a synergistic effect in increasing a blood GLP-1 level in a subject, wherein the amount of the GPR119 agonist alone and the amount of the DPP-IV inhibitor alone are therapeutically ineffective in increasing a blood GLP-1 level in the subject. Determination of the amounts of GPR119 agonist and DPP-IV inhibitor providing a synergistic effect in increasing a blood GLP-1 level in a subject, wherein the amount of the GPR119 agonist alone and the amount of the DPP-IV inhibitor alone are therapeutically ineffective in increasing a blood GLP-1 level in the subject, is well within the capability of those skilled in the art, especially in light of the detailed disclosure provided herein.

The data obtained from animal studies, including but not limited to studies using mice, rats, rabbits, pigs, and non-human primates, can be used in formulating a range of dosage for use in humans. In general, one skilled in the art understands how to extrapolate in vivo data obtained in an animal model system to another, such as a human. In some circumstances, these extrapolations may merely be based on the weight of the animal model in comparison to another, such as a human; in other circumstances, these extrapolations are not simply based on weights but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

An exemplary and preferred animal model system is oral glucose tolerance test (oGTT) in mice (see, Example 1). In this model, by way of illustration and not limitation, an amount of a GPR119 agonist alone or a DPP-IV inhibitor alone which is therapeutically ineffective is an amount of the GPR119 agonist alone or the DPP-IV inhibitor alone producing an Area Under Curve (AUC) inhibition of glycemic excursion less than or equal to about 30%, less than about 25%, less than about 20%, less than about 15%, less than about 10%, or less than about 5%, more preferably less than about 25%, less than about 20%, less than about 15%, less than about 10%, or less than about 5%. In this model, by way of illustration and not limitation, an amount of a GPR119 agonist alone or a DPP-IV inhibitor alone which is therapeutically ineffective is an amount of the GPR119 agonist alone or the DPP-IV inhibitor alone producing an Area Under Curve (AUC) inhibition of glycemic excursion about 0-30%, about 0-25%, about 0-20%, about 0-15%, about 0-10%, or about 0-5%, more preferably about 0-25%, about 0-20%, about 0-15%, about 0-10%, or about 0-5%. In this model, by way of illustration and not limitation, a therapeutically effective amount of a combination of a GPR119 agonist and a DPP-IV inhibitor in accordance with the present invention is an amount of the combination producing an Area Under Curve (AUC) inhibition of glycemic excursion greater than about 30%, greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, or greater than about 95%, more preferably greater than about 35%, greater than about 40%, greater than about 45%, greater than about 50%, greater than about 55%, greater than about 60%, greater than about 65%, greater than about 70%, or greater than about 75%, greater than about 80%, greater than about 85%, greater than about 90%, or greater than about 95%.

Dosage amount and interval may be adjusted in order to provide a synergistic effect in lowering a blood glucose level in the subject in accordance with the present invention or to provide a synergistic effect in increasing a blood GLP-1 level in the subject in accordance with the present invention. In certain embodiments, the blood glucose level is an elevated blood glucose level. It will be appreciated that the exact dosage of a GPR119 agonist or DPP-IV inhibitor in accordance with the present invention will vary depending on the combination of the GPR119 agonist and DPP-IV inhibitor, its potency, the mode of administration, the age and weight of the patient and the severity of the condition to be treated. The exact formulation, route of administration and dosage can be chosen by the individual physician in view of the patient's condition. By way of illustration and not limitation, an amount of GPR119 agonist or DPP-IV inhibitor providing a synergistic effect in lowering a blood glucose level in the subject in accordance with the present invention or providing a synergistic effect in increasing a blood GLP-1 level in the subject in accordance with the present invention is less than about 0.001 mg/kg body weight, less than about 0.005 mg/kg body weight, less than about 0.01 mg/kg body weight, less than about 0.05 mg/kg body weight, less than about 0.1 mg/kg body weight, less than about 0.5 mg/kg body weight, less than about 1 mg/kg body weight, less than about 5 mg/kg body weight, less than about 10 mg/kg body weight, less than about 50 mg/kg body weight, or less than about 100 mg/kg body weight. In certain embodiments, the blood glucose level is an elevated blood glucose level. In some embodiments, an amount of GPR119 agonist or DPP-IV inhibitor providing a synergistic effect in lowering a blood glucose level in the subject in accordance with the present invention or providing a synergistic effect in increasing a blood GLP-1 level in the subject in accordance with the present invention is less than about 0.001-100 mg/kg body weight, less than about 0.001-50 mg/kg body weight, less than about 0.001-10 mg/kg body weight, less than about 0.001-5 mg/kg body weight, less than about 0.001-1 mg/kg body weight, less than about 0.001 to 0.5 mg/kg body weight, less than about 0.001-0.1 mg/kg body weight, less than about 0.001-0.05 mg/kg body weight, less than about 0.001-0.01 mg/kg body weight, or less than about 0.001-0.005 mg/kg body weight. In certain embodiments, the blood glucose level is an elevated blood glucose level. In some embodiments, an amount of GPR119 agonist or DPP-IV inhibitor providing a synergistic effect in lowering a blood glucose level in the subject in accordance with the present invention or providing a synergistic effect in increasing a blood GLP-1 level in the subject in accordance with the present invention is about 0.001-100 mg/kg body weight, about 0.001-50 mg/kg body weight, about 0.001-10 mg/kg body weight, about 0.001-5 mg/kg body weight, about 0.001 to 1 mg/kg body weight, about 0.001-0.5 mg/kg body weight, about 0.001-0.1 mg/kg body weight, about 0.001-0.05 mg/kg body weight, about 0.001-0.01 mg/kg body weight, or about 0.001-0.005 mg/kg body weight. In certain embodiments, the blood glucose level is an elevated blood glucose level.

An additional exemplary and preferred animal model system is increase of a blood GLP-1 level after glucose challenge in mice (see, Example 3).

Dosage amount and interval may be adjusted individually to provide plasma levels of GPR119 agonist according to the present invention and DPP-IV inhibitor according to the present invention which provide a synergistic effect in lowering a blood glucose level in the subject according to the present invention or provide a synergistic effect in increasing a blood GLP-1 level in the subject according to the present invention. In certain embodiments, the blood glucose level is an elevated blood glucose level. Dosage intervals can also be determined using the value for a selected range of GPR119 agonist concentration or the value for a selected range of DPP-IV inhibitor concentration providing a synergistic effect in lowering a blood glucose level in the subject according to the present invention or providing a synergistic effect in increasing a blood GLP-1 level in the subject according to the present invention. In certain embodiments, the blood glucose level is an elevated blood glucose level. GPR119 agonist and DPP-IV inhibitor should be administered using a regimen that maintains plasma levels within the selected range of GPR119 agonist concentration and DPP-IV inhibitor concentration, respectively, for 10-90% of the time, preferably between 30-99% of the time, and most preferably between 50-90% of the time. In cases of local administration or selective uptake, the range of GPR119 agonist concentration or the range of DPP-IV inhibitor concentration providing a synergistic effect in lowering a blood glucose level in the subject according to the present invention or providing a synergistic effect in increasing a blood GLP-1 level in the subject according to the present invention may not be related to plasma concentration. In certain embodiments, the blood glucose level is an elevated blood glucose level.

The amount of composition administered will, of course, be dependent on the subject being treated, on the subject's weight, the severity of the affliction, the manner of administration, and the judgement of the prescribing physician.

In one aspect, the present invention accordingly features a method of treating or preventing diabetes or a condition related thereto comprising administering to a subject in need thereof a therapeutically effective amount of a composition comprising or consisting essentially of an amount of a GPR119 agonist according to the present invention and an amount of a DPP-IV inhibitor according to the present invention.

In one aspect, the present invention relates to a method of treating or preventing diabetes or a condition related thereto comprising administering to a subject in need thereof a therapeutically effective amount of a composition comprising or consisting essentially of an amount of a GPR119 agonist according to the present invention and an amount of a DPP-IV inhibitor according to the present invention. In a related aspect, the present invention features said method wherein the GPR119 agonist and the DPP-IV inhibitor are administered in amounts sufficient to give an effect in lowering a blood glucose level in the subject. In certain embodiments, the blood glucose level is an elevated blood glucose level.

In one aspect, the present invention relates to a method of treating or preventing diabetes or a condition related thereto comprising administering to a subject in need thereof a therapeutically effective amount of a composition comprising or consisting essentially of an amount of a GPR119 agonist according to the present invention and an amount of a DPP-IV inhibitor according to the present invention. In a related aspect, the present invention features said method wherein the GPR119 agonist and the DPP-IV inhibitor are administered in amounts sufficient to give an effect in lowering a blood glucose level in the subject, and wherein the amount of the GPR119 agonist alone and the amount of the DPP-IV inhibitor alone are therapeutically ineffective in lowering the blood glucose level in the subject. In certain embodiments, the blood glucose level is an elevated blood glucose level.

In one aspect, the present invention relates to a method of treating or preventing diabetes or a condition related thereto comprising administering to a subject in need thereof a therapeutically effective amount of a composition comprising or consisting essentially of an amount of a GPR119 agonist according to the present invention and an amount of a DPP-IV inhibitor according to the present invention. In a related aspect, the present invention features said method wherein the GPR119 agonist and the DPP-IV inhibitor are administered in amounts sufficient to give an effect in lowering a blood glucose level in the subject, and wherein the effect is a synergistic effect. In certain embodiments, the blood glucose level is an elevated blood glucose level.

In one aspect, the present invention relates to a method of treating or preventing diabetes or a condition related thereto comprising administering to a subject in need thereof a therapeutically effective amount of a composition comprising or consisting essentially of an amount of a GPR119 agonist according to the present invention and an amount of a DPP-IV inhibitor according to the present invention. In a related aspect, the present invention features said method wherein the GPR119 agonist and the DPP-IV inhibitor are administered in amounts sufficient to give an effect in lowering a blood glucose level in the subject, wherein the effect is a synergistic effect, and wherein the amount of the GPR119 agonist alone and the amount of the DPP-IV inhibitor alone are therapeutically ineffective in lowering the blood glucose level in the subject. In certain embodiments, the blood glucose level is an elevated blood glucose level.

A combination therapy of the present invention is useful in treating or preventing diabetes or a condition related thereto in a mammal, including and most preferably in a human. In some embodiments, diabetes is Type 1 diabetes. In some preferred embodiments, diabetes is Type 2 diabetes. A condition related to diabetes includes, but is not limited to, hyperglycemia, impaired glucose tolerance, insulin resistance, pancreatic beta-cell insufficiency, enteroendocrine cell insufficiency, glucosuria, metabolic acidosis, cataracts, diabetic nephropathy, diabetic neuropathy, diabetic retinopathy, diabetic coronary artery disease, diabetic cerebrovascular disease, diabetic peripheral vascular disease, metabolic syndrome, hyperlipidemia, atherosclerosis, stroke, hypertension, and obesity. It is understood that conditions related to diabetes can be included in embodiments individually or in any combination.

In one aspect, the present invention accordingly features a method of treating or preventing a condition ameliorated by increasing a blood GLP-1 level comprising administering to a subject in need thereof a therapeutically effective amount of a composition comprising or consisting essentially of an amount of a GPR119 agonist according to the present invention and an amount of a DPP-IV inhibitor according to the present invention.

In one aspect, the present invention relates to a method of treating or preventing a condition ameliorated by increasing a blood GLP-1 level comprising administering to a subject in need thereof a therapeutically effective amount of a composition comprising or consisting essentially of an amount of a GPR119 agonist according to the present invention and an amount of a DPP-IV inhibitor according to the present invention. In a related aspect, the present invention features said method wherein the GPR119 agonist and the DPP-IV inhibitor are administered in amounts sufficient to give an effect in increasing a blood GLP-1 level in the subject.

In one aspect, the present invention relates to a method of treating or preventing a condition ameliorated by increasing a blood GLP-1 level comprising administering to a subject in need thereof a therapeutically effective amount of a composition comprising or consisting essentially of an amount of a GPR119 agonist according to the present invention and an amount of a DPP-IV inhibitor according to the present invention. In a related aspect, the present invention features said method wherein the GPR119 agonist and the DPP-IV inhibitor are administered in amounts sufficient to give an effect in increasing a blood GLP-1 level in the subject, and wherein the amount of the GPR119 agonist alone and the amount of the DPP-IV inhibitor alone are therapeutically ineffective in increasing a blood GLP-1 level in the subject.

In one aspect, the present invention relates to a method of treating or preventing a condition ameliorated by increasing a blood GLP-1 level comprising administering to a subject in need thereof a therapeutically effective amount of a composition comprising or consisting essentially of an amount of a GPR119 agonist according to the present invention and an amount of a DPP-IV inhibitor according to the present invention. In a related aspect, the present invention features said method wherein the GPR119 agonist and the DPP-IV inhibitor are administered in amounts sufficient to give an effect in increasing a blood GLP-1 level in the subject, and wherein the effect is a synergistic effect.

In one aspect, the present invention relates to a method of treating or preventing a condition ameliorated by increasing a blood GLP-1 level comprising administering to a subject in need thereof a therapeutically effective amount of a composition comprising or consisting essentially of an amount of a GPR119 agonist according to the present invention and an amount of a DPP-IV inhibitor according to the present invention. In a related aspect, the present invention features said method wherein the GPR119 agonist and the DPP-IV inhibitor are administered in amounts sufficient to give an effect in increasing a blood GLP-1 level in the subject, wherein the effect is a synergistic effect, and wherein the amount of the GPR119 agonist alone and the amount of the DPP-IV inhibitor alone are therapeutically ineffective in increasing a blood GLP-1 level in the subject.

A combination therapy of the present invention is useful in treating or preventing a condition ameliorated by increasing a blood GLP-1 level in a mammal, including and most preferably in a human. A condition ameliorated by increasing a blood GLP-1 level includes, but is not limited to, diabetes, a condition related to diabetes, myocardial infarction, learning impairment, memory impairment, and a neurodegenerative disorder, wherein a condition related to diabetes includes, but is not limited to, hyperglycemia, impaired glucose tolerance, insulin resistance, pancreatic beta-cell insufficiency, enteroendocrine cell insufficiency, glucosuria, metabolic acidosis, cataracts, diabetic nephropathy, diabetic neuropathy, diabetic retinopathy, diabetic coronary artery disease, diabetic cerebrovascular disease, diabetic peripheral vascular disease, metabolic syndrome, hyperlipidemia, atherosclerosis, stroke, hypertension, and obesity, wherein a neurodegenerative disorder includes, but is not limited to, excitotoxic brain damage caused by severe epileptic seizures, Alzheimer's disease, Parkinson's disease, Huntington's disease, prion-associated disease, motor-neuron disease, traumatic brain injury, spinal cord injury, and peripheral neuropathy. In some embodiments, diabetes is Type 1 diabetes. In some preferred embodiments, diabetes is Type 2 diabetes. It is understood that conditions ameliorated by increasing a blood GLP-1 level can be included in embodiments individually or in any combination.

Without further elaboration, it is believed that one skilled in the art can, using the preceding description, practice the present invention to its fullest extent. The foregoing detailed description is given for clearness of understanding only, and no unnecessary limitation should be understood therefrom, as modifications within the scope of the invention may become apparent to those skilled in the art.

The inventions described in this application were made by Arena Pharmaceuticals, Inc as a result of activities undertaken within the scope of a Dec. 20, 2004 joint research agreement between Ortho-McNeil Pharmaceutical, Inc. and Arena Pharmaceuticals, Inc.

Throughout this application, various publications, patents and patent applications are cited. The disclosures of these publications, patents and patent applications referenced in this application are herein incorporated by reference in their entirety into the present disclosure. Citation herein by Applicant of a publication, patent, or patent application is not an admission by Applicant of said publication, patent, or patent application as prior art.

EXAMPLES

Without further elaboration, it is believed that one skilled in the art can, using the preceding description, practice the present invention to its fullest extent. The following detailed examples are to be construed as merely illustrative, and not limitations of the preceding disclosure in any way whatsoever. Those skilled in the art will promptly recognize appropriate variations from the procedures.

Example 1

Synergistic Effect of GPR119 Agonist and DPP-IV Inhibitor in Lowering an Elevated Blood Glucose Level in Oral Glucose Tolerance Test (oGTT) in Mice Oral glucose tolerance test (oGTT) in mice was carried out as described here. Overnight fasted mice (n=6 mice per treatment) were administered via oral gavage with vehicle (PET), a GPR119 agonist (AR231453) at 1 mkg (milligram compound per kilogram of body weight), a DPP-IV inhibitor (AR247810) at 0.1 mkg, or a combination of the GPR119 agonist (1 mkg) and the DPP-IV inhibitor (0.1 mkg). Thirty minutes later, a glucose bolus (3 gram/kg) was then delivered per orally. Plasma glucose levels were determined at the indicated time points over a two hour period using blood (~5 μl) collected from tail nick and a glucose meter. Glycemic excursion curve was graphed based on data from 6 mice and given in mean values +/−SEM (FIG. 1A). Area Under Curve (AUC) of the glycemic excursion was calculated for each mouse and AUC inhibition (%) was reported in FIG. 1B.

In this Example, GPR119 agonist given at 1 mkg alone, or DPP-IV inhibitor given at 0.1 mkg alone produced an AUC inhibition of glycemic excursion less than 15-20% in this mouse model, which is regarded as therapeutically ineffective for the long term glycemic control in diabetic patients. On the other hand, the combination of both compounds at their therapeutically ineffective dose (0.1 mkg for the DPP-IV inhibitor, and 1 mkg for the GPR119 agonist in this Example) produced an AUC inhibition over 60%. Typically, a therapeutically effective dose would create an AUC inhibition above 30% in this mouse model study, such as that observed for the incretin mimetic exendin-4 at ~60%.

Figure 1C:
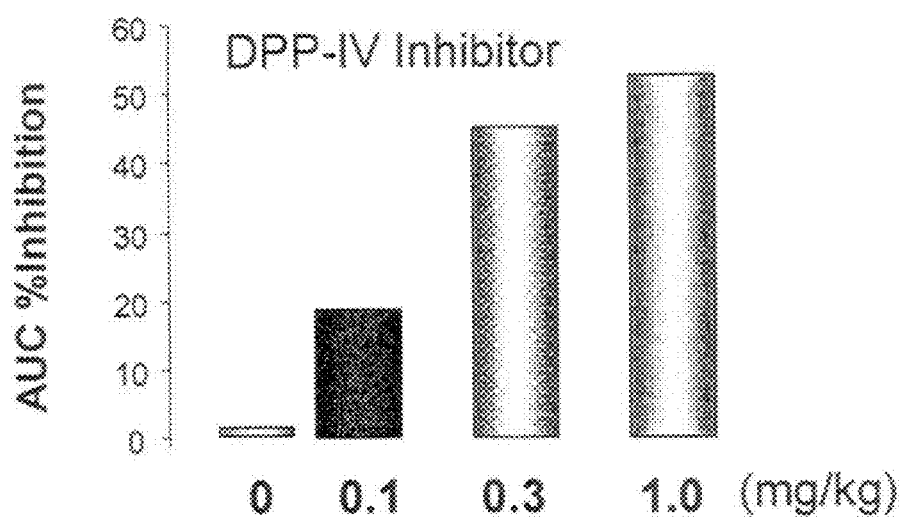
Figure 1D:
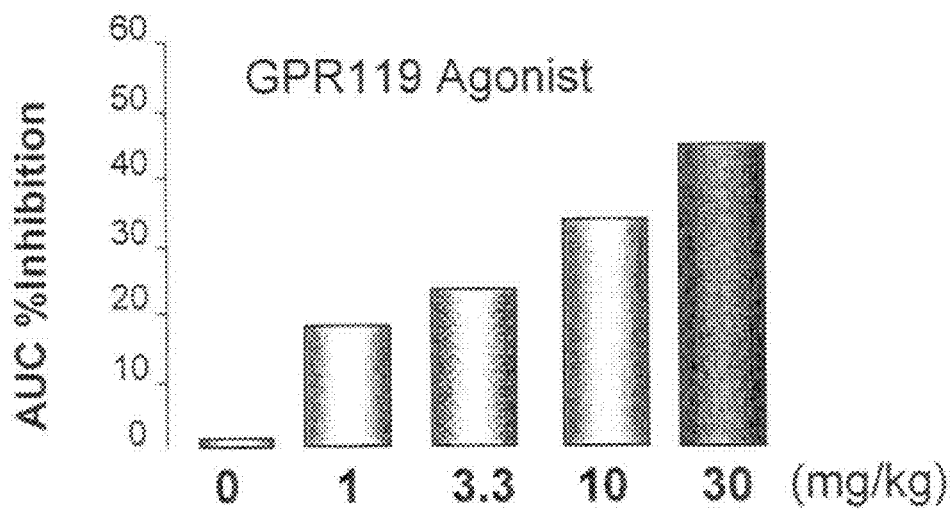

Both the DPP-IV inhibitor and the GPR119 agonist alone can produce an effective therapeutic response (at around 40% AUC inhibition) in this type of mouse model study, but only at significantly higher doses (FIG. 1C and FIG. 1D, respectively).

Example 2

Combination of GPR119 Agonist and DPP-IV Inhibitor for Treating or Preventing Diabetes and Conditions Related Thereto A GPR119 agonist in accordance with the present invention is selected. A DPP-IV inhibitor in accordance with the present invention is selected.

Titration of the GPR119 agonist with respect to percent inhibition of Area Under Curve (AUC) in mouse oral glucose tolerance test (oGTT) is determined across a dose range from about 0.01 mkg (milligram compound per kilogram of body weight) to about 100 mkg. See Example 1. A dose of the GPR119 agonist producing an AUC inhibition of glycemic excursion of about 15-20% is chosen. Typically, a dose of GPR119 agonist producing an AUC inhibition 30% or less is therapeutically ineffective in this mouse model.

Titration of the DPP-IV inhibitor with respect to percent inhibition of Area Under Curve (AUC) in mouse oral glucose tolerance test (oGTT) is determined across a dose range from about 0.01 mkg (milligram compound per kilogram of body weight) to about 100 mkg. See Example 1. A dose of the DPP-IV inhibitor producing an AUC inhibition of glycemic excursion of about 15-20% is chosen. Typically, a dose of DPP-IV inhibitor producing an AUC inhibition 30% or less is therapeutically ineffective in this mouse model.

The AUC inhibition of glycemic excursion produced by the combination of the chosen dose of the GPR119 agonist and the chosen dose of the DPP-IV inhibitor is determined in mouse oGTT assay. Therapeutic efficacy of the combination of the GPR119 agonist and the DPP-IV inhibitor is determined. Typically, an amount of the combination producing an AUC inhibition above 30% is therapeutically effective in this mouse model. Synergism between the GPR119 agonist and the DPP-IV inhibitor is determined.

Data obtained from this mouse model can be used to formulate a range of dosage for use in humans. In general, one skilled in the art understands how to extrapolate in vivo data obtained in an animal model system to another, such as a human. A combination of GPR119 agonist and DPP-IV inhibitor in accordance with the present invention is useful in treating or preventing diabetes and conditions related thereto.

It is understood that the foregoing is intended to be illustrative and not limiting.

Example 3

Synergistic Effect of GPR119 Agonist and DPP-IV Inhibitor in Increasing a Blood GLP-1 Level after Glucose Challenge in Mice C57blk/6 male mice (8 weeks of age) were fasted for 18 hours, and randomly assigned into twelve groups with n=6 for each group. Mice were administered per orally with vehicle (PET), GPR119 agonist (10 mg/kg) DPP-IV inhibitor (1 mg/kg), or a combination of GPR119 agonist and DPP-IV inhibitor, as indicated. The GPR119 agonist (AR231453) and the DPP-IV inhibitor (AR247810) used here are identical to those used in Example 1. Thirty minutes after treatment, a glucose bolus at 3 g/kg were delivered per orally, and plasma were collected at 0 minute (no glucose bolus), and at 2 minutes and 5 minutes after glucose bolus. Plasma GLP-1 levels were determined by using a GLP-1 ELISA kit purchased from Linco Research Laboratory [Glucagon-Like Peptide-1 (Active) ELISA kit, Catalog #EGLP-35K].

Figure 2:
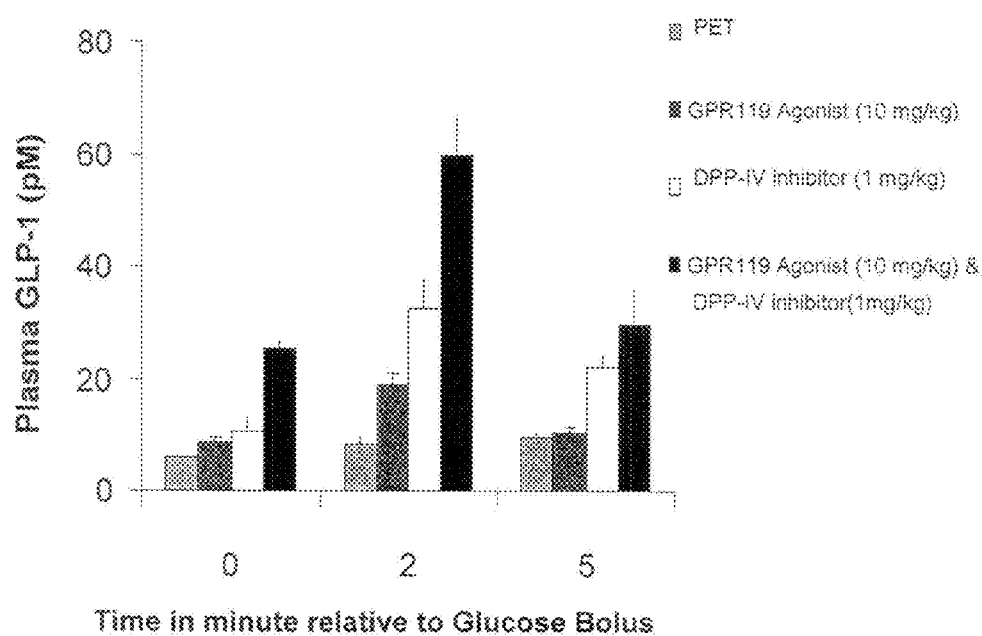
FIG. 2 shows a synergistic effect of GPR119 agonist and DPP-IV inhibitor in increasing a blood GLP-1 level after glucose challenge in mice. See Example 3.

Administration of a GPR119 agonist together with a DPP-IV inhibitor was found to produce a synergistic effect in increasing a blood GLP-1 level. See FIG. 2.

Example 4

Melanophore Assay for GPR119 Agonist Activity

Melanophores are maintained in culture as reported by Potenza et al [Pigment Cell Research (1992) 5:372-378] and transfected with an expression vector encoding a GPR119 receptor (GPR119; e.g., human GP 119, GenBank® Accession No. AAP72125 and alleles thereof) using electroporation. Following electroporation, the transfected cells are plated into 96 well plates for the assay. The cells are then allowed to grow for 48 hours in order to both recover from the electroporation procedure and attain maximal receptor expression levels.

On the assay day, the growth medium on the cells is replaced with serum-free buffer containing 10 nM melatonin. The melatonin acts via an endogenous Gi-coupled GPCR in the melanophores to lower intracellular cAMP levels. In response to lowered cAMP levels, the melanophores translocate their pigment to the center of the cell. The net effect of this is a significant decrease in the absorbance reading of the cell monolayer in the well, measured at 600-650 nM.

After a 1-hour incubation in melatonin, the cells become completely pigment-aggregated. At this point a baseline absorbance reading is collected. Serial dilutions of test compounds are then added to the plate, and compounds having GPR119 agonist activity produce increases in intracellular cAMP levels. In response to these increased cAMP levels, the melanophores translocate their pigment back into the cell periphery. After one hour, stimulated cells are fully pigment-dispersed. The cell monolayer in the dispersed state absorbs much more light in the 600-650 nm range. The measured increase in absorbance compared to the baseline reading allows one to quantitate the degree of receptor stimulation and plot a dose-response curve.

Materials and methods relating to melanophore assay are found in U.S. Pat. Nos. 5,462,856 and 6,051,386, the disclosure of each of which is herein incorporated by reference in its entirety.

Other assays for identifying a compound as a GPR119 agonist will be readily apparent to the skilled artisan (see, e.g., Example 7, infra).

Example 5

Full-Length Cloning of Endogenous Human GPR119

Polynucleotide encoding endogenous human GPR119 was cloned by PCR using the GPR119 specific primers:

5'-GTCCTGCCACTTCGAGACATGG-3' (SEQ ID NO: 3; sense, ATG as initiation codon)

5'-GAAACTTCTCTGCCCTTACCGTC-3' (SEQ ID NO: 4; antisense, 3' of stop codon)

and human genomic DNA as template. TaqPlus Precision™ DNA polymerase (Stratagene) was used for amplification by the following cycle with step 2 to step 4 repeated 35 times: 94° C., 3 minutes; 94° C., 1 minute; 58° C., 1 minute; 72° C., 2 minutes; 72° C., 10 minutes.

A 1.0 Kb PCR fragment of predicted size was isolated and cloned into the pCRII-TOPO™ vector (Invitrogen) and completely sequenced using the T7 DNA sequenase kit (Amersham). See, SEQ ID NO:1 for nucleic acid sequence and SEQ ID NO:2 for the deduced amino acid sequence.

Example 6

Receptor Expression

Although a variety of cells are available to the art for the expression of G protein-coupled receptors, it is most preferred that mammalian cells or melanophores be utilized. The following are illustrative; those of ordinary skill in the art are credited with the ability to determine those techniques that are preferentially beneficial for the needs of the artisan. See, e.g., Example 4, supra, as it relates to melanophores.

a. Transient Transfection

On day one, 6×10⁶/10 cm dish of 293 cells are plated out. On day two, two reaction tubes are prepared (the proportions to follow for each tube are per plate): tube A is prepared by mixing 4 µg DNA (e.g., pCMV vector; pCMV vector with receptor cDNA, etc.) in 0.5 ml serum free DMEM (Gibco BRL); tube B is prepared by mixing 24 µl lipofectamine (Gibco BRL) in 0.5 ml serum free DMEM. Tubes A and B are admixed by inversions (several times), followed by incubation at room temperature for 30-45 min. The admixture is referred to as the "transfection mixture". Plated 293 cells are washed with 1XPBS, followed by addition of 5 ml serum free DMEM. 1 ml of the transfection mixture is added to the cells, followed by incubation for 4 hrs at 37° C./5% $CO_2$. The transfection mixture is removed by aspiration, followed by the addition of 10 ml of DMEM/10% Fetal Bovine Serum. Cells are incubated at 37° C./5% $CO_2$. After 48 hr incubation, cells are harvested and utilized for analysis.

b. Stable Cell Lines

Approximately $12 \times 10^6$ 293 cells are plated on a 15 cm tissue culture plate. Grown in DME High Glucose Medium containing ten percent fetal bovine serum and one percent sodium pyruvate, L-glutamine, and antibiotics. Twenty-four hours following plating of 293 cells (or to ~80% confluency), the cells are transfected using 12 µg of DNA (e.g., pCMV-neo$^r$ vector with receptor cDNA). The 12 µg of DNA is combined with 60 µl of lipofectamine and 2 ml of DME High Glucose Medium without serum. The medium is aspirated from the plates and the cells are washed once with medium without serum. The DNA, lipofectamine, and medium mixture are added to the plate along with 10 ml of medium without serum. Following incubation at 37° C. for four to five hours, the medium is aspirated and 25 ml of medium containing serum is added. Twenty-four hours following transfection, the medium is aspirated again, and fresh medium with serum is added. Forty-eight hours following transfection, the medium is aspirated and medium with serum is added containing geneticin (G418 drug) at a final concentration of approximately $12 \times 10^6$ 293 cells are plated on a 15 cm tissue culture plate. Grown in DME High Glucose Medium containing ten percent fetal bovine serum and one percent sodium pyruvate, L-glutamine, and antibiotics. Twenty-four hours following plating of 293 cells (or to ~80% confluency), the cells are transfected using 12 µg of DNA (e.g., pCMV vector with receptor cDNA). The 12 µg of DNA is combined with 60 µl of lipofectamine and 2 ml of DME High Glucose Medium without serum. The medium is aspirated from the plates and the cells are washed once with medium without serum. The DNA, lipofectamine, and medium mixture are added to the plate along with 10 ml of medium without serum. Following incubation at 37° C. for four to five hours, the medium is aspirated and 25 ml of medium containing serum is added. Twenty-four hours following transfection, the medium is aspirated again, and fresh medium with serum is added. Forty-eight hours following transfection, the medium is aspirated and medium with serum is added containing geneticin (G418 drug) at a final concentration of 500 µg/ml. The transfected cells now undergo selection for positively transfected cells containing the G418 resistance gene. The medium is replaced every four to five days as selection occurs. During selection, cells are grown to create stable pools, or split for stable clonal selection.

Example 7

Assays for Screening Candidate Compounds as GPR119 Agonists

A variety of approaches are available for screening candidate compounds as GPR119 agonists. The following are illustrative; those of ordinary skill in the art are credited with the ability to determine those techniques that are preferentially beneficial for the needs of the artisan. Assays for screening compounds as agonists of a G protein-coupled receptor are well known to the skilled artisan (see, e.g., International Application WO 02/42461).

1. Membrane Binding Assays: [$^{35}$S]GTPγS Assay

When a G protein-coupled receptor is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyzes the GTP to GDP, at which point the receptor normally is deactivated. Activated receptors continue to exchange GDP for GTP. The non-hydrolyzable GTP analog, [$^{35}$S]GTPγS, can be utilized to demonstrate enhanced binding of [$^{35}$S]GTPγS to membranes expressing activated receptors. The advantage of using [$^{35}$S]GTPγS binding to measure activation is that: (a) it is generically applicable to all G protein-coupled receptors; (b) it is proximal at the membrane surface making it less likely to pick-up molecules which affect the intracellular cascade.

The assay utilizes the ability of G protein coupled receptors to stimulate [$^{35}$S]GTPγS binding to membranes expressing the relevant receptors. The assay is generic and has application to drug discovery at all G protein-coupled receptors.

Membrane Preparation

In some embodiments, membranes comprising a G protein-coupled receptor of the invention and for use in the identification of candidate compounds as, e.g., agonists of the receptor, are preferably prepared as follows:

a. Materials

"Membrane Scrape Buffer" is comprised of 20 mM HEPES and 10 mM EDTA, pH 7.4; "Membrane Wash Buffer" is comprised of 20 mM HEPES and 0.1 mM EDTA, pH 7.4; "Binding Buffer" is comprised of 20 mM HEPES, 100 mM NaCl, and 10 mM $MgCl_2$, pH 7.4.

b. Procedure

All materials will be kept on ice throughout the procedure. Firstly, the media will be aspirated from a confluent monolayer of cells, followed by rinse with 10 ml cold PBS, followed by aspiration. Thereafter, 5 ml of Membrane Scrape Buffer will be added to scrape cells; this will be followed by transfer of cellular extract into 50 ml centrifuge tubes (centrifuged at 20,000 rpm for 17 minutes at 4° C.). Thereafter, the supernatant will be aspirated and the pellet will be resuspended in 30 ml Membrane Wash Buffer followed by centrifuge at 20,000 rpm for 17 minutes at 4° C. The supernatant will then be aspirated and the pellet resuspended in Binding Buffer. This will then be homogenized using a Brinkman Polytron™ homogenizer (15-20 second bursts until the all material is in suspension). This is referred to herein as "Membrane Protein".

Bradford Protein Assay

Following the homogenization, protein concentration of the membranes will be determined using the Bradford Protein Assay (protein can be diluted to about 1.5 mg/ml, aliquoted and frozen (−80° C.) for later use; when frozen, protocol for use will be as follows: on the day of the assay, frozen Membrane Protein is thawed at room temperature, followed by vortex and then homogenized with a Polytron at about 12×1, 000 rpm for about 5-10 seconds; it is noted that for multiple preparations, the homogenizer should be thoroughly cleaned between homogenization of different preparations).

a. Materials

Binding Buffer (as per above); Bradford Dye Reagent; Bradford Protein Standard will be utilized, following manufacturer instructions (Biorad, cat. no. 500-0006).

b. Procedure

Duplicate tubes will be prepared, one including the membrane, and one as a control "blank". Each contained 800 µl Binding Buffer. Thereafter, 10 µl of Bradford Protein Standard (1 mg/ml) will be added to each tube, and 10 µl of membrane Protein will then be added to just one tube (not the blank). Thereafter, 200 µl of Bradford Dye Reagent will be added to each tube, followed by vortex of each. After five (5) minutes, the tubes will be re-vortexed and the material therein will be transferred to cuvettes. The cuvettes will then be read using a CECIL 3041 spectrophotometer, at wavelength 595.

Identification Assay a. Materials

GDP Buffer consists of 37.5 ml Binding Buffer and 2 mg GDP (Sigma, cat. no. G-7127), followed by a series of dilutions in Binding Buffer to obtain 0.2 µM GDP (final concentration of GDP in each well was 0.1 µM GDP); each well comprising a candidate compound, has a final volume of 200 µl consisting of 100 µl GDP Buffer (final concentration, 0.1 µM GDP), 50 µl Membrane Protein in Binding Buffer, and 50 µl [$^{35}$S]GTPγS (0.6 nM) in Binding Buffer (2.5 µl [$^{35}$S]GTPγS per 10 ml Binding Buffer).

b. Procedure

Candidate compounds will be preferably screened using a 96-well plate format (these can be frozen at –80° C.). Membrane Protein (or membranes with expression vector excluding the Target GPCR, as control), will be homogenized briefly until in suspension. Protein concentration will then be determined using the Bradford Protein Assay set forth above. Membrane Protein (and control) will then be diluted to 0.25 mg/ml in Binding Buffer (final assay concentration, 12.5 µg/well). Thereafter, 100 µl GDP Buffer was added to each well of a Wallac Scintistrip™ (Wallac). A 5 ul pin-tool will then be used to transfer 5 µl of a candidate compound into such well (i.e., 5 µl in total assay volume of 200 µl is a 1:40 ratio such that the final screening concentration of the candidate compound is 10 µM). Again, to avoid contamination, after each transfer step the pin tool should be rinsed in three reservoirs comprising water (1×), ethanol (1×) and water (2×)—excess liquid should be shaken from the tool after each rinse and dried with paper and kimwipes. Thereafter, 50 µl of Membrane Protein will be added to each well (a control well comprising membranes without the Target GPCR was also utilized), and pre-incubated for 5-10 minutes at room temperature. Thereafter, 50 µl of [$^{35}$S]GTPγS (0.6 nM) in Binding Buffer will be added to each well, followed by incubation on a shaker for 60 minutes at room temperature (again, in this example, plates were covered with foil). The assay will then be stopped by spinning of the plates at 4000 RPM for 15 minutes at 22° C. The plates will then be aspirated with an 8 channel manifold and sealed with plate covers. The plates will then be read on a Wallac 1450 using setting "Prot. #37" (as per manufacturer's instructions).

2. Adenylyl Cyclase Assay

A Flash Plate™ Adenylyl Cyclase kit (New England Nuclear; Cat. No. SMP004A) designed for cell-based assays can be modified for use with crude plasma membranes. The Flash Plate wells can contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

In certain embodiments, a modified Flash Plate™ Adenylyl Cyclase kit (New England Nuclear; Cat. No. SMP004A) is utilized for identification of candidate compounds as, e.g., GPR119 agonists in accordance with the following protocol.

Cells transfected with a G protein-coupled receptor of the invention are harvested approximately three days after transfection. Membranes are prepared by homogenization of suspended cells in buffer containing 20 mM HEPES, pH 7.4 and 10 mM MgCl$_2$. Homogenization is performed on ice using a Brinkman Polytron™ for approximately 10 seconds. The resulting homogenate is centrifuged at 49,000×g for 15 minutes at 4° C. The resulting pellet is then resuspended in buffer containing 20 mM HEPES, pH 7.4 and 0.1 mM EDTA, homogenized for 10 seconds, followed by centrifugation at 49,000×g for 15 minutes at 4° C. The resulting pellet is then stored at –80° C. until utilized. On the day of direct identification screening, the membrane pellet is slowly thawed at room temperature, resuspended in buffer containing 20 mM HEPES, pH 7.4 and 10 mM MgCl$_2$, to yield a final protein concentration of 0.60 mg/ml (the resuspended membranes are placed on ice until use).

cAMP standards and Detection Buffer (comprising 2 µCi of tracer {[$^{125}$I]cAMP (100 µl) to 11 ml Detection Buffer] are prepared and maintained in accordance with the manufacturer's instructions. Assay Buffer was prepared fresh for screening and contained 20 mM HEPES, pH 7.4, 10 mM MgCl$_2$, 20 mM phosphocreatine (Sigma), 0.1 units/ml creatine phosphokinase (Sigma), 50 µM GTP (Sigma), and 0.2 mM ATP (Sigma); Assay Buffer was then stored on ice until utilized.

Candidate compounds are added, preferably, to e.g. 96-well plate wells (3 µl/well; 12 µM final assay concentration), together with 40 µl Membrane Protein (30 µg/well) and 50 µl of Assay Buffer. This admixture was then incubated for 30 minutes at room temperature, with gentle shaking.

Following the incubation, 100 µl of Detection Buffer is added to each well, followed by incubation for 2-24 hours. Plates are then counted in a Wallac MicroBeta™ plate reader using "Prot. #31" (as per manufacturer's instructions).

3. CRE-Luc Reporter Assay 293 and 293T cells are plated-out on 96 well plates at a density of 2×10$^4$ cells per well and were transfected using Lipofectamine Reagent (BRL) the following day according to manufacturer instructions. A DNA/lipid mixture is prepared for each 6-well transfection as follows: 260 ng of plasmid DNA in 100 µl of DMEM is gently mixed with 2 µl of lipid in 100 µl of DMEM (the 260 ng of plasmid DNA consists of 200 ng of a 8xCRE-Luc reporter plasmid, 50 ng of pCMV comprising a G protein-coupled receptor of the invention or pCMV alone, and 10 ng of a GPRS expression plasmid [GPRS in pcDNA3 (Invitrogen)]. The 8XCRE-Luc reporter plasmid was prepared as follows: vector SRIF-β-gal was obtained by cloning the rat somatostatin promoter (–71/+51) at BglV-HindIII site in the pβgal-Basic Vector (Clontech). Eight (8) copies of cAMP response element were obtained by PCR from an adenovirus template AdpCF126CCRE8 [see, Suzuki et al., Hum Gene Ther (1996) 7:1883-1893; the disclosure of which is herein incorporated by reference in its entirety) and cloned into the SRIF-β-gal vector at the Kpn-BglV site, resulting in the 8xCRE-β-gal reporter vector. The 8xCRE-Luc reporter plasmid was generated by replacing the beta-galactosidase gene in the 8xCRE-β-gal reporter vector with the luciferase gene obtained from the pGL3-basic vector (Promega) at the HindIII-BamHI site. Following 30 min. incubation at room temperature, the DNA/lipid mixture is diluted with 400 µl of DMEM and 100 µl of the diluted mixture is added to each well. 100 µl of DMEM with 10% FCS are added to each well after a 4 hr incubation in a cell culture incubator. The following day the transfected cells are changed with 200 µl/well of DMEM with 10% FCS. Eight (8) hours later, the wells are changed to 100 µl/well of DMEM without phenol red, after one wash with PBS. Luciferase activity is measured the next day using the LucLite™ reporter gene assay kit (Packard) following manufacturer instructions and read on a 1450 MicroBeta™ scintillation and luminescence counter (Wallac).

Example 8

Radiolabeled Compound

In certain embodiments, a compound known to be a ligand of a G protein-coupled receptor of the invention is radiolabeled. A radiolabeled compound as described herein can be used in a screening assay to identify/evaluate compounds. In general terms, a newly synthesized or identified compound (i.e., test compound) can be evaluated for its ability to reduce binding of the radiolabeled known ligand to the receptor, by its ability to reduce formation of the complex between the radiolabeled known ligand and the receptor. Suitable radionuclides that may be incorporated in compounds of the present invention include but are not limited to $^3$H (also written as T), $^{11}$C, $^{14}$C, $^{18}$F, $^{125}$I, $^{82}$Br, $^{123}$I, $^{124}$I, $^{125}$I, $^{131}$I, $^{75}$Br, $^{76}$Br, $^{15}$O, $^{13}$N, $^{35}$S and $^{77}$Br. Compounds that incorporate $^3$H, $^{14}$C, $^{125}$I, $^{131}$I, $^{35}$S or $^{82}$Br will generally be most useful.

It is understood that a "radiolabelled" compound is a compound that has incorporated at least one radionuclide. In some embodiments, the radionuclide is selected from the group consisting of $^3$H, $^{14}$C, $^{125}$I, $^{35}$S and $^{82}$Br. In some embodiments, the radionuclide $^3$H or $^{14}$C. Moreover, it should be understood that all of the atoms represented in the compounds known to be ligands of a G protein-coupled receptor of the invention can be either the most commonly occurring isotope of such atoms or the more scarce radioisotope or nonradioactive isotope.

Synthetic methods for incorporating radioisotopes into organic compounds including those applicable to those compounds known to be ligands of a G protein-coupled receptor of the invention are well known in the art and include incorporating activity levels of tritium into target molecules include: A. Catalytic Reduction with Tritium Gas—This procedure normally yields high specific activity products and requires halogenated or unsaturated precursors. B. Reduction with Sodium Borohydride [$^3$H]—This procedure is rather inexpensive and requires precursors containing reducible functional groups such as aldehydes, ketones, lactones, esters, and the like. C. Reduction with Lithium Aluminum Hydride [$^3$H]—This procedure offers products at almost theoretical specific activities. It also requires precursors containing reducible functional groups such as aldehydes, ketones, lactones, esters, and the like. D. Tritium Gas Exposure Labeling—This procedure involves exposing precursors containing exchangeable protons to tritium gas in the presence of a suitable catalyst. E. N-Methylation using Methyl Iodide [$^3$H]—This procedure is usually employed to prepare O-methyl or N-methyl ($^3$H) products by treating appropriate precursors with high specific activity methyl iodide ($^3$H). This method in general allows for high specific activity, such as about 80-87 Ci/mmol.

Synthetic methods for incorporating activity levels of $^{125}$I into target molecules include: A. Sandmeyer and like reactions—This procedure transforms an aryl or heteroaryl amine into a diazonium salt, such as a tetrafluoroborate salt, and subsequently to $^{125}$I labelled compound using Na$^{125}$I. A represented procedure was reported by Zhu, D.-G. and co-workers in *J. Org. Chem.* 2002, 67, 943-948. B. Ortho $^{125}$Iodination of phenols—This procedure allows for the incorporation of $^{125}$I at the ortho position of a phenol as reported by Collier, T. L. and co-workers in *J. Labelled Compd Radiopharm.* 1999, 42, S264-S266. C. Aryl and heteroaryl bromide exchange with $^{125}$I—This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A represented procedure was reported by Bas, M.-D. and co-workers in *J. Labelled Compd Radiopharm.* 2001, 44, S280-S282.

The foregoing techniques are intended to be illustrative and not limiting. Other techniques for radiolabeling a compound known to be a ligand of a G protein-coupled receptor of the invention are well known to the skilled artisan.

Example 9

Receptor Binding Assay

A test compound can be evaluated for its ability to reduce formation of the complex between a compound known to be a ligand of a G protein-coupled receptor of the invention and the receptor. In certain embodiments, the known ligand is radiolabeled. The radiolabeled known ligand can be used in a screening assay to identify/evaluate compounds. In general terms, a newly synthesized or identified compound (i.e., test compound) can be evaluated for its ability to reduce binding of the radiolabeled known ligand to the receptor, by its ability to reduce formation of the complex between the radiolabeled known ligand and the receptor.

Assay Protocol for Detecting the Complex Between a Compound Known to be a Ligand of a G Protein-Coupled Receptor of the Invention and the Receptor A. Preparation of the Receptor 293 cells are transiently transfected with 10 ug expression vector comprising a polynucleotide encoding a G protein-coupled receptor of the invention using 60 ul Lipofectamine (per 15-cm dish). The transiently transfected cells are grown in the dish for 24 hours (75% confluency) with a media change and removed with 10 ml/dish of Hepes-EDTA buffer (20 mM Hepes+10 mM EDTA, pH 7.4). The cells are then centrifuged in a Beckman Coulter centrifuge for 20 minutes, 17,000 rpm (JA-25.50 rotor). Subsequently, the pellet is resuspended in 20 mM Hepes+1 mM EDTA, pH 7.4 and homogenized with a 50-ml Dounce homogenizer and again centrifuged. After removing the supernatant, the pellets are stored at −80° C., until used in binding assay. When used in the assay, membranes are thawed on ice for 20 minutes and then 10 mL of incubation buffer (20 mM Hepes, 1 mM MgCl$_2$, 100 mM NaCl, pH 7.4) added. The membranes are then vortexed to resuspend the crude membrane pellet and homogenized with a Brinkmann PT-3100 Polytron homogenizer for 15 seconds at setting 6. The concentration of membrane protein is determined using the BRL Bradford protein assay.

B. Binding Assay

For total binding, a total volume of 50 ul of appropriately diluted membranes (diluted in assay buffer containing 50 mM Tris HCl (pH 7.4), 10 mM $MgCl_2$, and 1 mM EDTA; 5-50 ug protein) is added to 96-well polyproylene microtiter plates followed by addition of 100 ul of assay buffer and 50 ul of a radiolabeled known ligand. For nonspecific binding, 50 ul of assay buffer is added instead of 100 ul and an additional 50 ul of 10 uM said known ligand which is not radiolabeled is added before 50 ul of said radiolabeled known ligand is added. Plates are then incubated at room temperature for 60-120 minutes. The binding reaction is terminated by filtering assay plates through a Microplate Devices GF/C Unifilter filtration plate with a Brandell 96-well plate harvestor followed by washing with cold 50 mM Tris HCl, pH 7.4 containing 0.9% NaCl. Then, the bottom of the filtration plate are sealed, 50 ul of Optiphase Supermix is added to each well, the top of the plates are sealed, and plates are counted in a Trilux MicroBeta scintillation counter. For determining whether less of the complex between said radiolabeled known ligand and said receptor is formed in the presence of a test compound, instead of adding 100 ul of assay buffer, 100 ul of appropriately diluted said test compound is added to appropriate wells followed by addition of 50 ul of said radiolabled known ligand.

A level of specific binding of the radiolabled known ligand in the presence of the test compound less than a level of specific binding of the radiolabeled known ligand in the absence of the test compound is indicative of less of the complex between said radiolabeled known ligand and said receptor being formed in the presence of the test compound than in the absence of the test compound.

Example 10

Expression of GPR119 in Gut

The expression of GPR119 mRNA in various tissues was determined using RNase Protection Assay (RPA).

Mouse tissue RNA was obtained commercially (Clontech). A 255 bp protected fragment of mouse GPR119 was cloned into pCRII-TOPO cloning vector (Invitrogen). The sequence of the 255 bp protected fragment was as follows (nucleotides that comprise mouse GPR119 coding region are underlined):

```
                                             (SEQ ID NO: 5)
5'-CTGGCCTGCCAGTAATGGCCAGAACGGTGCTGTGACTCTGAGCCTAT

AGCACATCTAATCCTGTCCCATGAGAATCTGAGCTCGCCATCCAGCATGC

CTTTGTAAGTGGAAGTGCTGCTACCTCACCATGGAGTCATCCTTCTCAT

TTGGAGTGATCCTTGCTGTCCTAACCATCCTCATCATTGCTGTTAATGC

ACTGGTAGTTGTGGCTATGCTGCTATCAATCTACAAGAATGATGGTGTT

GGCCTTTGCTT-3'.
```

The full length probe size was 356 bp. The plasmid was linearized with BamHI and gel purified using the Sephaglass Bandprep Kit (Amersham). After gel purification of the fragment, a riboprobe was made by in vitro transcription with using T7 RNA polymerase (Ambion Maxiscript Kit). The probe was purified by acrylamide gel electrophoresis and hybridized with 20 ug of total RNA at 45° C. overnight. The hybrids were digested with RNAse the following day and run on a 5% acrylamide gel to detect the results (Ambion, RPA III kit). All the procedures for in vitro transcription and RPA reactions were following the manufacturer's instructions.

The highest level of GPR119 expression was found in pancreatic islets, although GPR119 was also found to be expressed in colon and to lesser extent in small intestine. See FIG. 3.

Example 11

Expression of GPR119 in GLUTag Enteroendocrine Cell Line

Northern blot analysis was used to determine the level of GPR119 mRNA expression in GLUTag (Fla subline; see Example 12, infra), HIT-T15 (a hamster pancreatic beta cell line; ATCC No. CRL-1777), and NCI-H716 (a human endocrine cell line; ATCC No. CRL-251). GLUTag is a mouse enteroendocrine cell line that secretes GLP-1 [Brubaker et al., Endocrinology (1998) 139:4108-4114].

RNA was extracted from tissue cultured cells by using RNA Bee (Tel-Test). Ten (10) μg of total RNA was separated on a 0.8% agarose gel electrophoresis, and blotted onto nylon membrane (Amersham). The RNA blot was hybridized with a $^{32}$P-labeled mouse GPR119 cDNA probe (see, e.g., mouse GPR119, GenBank® Accession No. AY288423), followed by reprobing with a $^{32}$P-labeled cDNA probe for mouse preproglucagon mRNA as a control. The hybridization signals were visualized by autoradiography.

GLUTag cells (Fla subline; see Example 12, infra) were found to express GPR119 and preproglucagon. See FIG. 4.

Example 12

GPR119 Agonist Elevates Intracellular Camp in GLUTag Cells

GLUTag is a mouse enteroendocrine cell line that secretes GLP-1 [Brubaker et al., Endocrinology (1998) 139:4108-4114]. The effect of GPR119 agonist on the level of intracellular cAMP in GLUTag (Fla subline) enteroendocrine cells was determined. The Fro subline of GLUTag was used as a negative control. Northern blot analysis (inset) using mouse GPR119 cDNA as probe (see, e.g., mouse GPR119, GenBank® Accession No. AY288423) indicated that the Fla subline of GLUTag expresses GPR119, whereas the Flo subline of GLUTag does not detectably express GPR119.

GluTag (GLUTag-Fla and GLUTag-Fro) cells were plated at ~85% confluency in 15-cm tissue culture plate with regular growth medium. On the next day, cells were scraped off with cold Scraping Buffer (20 mM HEPES, 10 mM EDTA, pH7.4) and spinned down at 1000 rpm for 17 mins at 4° C. Cell pellets were washed with cold Membrane Wash Buffer (20 mM HEPES, 0.1 mM EDTA, pH7.4) and spun again as above. The membrane pellets were resuspended in cold Binding Buffer (20 mM HEPES, 1 mM $MgCl_2$, 100 mMNaCl, pH7.4) and homogenized twice using a Polytron™ homogenizer (Model No. PT3100; Brinkman) at 7000 rpm for 10 seconds. Protein concentration was determined by Bradford Assay. Cell membranes were diluted to a protein concentration of 0.2 mg/ml in Binding Buffer. (The final assay concentration was 10 ug/well).

The cyclase assay was done with a Flash Plate™ Adenylyl Cyclase kit (New England Nuclear; Cat. No. SMP004A). The Flash Plate wells contain a scintillant coating which also contains a specific antibody recognizing cAMP. The cAMP generated in the wells can be quantitated by a direct competition for binding of radioactive cAMP tracer to the cAMP antibody.

Details of the cyclase assay as it was carried out are described here. cAMP standards and Detection Buffer (comprising 1 µCi of tracer [125I]cAMP (50 µl) to 11 ml Detection Buffer) were prepared and maintained in accordance with the manufacturer's instructions. GPR119 agonist AR231453 was freshly prepared and serially diluted in 50 ul freshly prepared 2× Reconstitution Buffer (20 mM Phosphocreatine, 20 units/ 50 ul Creatine Phosphokinase, 20 uM GTP, 0.2 mM ATP, 1 mM IBMX). Eight doses of GPR119 agonist, from 10 uM down to 1.27 nM, were tested. The assay was carried out in a 96-well Flash Plate. GPR1119 agonist and cAMP standards were first added to appropriate wells. The cell membranes were then added to the wells, and the plate was incubated for 60 minutes at room temperature. 100 ul of Detection Mix containing tracer $^3$H-cAMP was then added to each well. Plates were incubated for an additional two hours, after which the samples were counted in a Wallac MicroBeta scintillation counter. Values of cAMP/well were then extrapolated from a standard cAMP curve which was contained within each assay plate.

GPR119 agonist was found to elevate the level of intracellular cAMP in GLUTag-Fla cells which express GPR119, but not in GLUTag-Fro cells which do not express GPR119. GPR119 agonist was found to elevate cAMP in GLUTag cells with an EC50 of about 4.3 nM. See FIG. 5.

Example 13

GPR119 Agonist Stimulates GLP-1 Secretion in GLUTag Cells

GLUTag-Fla cells (see Example 12, supra) were plated in 24-well plates on day one in complete culture medium (DMEM/10% FBS). On day two the culture medium was replaced with a low glucose medium (DMEM/3 mM Glucose/10% FBS). On day three cells were washed twice with 1XPBS. The washed GLUTag-Fla cells were stimulated with GPR119 agonist (AR231453) at various concentrations or with forskolin (1 uM) as a positive control in serum free DMEM with 15 mM glucose for one hour at 37° C. and 5% CO2 in a tissue culture incubator. The supernatants were then collected and clarified by centrifugation at 500 g and 4° C. for 5 minutes. GLP-1 released into the supernatant was determined by ELISA using reagents purchased from LINCO Research Laboratory [Glucagon-Like Peptide-1 (Active) ELISA Kit. Cat. #EGLP-35K].

GLUTag-Fla cells were found to secrete GLP-1 when stimulated with GPR119 agonist. See FIG. 6.

Example 14

Figure 7B:
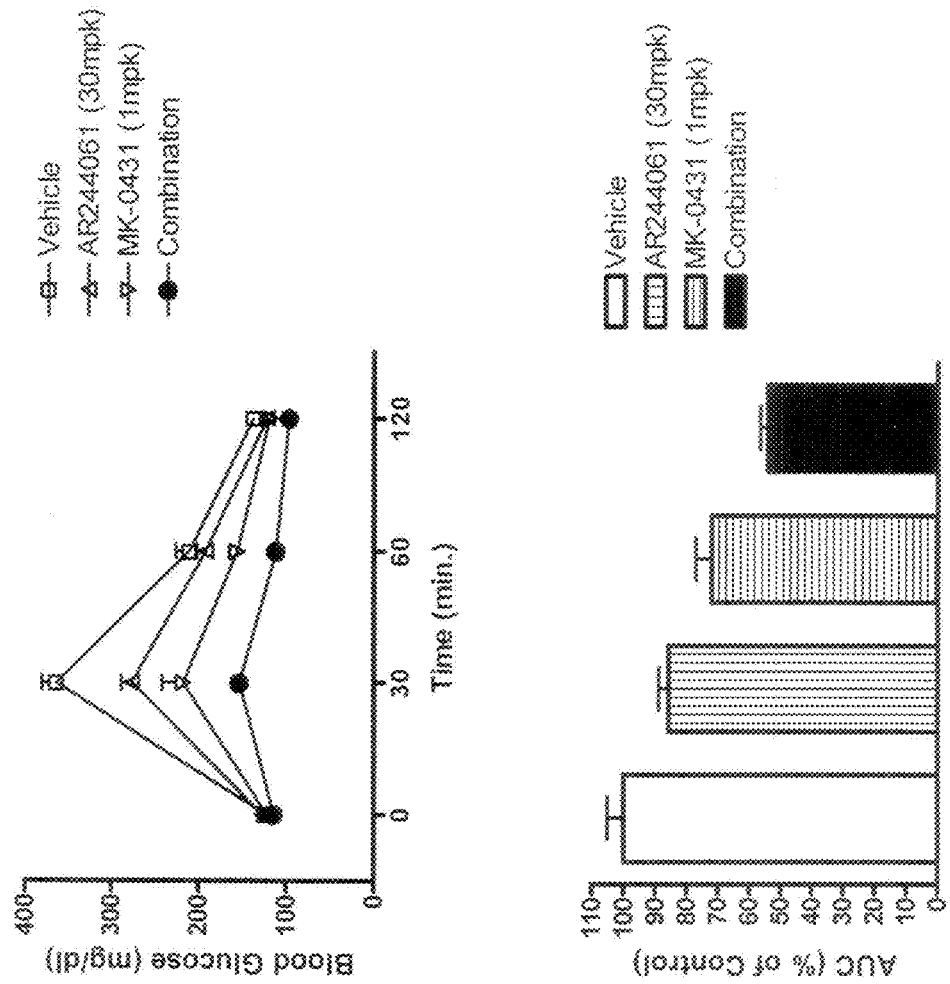
FIG. 7 shows an effect of GPR119 agonist AR244061 and DPP-IV inhibitor MK-0431 in lowering blood glucose level in oral glucose tolerance test (oGTT) in mice. See Example 14.
Figure 8B:
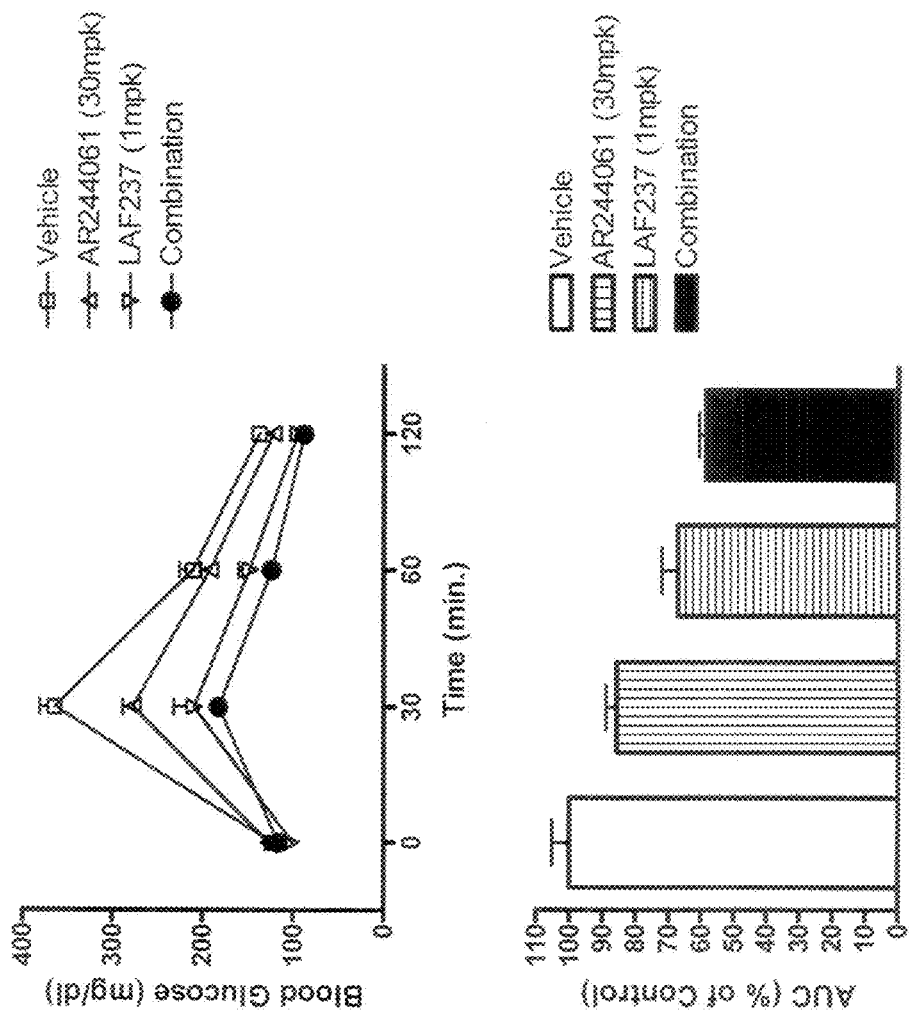
FIG. 8 shows an effect of GPR119 agonist AR244061 and DPP-IV inhibitor LAF237 in lowering blood glucose level in oral glucose tolerance test (oGTT) in mice. See Example 14.

Effect of GPR119 Agonist AR244061 and DPP-IV Inhibitors in Lowering Blood Glucose Level in Oral Glucose Tolerance Test (oGTT) in Mice Oral glucose tolerance test (oGTT) in 7-8 week old C57BL/6J mice was carried out as described here. Overnight fasted mice (n=8 mice per treatment group) were administered via oral gavage with vehicle, a GPR119 agonist (AR244061, different to that used in Example 1), a DPP-IV inhibitor (MK-0431, LAF237 or FE107542), or a combination of the GPR119 agonist and the DPP-IV inhibitor. GPR119 agonist AR244061 was administered at 10 mpk or 30 mpk (milligram compound per kilogram of body weight). DPP-IV inhibitors MK-0431 and LAF237 were administered at 1 mpk, and FE107542 was administered at 10 mpk. One hour after compound dosing, a glucose bolus (2 gram/kg) was delivered per orally, and tail blood samples were collected to measure blood glucose at 0, 30, 60 and 120 minutes. Results obtained for MK-0431 are shown in FIG. 7; results obtained for LAF237 are shown in FIG. 8; and results obtained for FE107542 are shown in FIG. 9. For each treatment group, glycemic excursion curve was graphed and is presented with blood glucose concentration given in mean values +/−standard error of the mean (SEM). Area Under Curve (AUC) of the glycemic excursion was calculated and reported as AUC (% of vehicle control).

From inspection of FIG. 7, FIG. 8 and FIG. 9, it is apparent that whereas at the concentrations used both the GPR119 agonist (a GPR119 agonist different to that used in Example 1) and the DPP-IV inhibitor alone (for each of three different DPP-IV inhibitors) provided measurable glycemic control, combination of the GPR119 agonist and the DPP-IV inhibitor provided a dose-dependent level of glycemic control over that provided by the GPR119 agonist or DPP-IV inhibitor alone.

While the foregoing specification teaches the principles of the present invention, with examples provided for the purpose of illustration, it will be understood that the practice of the invention encompasses all of the usual variations, adaptions, or modifications, as come within the scope of the following claims and its equivalents.

What is claimed is:

1. A method for identifying a Glucagon-like Peptide-1 (GLP-1) secretagogue, comprising:
   (a) contacting a G protein-coupled receptor (GPCR) with a ligand to the GPCR in the presence of a test compound, wherein the GPCR comprises an amino acid sequence selected from the group consisting of:
      (i) SEQ ID NO: 2; and
      (ii) the amino acid sequence of a GPCR encoded by the nucleotide sequence set forth in SEQ ID NO: 1;
   (b) detecting a complex between the GPCR and the ligand;
   (c) determining whether less of the complex is formed in the presence of the test compound than in the absence of the test compound;
   (d) determining the blood GLP-1 level in a blood or a plasma sample obtained from a mammal, the mammal having been administered with the test compound in the presence of which less of the complex is formed in step (c),
   wherein the ability of the test compound to increase a blood GLP-1 level in the blood or the plasma sample obtained from the mammal identifies the test compound as a GLP-1 secretagogue.

2. The method of claim 1, wherein the mammal is a non-human mammal.

3. The method of claim 1, wherein the mammal is a human.

4. The method of claim 1, wherein the GPCR is recombinant.

5. The method of claim 1, wherein the test compound is a small molecule.

6. The method of claim 1, wherein the test compound is a polypeptide.

7. The method of claim 1, wherein the test compound is an antibody or an antigen-binding fragment thereof.

8. The method of claim 1, wherein the ligand is labeled.

9. The method of claim 8, wherein the labeled ligand is a radiolabeled known ligand.

* * * * *

```
                        SEQUENCE LISTING

<160> NUMBER OF SEQ ID NOS: 5

<210> SEQ ID NO 1
<211> LENGTH: 1008
<212> TYPE: DNA
<213> ORGANISM: Homo sapien

<400> SEQUENCE: 1
atggaatcat ctttctcatt tggagtgatc cttgctgtcc tggcctccct catcattgct        60
actaacacac tagtggctgt ggctgtgctg ctgttgatcc acaagaatga tggtgtcagt       120
ctctgcttca ccttgaatct ggctgtggct gacaccttga ttggtgtggc catctctggc       180
ctactcacag accagctctc cagcccttct cggcccacac agaagaccct gtgcagcctg       240
```

-continued

```
cggatggcat tgtcacttc ctccgcagct gcctctgtcc tcacggtcat gctgatcacc      300
tttgacaggt accttgccat caagcagccc ttccgctact tgaagatcat gagtgggttc      360
gtggccgggg cctgcattgc cgggctgtgg ttagtgtctt acctcattgg cttcctccca      420
ctcggaatcc ccatgttcca gcagactgcc tacaaagggc agtgcagctt ctttgctgta      480
tttcacccte acttcgtgct gaccctctcc tgcgttggct tcttcccagc catgctcctc      540
tttgtcttct tctactgcga catgctcaag attgcctcca tgcacagcca gcagattcga      600
aagatggaac atgcaggagc catggctgga ggttatcgat ccccacggac tcccagcgac      660
ttcaaagctc tccgtactgt gtctgttctc attgggagct tgctctatc ctggacccccc      720
ttccttatca ctggcattgt gcaggtggcc tgccaggagt gtcacctcta cctagtgctg      780
gaacggtacc tgtggctgct cggcgtgggc aactccctgc tcaacccact catctatgcc      840
tattggcaga aggaggtgcg actgcagctc taccacatgg ccctaggagt gaagaaggtg      900
ctcacctcat tcctcctctt tctctcggcc aggaattgtg gcccagagag gcccagggaa      960
agttcctgtc acatcgtcac tatctccagc tcagagtttg atggctaa               1008
```

<210> SEQ ID NO 2
<211> LENGTH: 335
<212> TYPE: PRT
<213> ORGANISM: Homo sapien

<400> SEQUENCE: 2

```
Met Glu Ser Ser Phe Ser Phe Gly Val Ile Leu Ala Val Leu Ala Ser
1               5                   10                  15

Leu Ile Ile Ala Thr Asn Thr Leu Val Ala Val Ala Val Leu Leu Leu
                20                  25                  30

Ile His Lys Asn Asp Gly Val Ser Leu Cys Phe Thr Leu Asn Leu Ala
            35                  40                  45

Val Ala Asp Thr Leu Ile Gly Val Ala Ile Ser Gly Leu Leu Thr Asp
        50                  55                  60

Gln Leu Ser Ser Pro Ser Arg Pro Thr Gln Lys Thr Leu Cys Ser Leu
65                  70                  75                  80

Arg Met Ala Phe Val Thr Ser Ser Ala Ala Ala Ser Val Leu Thr Val
                85                  90                  95

Met Leu Ile Thr Phe Asp Arg Tyr Leu Ala Ile Lys Gln Pro Phe Arg
            100                 105                 110

Tyr Leu Lys Ile Met Ser Gly Phe Val Ala Gly Ala Cys Ile Ala Gly
        115                 120                 125

Leu Trp Leu Val Ser Tyr Leu Ile Gly Phe Leu Pro Leu Gly Ile Pro
130                 135                 140

Met Phe Gln Gln Thr Ala Tyr Lys Gly Gln Cys Ser Phe Phe Ala Val
145                 150                 155                 160

Phe His Pro His Phe Val Leu Thr Leu Ser Cys Val Gly Phe Phe Pro
                165                 170                 175

Ala Met Leu Leu Phe Val Phe Phe Tyr Cys Asp Met Leu Lys Ile Ala
            180                 185                 190

Ser Met His Ser Gln Gln Ile Arg Lys Met Glu His Ala Gly Ala Met
        195                 200                 205

Ala Gly Gly Tyr Arg Ser Pro Arg Thr Pro Ser Asp Phe Lys Ala Leu
    210                 215                 220

Arg Thr Val Ser Val Leu Ile Gly Ser Phe Ala Leu Ser Trp Thr Pro
225                 230                 235                 240

Phe Leu Ile Thr Gly Ile Val Gln Val Ala Cys Gln Glu Cys His Leu
```

-continued

```
                        245                 250                 255
Tyr Leu Val Leu Glu Arg Tyr Leu Trp Leu Leu Gly Val Gly Asn Ser
            260                 265                 270

Leu Leu Asn Pro Leu Ile Tyr Ala Tyr Trp Gln Lys Glu Val Arg Leu
            275                 280                 285

Gln Leu Tyr His Met Ala Leu Gly Val Lys Lys Val Leu Thr Ser Phe
        290                 295                 300

Leu Leu Phe Leu Ser Ala Arg Asn Cys Gly Pro Glu Arg Pro Arg Glu
305                 310                 315                 320

Ser Ser Cys His Ile Val Thr Ile Ser Ser Ser Glu Phe Asp Gly
                325                 330                 335

<210> SEQ ID NO 3
<211> LENGTH: 22
<212> TYPE: DNA
<213> ORGANISM: Artificial
<220> FEATURE:
<223> OTHER INFORMATION: Primer

<400> SEQUENCE: 3
gtcctgccac ttcgagacat gg                                       22

<210> SEQ ID NO 4
<211> LENGTH: 23
<212> TYPE: DNA
<213> ORGANISM: Artificial
<220> FEATURE:
<223> OTHER INFORMATION: Primer

<400> SEQUENCE: 4
gaaacttctc tgcccttacc gtc                                      23

<210> SEQ ID NO 5
<211> LENGTH: 255
<212> TYPE: DNA
<213> ORGANISM: Artificial
<220> FEATURE:
<223> OTHER INFORMATION: Probe

<400> SEQUENCE: 5
ctggcctgcc agtaatggcc agaacggtgc tgtgactctg agcctatagc acatctaatc    60
ctgtcccatg agaatctgag ctcgccatcc agcatgcctt tgtaagtgga agtgctgcta   120
cctcaccatg gagtcatcct tctcatttgg agtgatcctt gctgtcctaa ccatcctcat   180
cattgctgtt aatgcactgg tagttgtggc tatgctgcta tcaatctaca agaatgatgg   240
tgttggcctt tgctt                                                   255
```